US012576150B2

(12) United States Patent
De Vries et al.

(10) Patent No.: US 12,576,150 B2
(45) Date of Patent: Mar. 17, 2026

(54) CD4+ T CELLS EXPRESSING IL-10 AND CHIMERIC ANTIGEN RECEPTORS AND USES THEREOF

(71) Applicant: TR1X, INC., La Jolla, CA (US)

(72) Inventors: Jan Egbert De Vries, La Jolla, CA (US); Maria Grazia Roncarolo, La Jolla, CA (US); Xavier Paliard, La Jolla, CA (US); David De Vries, La Jolla, CA (US)

(73) Assignee: Tr1x, Inc., San Diego, CA (US)

( * ) Notice: Subject to any disclaimer, the term of this patent is extended or adjusted under 35 U.S.C. 154(b) by 0 days.

(21) Appl. No.: 19/064,325

(22) Filed: Feb. 26, 2025

(65) Prior Publication Data

US 2025/0195656 A1 Jun. 19, 2025

Related U.S. Application Data

(63) Continuation of application No. 18/725,665, filed as application No. PCT/US2022/082431 on Dec. 27, 2022.

(60) Provisional application No. 63/295,491, filed on Dec. 30, 2021.

(51) Int. Cl.

| | |
|---|---|
| *A61K 40/42* | (2025.01) |
| *A61K 38/20* | (2006.01) |
| *A61K 40/11* | (2025.01) |
| *A61K 40/31* | (2025.01) |
| *A61K 40/41* | (2025.01) |
| *A61P 35/00* | (2006.01) |
| *A61P 37/06* | (2006.01) |
| *C07K 14/54* | (2006.01) |
| *C07K 14/725* | (2006.01) |
| *C07K 16/28* | (2006.01) |
| *C12N 5/0783* | (2010.01) |
| *C12N 15/86* | (2006.01) |

(52) U.S. Cl.
CPC ...... *A61K 40/4211* (2025.01); *A61K 38/2066* (2013.01); *A61K 40/11* (2025.01); *A61K 40/31* (2025.01); *A61P 35/00* (2018.01); *A61P 37/06* (2018.01); *C07K 14/5428* (2013.01); *C07K 14/7051* (2013.01); *C07K 16/2803* (2013.01); *C12N 15/86* (2013.01); *C07K 2317/24* (2013.01); *C07K 2317/622* (2013.01); *C12N 2740/15043* (2013.01)

(58) Field of Classification Search
CPC ................ A61K 38/2066; A61K 40/31; C07K 14/5428; C07K 14/7051
See application file for complete search history.

(56) References Cited

U.S. PATENT DOCUMENTS

| | | | |
|---|---|---|---|
| 9,765,342 B2 | 9/2017 | Kochenderfer | |
| 10,703,794 B2 | 7/2020 | Maher et al. | |
| 2004/0043401 A1 | 3/2004 | Sadelain et al. | |
| 2013/0287748 A1 | 10/2013 | June et al. | |
| 2014/0050708 A1 | 2/2014 | Powell et al. | |
| 2014/0099309 A1 | 4/2014 | Powell et al. | |
| 2014/0227237 A1 | 8/2014 | June et al. | |
| 2014/0322275 A1 | 10/2014 | Brogdon et al. | |
| 2016/0053017 A1 | 2/2016 | Orentas et al. | |
| 2016/0355590 A1* | 12/2016 | Epstein ................... A61P 35/00 |
| 2017/0369585 A1 | 12/2017 | Orentas et al. | |
| 2018/0346544 A1 | 12/2018 | Mackall et al. | |
| 2018/0355052 A1 | 12/2018 | Orentas et al. | |
| 2019/0112380 A1 | 4/2019 | Chaudhary | |
| 2019/0345217 A1 | 11/2019 | Ma et al. | |
| 2020/0031904 A1 | 1/2020 | Jantz et al. | |
| 2020/0392200 A1 | 12/2020 | Orentas et al. | |
| 2021/0128615 A1* | 5/2021 | Wels ................... C07K 16/244 |

FOREIGN PATENT DOCUMENTS

| | | | |
|---|---|---|---|
| WO | WO 2010/104949 A2 | 9/2010 | |
| WO | WO 2012/079000 A1 | 6/2012 | |
| WO | WO 2015/157252 A1 | 10/2015 | |
| WO | WO-2016146542 A1 * | 9/2016 | ............. A61K 35/17 |
| WO | WO-2017058752 A1 * | 4/2017 | ............. A61K 35/17 |
| WO | WO 2019/002633 A1 | 1/2019 | |
| WO | WO-2019245817 A1 * | 12/2019 | ............. A61K 35/17 |
| WO | WO 2020/010235 A1 | 1/2020 | |
| WO | WO 2020/183158 A1 | 9/2020 | |
| WO | WO-2020194306 A1 * | 10/2020 | ............... A61P 1/00 |
| WO | WO 2020/247805 A1 | 12/2020 | |
| WO | WO 2022/006020 A1 | 1/2022 | |
| WO | WO 2023/025788 A1 | 3/2023 | |

OTHER PUBLICATIONS

Mohseni et al. European Journal of Immunology. 51: 2522-2530; Published Online: Aug. 8, 2021 (Year: 2021).*
Imura et al. JCI Insight. 5(14): e136185; Published: Jul. 23, 2020 (Year: 2020).*
Casucci et al. Frontiers in Immunology. 9: 507; Published: Mar. 21, 2018 (Year: 2018).*
Huang et al. Journal of Hematology & Oncology. 13: 86: Published: Jul. 2, 2020 (Year: 2020).*
Bertaina et al. Frontiers in Immunology. 10: 1342; Published: Jul. 10, 2019 (Year: 2019).*
Hombach et al. Cancer. 9: 112; Published: Aug. 29, 2017 (Year: 2017).*

(Continued)

*Primary Examiner* — Daniel E Kolker
*Assistant Examiner* — Katherine Ann Holtzman
(74) *Attorney, Agent, or Firm* — Goodwin Procter LLP

(57) ABSTRACT

The present disclosure provides a population of $CD4^{IL-10/CAR}$ cells (autologous or allogeneic single-donor and allogeneic polydonor) generated by genetically modifying $CD4^+$ T cells to express IL-10 and a chimeric antigen receptor. Further provided are methods of generating the $CD4^{IL-10/CAR}$ cells and methods of using the $CD4^{IL-10/CAR}$ cells for immune tolerization, treating GvHD, cell and organ transplantation, cancer, and other autoimmune and inflammatory disorders.

5 Claims, 72 Drawing Sheets

Specification includes a Sequence Listing.

(56)     References Cited

OTHER PUBLICATIONS

Greenhill et al. Arthritis Research & Therapy. 16: 419; Published: Apr. 30, 2014 (Year: 2014).*

Yao et al. The Journal of Immunology. 195(2): 488-497; Published: Jul. 15, 2015 (Year: 2015).*

Zeng et al. Cellular & Molecular Immunology. 12: 566-571: Published: Jun. 8, 2015 (Year: 2015).*

Song et al. Frontiers in Immunology. 12: 671579; Published: Apr. 26, 2021 (Year: 2021).*

Selck et al. Frontiers in Immunology. 12: 661875; Published; May 14, 2021 (Year: 2021).*

Roncarlo et al. Immunity. 49(6): 1004-1019; Published: Dec. 18, 2018 (Year: 2018).*

Liu et al. DNA and Cell Biology. 35(12): 845-852; Published: Oct. 5, 2016 (Year: 2016).*

Zhou et al. Oncoimmunology. 4(11): e1047582; Published: May 26, 2015 (Year: 2015).*

Tenspolde et al. Journal of Autoimmunity. 103(2019): 102289: Published: Jun. 5, 2019 (Year: 2019).*

Andolfi, G. et al., "Enforced IL-10 Expression Confers Type 1 Regulatory T Cell (Tr1) Phenotype and Function to Human CD4+ T Cells", Molecular Therapy, vol. 20, No. 9, Sep. 2012, pp. 1778-1790.

Boardman, D.A. et al., "Expression of a Chimeric Antigen Receptor Specific for Donor HLA Class I Enhances the Potency of Human Regulatory T Cells in Preventing Human Skin Transplant Rejection," American Journal of Transplantation, vol. 17, Dec. 17, 2016, pp. 931-943.

Castella, M. et al., "Point-Of-Care CAR T-Cell Production (ARI-0001) Using a Closed Semi-automatic Bioreactor: Experience From an Academic Phase | Clinical Trial," Frontiers in Immunology 11:482, Mar. 20, 2020, pp. 1-13.

clinicaltrials.gov, "Ph I/II Study of CAR19 Regulatory T Cells (CAR19-tTreg) for R/R CD19+ B-All," ClinicalTrials.gov ID NCT05114837, Study Started: Sep. 2024, Retrieved from the Internet <URL: https://www.clinicaltrials.gov/ct2/show/NCT05114837?term=CD19+ttreg&draw=2&rank=1>.

Good, Z. et al., "Post-infusion CAR TReg cells identify patients resistant to CD19-CAR therapy," Nature Medicine, vol. 28, Sep. 12, 2022, pp. 1860-1871.

Mátrai, J. et al., "Hepatocyte-Targeted Expression by Integrase-Defective Lentiviral Vectors Induces Antigen-Specific Tolerance in Mice with Low Genotoxic Risk," Hepatology vol. 53, No. 5, 2011, pp. 1696-1707.

Mátrai, J. et al., "Recent Advances in Lentiviral Vector Development and Applications," Molecular Therapy 18(3), Mar. 2010, pp. 477-490.

Nicholson, I.C. et al., "Construction and characterisation of a functional CD19 specific single chain Fv fragment for immunotherapy of B lineage leukaemia and lymphoma," Mol. Immunol., 34(16-17), 1997, pp. 1157-1165.

Oh, J-W. et al., "CD4 T-helper cells engineered to produce IL-10 prevent allergen-induced airway hyperreactivity and inflammation," Journal of Allergy and Clinical Immunology, vol. 110, No. 3, Sep. 2002, pp. 460-468.

PCT International Search Report and Written Opinion, PCT Application No. PCT/US2022/082422, Mar. 29, 2023, 17 pages.

PCT International Search Report and Written Opinion, PCT Application No. PCT/US2022/082431, May 24, 2023, 22 pages.

Rafiq, S. et al., "Engineering strategies to overcome the current roadblocks in CAR T cell therapy," Nature Reviews Clinical Oncology, vol. 17, Dec. 17, 2019, pp. 147-167.

Segal, B.M. et al., "Cutting Edge: IL-10-Producing CD4+ T Cells Mediate Tumor Rejection", The Journal of Immunology, vol. 168, Jan. 2002, pp. 1-4.

Setoguchi, K. et al., "Antigen-specific T cells transduced with IL-10 ameliorate experimentally induced arthritis without impairing the systemic immune response to the antigen", The Journal of Immunology, vol. 165, No. 10, Nov. 15, 2000, pp. 5980-5986.

Tiercy, J-M., "How to select the best available related or unrelated donor of hematopoietic stem cells?" Haematologica 101(6), Jun. 2016, pp. 680-687.

Van Montfrans, C. et al., "Generation of regulatory gut-homing human T lymphocytes using ex vivo interleukin 10 gene transfer", Gastroenterology, vol. 123, No. 6, Dec. 2002, pp. 1877-1888.

Wang, X. et al., "A transgene-encoded cell surface polypeptide for selection, in vivo tracking, and ablation of engineered cells," Blood 118(5), Aug. 4, 2011, pp. 1255-1263.

Yao, Y. et al., "Tr1 Cells, but Not Foxp3+ Regulatory T Cells, Suppress NLRP3 Inflammasome Activation via an IL-10-Dependent Mechanism," The Journal of Immunology, vol. 195, Jun. 8, 2015, pp. 488-497.

* cited by examiner

Expression of CD19, CD20, CD22, CD27, CD38, and BCMA during B-cell differentiation in bone marrow and periphery

```
(SEQ ID NO: 1)  IL-10_HUMAN          1  --MHSSALLCCLVLLTGVRASPGQGTQSENSCTHFPGNLPNMLRDLRDAFSRVKTFFQMKDQLDNLLLKE
(SEQ ID NO: 58) IL-10_MOUSE          1  --MPGSALLCCLVLLTGMRTSRGQSGDNCTHFPYGQSHMLRDLRDAFSRVKTFFQTKDQLDNLLLKE
(SEQ ID NO: 59) IL-10_RAT            1  --MPGSALLCCLLLAGVNTSRGQGIGKGDNKCTHFPYGQGHGIKGDNKCTHFPYGQGHGIKGDNKCTHFP...
(SEQ ID NO: 60) IL-10_MACMU          1  --MHSSALLCCLVLLTGVRASPGQGTQSENSCTHFPGNLPNMLRDLRDAFSRVKTFFQMKDQLDNLLLKE
(SEQ ID NO: 61) IL-10_GORILLA        1  --MHSSALLCCLVLLTGVRASPGQGTQSENSCTHFPGNLPNMLRDLRDAFSRVKTFFQMKDQLDNLLLKE
(SEQ ID NO: 62) IL-10_CYNO           1  --MHSSALLCCLVLVLVLLTGVRASPGQGTQSENSCTHFPGNLPNMLRDLRDAFSRVKTFFQMKDQLDNLLLKE
(SEQ ID NO: 63) IL-10_OLIVE BABOON   1  --MHSSALLCCLVLLTGVRASPGQGTQSENSCTHFPGNLPNMLRDLRDAFSRVKTFFQMKDQLDNLLLKE
(SEQ ID NO: 64) IL-10-BONOBO         1  --MHSSALLCCLVLLTGVRASPGQGTQSENSCTHFPGNLPNMLRDLRDAFSRVKTFFQMKDQLDNLLLKE
(SEQ ID NO: 65) IL-10-CHIMP          1  --MHSSALLCCLVLLTGVRASPGQGTQSENSCTHFPGNLPNMLRDLRDAFSRVKTFFQMKDQLDNLLLKE
(SEQ ID NO: 66) IL-10H_EBVB9         1  MERRLVVTLQCLVLL-----VRPRG------GTQCDNFP-----QMLRDLRDAFSRVKTFFQMKDEVDNLLLKE

IL-10_HUMAN         69  SLLEDFKGYLGCQALSEMIQFYLEEVMPQAENQDPDIKAHVNSLGENLKTLRLRLRRCHRFLPCENKSKA
                IL-10_MOUSE         69  SLLEDFKGYLGCQALSEMIQFYLEEVMPQAENQDPEIKEHVNSLGENLKTLRLRLRRCHRFLPCENKSKA
                IL-10_RAT           69  SLLEDFKGYLGCQALSEMIKFYLEEVMPQAENQDPDIKEHVNSLGENLKTLRLRLRRCHRFLPCENKSKA
                IL-10_MACMU         69  SLLEDFKGYLGCQALSEMIQFYLEEVMPQAENQDPDIKEHVNSLGENLKTLELKTLELKTLRLRLRRCHRFLPCENKSKA
                IL-10_GORILLA       69  SLLEDFKGYLGCQALSEMIQFYLEEVMPQAENQDPDIKAHVNSLGENLKTLRLRLRRCHRFLPCENKSKA
                IL-10_CYNO          69  SLLEDFKGYLGCQALSEMIQFYLEEVMPQAENQDPDIKAHVNSLGENLKTLRLRLRRCHRFLPCENKSKA
                IL-10_OLIVE BABOON  69  SLLEDFKGYLGCQALSEMIQFYLEEVMPQAENQDPDIKAHVNSLGENLKTLRLRLRRCHRFLPCENKSKA
                IL-10-BONOBO        69  SLLEDFKGYLGCQALSEMIQFYLEEVMPQAENQDPDIKAHVNSLGENLKTLRLRLRRCHRFLPCENKSKA
                IL-10-CHIMP         69  SLLEDFKGYLGCQALSEMIQFYLEEVMPQAENQDPDIKAHVNSLGENLKTLRLRLRRCHRFLPCENKSKA
                IL-10H_EBVB9        62  SLLEDFKGYLGCQALSEMIQFYLEEVMPQAENQDPDIKAHVNSLGENLKTLRLRLRRCHRFLPCENKSKA

IL-10_HUMAN        139  VEQVKNAFNKLQEKGIYKAMSEFDIFINYIEAYMTMKIRN
                IL-10_MOUSE        139  VEQVKSVFNKLQDKGIYKAMSEFDIFINCIEAYMTMKIRN
                IL-10_RAT          139  VEQVKNVFNKLQDKGIYKAMKEFDIFINCIEAYMTMKIRN
                IL-10_MACMU        139  VEQVKNAFSKLQEKGIYKAMSEFDIFINYIEAYMTMKIRN
                IL-10_GORILLA      139  VEQVKNAFNKLQEKGIYKAMSEFDIFINYIEAYMTMKIRN
                IL-10_CYNO         139  VEQVKNAFNKLQEKGIYKAMSEFDIFINYIEAYMTMKIRN
                IL-10_OLIVE BABOON 139  VEQVKNAFSKLQEKGIYKAMSEFDIFINYIEAYMTMKIRN
                IL-10-BONOBO       139  VEQVKNAFNKLQEKGIYKAMSEFDIFINYIEAYMTMKIRN
                IL-10-CHIMP        139  VEQVKNAFNKLQEKGIYKAMSEFDIFINYIEAYMTMKIRN
                IL-10H_EBVB9       132  VEQVKNAFNKLQEKGIYKAMSEFDIFINYIEAYMTMKIRN-
```

FIG. 43A

Possible huIL-10 HYBRID#1 (SEQ ID NO: 67)
any combination of  Change of amino acids (*)

MHSSALLCCLVLLTGVRASPGQGTQSENSCTHFPGNLPNMLRDLRDAFSRVKTFFQTKDEVDNLLLKESLLEDFKGY
LGCQALSEMIQFYLEEVMPQAENQDPEAKDHVNSLGENLKTLRLRRCHRFLPCENKSKAVEQIKNAFNKLQEKGI
YKAMSEFDIFINYIEAYMTMKIRN

Possible huIL-10 HYBRID#2 (SEQ ID NO: 68)
Preferred single aa change I105 to A105  Change of amino acids (#)

MHSSALLCCLVLLTGVRASPGQGTQSENSCTHFPGNLPNMLRDLRDAFSRVKTFFQMKDQLDNLLLLKESLLEDFKGY
LGCQALSEMIQFYLEEVMPQAENQDPDAKAHVNSLGENLKTLRLRRCHRFLPCENKSKAVEQVKNAFNKLQEKGI
YKAMSEFDIFINYIEAYMTMKIRN

FIG. 43B (SEQ ID NO: 1) IL10_HUMAN   1   --MHSSALLCCLVLLTGVRASPGQGTQSENSCTHFPGNLPNMLRDLRDAFSRVKTFFQ[M]KD[P]DNLLLKE (SEQ ID NO: 66) IL10H_EBVB9   1   M[ ]L[ ]CLVLL[ ]G[ ]FP----[ ]MLRDLRDAFSRVKTFFQ[K]KD[ ]DNLLLKE

* #  *               * *     * *

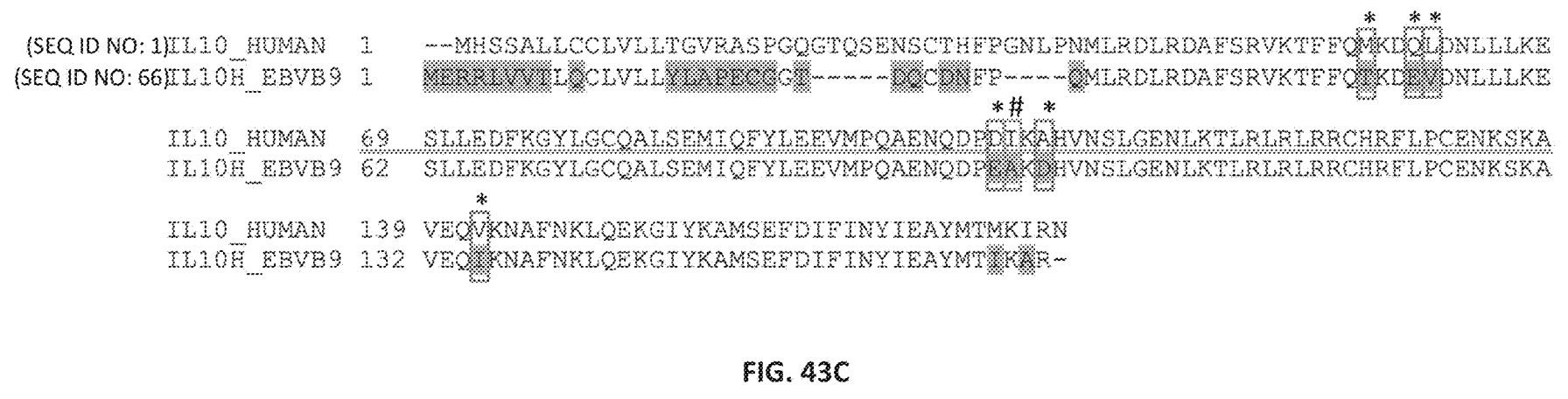

IL10_HUMAN   69   SLLEDFKGYLGCQALSEMIQFYLEEVMPQAENQDP[D]IKAHVNSLGENLKTLRLRRCHRFLPCENKSKA

IL10H_EBVB9   62   SLLEDFKGYLGCQALSEMIQFYLEEVMPQAEMQDF[ ][ ]HVNSLGENLKTLRLRRCHRFLPCENKSKA

*                              *

IL10_HUMAN   139   VEQ[V]KNAFNKLQEKGIYKAMSEFDIFINYIEAYMTMKIRN

IL10H_EBVB9   132   VEQ[ ]KNAFNKLQEKGIYKAMSEFDIFINYIEAYMT[ ][ ]R-

FIG. 43C

SEQUENCE LISTING

Sequence total quantity: 68
SEQ ID NO: 1              moltype = AA  length = 178
FEATURE                   Location/Qualifiers
source                    1..178
                          mol_type = protein
                          organism = Homo sapiens
SEQUENCE: 1
MHSSALLCCL VLLTGVRASP GQGTQSENSC THFPGNLPNM LRDLRDAFSR VKTFFQMKDQ   60
LDNLLLKESL LEDFKGYLGC QALSEMIQFY LEEVMPQAEN QDPDIKAHVN SLGENLKTLR  120
LRLRRCHRFL PCENKSKAVE QVKNAFNKLQ EKGIYKAMSE FDIFINYIEA YMTMKIRN    178

SEQ ID NO: 2              moltype = DNA  length = 537
FEATURE                   Location/Qualifiers
source                    1..537
                          mol_type = other DNA
                          organism = Homo sapiens
SEQUENCE: 2
atgcacagct cagcactgct ctgttgcctg gtcctcctga ctgggggtgag ggccagccca   60
ggccagggca cccagtctga gaacagctgc acccacttcc caggcaacct gcctaacatg  120
cttcgagatc tccgagatgc cttcagcaga gtgaagactt tctttcaaat gaaggatcag  180
ctggacaact tgttgttaaa ggagtccttg ctggaggact ttaagggtta cctgggttgc  240
caagccttgt ctgagatgat ccagtttttac ctggaggagg tgatgcccca agctgagaac  300
caagacccag acatcaaggc gcatgtgaac tccctggggg agaacctgaa gaccctcagg  360
ctgaggctac ggcgctgtca tcgatttctt ccctgtgaaa acaagagcaa ggccgtggag  420
caggtgaaga atgcctttaa taagctccaa gagaaaggca tctacaaagc catgagtgag  480
tttgacatct tcatcaacta catagaagcc tacatgacaa tgaagatacg aaactga     537

SEQ ID NO: 3              moltype = AA  length = 280
FEATURE                   Location/Qualifiers
source                    1..280
                          mol_type = protein
                          organism = synthetic construct
SEQUENCE: 3
MGAGATGRAM DGPRLLLLLL LGVSLGGAKE ACPTGLYTHS GECCKACNLG EGVAQPCGAN   60
QTVCEPCLDS VTFSDVVSAT EPCKPCTECV GLQSMSAPCV EADDAVCRCA YGYYQDETTG  120
RCEACRVCEA GSGLVFSCQD KQNTVCEECP DGTYSDEANH VDPCLPCTVC EDTERQLREC  180
TRWADAECEE IPGRWITRST PPEGSDSTAP STQEPEAPPE QDLIASTVAG VVTTVMGSSQ  240
PVVTRGTTDN LIPVYCSILA AVVVGLVAYI AFKRWNRGIL                         280

SEQ ID NO: 4              moltype = DNA  length = 843
FEATURE                   Location/Qualifiers
source                    1..843
                          mol_type = other DNA
                          organism = synthetic construct
SEQUENCE: 4
atgggggcag gtgccaccgg ccgcgccatg gacgggccgc gcctgctgct gttgctgctt   60
ctgggggtgt cccttggagg tgccaaggag gcatgcccca caggcctgta cacacacagc  120
ggtgagtgct gcaaagcctg caacctgggc gaggtgtgtg gccagccttg tggagccaac  180
cagaccgtgt gtgagccctg cctggacagc gtgacgttct ccgacgtggt gagcgcgacc  240
gagccgtgca gccgtgcac cgagtgcgtg gggctccaga gcatgtcggc gccgtgcgtg  300
gaggccgacg acgccgtgtg ccgctgcgcc tacggctact accaggatga gacgactggg  360
cgctgcgagg cgtgccgcgt gtgcgaggcg ggctcgggcc tcgtgttctc ctgccaggac  420
aagcagaaca ccgtgtgcga ggagtgcccc gacggcacgt attccgacga ggccaaccac  480
gtggacccgt gcctgccctg caccgtgtgc gaggacaccg agcgccagct ccgcgagtgc  540
acacgctggg ccgacgccga gtgcgaggag atccctggcc gttggattac acggtccaca  600
ccccagagg gctcggacag cacagccccc agcacccagg agcctgaggc acctccagaa  660
caagacctca tagccagcac ggtggcaggt gtggtgacca cagtgatggg cagctcccag  720
cccgtggtga cccgaggcac caccgacaac ctcatccctg tctattgctc catcctggct  780
gctgtggttg tgggccttgt ggcctacata gccttcaaga ggtggaacag ggggatcctc  840
tag                                                                 843

```
SEQ ID NO: 5           moltype = DNA  length = 8475
FEATURE                Location/Qualifiers
source                 1..8475
                       mol_type = other DNA
                       organism = synthetic construct
SEQUENCE: 5
tggccattgc atacgttgta tccatatcat aatatgtaca tttatattgg ctcatgtcca   60
acattaccgc catgttgaca ttgattattg actagttatt aatagtaatc aattacgggg  120
tcattagttc atagcccata tatggagttc cgcgttacat aacttacggt aaatggcccg  180
cctggctgac cgcccaacga cccccgccca ttgacgtcaa taatgacgta tgttcccata  240
gtaacgccaa tagggacttt ccattgacgt caatgggtgg agtatttacg gtaaactgcc  300
cacttggcag tacatcaagt gtatcatatg ccaagtacgc cccctattga cgtcaatgac  360
ggtaaatggc ccgcctggca ttatgcccag tacatgacct tatgggactt tcctacttgg  420
cagtacatct acgtattagt catcgctatt accatggtga tgcggttttg gcagtacatc  480
aatgggcgtg gatagcggtt tgactcacgg ggatttccaa gtctccaccc cattgacgtc  540
aatgggagtt tgttttggca ccaaaatcaa cgggactttc caaaatgtcg taacaactcc  600
gccccattga cgcaaatggg cggtaggcgt gtacggtggg aggtctatat aagcagagct  660
cgtttagtga accggggtct ctctggttag accagatctg agcctgggag ctctctggct  720
aactagggaa cccactgctt aagcctcaat aaagcttgcc ttgagtgctt caagtagtgt  780
gtgcccgtct gttgtgtgac tctggtaact agagatccct cagacccttt tagtcagtgt  840
ggaaaatctc tagcagtggc gcccgaacag ggacttgaaa gcgaaaggga aaccagagga  900
gctctctcga cgcaggactc ggcttgctga agcgcgcacg gcaagaggcg aggggcggcg  960
actggtgagt acgccaaaaa ttttgactag cggaggctag aaggagagag atgggtgcga 1020
gagcgtcagt attaagcggg ggagaattag atcgcgatgg gaaaaaattc ggttaaggcc 1080
agggggaaag aaaaaatata aattaaaaca tatagtatgg gcaagcaggg agctagaacg 1140
attcgcagtt aatcctggcc tgttagaaac atcagaaggc tgtagacaaa tactgggaca 1200
gctacaacca tcccttcaga caggatcaga agaacttaga tcattatata atacagtagc 1260
aaccctctat tgtgtgcatc aaaggataga gataaaagac accaaggaag ctttagacaa 1320
gatagaggaa gagcaaaaca aaagtaagac caccgcacag caagcggccg ctgatcttca 1380
gacctggagg aggagatatg agggacaatt ggagaagtga attatataaa tataaagtag 1440
taaaaattga accattagga gtagcaccca ccaaggcaaa gagaagagtg gtgcagagag 1500
aaaaaagagc agtgggaata ggagctttgt tccttgggtt cttgggagca gcaggaagca 1560
ctatgggcgc agcgtcaatg acgctgacgg tacaggccag acaattattg tctggtatag 1620
tgcagcagca gaacaatttg ctgagggcta ttgaggcgca acagcatctg ttgcaactca 1680
cagtctgggg catcaagcag ctccaggcaa gaatcctggc tgtggaaaga tacctaaagg 1740
atcaacagct cctggggatt tggggttgct ctggaaaact catttgcacc actgctgtgc 1800
cttggaatgc tagttggagt aataaatctc tggaacagat ttggaatcac acgacctgga 1860
tggagtggga cagagaaatt aacaattaca caagcttaat acactcctta attgaagaat 1920
cgcaaaacca gcaagaaaag aatgaacaag aattattgga attagataaa tgggcaagtt 1980
tgtggaattg gtttaacata acaaattggc tgtggtatat aaaattattc ataatgatag 2040
taggaggctt ggtaggttta agaatagttt ttgctgtact ttctatagtg aatagagtta 2100
ggcagggata ttcaccatta tcgtttcaga cccacctccc aaccccgagg ggacccgaca 2160
ggcccgaagg aatagaagaa gaaggtggag agagagacag agacagatcc attcgattag 2220
tgaacggatc tcgacggtat cggttaactt ttaaaagaaa aggggggatt ggggggtaca 2280
gtgcagggga agaatagta gacataatag caacagacat acaaactaaa gaattacaaa 2340
aacaaattac aaaaattcaa aattttatcg atcacgagac tagcctcgag agatctgatc 2400
ataatgatct ataccacatt tgtagaggtt ttacttgctt taaaaaacct cccacacctc 2460
cccctgaacc tgaaacataa aatgaatgca attgttgttg ttaacttgtt tattgcagct 2520
tataatggtt acaaataagg caatagcatc acaaatttca caataaggc attttttttca 2580
ctgcattcta gttttggttt gtccaaactc atcaatgtat cttatcatgt ctggatctca 2640
aatccctcgg aagctgcgcc tgtcttaggt tggagtgata cattttttatc acttttaccc 2700
gtctttggat taggcagtag ctctgacggc cctcctgtct taggttagtg aaaaatgtca 2760
ctctcttacc cgtcattggc tgtccagctt agctcgcagg ggaggtggtc tggatccacc 2820
atgtctagag gatcccctg ttccacctct tgaaggctat gtaggccaca aggcccacaa 2880
ccacagcagc caggatggag caatagacag ggatgaggtt gtcggtggtg cctcgggtca 2940
ccacgggctg ggagctgccc atcactgtgg tcaccacacc tgccaccgtg ctggctatga 3000
ggtcttgttc tggaggtgcc tcaggctcct gggtgctggg ggctgtgctg tccgagccct 3060
ctggggggtgt ggaccgtgta atccaacggc cagggatctc ctcgcactcg gcgtcggccc 3120
agcgtgtgca ctcgcggagc tggcgctcgg tgtcctcgca cacggtgcag ggcaggcacg 3180
ggtccacgtg gttggcctcg tcggaatacg tgccgtcggg gcactcctcg cacacggtgt 3240
tctgcttgtc ctggcaggag aacacgaggc ccgagcccgc ctcgcacacg cggcacgcct 3300
cgcagcgccc agtcgtctca tcctggtagt agccgtaggc gcagcggcac acggcgtcgt 3360
cggcctccac gcacggcgcc gacatgctct ggagcccac gcactcggtg cacggcttgc 3420
acggctcggt cgcgctcacc acgtcggaga acgtcacgct gtccaggcag ggctcacaca 3480
cggtctggtt ggctccacaa ggctgggcca caccctcgcc caggttcag gctttgcagc 3540
actcaccgct gtgtgtgtac aggcctgtgg ggcatgcctc cttggcacct ccaagggaca 3600
cccccagaag cagcaacagc agcaggcgcg gcccgtccat ggcgcggccg gtggcacctg 3660
ccccatcgc ccgcctcccg cggcagcgct cgacttccag ctcggtccgc tttcggact 3720
gatgggggtcg cgctgcgctg cgctccagcg cccccccctgc ccgccggagc tggccgccgt 3780
ccgaattcct gcaggaattc gatgaggct ggatcggtcc cggtgtcttc tatggaggtc 3840
aaaacagcgt ggatggcgtc tccaggcgat ctgacggttc actaaacgag ctctgcttat 3900
ataggcctcc caccgtacac gcctaccctc gagaagcttg atatcgaatt cccacggggt 3960
tggggttgcg ccttttccaa ggcagccctg ggtttgcgca gggacgcggc tgctctgggc 4020
gtggtccgg gaaacgcagc ggcgccgacc ctgggtctcg cacattcttc acgtccgttc 4080
gcagcgtcac ccggatcttc gccgctaccc ttgtggggcc cccggcgacg cttcctgctc 4140
cgcccctaag tcgggaaggt tccttgcggt tcgcggcgtg ccggacgtga caaacggaag 4200
ccgcacgtct cactagtacc ctcgcagacg gacagcgcca gggagcaatg gcagcgcgcc 4260
gaccgcgatg ggctgtggcc aatagcggct gctcagcggg gcgcgccgag agcagcggcc 4320
gggaaggggc ggtgcgggag gcggggtgtg gggcggtagt gtgggccctg ttcctgcccg 4380
```

```
cgcggtgttc cgcattctgc aagcctccgg agcgcacgtc ggcagtcggc tccctcgttg  4440
accgaatcac cgacctctct ccccagggg atccccggtc tgcaggaatt catgcacagc  4500
tcagcactgc tctgttgcct ggtcctcctg actgggtga gggccagccc aggccagggc  4560
acccagtctg agaacagctg cacccacttc ccaggcaacc tgcctaacat gcttcgagat  4620
ctccgagatg ccttcagcag agtgaagact ttctttcaa tgaaggatca gctggacaac  4680
ttgttgttaa aggagtcctt gctggaggac tttaagggtt acctgggttg ccaagccttg  4740
tctgagatga tccagtttta cctggaggag gtgatgcccc aagctgagaa ccaagaccca  4800
gacatcaagg cgcatgtgaa ctccctgggg gagaacctga agaccctcag gctgaggcta  4860
cggcgctgtc atcgatttct tccctgtgaa aacaagagca aggccgtgga gcaggtgaag  4920
aatgccttta ataagctcca agagaaaggc atctacaaag ccatgagtga gtttgacatc  4980
ttcatcaact acatagaagc ctacatgaca atgaagatac gaaactgagt cgagaatcaa  5040
cctctggatt acaaaatttg tgaaagattg actggtattc ttaactatgt tgctcctttt  5100
acgctatgtg gatacgctgc tttaatgcct ttgtatcatg ctattgcttc ccgtatggct  5160
ttcattttct cctccttgta taaatcctgg ttgctgtcct tttatgagga gttgtggccc  5220
gttgtcaggc aacgtggcgt ggtgtgcact gtgtttgctg acgcaacccc cactggttgg  5280
ggcattgcca ccacctgtca gctcctttcc gggactttcg ctttccccct ccctattgcc  5340
acggcggaac tcatcgccgc ctgccttgcc cgctgctgga caggggctcg gctgttgggc  5400
actgacaatt ccgtggtgtt gtcggggaaa tcatcgtcct ttccttggct gctcgcctgt  5460
gttgccacct ggattctgcg cgggacgtcc ttctgctacg tcccttcggc cctcaatcca  5520
gcggaccttc cttcccgcgg cctgctgccg gctctgcggc ctcttccgcg tcttcgcctt  5580
cgccctcaga cgagtcggat ctccctttgg ccgcctccc cgcctggaat tcgagctcgg  5640
tacctttaag accaatgact tacaaggcag ctgtagatct tagccacttt taaaagaaa  5700
aggggggact ggaagggcta attcactccc aacgaagaca agatctgctt tttgcttgta  5760
ctgggtctct ctggttagac cagatctgag cctgggagct ctctggctaa ctagggaacc  5820
cactgcttaa gcctcaataa agcttgcctt gagtgcttca agtagtgtgt gcccgtctgt  5880
tgtgtgactc tggtaactag agatccctca gacccttta gtcagtgtgg aaaatctcta  5940
gcagtagtag ttcatgtcat cttattattc agtatttata acttgcaaag aaatgaatat  6000
cagagagtga gaggaacttg tttattgcag cttataatgg ttacaaataa agcaatagca  6060
tcacaaattt cacaaataaa gcattttttt cactgcattc tagttgtggt ttgtccaaac  6120
tcatcaatgt atcttatcat gtctggctct agctatcccg cccctaactc cgcccatccc  6180
gcccctaact ccgcccagtt ccgcccattc tccgccccat ggctgactaa ttttttttat  6240
ttatgcagag gccgaggccg cctcggcctc tgagctattc cagaagtagt gaggaggctt  6300
ttttggaggc ctaggctttt gcgtcgagac gtacccaatt cgccctatag tgagtcgtat  6360
tacgcgcgct cactggccgt cgttttacaa cgtcgtgact gggaaaaccc tggcgttacc  6420
caacttaatc gccttgcagc acatccccct ttcgccagct ggcgtaatag cgaagaggcc  6480
cgcaccgatc gcccttccca gcggccgca cgctcagtgg aacgaaaact cacgttaagg  6540
gattttggtc atgaacaata aaactgtctg cttacataaa cagtaataca aggggtgtta  6600
tgagccatat tcaacgggaa acgtcttgct ctaggccgcg attaaattcc aacatggatg  6660
ctgatttata tgggtataaa tgggctcgcg ataatgtcgg gcaatcaggt gcgacaatct  6720
atcgattgta tgggaagccc gatgcgccag agttgtttct gaaacatggc aaaggtagcg  6780
ttgccaatga tgttacagat gagatggtca gactaaactg gctgacggaa tttatgcctc  6840
ttccgaccat caagcatttt atccgtactc ctgatgatgc atggttactc accactgcga  6900
tccccgggaa aacagcattc caggtattag aagaatatcc tgattcaggt gaaaacattg  6960
ttgatgcgct ggcagtgttc ctgcgccggt tgcattcgat tcctgtttgt aattgtcctt  7020
ttaacagcga tcgcgtattt cgtctcgctc aggcgcaatc acgaatgaat aacggtttgg  7080
ttgatgcgag tgattttgat gacgagcgta atggctggcc tgttgaacaa gtctggaaag  7140
aaatgcataa acttttgcca ttctcaccgg attcagtcgt cactcatggt gatttctcac  7200
ttgataacct tatttttgac gaggggaaat taataggttg tattgatgtt ggacgagtcg  7260
gaatcgcaga ccgataccag gatcttgcca tcctatggaa ctgcctcggt gagttttctc  7320
cttcattaca gaaacggctt tttcaaaaat atggtattga taatcctgat atgaataaat  7380
tgcagtttca tttgatgctc gatgagtttt tctaagaatt aattcatgag cggatacata  7440
tttgaatgta tttagaaaaa taaacaaata ggggttccgc gactatgtct ttgataatct  7500
catgaccaaa atcccttaac gtgagttttc gttccactga gcgtcagacc ccgtagaaaa  7560
gatcaaagga tcttcttgag atcctttttt tctgcgcgta atctgctgct tgcaaacaaa  7620
aaaaccaccg ctaccagcgg tggtttgttt gccggatcaa gagctaccaa ctctttttcc  7680
gaaggtaact ggcttcagca gagcgcagat accaaatact gtccttctag tgtagccgta  7740
gttaggccac cacttcaaga actctgtagc accgcctaca tacctcgctc tgctaatcct  7800
gttaccagtg gctgctgcca gtggcgataa gtcgtgtctt accgggttgg actcaagacg  7860
atagttaccg gataaggcgc agcggtcggg ctgaacgggg ggttcgtgca cacagcccag  7920
cttggagcga acgacctaca ccgaactgag atacctacag cgtgagctat gagaaagcgc  7980
cacgcttccc gaagggagaa aggcggacag gtatccggta agcggcaggg tcggaacagg  8040
agagcgcacg agggagcttc cagggggaaa cgcctggtat ctttatagtc ctgtcgggtt  8100
tcgccacctc tgacttgagc gtcgattttt gtgatgctcg tcagggggc ggagcctatg  8160
gaaaaacgcc agcaacgcgg cctttttacg gttcctggcc ttttgctggc cttttgctca  8220
cacgcttccc gaagggagaa aggcggacag gtatccggta agcggcaggg tcggaacagg  8220
gattctgtgg ataaccgtat taccgccttt gagtgagctg ataccgctcg ccgcagccga  8280
acgaccgagc gcagcgagtc agtgagcgag gaagcggaag agcgcccaat acgcaaaccg  8340
cctctccccg cgcgttgtat gcttccggct cgtatgttgt gtggaattgt gagcggataa  8400
caatttcaca caggaaacag ctatgaccat gattacgcca agccgaatta accctcacta  8460
aagggaacag ctagc                                                   8475
```

SEQ ID NO: 6          moltype = AA   length = 170
FEATURE               Location/Qualifiers
source                1..170
                      mol_type = protein
                      organism = synthetic construct
SEQUENCE: 6
MERRLVVTLQ CLVLLYLAPE CGGTDQCDNF PQMLRDLRDA FSRVKTFFQT KDEVDNLLLK   60
ESLLEDFKGY LGCQALSEMI QFYLEEVMPQ AENQDPEAKD HVNSLGENLK TLRLRLRRCH  120
RFLPCENKSK AVEQIKNAFN KLQEKGIYKA MSEFDIFINY IEAYMTIKAR              170

```
SEQ ID NO: 7            moltype = DNA   length = 513
FEATURE                Location/Qualifiers
source                 1..513
                       mol_type = other DNA
                       organism = synthetic construct
SEQUENCE: 7
atggagcgaa ggttagtggt cactctgcag tgcctggtgc tgctttacct ggcacctgag   60
tgtggaggta cagaccaatg tgacaatttt ccccaaatgt tgagggacct aagagatgcc   120
ttcagtcgtg ttaaaacctt tttccagaca aaggacgagg tagataacct tttgctcaag   180
gagtctctgc tagaggactt taagggctac cttggatgcc aggccctgtc agaaatgatc   240
caattctacc tggaggaagt catgccacag gctgaaaacc aggaccctga agccaaagac   300
catgtcaatt ctttgggtga aaatctaaag accctacggc tccgcctgcg caggtgccac   360
aggttcctgc cgtgtgagaa caagagtaaa gctgtggaac agataaaaaa tgcctttaac   420
aagctgcagg aaaaaggaat ttacaaagcc atgagtgaat ttgacatttt tattaactac   480
atagaagcat acatgacaat taaagccagg tga                                513

SEQ ID NO: 8            moltype =     length =
SEQUENCE: 8
000

SEQ ID NO: 9            moltype = AA   length = 489
FEATURE                Location/Qualifiers
source                 1..489
                       mol_type = protein
                       organism = synthetic construct
SEQUENCE: 9
MLLLVTSLLL CELPHPAFLL IPDIQMTQTT SSLSASLGDR VTISCRASQD ISKYLNWYQQ   60
KPDGTVKLLI YHTSRLHSGV PSRFSGSGSG TDYSLTISNL EQEDIATYFC QQGNTLPYTF   120
GGGTKLEITG GGGSGGGGSG GGGSEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
KHYYYGGSYA MDYWGQGTSV TVSSAAAPAP RPPTPAPTIA SQPLSLRPEA CRPAAGGAVH   300
TRGLDFDTAL AAVICSALAT VLLALLILCV IYCKRQPRRK KLLYIFKQPF MRPVQTTQEE   360
DGCSCRFPEE EEGGCELRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                          489

SEQ ID NO: 10           moltype = DNA   length = 1467
FEATURE                Location/Qualifiers
source                 1..1467
                       mol_type = other DNA
                       organism = synthetic construct
SEQUENCE: 10
atgctgctgc tggtcaccag cctgctgctg tgcgagctcc ctcacccgc ctttctgctt     60
atcccggaca ttcagatgac acagaccacc tcgagcttgt ccgcgtcgct gggcgatcgc   120
gtgaccatct cctgccgggc ctcccaagac atttcaaagt atctcaactg gtaccagcag   180
aagccggacg gaaccgtgaa actgctgatc taccatacca gccgcctgca ctccggcgtg   240
ccgtccgct tctccggatc gggttccgga actgactact cactgactat ctccaacttg   300
gaacaagagg acatcgccac ttacttctgt caacaaggaa ataccttcc ctacaccttc   360
ggggggggta ccaagctgga gatcactggg ggcggaggct ccggtggagg cggatccggc   420
ggtggaggga gcgaagtcaa gctgcaggaa tcaggaccag gactcgtgc gccatcccag   480
tccctgtcgg tgacctgtac tgtctccgga gtcagcctcc ccgattacgg agtgtcatg   540
attaggcaac cccaagaaa agggctggaa tggctcggag tgatctgggg ctccgaaacc   600
acctactaca actcggcgct gaagtcccgg ctgaccatca tcaaggacaa ctccaagagc   660
caagtgttct tgaagatgaa cagcttgcag accgacgata ccgcaatcta ctactgtgcc   720
aagcactatt actacggggg gtcttacgcc atggactact ggggacaggg cacctccgtg   780
actgtgtcgt ccgcggccgc gcccgcccct cggcccccga ctcctgcccc gacgatcgct   840
tcccaacctc tctcgctgcg cccggaagca tgccggcccg ccgccggtgg cgctgtccac   900
actcgcggac tggactttga taccgcactg gcggccgtga tctgtagcgc cctggccacc   960
gtgctgctgg cgctgctcat cctttgcgtg atctactgca agcggcagcc taggcgaaag   1020
aagtcctct acattttcaa gcaacccttc atgcgccccg tgcaaaccac ccaggaggag   1080
gatgatgct catgccggtt ccctgaggaa gaagaggcg gttgcgagct cagagtgaa   1140
ttcagccggt cggctgacgc cccggcgtac cagcagggc agaaccagct gtacaatgag   1200
ctcaacctgg ggcggccgga gagtacgac gtgctggaca agaggaggg cagagatccg   1260
gaaatgggcg gaaagccaag gcggaagaac ccgcaggaag gtctttacaa cgaactgcag   1320
aaggacaaga tggccgaggc ctactccgag attgggatga aggagaaag acggaggga   1380
aagggacatg acggacttta ccagggcctg agcactgcca cgaaggacac ctatgatgcc   1440
ctgcacatgc aggcgctgcc gcctcgg                                       1467

SEQ ID NO: 11           moltype = AA   length = 264
FEATURE                Location/Qualifiers
source                 1..264
                       mol_type = protein
                       organism = synthetic construct
SEQUENCE: 11
MLLLVTSLLL CELPHPAFLL IPDIQMTQTT SSLSASLGDR VTISCRASQD ISKYLNWYQQ   60
KPDGTVKLLI YHTSRLHSGV PSRFSGSGSG TDYSLTISNL EQEDIATYFC QQGNTLPYTF   120
GGGTKLEITG GGGSGGGGSG GGGSEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
```

-continued

```
KHYYYGGSYA MDYWGQGTSV TVSS                                                        264

SEQ ID NO: 12             moltype = DNA   length = 1470
FEATURE                   Location/Qualifiers
source                    1..1470
                          mol_type = other DNA
                          organism = synthetic construct
SEQUENCE: 12
atgcttctcc tggtcacctc cctgctcctc tgcgaactgc ctcaccctgc cttccttctg          60
attcctgaca ttcagatgac tcagaccacc tcttccttgt ccgcgtcact gggagacaga         120
gtgaccatct cgtgtcgcgc aagccaggat atctccaagt acctgaactg gtaccaacag         180
aagcccgacg ggactgtgaa gctgctgatc taccacacct cacgcctgca cagcggagtg         240
ccaagcagat tctccggctc cggctcggga accgattact cgcttaccat tagcaacctc         300
gagcaggagg acatcgctac ctacttctgc cagcaaggaa ataccctgcc ctacaccttc         360
ggcggaggaa ccaaattgga aatcaccggc ggaggaggct ccgggggagg aggttccggg         420
ggcggggggtt ccgaagtgaa gctccaggag tccggccccg gcctggtggc gccgtcgcaa        480
tcactctctg tgacctgtac cgtgtcggga gtgtccctgc ctgattacgg cgtgagctgg         540
attcggcagc cgccgcggaa gggcctggaa tggctgggtg tcatctgggg atccgagact         600
acctactaca actcggccct gaagtcccgc ctgactatca tcaaagacaa ctcgaagtcc         660
caggtctttc tgaagatgaa ctccctgcaa actgacgaca ccgccatcta ttactgtgct         720
aagcactact actacggtgg aagctatgct atggactact gggggcaagg cacttcggtg         780
actgtgtcaa gcgcggccgc aactaccacc cctgccccctc ccggccccac tccggcccca        840
accatcgcaa gccaaccccct ctccttgcgc cccgaagctt gccgcccggc cgcgggtgga        900
gccgtgcata cccgggggct ggactttgcc tgcgatatct acatttgggc cccgctggcc         960
ggcacttgcg gcgtgctcct gctgtcgctg gtcatcaccc tttactgcaa gaggggccgg        1020
aagaagctgc tttacatctt caagcagccg ttcatgcggc ccgtgcaaac gactcaggaa        1080
gaggacggat gctcgtgcag attccctgag gaggaagagg ggggatgcga actgcgcgtc        1140
aagttctcac ggtccgccga cgcccccgca tatcaacagg gccagaatca gctctacaac        1200
gagctgaacc tgggaaggag agaggagtac gacgtgctgg acaagcgacg cggacgcgac        1260
ccggaagatgg gggggaaacc acggcggaaa aaccctccagg aaggactgta caacgaactc       1320
cagaaagaca agatggcgaa agcctactca gaaatcggga tgaaggaga gcggaggagg         1380
ggaaagggtc acgacgggct gtaccaggga ctgagcaccg ccactaagga tacctacgat        1440
gccttgcata tgcaagcact cccacccccgg                                          1470

SEQ ID NO: 13             moltype = AA   length = 129
FEATURE                   Location/Qualifiers
source                    1..129
                          mol_type = protein
                          organism = synthetic construct
SEQUENCE: 13
MLLLVTSLLL CELPHPAFLL IPDIQMTQTT SSLSASLGDR VTISCRASQD ISKYLNWYQQ          60
KPDGTVKLLI YHTSRLHSGV PSRFSGSGSG TDYSLTISNL EQEDIATYFC QQGNTLPYTF         120
GGGTKLEIT                                                                  129

SEQ ID NO: 14             moltype = AA   length = 120
FEATURE                   Location/Qualifiers
source                    1..120
                          mol_type = protein
                          organism = synthetic construct
SEQUENCE: 14
EVKLQESGPG LVAPSQSLSV TCTVSGVSLP DYGVSWIRQP PRKGLEWLGV IWGSETTYYN          60
SALKSRLTII KDNSKSQVFL KMNSLQTDDT AIYYCAKHYY YGGSYAMDYW GQGTSVTVSS         120

SEQ ID NO: 15             moltype =    length =
SEQUENCE: 15
000

SEQ ID NO: 16             moltype = AA   length = 491
FEATURE                   Location/Qualifiers
source                    1..491
                          mol_type = protein
                          organism = synthetic construct
SEQUENCE: 16
MLLLVTSLLL CELPHPAFLL IPEVQLQQSG AELVKPGASV KMSCKASGYT FTSYNMHWVK          60
QTPGQGLEWI GAIYPGNGDT SYNQKFKGKA TLTADKSSST AYMQLSSLTS EDSADYYCAR         120
SNYYGSSYWF FDVWGAGTTV TVSSGGGGSG GGGSGGGGSD IVLTQSPAIL SASPGEKVTM         180
TCRASSSVNY MDWYQKKPGS SPKPWIYATS NLASGVPARF SGSGSGTSYS LTISRVEAED         240
AATYYCQQWS FNPPTFGGGT KLEIKAAATT TPAPRPPTPA PTIASQPLSL RPEACRPAAG         300
GAVHTRGLDF ACDIYIWAPL AGTCGVLLLS LVITLYCKRG RKKLLYIFKQ PFMRPVQTTQ         360
EEDGCSCRFP EEEEGGCELR VKFSRSADAP AYQQGQNQLY NELNLGRREE YDVLDKRRGR         420
DPEMGGKPRR KNPQEGLYNE LQKDKMAEAY SEIGMKGERR RGKGHDGLYQ GLSTATKDTY         480
DALHMQALPP R                                                              491

SEQ ID NO: 17             moltype = DNA   length = 1473
FEATURE                   Location/Qualifiers
source                    1..1473
                          mol_type = other DNA
                          organism = synthetic construct
SEQUENCE: 17
```

```
atgctccttc tcgtgacctc cctgcttctc tgcgaactgc cccatcctgc cttcctgctg   60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct acccegggaa tggcgatact  240
tcgtacaacc agaagttcaa gggaaaggcc accctgaccg ccgacaagag ctcctccaca  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccggggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaagcggc cgcaactacc acccctgccc ctcggccgca gactccggca  840
ccaaccatcg caagccaacc cctctccttg cgccccgaag cttgccgccc ggccgcgggt  900
ggagccgtgc atacccgggg gctggacttt gcctgcgata tctacatttg ggccccgctg  960
gccggcactt gcgkgcgtgct cctgctgtcg ctggtcatca ccctttactg caagaggggc 1020
cggaagaagc tgctttacat cttcaagcag ccgttcatgc ggccgtgca gacgactcag  1080
gaagaggacg gatgctcgtg cagattccct gaggaggaag aggggggatg cgaactgcgc 1140
gtcaagttct cacggtccgc cgacgccccc gcatatcaac agggccagaa tcagctctac 1200
aacgagctga acctgggaag gagagaggag tacgacgtgc tggacaagcg acgcggacgc 1260
gacccggaga tggggggggaa accacggcgg aaaaaccctc aggaaggact gtacaacgaa 1320
ctccagaaag acaagatggc ggaagcctac tcagaaatcg ggatgaaggg agagcggagg 1380
aggggaaagg gtcacgacgg gctgtaccag ggactgagca ccgccactaa ggatacctac 1440
gatgccttgc atatgcaagc actcccaccc cgg                                1473
```

```
SEQ ID NO: 18            moltype = AA  length = 244
FEATURE                  Location/Qualifiers
source                   1..244
                         mol_type = protein
                         organism = Synthetic construct
SEQUENCE: 18
EVQLQQSGAE LVKPGASVKM SCKASGYTFT SYNMEIWVKQ TPGQGLEWIG AIYPGNGDTS   60
YNQKFKGKAT LTADKSSSTA YMQLSSLTSE DSADYYCARS NYYGSSYWFF DVWGAGTTVT  120
VSSGGGGSGG GGSGGGGSDI VLTQSPAILS ASPGEKVTMT CRASSSVNYM DWYQKKPGSS  180
PKPWIYATSN LASGVPARFS GSGSGTSYSL TISRVEAEDA ATYYCQQWSF NPPTFGGGTK  240
LEIK                                                                244
```

```
SEQ ID NO: 19            moltype = DNA  length = 729
FEATURE                  Location/Qualifiers
source                   1..729
                         mol_type = other DNA
                         organism = synthetic construct
SEQUENCE: 19
gaggtgcagt tgcaacagtc aggagctgaa ctggtcaagc caggagccag cgtgaagatg   60
agctgcaagg cctccggtta caccttcacc tcctacaaca tgcactgggt gaaacagacc  120
ccgggacaag ggctcgaatg gattggcgcc atctacccgc ggaatggcga tacttcgtac  180
aaccagaagt tcaagggaaa ggccaccctg accgccgaca gagctcctc caccgcgtat  240
atgcagttga gctccctgac ctccgaggac tccgccgact actactgcgc acggtccaac  300
tactatggaa gctcgtactg gttcttcgat gtctgggggg ccggcaccac tgtgaccgtc  360
agctccgggg gcggaggatc cggtggaggc ggaagcgggg gtggaggatc cgacattgtg  420
ctgactcagt ccccggcaat cctgtcggcc tcaccgggcg aaaaggtcac gatgacttgt  480
agagcgtcgt ccagcgtgaa ctacatggat tggtaccaaa agaagcctgg atcgtcaccc  540
aagccttgga tctacgctac atctaacctg gcctccggcg tgccagcgcg gttcagcggg  600
tccggctcgg gcacctcata ctcgctgacc atctcccgcg tggaggctga ggacgccgcg  660
acctactact gccagcagtg gtccttcaac ccgccgactt ttggaggcgg tactaagctg  720
gagatcaaa                                                           729
```

```
SEQ ID NO: 20            moltype = AA  length = 123
FEATURE                  Location/Qualifiers
source                   1..123
                         mol_type = protein
                         organism = synthetic construct
SEQUENCE: 20
EVQLQQSGAE LVKPGASVKM SCKASGYTFT SYNMEIWVKQ TPGQGLEWIG AIYPGNGDTS   60
YNQKFKGKAT LTADKSSSTA YMQLSSLTSE DSADYYCARS NYYGSSYWFF DVWGAGTTVT  120
VSS                                                                 123
```

```
SEQ ID NO: 21            moltype = AA  length = 106
FEATURE                  Location/Qualifiers
source                   1..106
                         mol_type = protein
                         organism = synthetic construct
SEQUENCE: 21
DIVLTQSPAI LSASPGEKVT MTCRASSSVN YMDWYQKKPG SSPKPWIYAT SNLASGVPAR   60
FSGSGSGTSY SLTISRVEAE DAATYYCQQW SFNPPTFGGG TKLEIK                  106
```

```
SEQ ID NO: 22            moltype = AA  length = 494
FEATURE                  Location/Qualifiers
```

```
source                    1..494
                          mol_type = protein
                          organism = synthetic construct
SEQUENCE: 22
MLLLVTSLLL CELPHPAFLL IPQVQLQQSG PGLVKPSQTL SLTCAISGDS VSSNSAAWNW  60
IRQSPSRGLE WLGRTYYRSK WYNDYAVSVK SRITINPDTS KNQFSLQLNS VTPEDTAVYY  120
CAREVTGDLE DAFDIWGQGT MVTVSSGGGG SGGGGSGGGG SDIQMTQSPS SLSASVGDRV  180
TITCRASQTI WSYLNWYQQR PGKAPNLLIY AASSLQSGVP SRFSGRGSGT DFTLTISSLQ  240
AEDFATYYCQ QSYSIPQTFG QGTKLEIKAA ATTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                    494

SEQ ID NO: 23             moltype = DNA  length = 1482
FEATURE                   Location/Qualifiers
source                    1..1482
                          mol_type = other DNA
                          organism = synthetic construct
SEQUENCE: 23
atgcttcttt tggtgacttc ccttttgctg tgcgagttgc cacacccccgc cttcctgctt   60
attccccagg tacagctcca gcagagtggc ccagggctcg tgaagccaag ccagacgctg  120
tccctgactt gtgcaatttc aggggattca gtttcatcaa atagcgcggc gtggaattgg  180
attcgacaat ctccttcccg agggttggaa tggcttggac gaacatatta cagatccaaa  240
tggtataacg actatgcggt atcagtaaag tcaagaataa ccattaaccc cgacacaagc  300
aagaaccaat tctcttttgca gcttaactct gtcacgccaa agacacggc agtctattat  360
tgcgctcgcg aggtaacggg tgacctggaa gacgctttttg acatttgggg gcagggtacg  420
atggtgacag tcagttcagg gggcggtggg agtggggag ggggtagcgg ggggggaggg  480
tcagacattc agatgaccca gtcccttca tccttgtctg cctccgtcgg tgacagggtg  540
acaataacat gcagagcaag ccaaacaatc tggagctatc tcaactggta ccagcagcga  600
ccaggaaaag cgccaaacct gctgatttac gctgcttcct ccctccaatc aggccgtgcct  660
agtagattta gcggtagggg ctccggcacc gattttacgc tcactataag ctctcttcaa  720
gcagaagatt ttgcgactta ttactgccag cagtcctata gtatacctca gactttcgga  780
cagggtacca agttggagat taaggcggc gcaactacaa cccctgcccc tcggccgccg  840
actccggccc caaccatcgc aagccaaccc ctctccttgc gccccgaagc ttgccgcccg  900
gccgcgggtg gagccgtgca tacccggggg ctggactttg cctgcgatat ctacatttgg  960
gccccgctgg ccggcacttg cggcgtgctc ctgctgtcgc tggtcatcac cctttactgc  1020
aagaggggc ggaagaagct gctttacatc ttcaagcagc cgttcatgcg gcccgtgcag  1080
acgactcagg aagaggacgg atgctcgtgc agattccctg aggaggaaga ggggggatgc  1140
gaactgcgcg tcaagttctc acggtccgcc gacgcccccg catatcaaca gggccagaat  1200
cagctctaca cgagctgaa cctgggaagg agagaggagt acgacgtgct ggacaagcga  1260
cgcggacgcg acccggagat gggggggaaa ccacggcgga aaaacccctca ggaaggactg  1320
tacaacgaac tccagaaaga caagatggcg gaagcctact cagaaatcgg gatgaaggga  1380
gagcggagga ggggaaaggg tcacgacggg ctgtaccagg gactgagcac cgccactaag  1440
gatacctacg atgccttgca tatgcaagca ctcccacccc gg                     1482

SEQ ID NO: 24             moltype = AA  length = 249
FEATURE                   Location/Qualifiers
source                    1..249
                          mol_type = protein
                          organism = synthetic construct
SEQUENCE: 24
QVQLQQSGPG LVKPSQTLSL TCAISGDSVS SNSAAWNWIR QSPSRGLEWL GRTYYRSKWY   60
NDYAVSVKSR ITINPDTSKN QFSLQLNSVT PEDTAVYYCA REVTGDLEDA FDIWGQGTMV  120
TVSSGGGGSG GGSGGGGSD IQMTQSPSSL SASVGDRVTI TCRASQTIWS YLNWYQQRPG  180
KAPNLLIYAA SSLQSGVPSR FSGRGSGTDF TLTISSLQAE DFATYYCQQS YSIPQTFGQG  240
TKLEIKAAA                                                          249

SEQ ID NO: 25             moltype = DNA  length = 747
FEATURE                   Location/Qualifiers
source                    1..747
                          mol_type = other DNA
                          organism = synthetic construct
SEQUENCE: 25
caggtacagc tccagcagag tggcccaggg ctcgtgaagc caagccagac gctgtccctg   60
acttgtgcaa tttcagggga ttcagtttca tcaaatagcg cggcgtggaa ttggattcga  120
caatctcctt cccgagggtt ggaatggctt ggacgaacat attacagatc caaatggtat  180
aacgactatg cggtatcagt aaagtcaaga ataaccatta accccgacac aagcaagaac  240
caattctctt tgcagcttaa ctctgtcacg ccagaagaca cggcgtcta ttattgcgct  300
cgcgaggtaa cgggtgacct ggaagacgct tttgacattt ggggggcaggg tacgatggtg  360
acagtcagtt caggggcggg tgggagtggg ggaggggta gcggggggg agggtcagac  420
attcagatga cccagtcccc ttcatccttg tctgcctccg tcggtgacag gtgacaata  480
acatgcagag caagccaaac aatctggagc tatctcaact ggtaccagca gcgaccagga  540
aaagcgccaa acctgctgat ttacgctgct tcctccctcc aatcaggccg tgcctagtaga  600
tttagcggta ggggctccgg caccgatttt acgctcacta taagctctct tcaagcagaa  660
gattttgcga cttattactg ccagcagtcc tatagtatac ctcagacttt cggacagggt  720
accaagttgg agattaaggc ggccgca                                      747

SEQ ID NO: 26             moltype = AA  length = 124
```

-continued

```
FEATURE                 Location/Qualifiers
source                  1..124
                        mol_type = protein
                        organism = synthetic construct
SEQUENCE: 26
QVQLQQSGPG LVKPSQTLSL TCAISGDSVS SNSAAWNWIR QSPSRGLEWL GRTYYRSKWY    60
NDYAVSVKSR ITINPDTSKN QFSLQLNSVT PEDTAVYYCA REVTGDLEDA FDIWGQGTMV   120
TVSS                                                                124

SEQ ID NO: 27           moltype = AA   length = 110
FEATURE                 Location/Qualifiers
source                  1..110
                        mol_type = protein
                        organism = synthetic construct
SEQUENCE: 27
DIQMTQSPSS LSASVGDRVT ITCRASQTIW SYLNWYQQRP GKAPNLLIYA ASSLQSGVPS    60
RFSGRGSGTD FTLTISSLQA EDFATYYCQQ SYSIPQTFGQ GTKLEIKAAA              110

SEQ ID NO: 28           moltype = AA   length = 72
FEATURE                 Location/Qualifiers
source                  1..72
                        mol_type = protein
                        organism = synthetic construct
SEQUENCE: 28
AAATTTPAPR PPTPAPTIAS QPLSLRPEAC RPAAGGAVHT RGLDFACDIY IWAPLAGTCG    60
VLLLSLVITL YC                                                        72

SEQ ID NO: 29           moltype = AA   length = 30
FEATURE                 Location/Qualifiers
source                  1..30
                        mol_type = protein
                        organism = synthetic construct
SEQUENCE: 29
DTALAAVICS ALATVLLALL ILCVIYCKRQ                                     30

SEQ ID NO: 30           moltype = AA   length = 112
FEATURE                 Location/Qualifiers
source                  1..112
                        mol_type = protein
                        organism = synthetic construct
SEQUENCE: 30
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 31           moltype = AA   length = 42
FEATURE                 Location/Qualifiers
source                  1..42
                        mol_type = protein
                        organism = synthetic construct
SEQUENCE: 31
KRGRKKLLYI FKQPFMRPVQ TTQEEDGCSC RFPEEEEGGC EL                       42

SEQ ID NO: 32           moltype = AA   length = 41
FEATURE                 Location/Qualifiers
source                  1..41
                        mol_type = protein
                        organism = synthetic construct
SEQUENCE: 32
RSKRSRLLHS DYMNMTPRRP GPTRKHYQPY APPRDFAAYR S                        41

SEQ ID NO: 33           moltype = AA   length = 30
FEATURE                 Location/Qualifiers
source                  1..30
                        mol_type = protein
                        organism = synthetic construct
SEQUENCE: 33
RAKRGSGATN FSLLKQAGDV EENPGPRAKR                                     30

SEQ ID NO: 34           moltype = AA   length = 492
FEATURE                 Location/Qualifiers
source                  1..492
                        mol_type = protein
                        organism = synthetic construct
SEQUENCE: 34
MLLLVTSLLL CELPHPAFLL IPQVQLQQSG AEVKKPGSSV KVSCKASGGT FSSYAISWVR    60
QAPGQGLEWM GGIIPILGIA NYAQKFQGRV TITADESTST AYMELSSLRS EDTAVYYCAR   120
GGAGGSGSYY PLIWGQGTTV TVSSGGGGSG GGGSGGGGSE IVLTQSPATL SLSPGERATL   180
SCGASQSVSS SYLAWYQQKP GQAPRLLIYD ASSRATGIPA RFSGSGSGTD FTLTISSLEP   240
EDFAVYYCQQ RSSWPPTWTF GQGTKLEIKR AAAIEVMYPP PYLDNEKSNG TIIHVKGKHL   300
```

-continued

```
CPSPLFPGPS KPFWVLVVVG GVLACYSLLV TVAFIIFWVR SKRSRLLHSD YMNMTPRRPG   360
PTRKHYQPYA PPRDFAAYRS RVKFSRSADA PAYQQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                      492

SEQ ID NO: 35              moltype = DNA   length = 1476
FEATURE                    Location/Qualifiers
source                     1..1476
                           mol_type = other DNA
                           organism = synthetic construct
SEQUENCE: 35
atgctgctgc tggtgaccag cctgctgctg tgcgaactgc cgcatccggc gtttctgctg   60
attccgcagg tgcagctgca gcagagcggc gcggaagtga aaaaaccggg cagcagcgtg  120
aaagtgagct gcaaagcgag cggcggcacc tttagcagct atgcgattag ctgggtgcgc  180
caggcgccgg gccagggcct ggaatggatg ggcggcatta ttccgattct gggcattgcg  240
aactatgcgc agaaatttca gggccgcgtg accattaccg cggatgaaag caccagcacc  300
gcgtatatgg aactgagcag cctgcgcagc gaagataccg cggtgtatta ttgcgcgcgc  360
ggcggcggcg gcggcagcgg cagctattat ccgctgattt ggggccaggg caccaccgtg  420
accgtgagca gcggcggcgg cggcagcggc ggcggcggca gcggcggcgg cggcagcgaa  480
attgtgctga cccagagccc ggcgaccctg agcctgagcc cgggcgaacg cgcgaccctg  540
agctgcggc cgagccagag cgtgagcagc agctatctgg cgtggtatca gcagaaaccg  600
ggccaggcgc cgcgcctgct gatttatgat gcgagcagcc gcgccaccgtg cattccggcg  660
cgctttagcg gcagcggcag cggcaccgat tttaccctga ccattagcag cctggaaccg  720
gaagattttg cggtgtatta ttgccagcag cgcagcagct ggccgccgac ctggaccttt  780
ggccagggca ccaaactgga aattaaacgc gcggcggcga ttgaagtgat gtatccgccg  840
ccgtatctgg ataacgaaaa aagcaacggc accattattc atgtgaaagg caaacatctg  900
tgcccgagcc cgctgtttcc gggcccgagc aaaccgtttt gggtgctggt ggtggtgggc  960
ggcgtgctgc cgtgctatag cctgctggtg accgtggcgt ttattatttt ttgggtgcgc  1020
agcaaacgca gccgcctgct gcatagcgat tatatgaaca tgaccccgcg ccgcccgggc  1080
ccgacccgca aacattatca gccgtatgcg ccgcgcgacg attttgcggc gtatcgcagc  1140
cgcgtgaaat ttagccgcag cgcggatgcg ccggcgtatc agcagggcca gaaccagctg  1200
tataacgaac tgaacctggg ccgccgcgaa gaatatgatg tgctggataa acgccgcggc  1260
cgcgatccgg aaatgggcgg caaaccgcgc cgcaaaaacc cgcaggaagg cctgtataac  1320
gaactgcaga aagataaaat ggcggaagcg tatagcgaaa ttggcatgaa aggcgaacgc  1380
cgccgcggca aaggccatga tggcctgtat cagggcctga gcaccgcgac caaagatacc  1440
tatgatgcgc tgcatatgca ggcgctgccg ccgcgc                            1476

SEQ ID NO: 36              moltype = AA   length = 251
FEATURE                    Location/Qualifiers
source                     1..251
                           mol_type = protein
                           organism = synthetic construct
SEQUENCE: 36
QVQLQQSGAE VKKPGSSVKV SCKASGGTFS SYAISWVRQA PGQGLEWMGG IIPILGIANY   60
AQKFQGRVTI TADESTSTAY MELSSLRSED TAVYYCARGG AGGSGSYYPL IWGQGTTVTV  120
SSGGGGSGGG GSGGGGSEIV LTQSPATLSL SPGERATLSC GASQSVSSSY LAWYQQKPGQ  180
APRLLIYDAS SRATGIPARF SGSGSGTDFT LTISSLEPED FAVYYCQQRS SWPPTWTFGQ  240
GTKLEIKRAA A                                                       251

SEQ ID NO: 37              moltype = DNA   length = 753
FEATURE                    Location/Qualifiers
source                     1..753
                           mol_type = other DNA
                           organism = synthetic construct
SEQUENCE: 37
caggtgcagc tgcagcagag cggcgcggaa gtgaaaaaac cgggcagcag cgtgaaagtg   60
agctgcaaag cgagcggcgg cacctttagc agctatgcga ttagctgggt cgccaggcg  120
ccgggccagg gcctggaatg gatgggcggc attattccga ttctgggcat tgcgaactat  180
gcgcagaaat ttcagggccg cgtgaccatt accgcggatg aaagcaccag caccgcgtat  240
atggaactga gcagcctgcg cagcgaagat accgcggtgt attattgcgc gcgcggcggc  300
gcggcggca gcggcagcta ttatccgctg atttgggggc agggcaccac cgtgaccgtg  360
agcagcggcg gcggcggcag cggcggcggc ggcagcggcg gcggcggcag cgaaattgtg  420
ctgacccaga gcccggcgac cctgagcctg agcccgggca acgcgcgac cctgagctgc  480
ggcgcgagcc agagcgtgag cagcagctat ctggcgtggt atcagcagaa accgggccag  540
gcgccgcgcc tgctgattta tgatgcgagc agccgcgcga ccggcattcc ggcgcgcttt  600
agcggcagcg gcagcggcac cgattttacc ctgaccatta gcagcctgga accggaagat  660
tttgcggtgt attattgcca gcagcgcagc agctggccgc cgacctggac ctttggccag  720
ggcaccaaac tggaaattaa acgcgcggcg gcg                               753

SEQ ID NO: 38              moltype = AA   length = 122
FEATURE                    Location/Qualifiers
source                     1..122
                           mol_type = protein
                           organism = synthetic construct
SEQUENCE: 38
QVQLQQSGAE VKKPGSSVKV SCKASGGTFS SYAISWVRQA PGQGLEWMGG IIPILGIANY   60
AQKFQGRVTI TADESTSTAY MELSSLRSED TAVYYCARGG AGGSGSYYPL IWGQGTTVTV  120
SS                                                                 122
```

```
SEQ ID NO: 39               moltype = AA   length = 114
FEATURE                     Location/Qualifiers
source                      1..114
                            mol_type = protein
                            organism = synthetic construct
SEQUENCE: 39
EIVLTQSPAT LSLSPGERAT LSCGASQSVS SSYLAWYQQK PGQAPRLLIY DASSRATGIP   60
ARFSGSGSGT DFTLTISSLE PEDFAVYYCQ QRSSWPPTWT FGQGTKLEIK RAAA        114

SEQ ID NO: 40               moltype = AA   length = 24
FEATURE                     Location/Qualifiers
source                      1..24
                            mol_type = protein
                            organism = synthetic construct
SEQUENCE: 40
IYIWAPLAGT CGVLLLSLVI TLYC                                          24

SEQ ID NO: 41               moltype = AA   length = 503
FEATURE                     Location/Qualifiers
source                      1..503
                            mol_type = protein
                            organism = synthetic construct
SEQUENCE: 41
MALPVTALLL PLALLLHAAR PDIVLTQSPP SLAMSLGKRA TISCRASESV TILGSHLIYW   60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFR  180
HYSMNWVKQA PGKGLKWMGR INTESGVPIY ADDFKGRFAF SVETSASTAY LVINNLKDED  240
TASYFCSNDY LYSLDFWGQG TALTVSSFVP VFLPAKPTTT PAPRPPTPAP TIASQPLSLR  300
PEACRPAAGG AVHTRGLDFA CDIYIWAPLA GTCGVLLLSL VITLYCNHRN RSKRSRLLHS  360
DYMNMTPRRP GPTRKHYQPY APPRDFAAYR SRVKFSRSAD APAYQQGQNQ LYNELNLGRR  420
EEYDVLDKRR GRDPEMGGKP RRKNPQEGLY NELQKDKMAE AYSEIGMKGE RRRGKGHDGL  480
YQGLSTATKD TYDALHMQAL PPR                                         503

SEQ ID NO: 42               moltype = AA   length = 503
FEATURE                     Location/Qualifiers
source                      1..503
                            mol_type = protein
                            organism = synthetic construct
SEQUENCE: 42
MALPVTALLL PLALLLHAAR PDIVLTQSPP SLAMSLGKRA TISCRASESV TILGSHLIHW   60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
DYSINWVKRA PGKGLKWMGW INTETREPAY AYDFRGRFAF SLETSASTAY LQINNLKNED  240
TATYFCALDY SYAMDYWGQG TSVTVSSFVP VFLPAKPTTT PAPRPPTPAP TIASQPLSLR  300
PEACRPAAGG AVHTRGLDFA CDIYIWAPLA GTCGVLLLSL VITLYCNHRN RSKRSRLLHS  360
DYMNMTPRRP GPTRKHYQPY APPRDFAAYR SRVKFSRSAD APAYQQGQNQ LYNELNLGRR  420
EEYDVLDKRR GRDPEMGGKP RRKNPQEGLY NELQKDKMAE AYSEIGMKGE RRRGKGHDGL  480
YQGLSTATKD TYDALHMQAL PPR                                         503

SEQ ID NO: 43               moltype = AA   length = 503
FEATURE                     Location/Qualifiers
source                      1..503
                            mol_type = protein
                            organism = synthetic construct
SEQUENCE: 43
MALPVTALLL PLALLLHAAR PDIVLTQSPP SLAMSLGKRA TISCRASESV TILGSHLIYW   60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
HYSMNWVKQA PGKGLKWMGR INTETGEPLY ADDFKGRFAF SLETSASTAY LVINNLKNED  240
TATFFCSNDY LYSCDYWGQG TTLTVSSFVP VFLPAKPTTT PAPRPPTPAP TIASQPLSLR  300
PEACRPAAGG AVHTRGLDFA CDIYIWAPLA GTCGVLLLSL VITLYCNHRN RSKRSRLLHS  360
DYMNMTPRRP GPTRKHYQPY APPRDFAAYR SRVKFSRSAD APAYQQGQNQ LYNELNLGRR  420
EEYDVLDKRR GRDPEMGGKP RRKNPQEGLY NELQKDKMAE AYSEIGMKGE RRRGKGHDGL  480
YQGLSTATKD TYDALHMQAL PPR                                         503

SEQ ID NO: 44               moltype = AA   length = 507
FEATURE                     Location/Qualifiers
source                      1..507
                            mol_type = protein
                            organism = synthetic construct
SEQUENCE: 44
MLLLVTSLLL CELPHPAFLL IPDIVLTQSP PSLAMSLGKR ATISCRASES VTILGSHLIH   60
WYQQKPGQPP TLLIQLASNV QTGVPARFSG SGSRTDFTLT IDPVEEDDVA VYYCLQSRTI  120
PRTFGGGTKL EIKGSTSGSG KPGSGEGSTK GQIQLVQSGP ELKKPGETVK ISCKASGYTF  180
TDYSINWVKR APGKGLKWMG WINTETREPA YAYDFRGRFA FSLETSASTA YLQINNLKYE  240
DTATYFCALD YSYAMDYWGQ GTSVTVSSAA AFVPVFLPAK PTTTPAPRPP TPAPTIASQP  300
LSLRPEACRP AAGGAVHTRG LDFACDIYIW APLAGTCGVL LLSLVITLYC NHRNRSKRSR  360
LLHSDYMNMT PRRPGPTRKH YQPYAPPRDF AAYRSRVKFS RSADAPAYQQ GQNQLYNELN  420
LGRREEYDVL DKRRGRDPEM GGKPRRKNPQ EGLYNELQKD KMAEAYSEIG MKGERRRGKG  480
```

```
HDGLYQGLST ATKDTYDALH MQALPPR                                           507

SEQ ID NO: 45              moltype = AA   length = 506
FEATURE                    Location/Qualifiers
source                     1..506
                           mol_type = protein
                           organism = synthetic construct
SEQUENCE: 45
MALPVTALLL PLALLLHAAR PDIVLTQSPP SLAMSLGKRA TISCRASESV TILGSHLIHW      60
YQQKPGQPPT LLIQLASNVQ TGVPARFSGS GSRTDFTLTI DPVEEDDVAV YYCLQSRTIP      120
RTFGGGTKLE IKGSTSGSGK PGSGEGSTKG QIQLVQSGPE LKKPGETVKI SCKASGYTFT      180
DYSINWVKRA PGKGLKWMGW INTETREPAY AYDFRGRFAF SLETSASTAY LQINNLKYED      240
TATYFCALDY SYAMDYWGQG TSVTVSSAAA FVPVFLPAKP TTTPAPRPPT PAPTIASQPL      300
SLRPEACRPA AGGAVHTRGL DFACDIYIWA PLAGTCGVLL LSLVITLYCN HRNRSKRSRL      360
LHSDYMNMTP RRPGPTRKHY QPYAPPRDFA AYRSRVKFSR SADAPAYQQG QNQLYNELNL      420
GRREEYDVLD KRRGRDPEMG GKPRRKNPQE GLYNELQKDK MAEAYSEIGM KGERRRGKGH      480
DGLYQGLSTA TKDTYDALHM QALPPR                                          506

SEQ ID NO: 46              moltype = AA   length = 512
FEATURE                    Location/Qualifiers
source                     1..512
                           mol_type = protein
                           organism = synthetic construct
SEQUENCE: 46
MALPVTALLL PLALLLHAAR PDIVLTQSPP SLAMSLGKRA TISCRASESV TILGSHLIHW      60
YQQKPGQPPT LLIQLASNVQ TGVPARFSGS GSRTDFTLTI DPVEEDDVAV YYCLQSRTIP      120
RTFGGGTKLE IKGSTSGSGK PGSGEGSTKG QIQLVQSGPE LKKPGETVKI SCKASGYTFT      180
DYSINWVKRA PGKGLKWMGW INTETREPAY AYDFRGRFAF SLETSASTAY LQINNLKYED      240
TATYFCALDY SYAMDYWGQG TSVTVSSAAA FVPVFLPAKP TTTPAPRPPT PAPTIASQPL      300
SLRPEACRPA AGGAVHTRGL DFACDIYIWA PLAGTCGVLL LSLVITLYCN HRNRFSVVKR      360
GRKKLLYIFK QPFMRPVQTT QEEDGCSCRF PEEEEGGCEL RVKFSRSADA PAYQQGQNQL      420
YNELNLGRRE EYDVLDKRRG RDPEMGGKPR RKNPQEGLYN ELQKDKMAEA YSEIGMKGER      480
RRGKGHDGLY QGLSTATKDT YDALHMQALP PR                                   512

SEQ ID NO: 47              moltype = AA   length = 502
FEATURE                    Location/Qualifiers
source                     1..502
                           mol_type = protein
                           organism = synthetic construct
SEQUENCE: 47
MALPVTALLL PLALLLHAAR PDIVLTQSPP SLAMSLGKRA TISCRASESV TILGSHLIHW      60
YQQKPGQPPT LLIQLASNVQ TGVPARFSGS GSRTDFTLTI DPVEEDDVAV YYCLQSRTIP      120
RTFGGGTKLE IKGSTSGSGK PGSGEGSTKG QIQLVQSGPE LKKPGETVKI SCKASGYTFT      180
DYSINWVKRA PGKGLKWMGW INTETREPAY AYDFRGRFAF SLETSASTAY LQINNLKYED      240
TATYFCALDY SYAMDYWGQG TSVTVSSAAA FVPVFLPAKP TTTPAPRPPT PAPTIASQPL      300
SLRPEACRPA AGGAVHTRGL DFACDIYIWA PLAGTCGVLL LSLVITLYCN HRNRRDQRLP      360
PDAHKPGGGG SFRTPIQEEQ ADAHSTLAKI RVKFSRSADA PAYQQGQNQL YNELNLGRRE      420
EYDVLDKRRG RDPEMGGKPR RKNPQEGLYN ELQKDKMAEA YSEIGMKGER RRGKGHDGLY      480
QGLSTATKDT YDALHMQALP PR                                              502

SEQ ID NO: 48              moltype = AA   length = 549
FEATURE                    Location/Qualifiers
source                     1..549
                           mol_type = protein
                           organism = synthetic construct
SEQUENCE: 48
MALPVTALLL PLALLLHAAR PDIVLTQSPP SLAMSLGKRA TISCRASESV TILGSHLIHW      60
YQQKPGQPPT LLIQLASNVQ TGVPARFSGS GSRTDFTLTI DPVEEDDVAV YYCLQSRTIP      120
RTFGGGTKLE IKGSTSGSGK PGSGEGSTKG QIQLVQSGPE LKKPGETVKI SCKASGYTFT      180
DYSINWVKRA PGKGLKWMGW INTETREPAY AYDFRGRFAF SLETSASTAY LQINNLKYED      240
TATYFCALDY SYAMDYWGQG TSVTVSSAAA FVPVFLPAKP TTTPAPRPPT PAPTIASQPL      300
SLRPEACRPA AGGAVHTRGL DFACDIYIWA PLAGTCGVLL LSLVITLYCN HRNRFSVVKR      360
GRKKLLYIFK QPFMRPVQTT QEEDGCSCRF PEEEEGGCEL RRDQRLPPDA HKPPGGGSFR      420
TPIQEEQADA HSTLAKIRVK FSRSADAPAY QQGQNQLYNE LNLGRREEYD VLDKRRGRDP      480
EMGGKPRRKN PQEGLYNELQ KDKMAEAYSE IGMKGERRRG KGHDGLYQGL STATKDTYDA      540
LHMQALPPR                                                             549

SEQ ID NO: 49              moltype = AA   length = 472
FEATURE                    Location/Qualifiers
source                     1..472
                           mol_type = protein
                           organism = synthetic construct
SEQUENCE: 49
DIVLTQSPPS LAMSLGKRAT ISCRASESVT ILGSHLIHWY QQKPGQPPTL LIQLASNVQT      60
GVPARFSGSG SRTDFTLTID PVEEDDVAVY YCLQSRTIPR TFGGGTKLEI KGSTSGSGKP      120
GSGEGSTKGQ IQLVQSGPEL KKPGETVKIS CKASGYTFD YSINWVKRAP GKGLKWMGWI      180
NTETREPAYA YDFRGRFAFS LETSASTAYL QINNLKYEDT ATYFCALDYS YAMDYWGQGT      240
SVTVSSAAAT TTPAPRPPTP APTIASQPLS LRPEACRPAA GGAVHTRGLD FACDIYIWAP      300
LAGTCGVLLL SLVITLYCKR GRKKLLYIFK QPFMRPVQTT QEEDGCSCRF PEEEEGGCEL      360
```

```
RVKFSRSADA PAYQQGQNQL YNELNLGRRE EYDVLDKRRG RDPEMGGKPR RKNPQEGLYN   420
ELQKDKMAEA YSEIGMKGER RRGKGHDGLY QGLSTATKDT YDALHMQALP PR           472

SEQ ID NO: 50              moltype = AA   length = 449
FEATURE                    Location/Qualifiers
source                     1..449
                           mol_type = protein
                           organism = synthetic construct
SEQUENCE: 50
QLQLQESGPG LVKPSETLSL TCTVSGGSIS SGSYFWGWIR QPPGKGLEWI GSIYYSGITY   60
YNPSLKSRVT ISVDTSKNQF SLKLSSVTAA DTAVYYCARH DGAVAGLFDY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEAAGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKQ                                     449

SEQ ID NO: 51              moltype = AA   length = 214
FEATURE                    Location/Qualifiers
source                     1..214
                           mol_type = protein
                           organism = synthetic construct
SEQUENCE: 51
SYVLTQPPSV SVAPGQTARI TCGGNNIGSK SVHWYQQPPG QAPVVVVYDD SDRPSGIPER   60
FSGSNSGNTA TLTISRVEAG DEAVYYCQVW DSSSDHVVFG GGTKLTVLGQ PKAAPSVTLF   120
PPSSEELQAN KATLVCLISD FYPGAVTVAW KGDSSPVKAG VETTTPSKQS NNKYAASSYL   180
SLTPEQWKSH RSYSCQVTHE GSTVEKTVAP TECS                              214

SEQ ID NO: 52              moltype = AA   length = 451
FEATURE                    Location/Qualifiers
source                     1..451
                           mol_type = protein
                           organism = synthetic construct
SEQUENCE: 52
QVQLVQSGAE VKKPGSSVKV SCKASGGTFS NYWMHWVRQA PGQGLEWMGA TYRGHSDTYY   60
NQKFKGRVTI TADKSTSTAY MELSSLRSED TAVYYCARGA IYDGYDVLDN WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 53              moltype = AA   length = 214
FEATURE                    Location/Qualifiers
source                     1..214
                           mol_type = protein
                           organism = synthetic construct
SEQUENCE: 53
DIQMTQSPSS LSASVGDRVT ITCSASQDIS NYLNWYQQKP GKAPKLLIYY TSNLHSGVPS   60
RFSGSGSGTD FTLTISSLQP EDFATYYCQQ YRKLPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 54              moltype = AA   length = 488
FEATURE                    Location/Qualifiers
source                     1..488
                           mol_type = protein
                           organism = synthetic construct
SEQUENCE: 54
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR   120
RIDAADFDSW GQGTQVTVSS GGGGSEVQLV ESGGGLVQAG GSLRLSCAAS GRTFTMGWFR   180
QAPGKEREFV AAISLSPTLA YYAESVKGRF TISRDNAKNT VVLQMNSLKP EDTALYYCAA   240
DRKSVMSIRP DYWGQGTQVT VSSTSTTTPA PRPPTPAPTI ASQPLSLRPE ACRPAAGGAV   300
HTRGLDFACD IYIWAPLAGT CGVLLLSLVI TLYCKRGRKK LLYIFKQPFM RPVQTTQEED   360
GCSCRFPEEE EGGCELRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                           488

SEQ ID NO: 55              moltype = DNA   length = 5869
FEATURE                    Location/Qualifiers
source                     1..5869
                           mol_type = other DNA
                           organism = synthetic construct
SEQUENCE: 55
tgtagtctta tgcaatactc ttgtagtctt gcaacatggt aacgatgagt tagcaacatg   60
ccttacaagg agagaaaaag caccgtgcat gccgattggt ggaagtaagg tggtacgatc   120
```

-continued

```
gtgccttatt aggaaggcaa cagacgggtc tgacatggat tggacgaacc actgaattgc   180
cgcattgcag agatattgta tttaagtgcc tagctcgata cataaacggg tctctctggt   240
tagaccagat ctgagcctgg gagctctctg gctaactagg gaacccactg cttaagcctc   300
aataaagctt gccttgagtg cttcaagtag tgtgtgcccg tctgttgtgt gactctggta   360
actagagatc cctcagaccc ttttagtcag tgtggaaaat ctctagcagt ggcgcccgaa   420
cagggacttg aaagcgaaag ggaaaccaga ggagctctct cgacgcagga ctcggcttgc   480
tgaagcgcgc acggcaagag gcgaggggcg gcgactggtg agtacgccaa aaattttgac   540
tagcggaggc tagaaggaga gagatgggtg cgagagcgtc agtattaagc gggggagaat   600
tagatcgcga tgggaaaaaa ttcggttaag gccaggggga aagaaaaaat ataaattaaa   660
acatatagta tgggcaagca gggagctaga acgattcgca gttaatcctg gcctgttaga   720
aacatcagaa ggctgtagac aaatactggg acagctacaa ccatcccttc agacaggatc   780
agaagaactt agatcattat ataatacagt agcaaccctc tattgtgtgc atcaaaggat   840
agagataaaa gacaccaagg aagctttaga caagatagag gaagagcaaa acaaaagtaa   900
gaccaccgca cagcaagcgg ccggccgctg atcttcagac ctggaggagg agatatgagg   960
gacaattgga gaagtgaatt atataaatat aaagtagtaa aaattgaacc attaggagta  1020
gcacccacca aggcaaagag aagagtggtg cagagagaaa aaagagcagt gggaatagga  1080
gctttgttcc ttgggttctt gggagcagca ggaagcacta tgggcgcagc gtcaatgacg  1140
ctgacggtac aggccagaca attattgtct ggtatagtgc agcagcagaa caatttgctg  1200
agggctattg aggcgcaaca gcatctgttg caactcacag tctggggcat caagcagctc  1260
caggcaagaa tcctggctgt ggaaagatac ctaaaggatc aacagctcct ggggatttgg  1320
ggttgctctg gaaaactcat ttgcaccact gctgtgcctt ggaatgctag ttggagtaat  1380
aaatctctgg aacagatttg gaatcacacg acctggatgg agtgggacag agaaattaac  1440
aattacacaa gcttaataca ctccttaatt gaagaatcgc aaaaccagca agaaaagaat  1500
gaacaagaat tattggaatt agataaatgg gcaagtttgt ggaattggtt taacataaca  1560
aattggctgt ggtatataaa attattcata atgatagtag gaggcttggt aggtttaaga  1620
atagtttttg ctgtactttc tatagtgaat agagttaggc agggatattc accattatcg  1680
tttcagaccc acctcccaac cccgagggga cccgacaggc ccgaaggaat agaagaagaa  1740
ggtggagaga gagacagaga cagatccatt cgattagtga acggatctcg acggtatcgc  1800
ctttaaaaga aaagggggga ttggggggta cagtgcaggg gaaagaatag tagacataat  1860
agcaacagac atacaaacta aagaattaca aaaacaaatt acaaaaattc aaaattttcg  1920
ggtttattac agggacagca gagatccagt ttatcgatga gtaattcata caaaaggact  1980
cgccctgcc ttggggaatc ccagggaccg tcgttaaact cccactaacg tagaacccag  2040
agatcgctgc gttcccgccc cctcacccgc ccgctctcgt catcactgag gtggagaaga  2100
gcatgcgtga ggctccggtg cccgtcagtg ggcagagcgc acatcgccca cagtccccga  2160
gaagttgggg ggaggggtcg gcaattgaac cggtgcctag agaaggtggc gcggggtaaa  2220
ctgggaaagt gatgtcgtgt actggctccg cctttttccc gagggtgggg gagaaccgta  2280
tataagtgca gtagtcgccg tgaacgttct ttttcgcaac gggtttgccg ccagaacaca  2340
ggtaagtgcc gtgtgtggtt cccgcgggcc tggcctcttt acgggttatg gcccttgcgt  2400
gccttgaatt acttccacgc ccctggctgc agtacgtgat tcttgatccc gagcttcggg  2460
ttggaagtgg gtgggagagt tcgaggcctt gcgcttaagg agcccttcg cctcgtgctt  2520
gagttgaggc ctggcttggg cgctggggcc gccgcgtgcg aatctggtgg caccttcgcg  2580
cctgtctcgc tgctttcgat aagtctctag ccatttaaaa tttttgatga cctgctgcga  2640
cgctttttt ctggcaagat agtcttgtaa atgcgggcca agatctgcac actggtattt  2700
cggtttttgg ggccgcgggc ggcgacgggg cccgtgcgtc ccagcgcaca tgttcggcga  2760
ggcggggcct gcgagcgcgg ccaccgagaa tcggacgggg gtagtctcaa gctggccggc  2820
ctgctctggt gcctggcctc gcgccgccgt gtatcgcccc gccctgggcg gcaaggctgg  2880
cccggtgggac accagttgcg tgagcggaaa gatggccgct tcccggcct gctgcaggga  2940
gctcaaaatg gaggacgcgg cgctcgggag agcgggcggg tgagtcaccc acacaaagga  3000
aaagggcctt tccgtcctca gccgtcgctt catgtgactc cacggagtac cgggcgccgt  3060
ccaggcacct cgattagttc tcgagctttt ggagtacgtc gtctttaggt tggggggagg  3120
ggttttatgc gatggagttt ccccacactg agtgggtgga gactgaagtt aggccagctt  3180
ggcacttgat gtaattctcc ttggaatttg cccttttga gtttggatct tggttcattc  3240
tcaagcctca gacagtggtt caaagttttt ttcttccatt tcaggtgtcg tgaggatcgc  3300
tagcgctacc ggactcagat ctcgagctca agcttcgaat tcgccgccac catggctctg  3360
cccgtcaccg ctctgctgct gcctctggct ctgctgctcg ccctcaggtc  3420
aaactggaag aatctggcgg aggcctggtg caggcaggac ggagcctgcg cctgagctgc  3480
gcagcatccg agcacacctt cagctcccac gtgatgggc ggtttcggca ggccccaggc  3540
aaggagagag agagcgtggc cgtgatcggc tggaggggaca tctccacatc ttacgccgat  3600
tccgtgaagg gccggttcac catcagccgg gacaacgcca agaagacact gtatctgcag  3660
atgaacagcc tgaagcccga ggacaccgcc gtgtactatt gcgcagcaag gagaatcgac  3720
gcagcagact ttgattcctg gggccaggc acccaggtga cagtgtctag cggaggagga  3780
ggatctgagg tgcagctggt ggagagcgga ggcggcctgg tgcaggccgg aggctctctg  3840
aggctgagct gtgcagcatc cggaagaacc ttcacaatgg ctggtttag gcaggcacca  3900
ggaaaggaga gggagttcgt ggcagcaatc agcctgtccc ctaccctggc ctactatgcc  3960
gagagcgtga agggcaggtt taccatctcc cgcgataacg ccaagaatac agtggtgctg  4020
cagatgaact ccctgaaacc tgaggacaca gccctgtact attgtgccgc cgatcggaag  4080
agcgtgatga gcattagacc agactattgg gggcagggaa cacaggtgac cgtgagcagc  4140
actagtacca cgacgccagc gccgcgacca ccaacaccgg cgcccaccat cgcgtcgcag  4200
cccctgtccc tgcgcccaga ggcgtgccgg ccagcggcgg gcacacgagg tgacacgagg  4260
gggctggact cgcctgtga tatctacatc tgggcgccct tggccgggac ttgtggggtc  4320
cttctcctgt cactggttat cacccttac tgcaaacggg gcagaaagaa actcctgtat  4380
atattcaaac aaccatttat gagaccagta caaactactc aagaggaaga tggctgtagc  4440
tgccgatttc cagaagaaga agaaggagga tgtgaactga gagtgaagtt cagcaggagc  4500
gcagacgccc ccgcgtacca gcagggccag aaccagctct ataacgagct caatctagga  4560
cgaagagag agtacgatgt tttggacaag agacgtggcc gggaccctga gatgggggga  4620
aagccgagaa ggaagaaccc tcaggaaggc ctgtacaatg aactgcagaa agataagatg  4680
gcggaggcct acagtgagat tgggatgaaa ggcgagcgcc ggaggggcaa ggggcacgat  4740
ggcctttacc agggtctcag tacagccacc aaggacacct acgacgccct tcacatgcag  4800
gccctgcccc ctcgctaatc tagatccgcg tctggaacaa tcaacctctg gattacaaaa  4860
```

```
tttgtgaaag attgactggt attcttaact atgttgctcc ttttacgcta tgtggatacg   4920
ctgctttaat gcctttgtat catgctattg cttcccgtat ggctttcatt ttctcctcct   4980
tgtataaatc ctggttgctg tctctttatg aggagttgtg gcccgttgtc aggcaacgtg   5040
gcgtggtgtg cactgtgttt gctgacgcaa cccccactgg ttggggcatt gccaccacct   5100
gtcagctcct ttccgggact ttcgctttcc ccctccctat tgccacggcg gaactcatcg   5160
ccgcctgcct tgcccgctgc tggacagggg ctcggctgtt gggcactgac aattccgtgg   5220
tgttgtcggg gaagctgacg tcctttccat ggctgctcgc ctgtgttgcc acctggattc   5280
tgcgcgggac gtccttctgc tacgtccctt cggccctcaa tccagcggac cttccttccc   5340
gcggcctgct gccggctctg cggcctcttc cgcgtcttcg ccttcgccct cagacgagtc   5400
ggatctccct ttgggccgcc tccccgcctg gaattaattc tgcagtcgag acctagaaaa   5460
acatggagca atcacaagta gcaatacagc agctaccaat gctgattgtg cctggctaga   5520
agcacaagag gaggaggagg tgggtttttcc agtcacacct caggtacctt taagaccaat   5580
gacttacaag gcagctgtag atcttagcca cttttttaaa gaaaagaggg gactggaagg   5640
gctaattatc tgagcctggg agctctctct gcttttttgct tgtactgggt ctctctggtt   5700
agaccagcac tcccaacgaa gacaagatgg ctaactaggg aacccactgc ttaagcctca   5760
ataaagcttg ccttgagtgc ttcaagtagt gtgtgcccgt ctgttgtgtg actctggtaa   5820
ctagagatcc ctcagaccct tttagtcagt gtggaaaatc tctagcagt              5869
```

```
SEQ ID NO: 56              moltype = AA  length = 178
FEATURE                    Location/Qualifiers
source                     1..178
                           mol_type = protein
                           organism = synthetic construct
SEQUENCE: 56
MHSSALLCCL VLLTGVRASP GQGTQSENSC THFPGNLPNM LRDLRDAFSR VKTFFQTKDE   60
VDNLLLKESL LEDFKGYLGC QALSEMIQFY LEEVMPQAEN QDPEAKDHVN SLGENLKTLR   120
LRLRRCHRFL PCENKSKAVE QIKNAFNKLQ EKGIYKAMSE FDIFINYIEA YMTMKIRN     178

SEQ ID NO: 57              moltype = AA  length = 178
FEATURE                    Location/Qualifiers
source                     1..178
                           mol_type = protein
                           organism = synthetic construct
SEQUENCE: 57
MHSSALLCCL VLLTGVRASP GQGTQSENSC THFPGNLPNM LRDLRDAFSR VKTFFQMKDQ   60
LDNLLLKESL LEDFKGYLGC QALSEMIQFY LEEVMPQAEN QDPDAKAHVN SLGENLKTLR   120
LRLRRCHRFL PCENKSKAVE QVKNAFNKLQ EKGIYKAMSE FDIFINYIEA YMTMKIRN     178

SEQ ID NO: 58              moltype = AA  length = 178
FEATURE                    Location/Qualifiers
source                     1..178
                           mol_type = protein
                           organism = Mus musculus
SEQUENCE: 58
MPGSALLCCL LLLTGMRISR GQYSREDNNC THFPVGQSHM LLELRTAFSQ VKTFFQTKDQ   60
LDNILLTDSL MQDFKGYLGC QALSEMIQFY LVEVMPQAEK HGPEIKEHLN SLGEKLKTLR   120
MRLRRCHRFL PCENKSKAVE QVKSDFNKLQ DQGVYKAMNE FDIFINCIEA YMMIKMKS     178

SEQ ID NO: 59              moltype = AA  length = 178
FEATURE                    Location/Qualifiers
source                     1..178
                           mol_type = protein
                           organism = Rattus norvegicus
SEQUENCE: 59
MPGSALLCCL LLLAGVKTSK GHSIRGDNNC THFPVSQTHM LRELRAAFSQ VKTFFQKKDQ   60
LDNILLTDSL LQDFKGYLGC QALSEMIKFY LVEVMPQAEN HGPEIKEHLN SLGEKLKTLW   120
IQLRRCHRFL PCENKSKAVE QVKNDFNKLQ DKGVYKAMNE FDIFINCIEA YVTLKMKN     178

SEQ ID NO: 60              moltype = AA  length = 178
FEATURE                    Location/Qualifiers
source                     1..178
                           mol_type = protein
                           organism = Macaca mulatta
SEQUENCE: 60
MHSSALLCCL VLLTGVRASP GQGTQSENSC TRFPGNLPHM LRDLRDAFSR VKTFFQMKDQ   60
LDNILLKESL LEDFKGYLGC QALSEMIQFY LEEVMPQAEN HDPDIKEHVN SLGENLKTLR   120
LRLRRCHRFL PCENKSKAVE QVKNAFSKLQ EKGVYKAMSE FDIFINYIEA YMTMKIQN     178

SEQ ID NO: 61              moltype = AA  length = 178
FEATURE                    Location/Qualifiers
source                     1..178
                           mol_type = protein
                           organism = Gorilla gorilla
SEQUENCE: 61
MHSSALLCCL VLLTGVRASP GHGTQSENSC THFPGNLPNM LRDLRDAFSR VKTFFQMKDQ   60
LDNLLLKESL LEDFKGYLGC QALSEMIQFY LEEVMPQAEN QDPDIKAHVN SLGENLKTLR   120
LRLRRCHRFL PCENKSKAVE QVKNAFNKLQ EKGVYKAMSE FDIFINYIEA YMTMKIRN     178

SEQ ID NO: 62              moltype = AA  length = 178
```

-continued

```
FEATURE               Location/Qualifiers
source                1..178
                      mol_type = protein
                      organism = Macaca fascicularis
SEQUENCE: 62
MHSSALLCCL VLLTGVRASP GQGTQSENSC TRFPGNLPHM LRDLRDAFSR VKTFFQMKDQ   60
LDNILLKESL LEDFKGYLGC QALSEMIQFY LEEVMPQAEN HDPDIKEHVN SLGENLKTLR   120
LRLRRCHRFL PCENKSKAVE QVKNAFSKLQ EKGVYKAMSE FDIFINYIEA YMTMKIQN     178

SEQ ID NO: 63         moltype = AA  length = 178
FEATURE               Location/Qualifiers
source                1..178
                      mol_type = protein
                      organism = Papio anubis
SEQUENCE: 63
MHSSALLCCL VVLTGVRASP GQGTQSENSC TRFPGNLPHM LRDLRDAFSR VKTFFQMKDQ   60
LDNILLKESL LEDFKGYLGC QALSEMIQFY LEEVMPQAEN HDPDIKEHVN SLGENLKTLR   120
LRLRRCHRFL PCENKSKAVE QVKNAFSKLQ EKGVYKAMSE FDIFINYIEA YMTMKIQN     178

SEQ ID NO: 64         moltype = AA  length = 178
FEATURE               Location/Qualifiers
source                1..178
                      mol_type = protein
                      organism = Pan paniscus
SEQUENCE: 64
MHSSALLCCL VLLTGVRASP GQGTQSENSC THFPGNLPNM LRDLRDAFSR VKTFFQMKDQ   60
LDNLLLKESL LEDFKGYLGC QALSEMIQFY LEEVMPQAEN QDPDIKVHVN SLGENLKTLR   120
LRLRRCHRFL PCENKSKAVE QVKNAFNKLQ EKGIYKAMSE FDIFINYIEA YMTMKIRN     178

SEQ ID NO: 65         moltype = AA  length = 178
FEATURE               Location/Qualifiers
source                1..178
                      mol_type = protein
                      organism = Pan troglodytes
SEQUENCE: 65
MHSSALLCCL VLLTGVRASP GQGTQSENSC THFPGNLPNM LRDLRDAFSR VKTFFQMKDQ   60
LDNLLLKESL LEDFKGYLGC QALXEMIQFY LEEVMPQAEN QDPDIKVHVN SLGENLKTLR   120
LRLRRCHRFL PCENKSKAVE QVKNAFNKLQ EKGIVKAMSE FDIFINYIEA YMTMKIRN     178

SEQ ID NO: 66         moltype = AA  length = 170
FEATURE               Location/Qualifiers
source                1..170
                      mol_type = protein
                      organism = synthetic construct
SEQUENCE: 66
MERRLVVTLQ CLVLLYLAPE CGGTDQCDNF PQMLRDLRDA FSRVKTFFQT KDEVDNLLLK   60
ESLLEDFKGY LGCQALSEMI QFYLEEVMPQ AENQDPEAKD HVNSLGENLK TLRLRLRRCH   120
RFLPCENKSK AVEQIKNAFN KLQEKGIYKA MSEFDIFINY IEAYMTIKAR             170

SEQ ID NO: 67         moltype = AA  length = 177
FEATURE               Location/Qualifiers
source                1..177
                      mol_type = protein
                      organism = synthetic construct
SEQUENCE: 67
MHSSALLCCL VLLTGRASPG QGTQSENSCT HFPGNIPNML RDIRDAFSRV KTEFQTKDEV   60
DNLLLKESLL EDEKGYLGCQ ALSEMIQFYL EEVMPQAENQ DPEAKDHVNS LGENLKTLRL   120
RIRRCHRFLP CENKSKAVEQ IKNAFNKLQE KGIYKAMSEF DIFINYIEAY MTMKIRN      177

SEQ ID NO: 68         moltype = AA  length = 177
FEATURE               Location/Qualifiers
source                1..177
                      mol_type = protein
                      organism = synthetic construct
SEQUENCE: 68
MHSSALLCCL VLLTGRASPG QGTQSENSCT HFPGNIPNML RDIRDAFSRV KTEFQMKDQL   60
DNLLLKESLL EDEKGYLGCQ ALSEMIQFYL EEVMPQAENQ DPDAKAHVNS LGENLKTLRL   120
RIRRCHRFLP CENKSKAVEQ VKNAFNKLQE KGIYKAMSEF DIFINYIEAY MTMKIRN      177
```

CD4+ T CELLS EXPRESSING IL-10 AND CHIMERIC ANTIGEN RECEPTORS AND USES THEREOF

1. CROSS-REFERENCE TO RELATED APPLICATIONS

This application is a continuation of U.S. patent application Ser. No. 18/725,665, filed Jun. 28, 2024, which is a National Stage on international Application No. PCT/US2022/082431, Filed Dec. 27, 2022, which claims the benefit of U.S. Provisional Application No. 63/295,491, filed Dec. 30, 2021, which is hereby incorporated in its entirety by reference.

2. SEQUENCE LISTING

The instant application contains a Sequence Listing, which has been submitted XML format and is hereby incorporated herein by reference in its entirety. Said XML copy, created on Feb. 25, 2025 is named 37104-62100SL.xml, and is 96 kilobytes (KB) in size.

3. BACKGROUND

Regulatory T cells belong to a small but important subset of T cells which maintain immunological tolerance to self and non-pathogenic antigens and maintain immune homeostasis. There are two major populations of regulatory T cells—CD4$^+$ FOXP3$^+$ CD25$^+$ T cells (FOXP3$^+$) cells and type 1 regulatory T (Tr1) cells. Both FOXP3$^+$ and Tr1 cells downregulate pathogenic T-cell responses in various preclinical models of organ and pancreatic islet transplantation, graft-versus-host disease (GvHD) and various autoimmune and inflammatory diseases.

Tr1 cells have been shown to be effective in clinical studies. Administration of cloned, antigen-specific, autologous Tr1 cells to patients with ongoing moderate to severe Crohn's disease resulted in objective, transient remissions (Desreumaux et al., *Gastroenterology.* 2012; 143(5):1207-1217.e2.). In addition, adoptive transfer of donor-derived CD4$^+$ T cell populations enriched for allo-specific Tr1 cells to leukemia patients following allogeneic hematopoietic stem cell transplantation (allo-HSCT) resulted in a rapid reconstitution of the immune system and protection against microbial and viral infections, without severe GvHD. In the responder patients, long term remissions and tolerance (>7 years) resulting in cures were achieved (Bacchetta et al., *Front Immunol.* 2014; 5:16).

Despite these encouraging results, the production of donor-derived or autologous Tr1 cells for large scale therapy for patients with high unmet medical needs is not always feasible, is very cumbersome, and does not allow for the generation of large quantities of pure Tr1 cells.

Recently, Locafaro and colleagues circumvented some of these problems by transducing purified CD4$^+$ T cells from a single donor with a bidirectional lentiviral vector containing a human IL-10 gene. The resulting single-donor CD4$^{IL-10}$ populations shared the major functions of naturally occurring Tr1 cells. Like Tr1 cells, single-donor CD4$^{IL-10}$ cells produce high levels of IL-10 and downregulate the proliferation of both allogeneic CD4$^+$ T cells and allogeneic CD8$^+$ T cells. In addition, they are directly cytotoxic for both normal myeloid cells (including antigen presenting cells, APC) and myeloid leukemia cells. In a humanized xenograft-versus-host disease (GvHD) model, these single-donor CD4$^{IL-10}$ cells were shown to be effective in reducing GvHD while retaining graft-versus-leukemia (GvL) activity. See Locafaro et al. Mol Ther. 2017; 25(10):2254-2269 and WO 2016/146,542.

There is a need for means of redirecting the cytotoxic capability of CD4$^{IL-10}$ cells to non-myeloid cells while simultaneously preserving the immune suppressive and immune homeostasis-maintaining activity of these cells.

4. SUMMARY

The present disclosure provides a new type of immune cell, CD4$^{IL-10/CAR}$ cells, which are engineered to express both exogenous IL-10 and a chimeric antigen receptor (CAR). We have discovered that expression of a CAR in addition to IL-10 redirects the cytotoxic properties of these Tr1-like cells to therapeutically useful targets other than myeloid targets, while surprisingly leaving intact the cells' immune-regulatory properties. Also described are methods of treatment using the CD4$^{IL-10/CAR}$ cells, use of CD4$^{IL-10/CAR}$ cells for treatment, and use of CD4$^{IL-10/CAR}$ cells in the manufacture of a medicament for treating various disorders in which the CAR directs the cytotoxic properties of these Tr1-like cells to therapeutically useful targets other than myeloid cells, while leaving intact the cells' immune-regulatory properties.

The present disclosure provides a genetically modified CD4$^+$ T cell (CD4$^{IL10/CAR}$) comprising: (a) a first exogenous polynucleotide segment encoding a chimeric antigen receptor (CAR); and (b) a second exogenous polynucleotide segment encoding interleukin-10 (IL-10)

In some embodiments, the first exogenous polynucleotide segment comprises a regulatory element operably linked to a coding sequence of the CAR. In some embodiments, the regulatory element drives constitutive expression of the CAR.

In some embodiments, the CAR comprises an antigen-binding domain, a hinge region, a transmembrane domain, and an intracellular signaling domain.

In some embodiments, the antigen-binding domain comprises a single chain antibody fragment. In some embodiments, the single chain antibody fragment comprises a single chain Fv (scFv).

In some embodiments, the antigen-binding domain targets an antigen associated with an autoimmune disease, inflammatory disorder, or cancer.

In some embodiments, the antigen is selected from the group consisting of: CD19, CD20, CD22, BCMA, CD27, CD38, B7-H3, CD23, Lym1, Lym2, CLEC5A, CDH179b, FLT3, GCC, Muc, CSF2RA, GFRa4, CD32, CD33, CEA, IL11Ra, IL13Ra, NYBRI, SLea, CD200R, TGFBetaR2, CD276, TROP2, LAMP1, PTK7, DLL3, CDH1, CDH6, CDH17, CDH19, TSHR, tyrosinase, HLA-A*02, HLA-A*24 or citrullinated peptides, insulin, MOG, GAD65, IA2, gliadin, and desmoglein in the context of relevant MHC molecules.

In some embodiments, the antigen-binding domain comprises an anti-CD19 antigen-binding domain. In some embodiments, the anti-CD19 antigen-binding domain comprises the sequence of SEQ ID NO: 11.

In some embodiments, the antigen-binding domain is an anti-CD20 antigen-binding domain. In some embodiments, the anti-CD20 antigen-binding domain comprises the sequence of SEQ ID NO: 18.

In some embodiments, the antigen-binding domain is an anti-BCMA antigen-binding domain. In some embodiments, the anti-BCMA antigen-binding domain comprises the sequence of SEQ ID NOs: 50-53.

In some embodiments, the binge region is selected from a human CD8 hinge region, a human CD28 hinge region, a IgG1 hinge region, or a IgG4 hinge region. In some embodiments, the hinge region is derived from human CD8.

In some embodiments, the transmembrane domain is selected from a TNERSF 19 transmembrane domain, a CD3zeta transmembrane domain, a CD8a transmembrane domain, a CD4 transmembrane domain, a CD28 transmembrane domain, or an B7-family inducible costimulatory (ICOS) transmembrane domain. In some embodiments, the transmembrane domain is derived from a CD8a transmembrane domain.

In some embodiments, the CAR further comprises one or more co-stimulatory domains. In some embodiments, the CAR comprises two co-stimulatory domains.

In some embodiments, the one or more co-stimulatory domains are selected from the group consisting of 4-1BB, CD28, OX40, ICOS, CD27, MYD88-CD40, and KIR2DS2.

In some embodiments, one of the one or more co-stimulatory domains is derived from CD28.

In some embodiments, a second co-stimulatory domain is derived from 4-1BB.

In some embodiments, the intracellular signaling domain comprises an immunoreceptor tyrosine-based activation motif (ITAM). In some embodiments, the immunoreceptor tyrosine-based activation motif (ITAM) is derived from CD3zeta.

In some embodiments, the CAR comprises: an anti-CD19 antigen binding domain, an anti-BCMA antigen binding domain, or an anti-CD20 antigen binding domain; a human CD8 hinge region; a TNFRSF 19 transmembrane region; a 4-1BB co stimulatory domain; and a CD3zeta chain intracellular signaling domain. In some embodiments, the CAR comprises: an anti-CD19 antigen binding domain, an anti-BCMA antigen binding domain, or an anti-CD20 antigen binding domain; a human CD8 binge region; a CD8a transmembrane region; a 4-1BB co stimulatory domain; and a CD3zeta chain intracellular signaling domain.

In some embodiments, the CAR comprises the sequence of SEQ ID NOs: 9, 16, 22, 34, 41-49, or 54.

In some embodiments, the first exogenous polynucleotide segment comprises the sequence of SEQ ID NOs: 10, 17, 23, 35, or 55.

In some embodiments, the first exogenous polynucleotide segment is integrated into the T cell nuclear genome.

In some embodiments, the first exogenous polynucleotide segment is not integrated into the T cell nuclear genome.

In some embodiments, the first exogenous polynucleotide segment is in a vector.

In some embodiments, the second exogenous polynucleotide segment comprises a regulatory element operably linked to a coding sequence of the IL-10. In some embodiments, the IL-10 is a human IL-10. In some embodiments, the IL-10 is a viral IL-10.

In some embodiments, the IL-10 is a protein having the sequence of SEQ ID NO: 1. In some embodiments, the second exogenous polynucleotide segment comprises the sequence of SEQ ID NO: 2.

In some embodiments, the regulatory element drives constitutive expression of the IL-10.

In some embodiments, the second exogenous polynucleotide segment is integrated into the T cell nuclear genome.

In some embodiments, the second exogenous polynucleotide segment is not integrated into the T cell nuclear genome.

In some embodiments, the second exogenous polynucleotide segment is in a vector.

In some embodiments, the first exogenous polynucleotide segment and the second exogenous polynucleotide segment are in the same vector. In some embodiments, the vector is a viral vector. In some embodiments, the vector is a lentiviral vector.

In some embodiments, the $CD4^+$ T cell constitutively expresses at least 100 pg IL-10 per $10^6$ of the $CD4^+$ T cells/mL of culture medium.

In some embodiments, the $CD4^+$ T cell constitutively expresses at least 100 pg, 200 pg, 500 pg, 1 ng, 5 ng, 10 ng, or 50 ng IL-10 per $10^6$ of the $CD4^+$ T cells/mL.

In some embodiments, the $CD4^+$ T cells expresses at least 1 ng IL-10 per $10^6$ of the $CD4^+$ T cells/mL after activation with anti-CD3 and anti-CD28 antibodies.

In some embodiments, the $CD4^+$ T cells expresses at least 2 ng, 5 ng, 10 ng, 100 ng, 200 ng, or 500 ng IL-10 per $10^6$ of the $CD4^+$ T cells/mL after activation with anti-CD3 and anti-CD28 antibodies.

In some embodiments, the $CD4^+$ T cell expresses IL-10 at a level at least 5-fold higher than unmodified $CD4^+$ T cells. In some embodiments, the $CD4^+$ T cell expresses IL-10 at a level at least 10-fold higher than unmodified $CD4^+$ T cells.

In some embodiments, the $CD4^+$ T cell expresses at least 100 pg IL-5 per $10^6$ of the $CD4^+$ T cells/mL. In some embodiments, the $CD4^+$ T cell expresses at least 100 pg, 200 pg, 500 pg, 1 ng, 5 ng, 10 ng, or 50 ng IL-5 per $10^6$ of the $CD4^+$ T cells/mL.

In some embodiments, the $CD4^+$ T cell expresses at least 1 ng IL-5 per 100 of the $CD4^+$ T cells/mL after activation with anti-CD3 and anti-CD28 antibodies.

In some embodiments, the $CD4^+$ T cells expresses at least 2 ng, 5 ng, 10 ng, 100 ng, 200 ng, or 500 ng IL-5 per $10^6$ of the $CD4^+$ T cells/mL after activation with anti-CD3 and anti-CD28 antibodies.

In some embodiments, the $CD4^+$ T cell expresses at least 100 pg IFN-γ per $10^6$ of the $CD4^+$ T cells/mL In some embodiments, the $CD4^+$ T cell expresses at least 100 pg, 200 pg, 500 pg, 1 ng, 5 ng, 10 ng, or 50 ng IFN-γ per $10^6$ of the $CD4^+$ T cells/mL.

In some embodiments, the $CD4^+$ T cell expresses at least 1 ng IFN-γ per $10^6$ of the $CD4^+$ T cells/mL after activation with anti-CD3 and anti-CD28 antibodies.

In some embodiments, the $CD4^+$ T cells expresses at least 2 ng, 5 ng, 10 ng, 100 ng, 200 ng, or 500 ng IFN-γ per $10^6$ of the $CD4^+$ T cells/mL after activation with anti-CD3 and anti-CD28 antibodies.

In some embodiments, the $CD4^+$ T cell expresses at least 25 pg IL-4 per $10^6$ of the $CD4^+$ T cells/mL.

In some embodiments, the $CD4^+$ T cell expresses at least 25 pg, 50 pg, 75 pg, 100 pg, 200 pg, 500 pg, 1 ng, 5 ng, 10 ng, or 50 ng IL-4 per $10^6$ of the $CD4^+$ T cells/mL.

In some embodiments, the $CD4^+$ T cell expresses at least 100 pg IL-4 per $10^6$ of the CD4" T cells/mL after activation with anti-CD3 and anti-CD28 antibodies.

In some embodiments, the $CD4^+$ T cells expresses at least 100 pg, 200 pg, 300 pg, 400 pg, 500 pg, 600 pg, 700 pg, 800 pg, 900 pg, 1000 pg, 2 ng, 5 ng, 10 ng, 100 ng, 200 ng, or 500 ng IL-4 per $10^6$ of the $CD4^+$ T cells/mL after activation with anti-CD3 and anti-CD28 antibodies.

In some embodiments, the expression one or more of IL-10, IL-4, IFN-γ, and IL-5 is stable after one or more re-stimulations.

In some embodiments, the first exogenous polynucleotide segment or the second exogenous polynucleotide segment, further comprises a sequence encoding a selection marker.

In some embodiments, the selection marker is ΔNGFR. In some embodiments, the ΔNGFR has the sequence of SEQ ID NO: 3. In some embodiments, the second exogenous polynucleotide segment comprises a sequence of SEQ ID NO: 4.

In some embodiments, the selection marker is a truncated form of an EGFR polypeptide.

In some embodiments, the CD4$^+$ T cell is capable of in vitro cytotoxicity to a CD19$^+$ target cell.

In some embodiments, the CD4$^+$ T cell is capable of in vivo cytotoxicity to a CD19$^+$ target cell.

In some embodiments, the CD19$^+$ target cell is an autoantibody producing B cell. In some embodiments, the CD19$^+$ target cell is a CD19$^+$ cancer cell.

In some embodiments, the CD4$^+$ T cell is capable of in vitro cytotoxicity to a myeloid target cell.

In some embodiments, the CD4$^+$ T cell is capable of in vivo cytotoxicity to a myeloid target cell.

In some embodiments, the CD4$^+$ T cell is capable of cytotoxicity to a CD19$^+$ target cell and a myeloid target cell.

In some embodiments, the myeloid target cell express one or more of Class I MHC, CD13, CD54 and CD112.

In some embodiments, the cytotoxicity to a CD19$^+$ target cell is maintained after one or more in vitro restimulations. In some embodiments, the cytotoxicity to a CD19$^+$ target cell is maintained after one or more in vitro expansions.

In some embodiments, the cytotoxicity to a myeloid target cell is maintained after one or more vitro restimulations. In some embodiments, the cytotoxicity to a myeloid target cell is maintained after one or more in vitro expansions.

In some embodiments, the CD4$^+$ T cell is capable of suppressing allogeneic CD4$^+$ T cell proliferation.

In some embodiments, the CD4$^+$ T cell is capable of suppressing allogeneic CD8$^+$ T cell proliferation.

In some embodiments, the CD4$^+$ T cell is capable of suppressing allogeneic CD4$^+$ T cell proliferation, allogenic CD8$^+$ T cell proliferation, and PBMC proliferation.

In some embodiments, the suppressive property is maintained after one or more restimulations.

In another aspect, the present disclosure features a population of CD4$^+$ T cells comprising any of the genetically modified CD4$^+$ cells provided herein.

In some embodiments, the CD4$^+$ T cells before the genetic modification were obtained from two, three, four, five, six, seven, eight, nine, or ten different T cell donors and pooled.

In some embodiments, the CD4$^+$ T cells in the population collectively have six, seven, eight, nine, ten, eleven, twelve, or more different HLA haplotypes.

In some embodiments, all the CD4$^+$ T cells in the population have at least 1/10, 2/10, 3/10, 4/10, 5/10, 6/10, 7/10, 8/10, or 9/10 match at the HLA-A, HLA-B, HLA-C, HLA-DRB1, and HLA-DQB1 loci to each other.

In some embodiments, all the CD4$^+$ T cells in the population have at least 1/8, 2/8, 3/8, 4/8, 5/8, 6/8, 7/8, or 8/8 match at the HLA-A, HLA-B, HLA-C, and HLA-DRB1 loci to each other.

In some embodiments, all the CD4$^+$ T cells in the population have 2/2 match at the HLA-A locus to each other.

In some embodiments, all the CD4$^+$ T cell in the population have 2/2 match at the HLA-B locus to each other.

In some embodiments, all the CD4$^+$ T cell in the population have 2/2 match at the HLA-C locus to each other.

In some embodiments, all the CD4$^+$ T cells in the population have at least 3/4 or 4/4 match at the HLA-DRB1 and HLA-DQB1 loci with each other.

In some embodiments, all the CD4$^+$ T cells in the population have less than 5/10, 6/10, 7/10, 8/10, or 9/10 match at the HLA-A, HLA-B, HLA C, HLA-DRB1, and HLA-DQB1 loci to each other.

In some embodiments, all the CD4$^+$ T cells in the population have less than 4/8, 5/8, 6/8, 7/8, or 8/8 match at the HLA-A, HLA-B, HLA C, and HLA DRB1 loci to each other.

In some embodiments, all the CD4$^+$ T cells in the population have less than 2/2 match at the HLA-A locus to each other.

In some embodiments, all the CD4$^+$ T cell in the population have less than 2/2 match at the HLA-B locus to each other.

In some embodiments, all the CD4$^+$ T cell in the population have less than 2/2 match at the HLA-C locus to each other.

In some embodiments, all the CD4$^+$ T cells in the population have less than 4/2, 3/4 or 4/4 match at the HLA-DRB1 and HLA DQB1 loci with each other.

In some embodiments, all the CD4$^+$ T cells in the population have an A*02 allele or are A*02 negative.

In some embodiments, all the CD4$^+$ T cells in the population have an A*24 allele or are A*24 negative.

In some embodiments, at least 30% of the CD4$^+$ T cells within the population of NGFR$^+$ cells express the CAR.

In some embodiments, at least 60% of the CD4$^+$ T cells within the population of NGFR$^+$ cells express the CAR.

In some embodiments, at least 90% of the CD4$^+$ T cells within the population of NGFR$^+$ cells express the CAR.

In some embodiments, the CD4$^+$ T cells are in a frozen suspension.

In some embodiments, the CD4$^+$ T cells are in a liquid suspension.

In some embodiments, the liquid suspension has previously been frozen.

In another aspect, this disclosure features any of the pharmaceutical compositions provided herein comprising any of the CD4$^+$ T cells provided herein or any of the populations of CD4$^+$ T cells provided herein.

In another aspect, this disclosure features a method of making CD4$^{IL10/CAR}$ cells, comprising the steps of: (a) obtaining primary CD4$^+$ T cells from one or more T cell donors; and (b) modifying the CD4$^+$ T cells by introducing (i) a first exogenous polynucleotide segment encoding a chimeric antigen receptor (CAR), and (ii) a second exogenous polynucleotide segment encoding IL-10.

In some embodiments, in step (a), the primary CD4$^+$ T cells are obtained from two, three, four, five, six, seven, eight, nine, or ten different T cell donors.

In some embodiments, the method further comprising pooling the genetically modified CD4$^+$ T cells from step (b).

In some embodiments, wherein in step (a), the primary CD4$^+$ T cells are autologous to the patient.

In some embodiments, the method further comprising the step, after step (a) and before step (b), or after step (b) of: incubating the CD4$^+$ T cells in the presence of an anti-CD3 antibody, and anti-CD28 antibody or anti-CD3 antibody and CD28 antibody coated beads.

In some embodiments, the method further incubating the CD4$^+$ T cells further in the presence of IL-2.

In some embodiments, the first exogenous polynucleotide segment, second exogenous polynucleotide segment, or both are introduced into the primary CD4$^+$ T cells using one or more viral vectors. In some embodiments, the viral vector is a lentiviral vector.

In some embodiments, the first exogenous polynucleotide segment comprises a coding sequence of a CAR.

In some embodiments, the CAR is specific to a target antigen associated with an autoimmune disease, inflammatory disorder or cancer.

In some embodiments, the target antigen is associated with an autoimmune disease, inflammatory disorder or cancer.

In some embodiments, the CAR is an anti-CD19 CAR, an anti-CD20 CAR, an anti-CD22 CAR, an anti BCMA CAR, an anti-B7-H3 CAR, an anti-CD27 CAR, or an anti-CD38 CAR.

In some embodiments, the CAR comprises the sequence of SEQ ID NOs: 9, 16, 22, 34, 41-49, or 54.

In some embodiments, the first exogenous polynucleotide segment comprises the sequence of SEQ ID NOs: 10, 17, 23, 35, or 55.

In some embodiments, the IL-10 comprises the sequence of SEQ ID NO: 1. In some embodiments, the second exogenous polynucleotide segment comprises the sequence of SEQ ID NO: 2.

In some embodiments, the first exogenous polynucleotide segment or the second exogenous polynucleotide segment, further comprising a segment encoding a selection marker.

In some embodiments, the encoded selection marker is ΔNGFR. In some embodiments, the encoded selection marker has the sequence of SEQ ID NO: 3.

In some embodiments, the selection marker is a truncated form of EGFR polypeptide.

In some embodiments, the method further comprising the step, after step (b), of: isolating the genetically-modified CD4$^+$ T cells expressing the selection marker, thereby generating an enriched population of genetically-modified CD4$^+$ T cells.

In some embodiments, at least 30% or at least 60% of the genetically-modified CD4$^+$ T cells in the enriched population express IL-10 and the CAR.

In some embodiments, at least 90% of the genetically-modified CD4$^+$ T cells in the enriched population express IL-10 and the CAR.

In some embodiments, at least 40% of the genetically-modified CD4$^+$ T cells in the enriched population express the selection marker.

In some embodiments, at least 75% of the genetically-modified CD4$^+$ T cells in the enriched population express the selection marker.

In some embodiments, at least 90% of the genetically-modified CD4$^+$ T cells in the enriched population express the selection marker.

In some embodiments, the method further comprising the step of incubating the enriched population of genetically-modified CD4$^+$ T cells.

In some embodiments, the step of incubating the enriched population of genetically-modified CD4$^+$ T cells is performed in the presence of anti-CD3 antibody and anti-CD28 antibody or CD3 antibody and CD28 antibody coated beads in the presence of IL-2.

In some embodiments, the method further comprising the later step of freezing the genetically-modified CD4$^+$ T cells.

In some embodiments, the at least two T cell donors have at least 1/10, 2/10, 3/10, 4/10, 5/10, 6/10, 7/10, 8/10, or 9/10 match at the HLA-A, HLA-B, HLA-C, HLA-DRB1, and HLA-DQB1 loci to each other.

In some embodiments, the at least two T cell donors have at least 1/8, 2/8, 3/8, 4/8, 5/8, 6/8, 7/8, or 8/8 match at the HLA-A, HLA-B, HLA-C, and HLA-DRB1 loci to each other.

In some embodiments, the at least two T cell donors have 2/2 match at the HLA-A locus to each other. In some embodiments, the at least two T cell donors have 2/2 match at the HLA-B locus to each other. In some embodiments, the at least two T cell donors have 2/2 match at the HLA-C locus to each other.

In some embodiments, the at least two T cell donors have at least 3/4 or 4/4 match at the HLA-DRB1 and HLA-DQB1 loci to each other.

In some embodiments, the at least two T cell donors have less than 5/10, 6/10, 7/10, 8/10, or 9/10 match at the HLA-A, HLA-B, HLA C, HLA-DRB1, and HLA-DQB1 loci to each other.

In some embodiments, the at least two T cell donors have less than 4/8, 5/8, 6/8, 7/8, or 8/8 match at the HLA-A, HLA-B, HLA C, and HLA DRB1 loci to each other.

In some embodiments, the at least two T cell donors have less than 2/2 match at the HLA-A locus to each other. In some embodiments, the at least two T cell donors have less than 2/2 match at the HLA-B locus to each other. In some embodiments, the at least two T cell donors have less than 2/2 match at the HLA-C locus to each other.

In some embodiments, the at least two T cell donors have less than 4/2, 3/4 or 4/4 match at the HLA-DRB1 and HLA DQB1 loci with each other.

In some embodiments, each of the at least two T cell donors has an A*02 allele or are A*02 negative. In some embodiments, each of the at least two T cell donors has an A*02 allele or are A*02 negative.

In some embodiments, in step (a), the primary CD4$^+$ T cells are obtained from one or more frozen stocks.

In some embodiments, in step (a), the primary CD4$^+$ T cells are obtained from unfrozen peripheral blood mononuclear cells of the at least two different T cell donors.

In some embodiments, the method further comprising the step of isolating CD4$^+$ T cells from the peripheral blood mononuclear cells.

In another aspect, this disclosure features a method for treating a hematological cancer, comprising: administering to a hematological cancer patient a therapeutically effective amount of any of the CD4$^{IL-10/CAR}$ cells provided, any of the population of CD4$^{IL-10/CAR}$ cells provided herein, or any of the pharmaceutical compositions provided herein sufficient to induce anti-cancer effect.

In some embodiments, the method further comprising the step of administering allo HSCT graft to the patient prior to or subsequent to administration of the CD4$^{IL-10/CAR}$.

In another aspect, this disclosure features a method of treating a patient with a malignancy, comprising: administering an allo-HSCT graft to the patient, and administering a therapeutically effective amount of any of the CD4$^{IL-10/CAR}$ cells provided, any of the population of CD4$^{IL-10/CAR}$ cells provided herein, or any of the pharmaceutical compositions provided herein.

In some embodiments, the amount of CD4$^{IL-10/CAR}$ cells is further sufficient to suppress or prevent graft versus host disease (GvHD) without suppressing graft versus leukemia (GvL) or graft versus tumor (GvT) efficacy of the allo HSCT.

In some embodiments, the malignancy or hematological cancer is a myeloid leukemia.

In some embodiments, the CD4$^{IL-10/CAR}$ cells target and kill cancer cells that express CD13.

In some embodiments, the CD4$^{IL-10/CAR}$ cells target and kill cancer cells that express HLA-class I.

In some embodiments, the myeloid leukemia is acute myeloid leukemia (AML).

In some embodiments, the malignancy or hematological cancer is a CD19$^+$, CD20$^+$, CD22$^+$, CD27$^+$, CD38$^+$, BCMA+, or B7-H3$^+$ hematological cancer.

In some embodiments, the CD19$^+$, CD20$^+$, CD22$^+$, CD27$^+$, CD38$^+$, BCMA+, or B7-H3$^+$ hematological cancer is selected from chronic lymphocytic leukemia, acute lymphoblastic leukemia (ALL), and non-Hodgkin's lymphomas.

In some embodiments, the allo-HSCT graft is obtained from a related or unrelated donor with respect to the patient.

In some embodiments, the CD4$^{IL-10/CAR}$ cells are non-autologous to the patient.

In some embodiments, the CD4$^{IL-10/CAR}$ cells are autologous to the patient.

In some embodiments, the CD4$^{IL-10/CAR}$ cells are allogeneic to the patient.

In some embodiments, the CD4$^{IL-10/CAR}$ cells are not anergized to host allo-antigens prior to administration to the patient.

In some embodiments, the CD4$^{IL-10/CAR}$ cells are Tr1-like cells.

In some embodiments, the CD4$^{IL-10/CAR}$ cells are polyclonal.

In some embodiments, the CD4$^{IL-10/CAR}$ cells are polyclonal and non-autologous to the patient.

In some embodiments, the CD4$^{IL-10/CAR}$ cells are polyclonal and autologous to the patient.

In some embodiments, the CD4$^{IL-10/CAR}$ cells are isolated from at least two donors prior to being genetically modified.

In some embodiments, none of the at least two donors is the same donor as the allo-HSCT donor.

In some embodiments, the allo-HSCT graft is obtained from a matched or mismatched donor with respect to the patient.

In some embodiments, the CD4$^{IL-10/CAR}$ cells target and kill cells that express CD19, CD20, or BCMA. In some embodiments, the CD4$^{IL-10/CAR}$ cells target and kill cells that express CD54. In some embodiments, the CD4$^{IL-10/CAR}$ cells target and kill cancer cells that express HLA-class I and CD54. In some embodiments, the CD4$^{IL-10/CAR}$ cells target and kill cancer cells that express CD112 and CD155. In some embodiments, the CD4$^{IL-10/CAR}$ cells target and kill cancer cells that express CD58.

In some embodiments, the CD4$^{IL-10/CAR}$ cells target and kill cancer cells in the patient.

In some embodiments, the CD4$^{IL-10/CAR}$ cells target and kill solid tumor cells in the patient.

In another aspect, this disclosure features a method of treating a hematological cancer by allogeneic hematopoietic stem cell transplant (allo-HSCT), comprising:

administering allo-HSCT graft to a patient;

administering to the patient an amount of CD4$^{IL-10/CAR}$ cells sufficient to suppress or prevent graft-versus-host disease (GvHD) without suppressing graft-versus-leukemia (GvL) or graft-versus-tumor (GvT) efficacy of the allo-HSCT graft, wherein the CD4$^{IL-10/CAR}$ cells comprise CD4$^+$ T cells genetically modified by vector-mediated gene transfer of one or more vectors comprising the coding sequence of human IL-10 under control of a constitutive promoter or inducible promoter and the coding sequence of a CAR under control of a constitutive promoter or inducible promoter;

wherein the CD4$^{IL-10/CAR}$ cells target and kill cancer cells in the patient;

wherein the wherein the CD4$^{IL-10/CAR}$ cells are not anergized to host allo-antigens prior to administration to the patient; and wherein the CD4$^{IL-10/CAR}$ cells are non-autologous to the patient, and are Tr1-like.

In another aspect, this disclosure features method of treating a hematological cancer by allogeneic hematopoietic stem cell transplant (allo-HSCT), comprising:

administering allo-HSCT graft to a patient;

administering to the patient an amount of CD4$^{IL-10/CAR}$ cells, optionally wherein the amount is sufficient to suppress or prevent graft-versus-host disease (GvHD) without suppressing graft-versus-leukemia (GvL) or graft-versus-tumor (GvT) efficacy of the allo-HSCT graft, wherein the CD4$^{IL-10/CAR}$ cells comprise CD4$^+$ T cells genetically modified by vector-mediated gene transfer of one or more vectors comprising the coding sequence of human IL-10 under control of a constitutive promoter or inducible promoter and the coding sequence of a CAR under control of a constitutive promoter or inducible promoter;

wherein the CD4$^{IL-10/CAR}$ cells target and kill cancer cells in the patient;

wherein the wherein the CD4$^{IL-10/CAR}$ cells are not anergized to host allo-antigens prior to administration to the patient; and wherein the CD4$^{IL-10/CAR}$ cells are autologous to the patient, and are Tr1-like.

In another aspect, this disclosure features a method for preventing relapse of a CD19$^+$, CD20$^+$, CD22$^+$, CD27$^+$, CD38$^+$, BCMA$^+$ or B7-H3$^+$ hematological cancer in a patient, comprising:

administering to a patient, identified as having a CD19$^+$, CD20$^+$, CD22$^+$, BCMA+, or B7-H3$^+$ hematological cancer or at risk of having a relapse of a CD19$^+$, CD20$^+$, CD22$^+$, BCMA$^+$ or B7-H3$^+$ hematological cancer, a therapeutically effective amount of any of the CD4$^{IL-10/CAR}$ cells provided, any of the population of CD4$^{IL-10/CAR}$ cells provided herein, or any of the pharmaceutical compositions provided herein sufficient to induce anti-cancer effect. In some embodiments, the CD4$^{IL-10/CAR}$ cells are administered after administration of HSCT.

In another aspect, this disclosure features a method for preventing relapse of a B7-H3$^+$ cancer in a patient, comprising: administering to a patient, identified as having a B7-H3$^+$ cancer, a therapeutically effective amount of any of the CD4$^{IL-10/CAR}$ cells provided, any of the population of CD4$^{IL-10/CAR}$ cells provided herein, or any of the pharmaceutical compositions provided herein sufficient to induce anti-cancer effect.

In some embodiments, the B7-H3+ cancer is solid tumor.

In some embodiments, the solid tumor is selected from the group consisting of: breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

In another aspect, this disclosure features a method for treating a patient with minimal residual disease, comprising: administering to a patient, identified as having minimal residual disease or at risk of having minimal residual disease, a therapeutically effective amount of any of the CD4$^{IL-10/CAR}$ cells provided, any of the population of CD4$^{IL-10/CAR}$ cells provided herein, or any of the pharmaceutical compositions provided herein sufficient to induce anti-cancer effect.

In another aspect, this disclosure features a method of treating a patient, comprising: administering a therapeutically effective amount of any of the CD4$^{IL-10/CAR}$ cells provided, any of the population of CD4$^{IL-10/CAR}$ cells provided herein, or any of the pharmaceutical compositions provided herein, to a patient in need of immune tolerization.

In some embodiments, the method further comprising the preceding step of thawing a frozen suspension of $CD4^{IL-10/CAR}$ cells or the population of $CD4^{IL-10/CAR}$ cells.

In some embodiments, the patient has an inflammatory or autoimmune disease.

In some embodiments, the inflammatory or autoimmune disease is selected from the group consisting of: autoimmune uveitis, psoriasis, vitiligo, alopecia areata, psoriatic arthritis, inflammatory bowel disease, Hashimoto's thyroiditis, autoimmune vasculitis, ulcerative colitis, bullous diseases, scleroderma, celiac disease, graves disease, systemic sclerosis, myasthenia gravis, anti-NMDA encephalitis, pemphigoid diseases (vulgaris and *foliaceus*), epidermolysis bullosa acquisita, thrombotic thrombocytopenia purpura, ididopathic thrombocytic purpora, autoantibody induced vascular inflammation, autoantibody induced carditis, rheumatoid arthritis, autoantibody induced rheumatoid arthritis, neuromyelitis optica spectrum disorders, systemic lupus erythematosus (SLE), multiple sclerosis (MS), sjögren's syndrome, autoimmune myopathies, type I diabetes, addison disease, pernicious anemia, autoimmune hepatitis, primary biliary cholangitis (PBC), autoimmune pancreatitis, goodpasture's disease, primary membranous nephropathy, ovarian insufficiency, autoimmune orchitis, dry eye disease, aplastic anemia, autoimmune neutropenia, and idiopathic interstitial pneumonias.

In some embodiments, the inflammatory or autoimmune disease is Crohn's disease, ulcerative colitis, celiac disease, type-1 diabetes, lupus, psoriasis, psoriatic arthritis, alkylosing spondylitis, or rheumatoid arthritis.

In some embodiments, the patient has a disease or disorder involving hyperactivity of NLPR3 inflammasome.

In some embodiments, the patient has type 2 diabetes, neurodegenerative disease, cardiovascular disease or inflammatory bowel disease.

In some embodiments, the patient has a disease or disorder involving increased IL-1β production by activated monocytes, macrophages or dendritic cells In some embodiments, the patient has a disease or disorder involving increased IL-18 production by activated monocytes, macrophages or dendritic cells.

In some embodiments, the patient has a disease or disorder involving increased mature caspase 1 production by activated monocytes, macrophages or dendritic cells.

In some embodiments, the patient has an allergic or atopic disease.

In some embodiments, wherein the allergic or atopic disease is selected from the group consisting of: asthma, atopic dermatitis, and rhinitis.

In some embodiments, the patient has a food allergy.

In some embodiments, the patient has a solid tumor.

In some embodiments, the solid tumor is selected from the group consisting of: breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

In some embodiments, the method further comprising the step of organ transplantation to the patient, either prior to or subsequent to administration of the $CD4^{IL-10/CAR}$ cells, the population of $CD4^{IL-10/CAR}$ cells or the pharmaceutical composition. In some embodiments, the $CD4^{IL-10/CAR}$ cells, the population of $CD4^{IL-10/CAR}$ cells, or the pharmaceutical composition prevents or reduces severity of host rejection of the organ transplantation.

In some embodiments, the method further comprising the step of transplanting iPS cell-derived cells or tissues to the patient, either prior to or subsequent to administration of the $CD4^{IL-10/CAR}$ cells, the population of $CD4^{IL-10/CAR}$ cells, or the pharmaceutical composition. In some embodiments, the $CD4^{IL-10/CAR}$ cells, the population of $CD4^{IL-10/CAR}$ cells, or the pharmaceutical composition prevents or reduces severity of host rejection of the cell transplantation.

In some embodiments, the method further comprising the step of administering a recombinant AAV to the patient, either prior to or subsequent to administration of the $CD4^{IL-10/CAR}$ cells, the population of $CD4^{IL-10/CAR}$ cells, or the pharmaceutical composition. In some embodiments, the $CD4^{IL-10/CAR}$ cells, the population of $CD4^{IL-10/CAR}$ cells, or the pharmaceutical composition reduces immune responses against the recombinant AAV.

In some embodiments, the method further comprising the step of administering a recombinant viral vector other than AAV to the patient, either prior to or subsequent to administration of the $CD4^{IL-10/CAR}$ cells, the population of $CD4^{IL-10/CAR}$ cells, or the pharmaceutical composition. In some embodiments, the $CD4^{IL-10/CAR}$ cells, the population of $CD4^{IL-10/CAR}$ cells, or the pharmaceutical composition reduces immune responses against the recombinant viral vector other than AAV.

In some embodiments, the method further comprises the step of administering an immunogenic therapeutic protein to the patient, either prior to or subsequent to administration of the $CD4^{IL-10/CAR}$ cells, the population of $CD4^{IL-10/CAR}$ cells, or the pharmaceutical composition. In some embodiments, the $CD4^{IL-10/CAR}$ cells, the population of $CD4^{IL-10/CAR}$ cells, or the pharmaceutical composition reduces immune responses against the immunogenic therapeutic protein. In some embodiments, the immunogenic therapeutic protein is selected from a therapeutic antibody, a factor VIII replacement, a cytokine, and a cytokine mutein.

In some embodiments, the patient has an excessive immune response against viral or bacterial infection. In some embodiments, the patient has a coronavirus infection. In some embodiments, the patient has organ and/or tissue damage.

In some embodiments, the method further comprising the step of detecting the selection marker in a biological sample obtained from the patient, thereby detecting presence or absence of $CD4^{IL-10/CAR}$ cells.

In some embodiments, the biological sample is a biopsy or blood from the patient.

In another aspect, this disclosure features a method of treating or inhibiting autoimmune disease, allergic disease, or inflammatory disease in a patient, comprising: administering to a patient, identified as having autoimmune disease, allergic disease, or inflammatory disease, a therapeutically effective amount of any of the $CD4^{IL-10/CAR}$ cells provided, any of the population of $CD4^{IL-10/CAR}$ cells provided herein, or any of the pharmaceutical compositions provided herein sufficient to treat or inhibit the autoimmune disease, allergic disease, or inflammatory disease.

In another aspect, this disclosure features a method for reducing transplant rejection in a patient transplanted with hematopoietic stem cells, bone marrow cells, cord blood cells, tissue stem cells or a solid organ, comprising: administering to a patient, identified as having rejection of transplanted hematopoietic stem cells, bone marrow cells, tissue stem cells or a solid organ, a therapeutically effective amount of any of the $CD4^{IL-10/CAR}$ cells provided, any of the population of $CD4^{IL-10/CAR}$ cells provided herein, or any of the pharmaceutical compositions provided herein sufficient to reduce transplant rejection.

In another aspect, this disclosure features a method for treating graft-versus-host disease (GvHD) in a patient, comprising: administering to a patient, identified as having a graft-versus-host disease (GvHD) or at risk of having graft-versus-host disease (GvHD), a therapeutically effective amount of any of the CD4$^{IL-10/CAR}$ cells provided, any of the population of CD4$^{IL-10/CAR}$ cells provided herein, or any of the pharmaceutical compositions provided herein sufficient to suppress or prevent GvHD.

In some embodiments, the graft-versus-host disease (GvHD) comprises acute GvHD.

In some embodiments, the graft-versus-host disease (GvHD) comprises chronic GvHD.

In another aspect, this disclosure features a method for treating tissue or organ damage in a patient, comprising: administering to a patient, identified as having tissue or organ damage or at risk of having tissue or organ damage, a therapeutically effective amount of any of the CD4$^{IL-10/}$ $_{CAR}$ cells provided herein, any of the populations of CD4$^{IL-}$ $_{10/CAR}$ cells provided herein, or the pharmaceutical composition provided herein sufficient to induce repair of tissue or organ damage.

In another aspect, this disclosure features a polynucleotide construct comprising: (a) a first polynucleotide segment encoding a chimeric antigen receptor (CAR); and (b) a second polynucleotide segment encoding interleukin-10 (IL-10).

In some embodiments, the first polynucleotide segment comprises a regulatory element operably linked to a coding sequence of the CAR. In some embodiments, the regulatory element drives constitutive expression of the CAR.

In some embodiments, the second polynucleotide segment comprises a regulatory element operably linked to a coding sequence of the IL-10. In some embodiments, the regulatory element drives constitutive expression of the IL-10.

In some embodiments, the method further comprising an internal ribosome entry site (IRES) or a self-cleaving peptide between the first polynucleotide segment and the second polynucleotide segment. In some embodiments, the self-cleaving peptide is selected from the group consisting of F2A, P2A, T2A and E2.A.

In some embodiments, the CAR comprises an antigen-binding domain, a hinge region, a transmembrane domain, and an intracellular signaling domain.

In some embodiments, the antigen-binding domain comprises a single chain antibody fragment. In some embodiments, the single chain antibody fragment comprises a single chain Fv (scFv).

In some embodiments, the antigen-binding domain targets an antigen associated with an autoimmune disease, inflammatory disorder, or cancer.

In some embodiments, the antigen is selected from the group consisting of: CD19, CD20, CD22, BCMA, B7-H3, CD27, CD38, CEA. BCMA, CD23, Lym1, Lym2, CLEC5A, CDH179b, FLT3, GCC, Muc, CSF2RA, GFRa4, CD32, CD33, IL11Ra, IL13Ra, NYBRI, SLea, CD200R, TGF-BetaR2, CD276, TROP2, LAMP1, PTK7, DLL3, CDH1, CDH6, CDH17, CDH19, TSHR, tyrosinase, HLA-A2, citrullinated peptides, insulin, GAD65, LA2, gliadin, and desmoglein.

In some embodiments, the antigen-binding domain is an anti-CD19 antigen binding domain. In some embodiments, the anti-CD19 antigen-binding domain comprises the sequence of SEQ ID NO: 11.

In some embodiments, the antigen-binding domain is an anti-CD20 antigen binding domain. In some embodiments, the anti-CD20 antigen-binding domain comprises the sequence of SEQ ID NO: 18.

In some embodiments, the antigen-binding domain is an anti-BCMA antigen binding domain. In some embodiments, the anti-BCMA antigen-binding domain comprises the sequence of SEQ ID NOs: 50-53.

In some embodiments, the hinge region is selected from a human CD8 hinge region, a human CD28 hinge region, a IgG1 hinge region, or a IgG4 hinge region. In some embodiments, the hinge region is derived from human CD8.

In some embodiments, the transmembrane domain is selected from a TNFRSF 19 transmembrane domain, a CD3zeta transmembrane domain, a CD8a transmembrane domain, a CD4 transmembrane domain, a CD28 transmembrane domain, or an B7-family inducible costimulatory (ICOS) transmembrane domain. In some embodiments, the transmembrane domain is derived from CD8.

In some embodiments, the CAR further comprises one or more co-stimulatory domains. In some embodiments, the CAR comprises two co-stimulatory domains.

In some embodiments, the one or more co-stimulatory domains are selected from the group consisting of 4-1BB, CD28, OX40, ICOS, CD27, MYD88-CD40, and KIR2DS2.

In some embodiments, one of the one or more co-stimulatory domain is derived from CD28.

In some embodiments, a second co-stimulatory domain is derived from 4-1BB.

In some embodiments, the intracellular signaling domain comprises an immunoreceptor tyrosine-based activation motif (ITAM). In some embodiments, the immunoreceptor tyrosine-based activation motif (ITAM) is derived from CD3zeta.

In some embodiments, the CAR comprises: an anti-CD19 antigen binding domain, a BCMA or an anti-CD20 antigen-binding domain; a human CD8 hinge region; a CD8 transmembrane region; a 4 a CD28 co-stimulatory domain; and a CD3zeta chain intracellular signaling domain.

In some embodiments, the CAR comprises the sequence of SEQ ID NOs: 9, 16, 22, or 34.

In some embodiments, the first polynucleotide segment comprises the sequence of SEQ ID NOs: 10, 17, 23, 35, or 55.

In some embodiments, the IL-10 is a human IL-10. In some embodiments, the IL-10 is a viral IL-10.

In some embodiments, the IL-10 is a protein having the sequence of SEQ ID NO: 1. In some embodiments, the second polynucleotide segment comprises the sequence of SEQ ID NO: 2.

In some embodiments, the first polynucleotide segment or the second polynucleotide segment, further comprising a sequence encoding a selection marker.

In some embodiments, the selection marker is ΔNGFR. In some embodiments, the ΔNGFR has the sequence of SEQ ID NO: 3. In some embodiments, the polynucleotide construct comprises a sequence of SEQ ID NO: 4.

In some embodiments, the selection marker is a truncated form of an EGFR polypeptide.

In some embodiments, the construct is a vector. In some embodiments, the vector is a viral vector. In some embodiments, the vector is a lentiviral vector.

In another aspect, this disclosure features a polynucleotide construct, comprising: a first polynucleotide segment having the sequence of SEQ ID NOs: 10, 17, 23, 35, or 55; and a second polynucleotide segment having the sequence of SEQ ID NO: 2.

In another aspect, this disclosure features a polynucleotide construct, comprising: a first polynucleotide segment having the sequence of SEQ ID NOs: 10, 17, 23, 35, or 55; a second polynucleotide segment having the sequence of SEQ ID NO: 2; and a third polynucleotide segment having the sequence of SEQ ID NO: 33 in between the first polynucleotide segment and the second polynucleotide segment.

In another aspect, this disclosure features a polynucleotide construct, comprising: a first polynucleotide segment having the sequence of SEQ ID NOs: 10, 17, 23, 35, or 55; a second polynucleotide segment having the sequence of SEQ ID NO: 2; a third polynucleotide segment having the sequence of SEQ ID NO: 27 in between the first polynucleotide segment and the second polynucleotide segment; and a fourth polynucleotide segment having the sequence of SEQ ID NO: 4.

In another aspect, this disclosure features CD4$^{IL-10}$ cells from a single donor or multiple donors, where the IL-10 is viral IL-10. The viral IL-10 having the sequence of SEQ ID NO: 6 or 18. In some embodiments, the viral IL-10 is encoded by a polynucleotide having the sequence of SEQ ID NO: 7. In some embodiments, the IL-10 is human IL-10 where one, two, three, four, five, six, seven, eight, nine or ten amino-acid from human IL-10 are replaced by the corresponding amino-acid sequence from viral IL-10. In some embodiments, the CD4$^+$ T cells are transduced with exogenous viral IL-10 under the control of constitutive promoter. In some embodiments, the expression control elements drive expression of viral IL-10 in activated CD4$^+$ T cells. In some embodiments, the exogenous polynucleotide encoding viral IL-10 is integrated into the T cell nuclear genome. In some embodiments, the exogenous polynucleotide encoding viral IL-10 is not integrated into the T cell nuclear genome. In some embodiments, the exogenous polynucleotide encoding viral IL-10 has the sequence of SEQ ID NO: 7.

In another aspect, this disclosure features CD4$^{IL-10}$ cells from a single donor or multiple donors, where the IL-10 is IL-10 of a *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66). In some embodiments, the IL-10 is a protein having at least 90%, 95%, 98%, or 99% sequence identity to IL-10 of a *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66).

In another aspect, this disclosure features CD4$^{IL-10}$ cells from a single donor or multiple donors, where the IL-10 is a variant of human IL-10. The variant of human IL-10 having the sequence of SEQ ID NO: 67 or SEQ ID NO: 68. In some embodiments, the IL-10 is human IL-10 where one, two, three, four, five, six, seven, eight, nine or ten amino-acid from human IL-10 are replaced by the corresponding amino-acid sequence from IL-10 of another species (e.g., IL-10 of a *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66). In some embodiments, the CD4$^+$ T cells are transduced with exogenous the IL-10 variant under the control of constitutive promoter. In some embodiments, the expression control elements drive expression of the IL-10 variant in activated CD4$^+$ T cells. In some embodiments, the exogenous polynucleotide encoding the IL-10 variant is integrated into the T cell nuclear genome. In some embodiments, the exogenous polynucleotide encoding the IL-10 variant is not integrated into the T cell nuclear genome.

In yet another aspect, the present disclosure provides a method of making viral IL-10 CD4$^{IL-10}$, comprising the steps of:
  (i) obtaining primary CD4$^+$ T cells from a single T cell donor; and
  (ii) modifying the donor CD4$^+$ T cells by introducing an exogenous polynucleotide encoding viral IL-10, thereby obtaining the genetically-modified CD4$^+$ T cells.

In some embodiments, the method further comprises the step, after step (i), or after step (ii), of: incubating the primary CD4$^+$ T cells in the presence of an anti-CD3 antibody, and anti-CD28 antibody or anti-CD3 antibody and CD28 antibody coated beads.

In some embodiments, the method comprises incubating the primary CD4$^+$ T cells further in the presence of IL-2. In some embodiments, the exogenous polynucleotide encoding viral IL-10 using a vector.

In some embodiments, the exogenous polynucleotide encoding viral IL-10 comprises a segment encoding a selection marker. In some embodiments, the encoded selection marker is ΔNGFR. In some embodiments, the encoded selection marker has the sequence of SEQ ID NO: 3. In some embodiments, the encoded selection marker is a truncated EGFR polypeptide. In some embodiments, the encoded selection marker is a truncated human EGFR polypeptide.

In some embodiments, the method further comprises the step, after step (ii), of: isolating the genetically-modified CD4$^+$ T cells expressing the selection marker, thereby generating an enriched population of genetically-modified CD4$^+$ T cells.

In some embodiments, the method further comprises the step of incubating the enriched population of genetically-modified CD4$^+$ T cells. In some embodiments, the step of incubating the enriched population of genetically-modified CD4$^+$ T cells is performed in the presence of anti-CD3 antibody and anti-CD28 antibody or CD3 antibody and CD28 antibody coated beads in the presence of IL-2.

In some embodiments, in step (i), the primary CD4$^+$ T cells are obtained from frozen stock. In some embodiments, in step (i), the primary CD4$^+$ T cells are obtained from unfrozen peripheral blood mononuclear cells of the single T cell donor.

In some embodiments, the method further comprises the step of isolating CD4$^+$ T cells from the peripheral blood mononuclear cells. In some embodiments, the peripheral blood mononuclear cells are obtained from buffy coat or apheresis.

5. BRIEF DESCRIPTION OF THE DRAWINGS

Figure 3A:
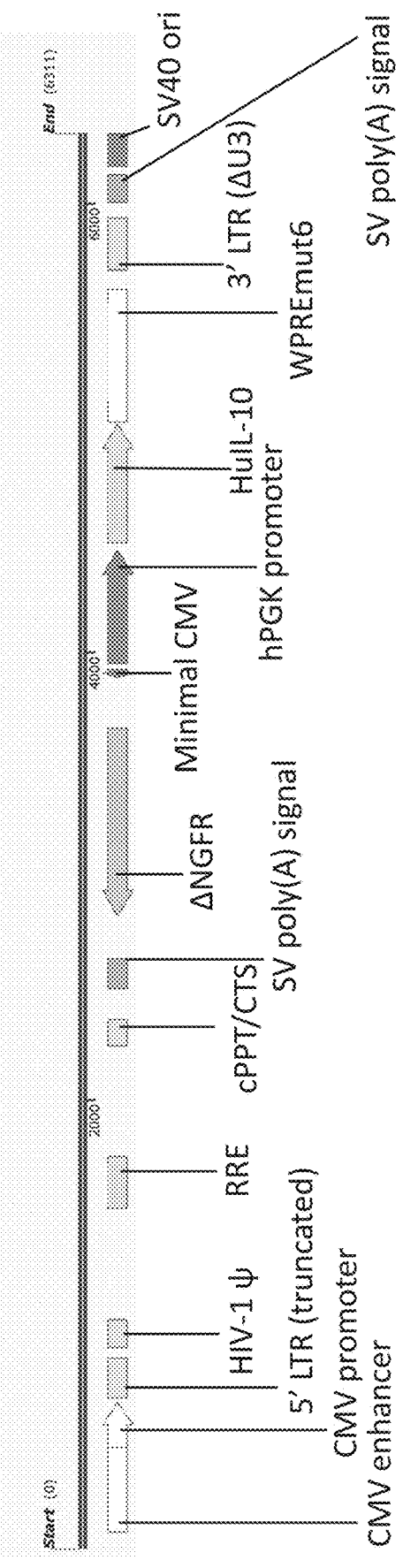
Figure 3B:
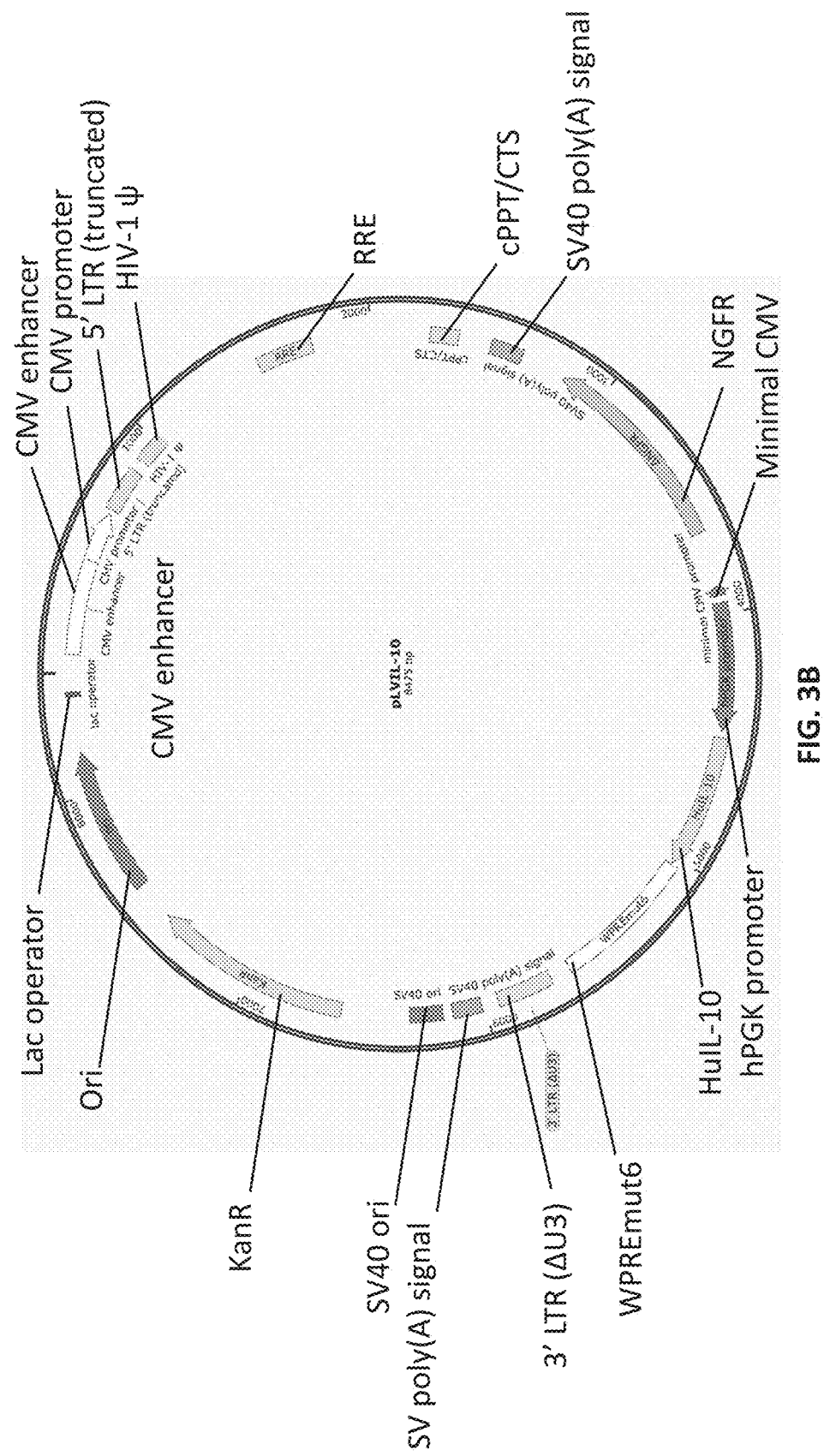

FIGS. 3A-3B illustrate a bidirectional plasmid (pLVIL-10) used to generate the lentiviral vector (LVV; LVV$^{IL-10-NGFR}$) used for delivering human IL-10 and ΔNGER coding sequences into CD4+ T cells to produce CD4$^{IL-10}$ cells or CD4$^{IL-10\ antiCD19CAR}$ cells. FIG. 3A illustrates the partial structure of a bidirectional lentiviral vector for delivering human IL-10 and ΔNGFR coding sequences into CD4+ T cells from multiple donors to produce polydonor CD4$^{IL-10}$ cells. FIG. 3B illustrates the complete and circular structure of a bidirectional lentiviral vector (hPGK.IL10.WPRE.mhCMV. ΔNGFR.SV40PA) for delivering human IL-10 and ΔNGFR coding sequences into CD4+ T cells from multiple donors to produce polydonor CD4$^{IL-10}$ cells.

Figure 4:
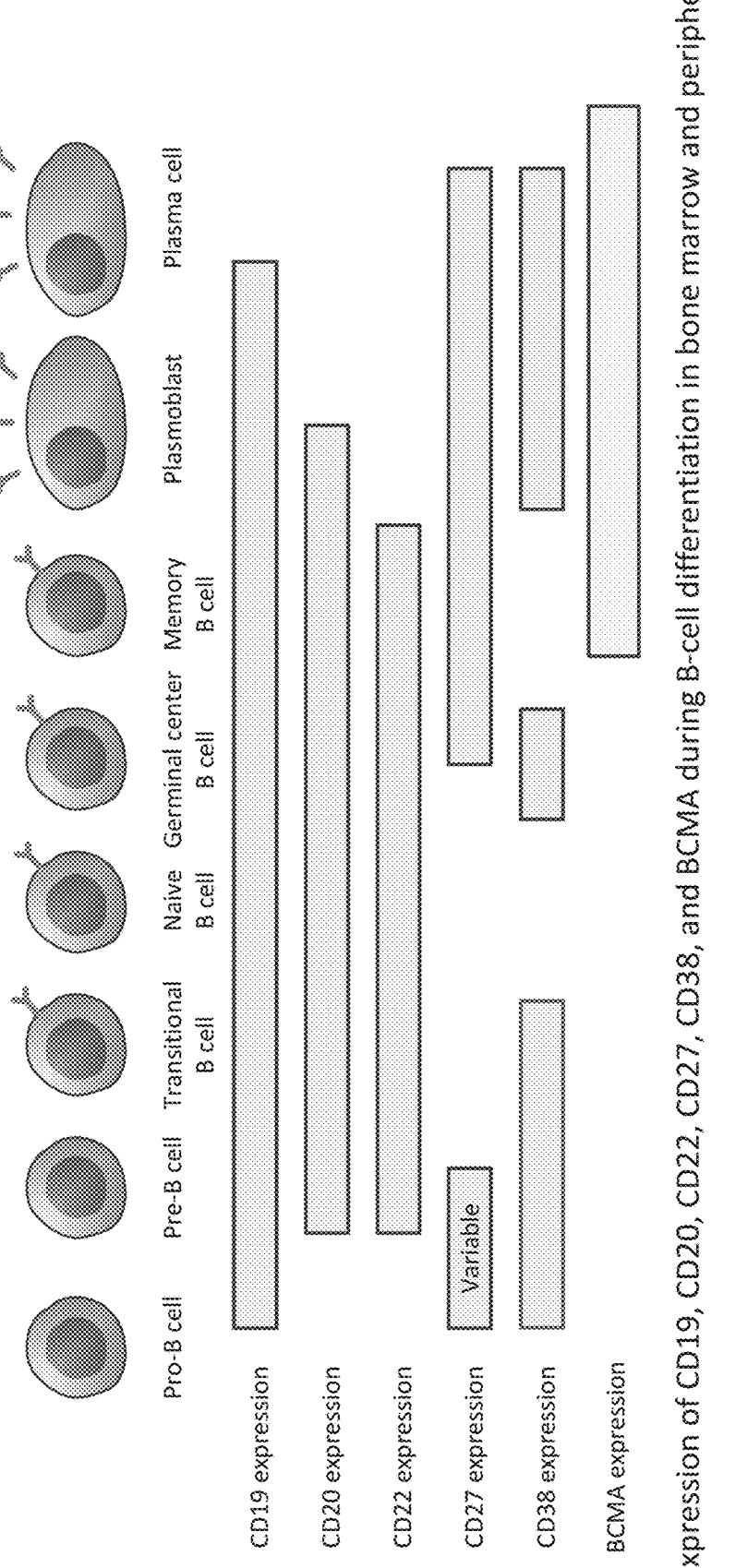

FIG. 4 shows for illustrative purposes antigen expression during natural B-cell differentiation.

Figure 5A:
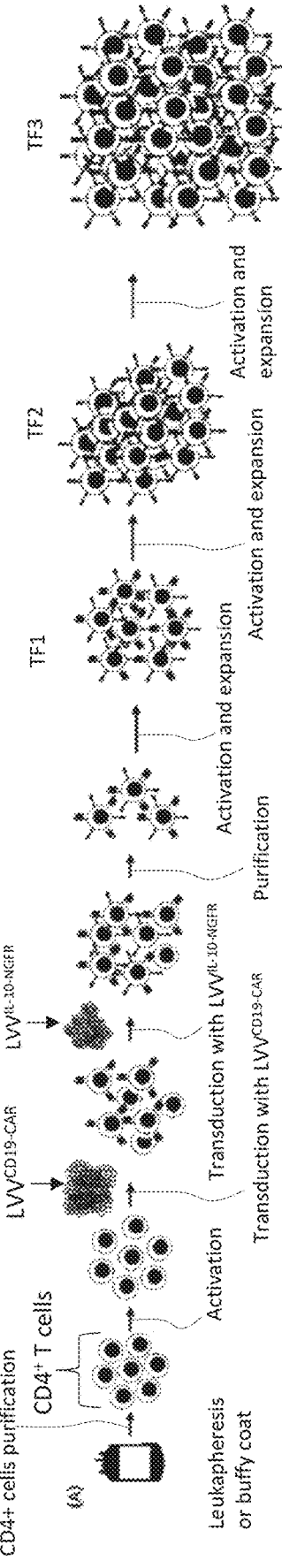
Figure 5B:
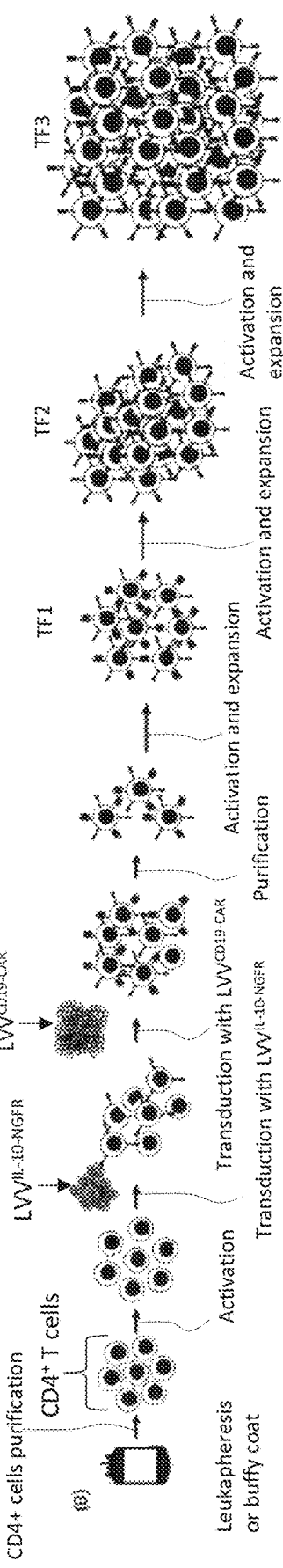
Figure 5C:
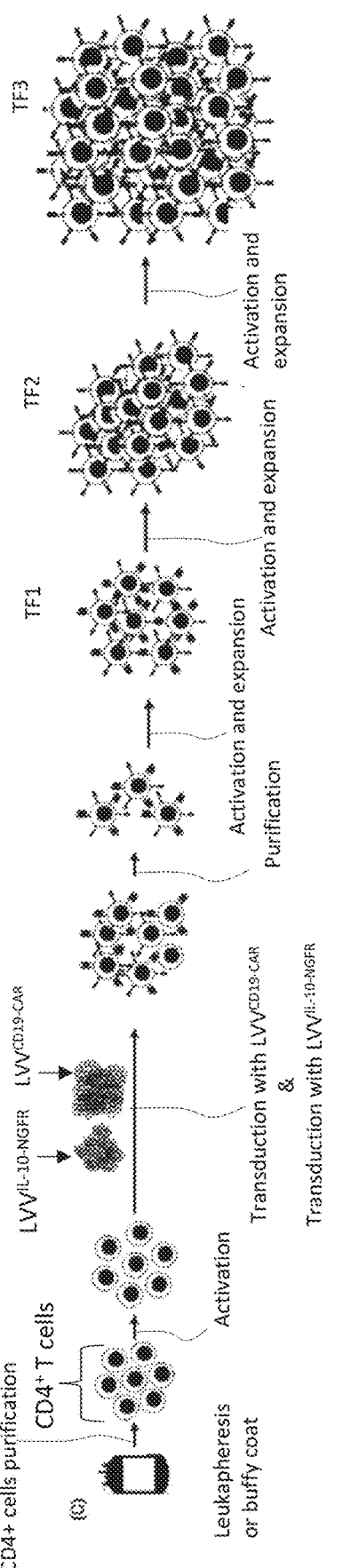

FIGS. 5A-5C show schematics for non-limiting examples of methods of generating CD4$^{IL-10antiCD19CAR}$ cells. In each method, human CD4+ T cells were activated with anti-CD3/anti-CD28 beads (Miltenyi) (3:1 cells:beads ratio), in complete culture medium (X-vivo supplemented with 5% human AB serum and rhIL-2 (50U/mL). FIG. 5A shows the activated CD4+ T cells were transduced with a lentiviral vector encoding an anti-CD19 CAR (LVV$^{CD19-CAR}$) 48 hours after activation and transduced 24 hours later (i.e., 72 hours after activation) with a bidirectional lentiviral vector encoding human IL-10 and a truncated form of the human NGF receptor (LVV$^{IL-10-NGFR}$). Both LVVs were used at a multiplicity of infection (MOI) of 20. FIG. 5B shows activated CD4+ T cells were transduced with the LVV$^{IL-10-NGFR}$ 48 hours after activation and transduced 24 hours later (i.e., 24 hours after activation) with LVV$^{CD19-CAR}$. FIG. 5C shows the activated CD4+ T cells were transduced simultaneously with LVV$^{IL-10-NGER}$ and LVV$^{CD19-CAR}$ 48 hours after activation. Controls (do not express the CAR) were generated by transducing activated CD4+ T cells 48 hours after activation with LVV$^{IL-10-NGFR}$ only. For each of FIGS. 5A-5C, the transductions were conducted in the presence of polybrene (8 μg/mL). Additionally, for each of FIGS. 5A-5C, 10-28 days after transduction, transduced cells (i.e., ΔNGFR+ cells) were purified using anti-CD271 microbeads (Miltenyi) and anti-CD19 CAR microbeads (Miltenyi). Purified cells were re-stimulated every 14 days as previously described (Andolfi et al. Mol. Ther. 20(9):1778-1790 (2012) and Locafaro et al. Mol. Ther. 25(10):2254-2269 (2017)). After the second (TF2) and third (TF3) re-stimulation the resulting cells (CD4$^{IL-10antiCD19CAR}$ cells or control CD4$^{IL-10}$ cells) were characterized in vitro and in vivo. Culture medium was refreshed every 2-3 days, as needed through the entire culture period.

Figure 6A:
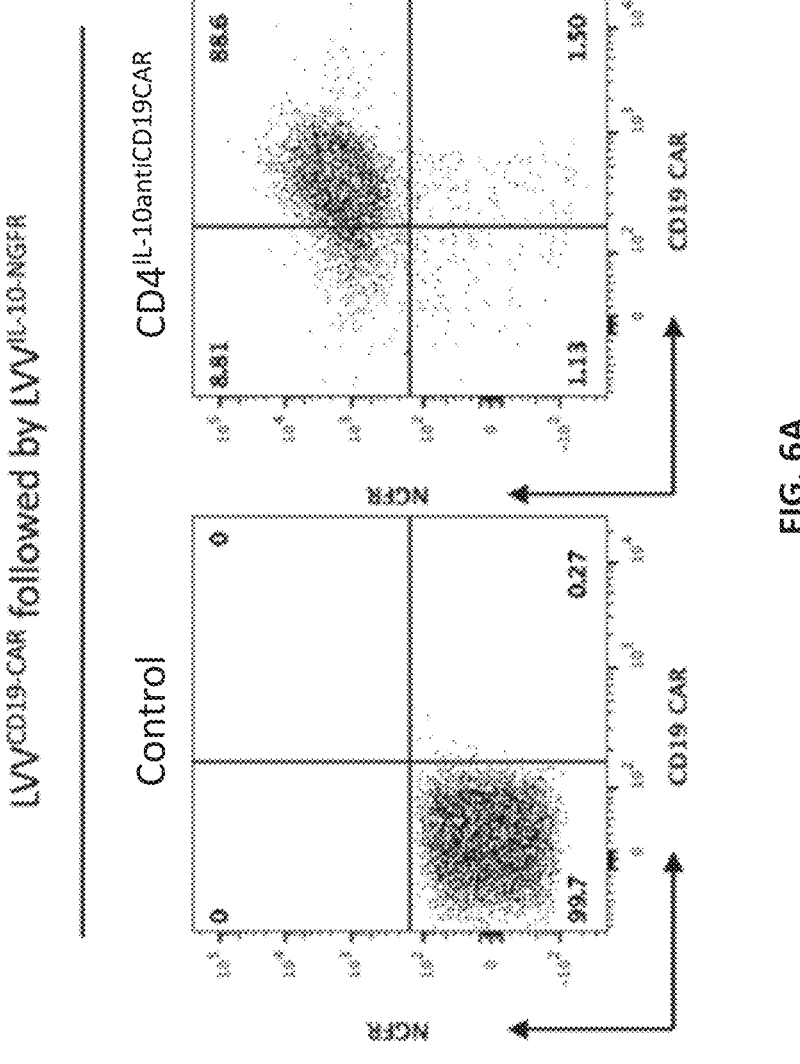
Figure 6B:
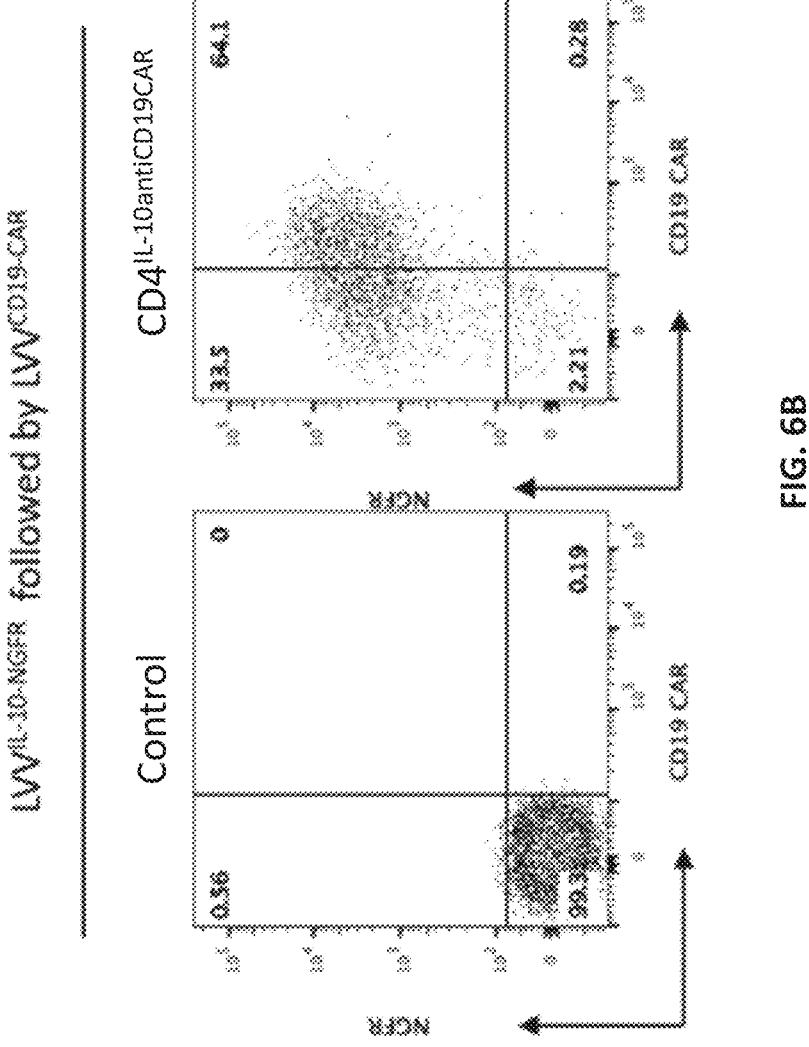
Figure 6C:
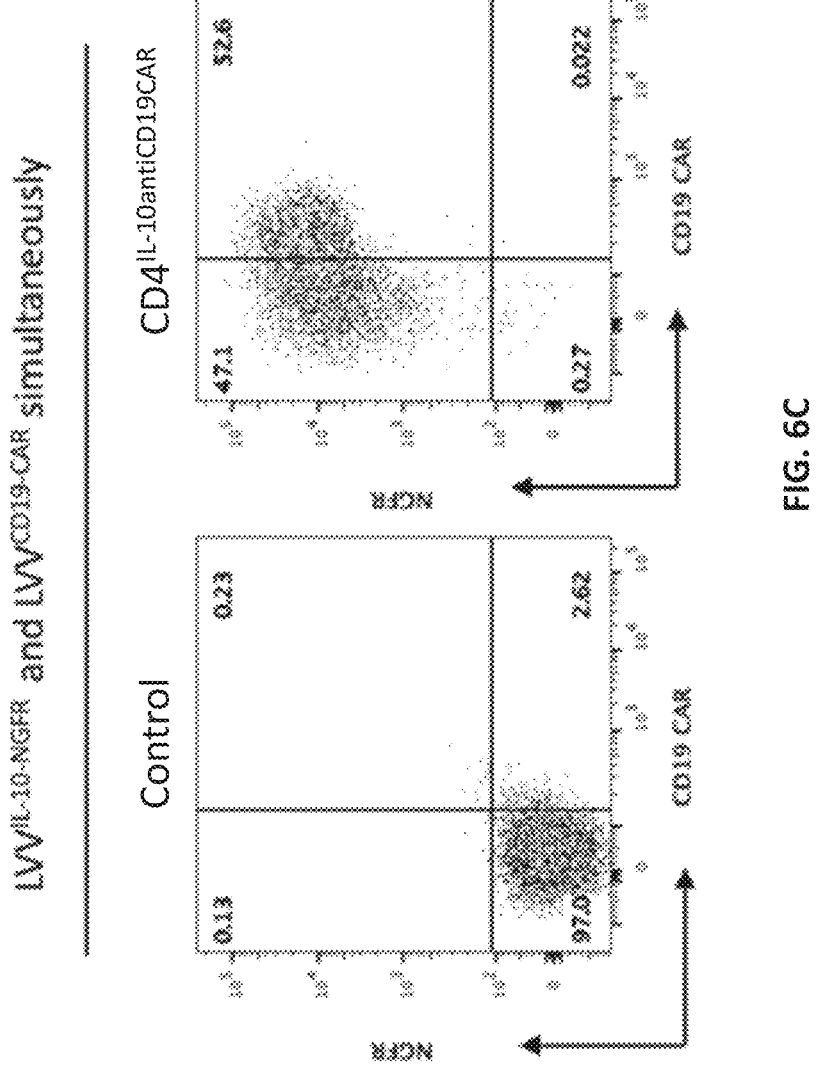

FIG. 6A shows flow cytometry plots (anti-CD19 CAR expression on x-axis and NGFR expression a proxy for IL-10, on y-axis) for control (left panel) and CD4$^{IL-10antiCD19\ CAR}$ ((right panel) produced according to the methods described in FIG. 5A. FIG. 6B shows flow cytometry plots (CD19 on x-axis and NGFR on y-axis) for control (left panel) and CD4$^{IL-10antiCD19CAR}$ (right panel) produced according to the methods described in FIG. 5B. FIG. 6C shows flow cytometry plots (CD19 on x-axis and NGFR on y-axis) for control (left panel) and CD4$^{IL-10antiCD19\ CAR}$ (right panel) produced according to the methods described in FIG. 5C.

Figure 7:
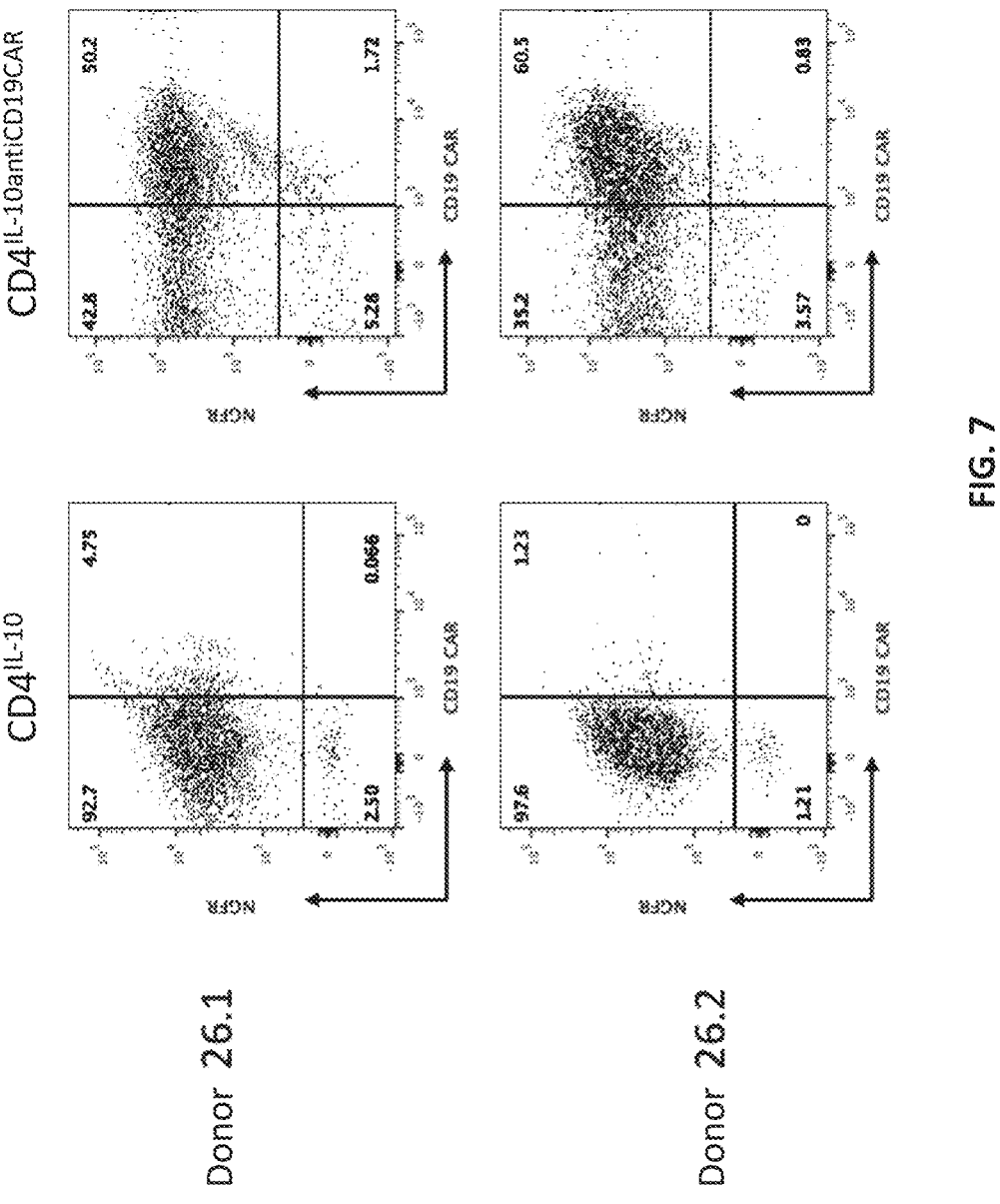

FIG. 7 shows flow cytometry plots (anti-CD19 CAR expression on x-axis and NGFR expression on y-axis) for CD4$^{IL-10}$ T cells (control) and CD4$^{IL-10anti-CD19\ CAR}$ T cells. Top panel shows CD4$^{IL-10}$ T cells (control) and CD4$^{IL-10antiCD19\ CAR}$ T cells generated from donor 26.1 according to the method shown in FIG. 5C. Bottom panel shows CD4$^{RL-10}$ T cells (control) and CD4$^{IL-10antiCD19CAR}$ T cells generated from donor 26.2 according to the methods shown in FIG. 5C.

Figure 8A:
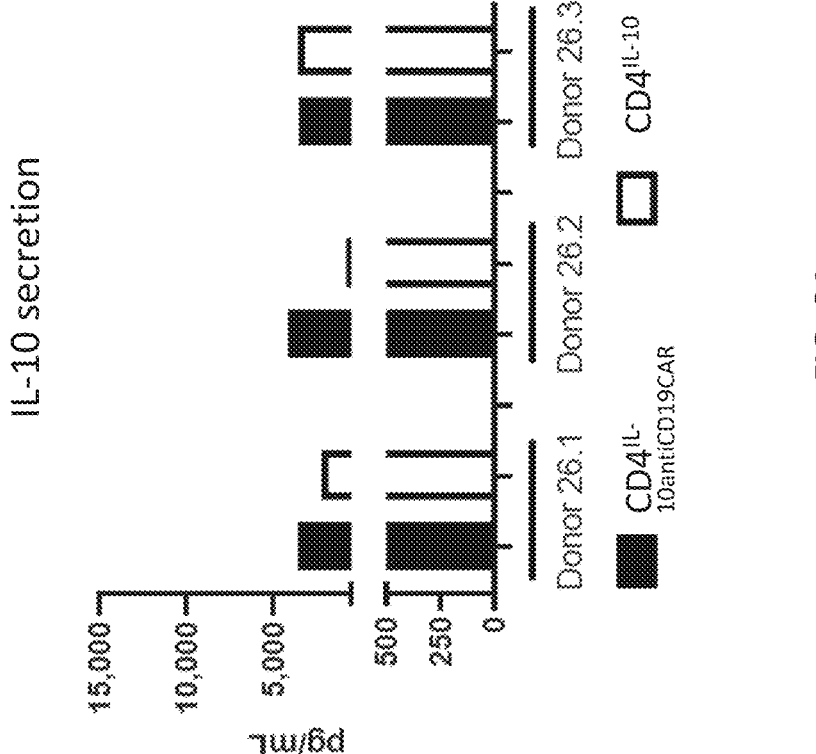
Figure 8B:
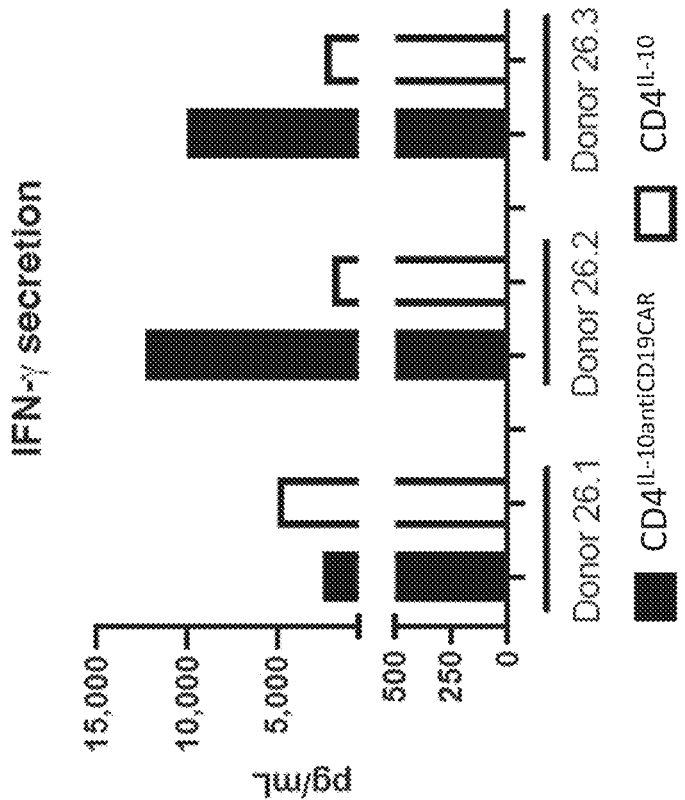
Figure 8C:
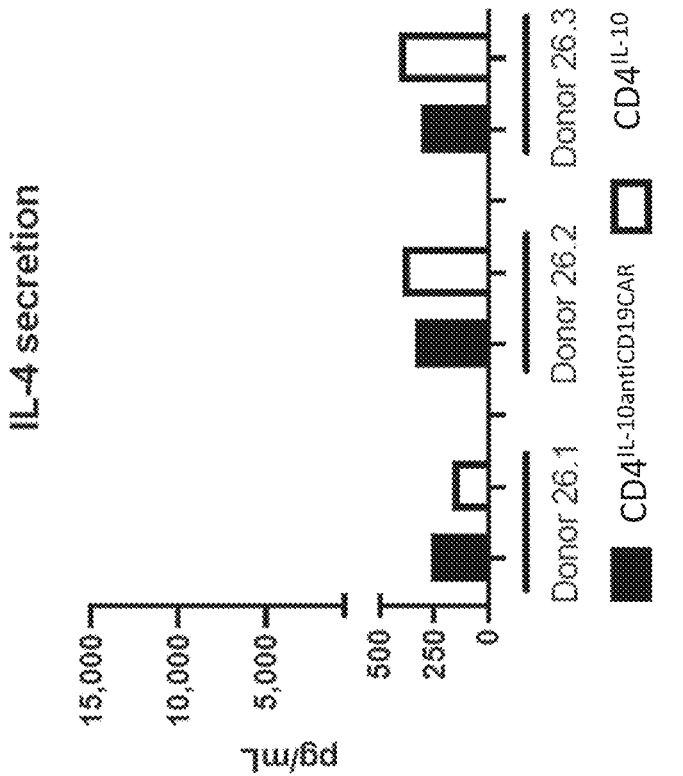
Figure 8D:
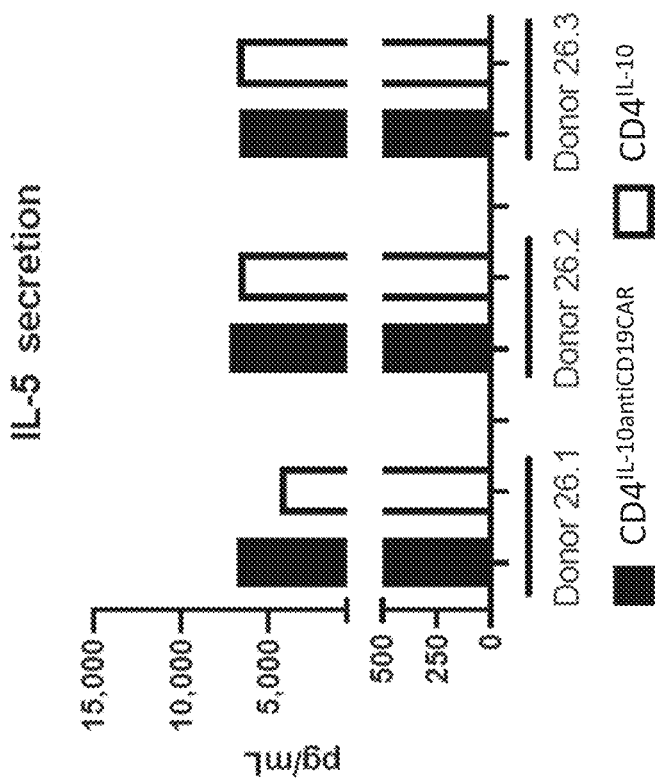

FIGS. 8A-8D shows cytokine production profiles for CD4$^{IL-10}$ T cells (control) and CD4$^{IL-10/CAR}$ T cells generated from CD4+ T cells isolated from three different donors (26.1, 26.2, and 26.3). Cytokine production profile includes IL-10 (FIG. 8A), IFN-γ (FIG. 8B), IL-4 (FIG. 8C), and IL-5 (FIG. 8D).

Figure 9:
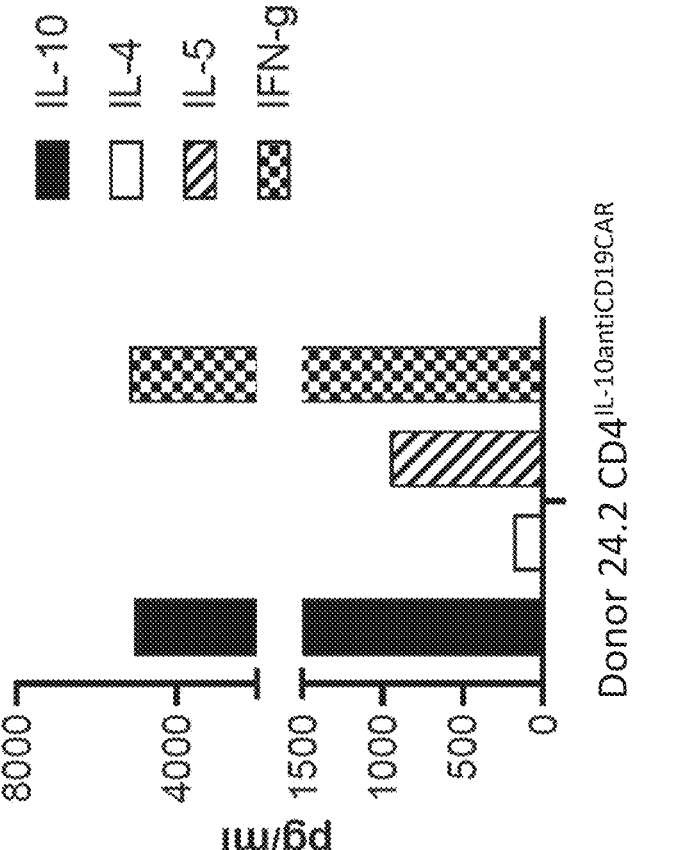
Figure 9:
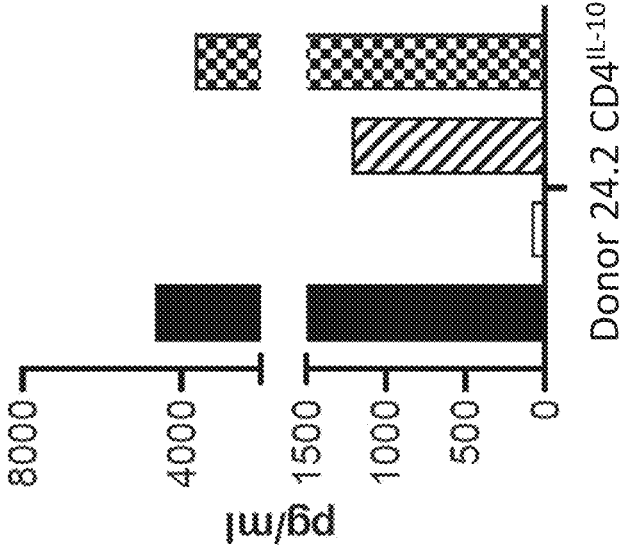

FIG. 9 shows cytokine production profiles for CD4$^{IL-10}$ T cells (control) and CD4$^{IL-10/CAR}$ T cells generated from CD4+ T cells isolated from donor 24.2.

Figure 10:
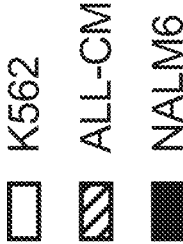
Figure 10:
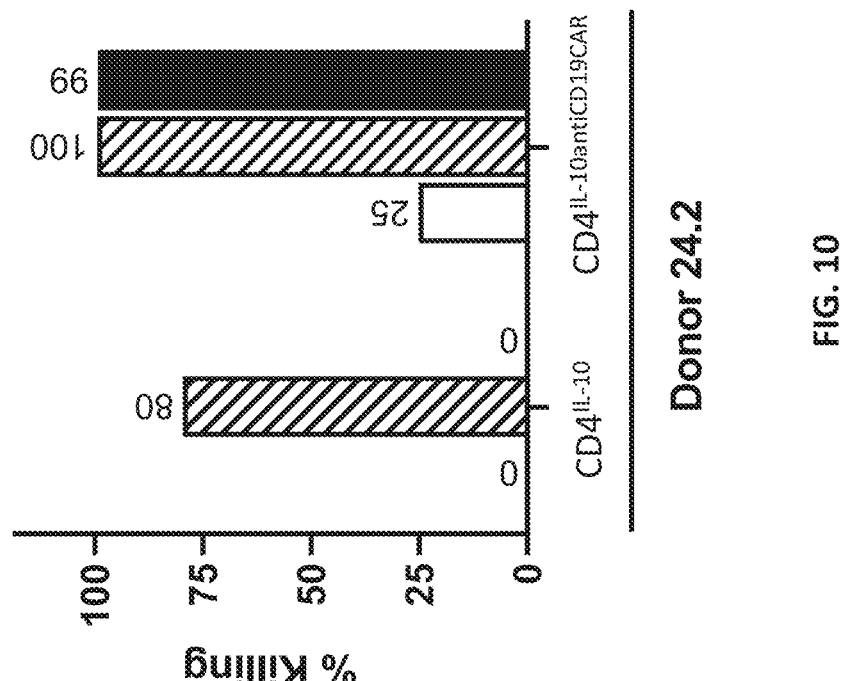

FIG. 10 shows that CD4$^{IL-10antiCD19CAR}$ cells generated from CD4+ T cells isolated from donor 24.2 killed the CD19 expressing NALM6 cells in vitro. ALL-CM is a myeloid cell line and K562, a cell line sensitive to NK killing, was included as a control.

Figure 11A:
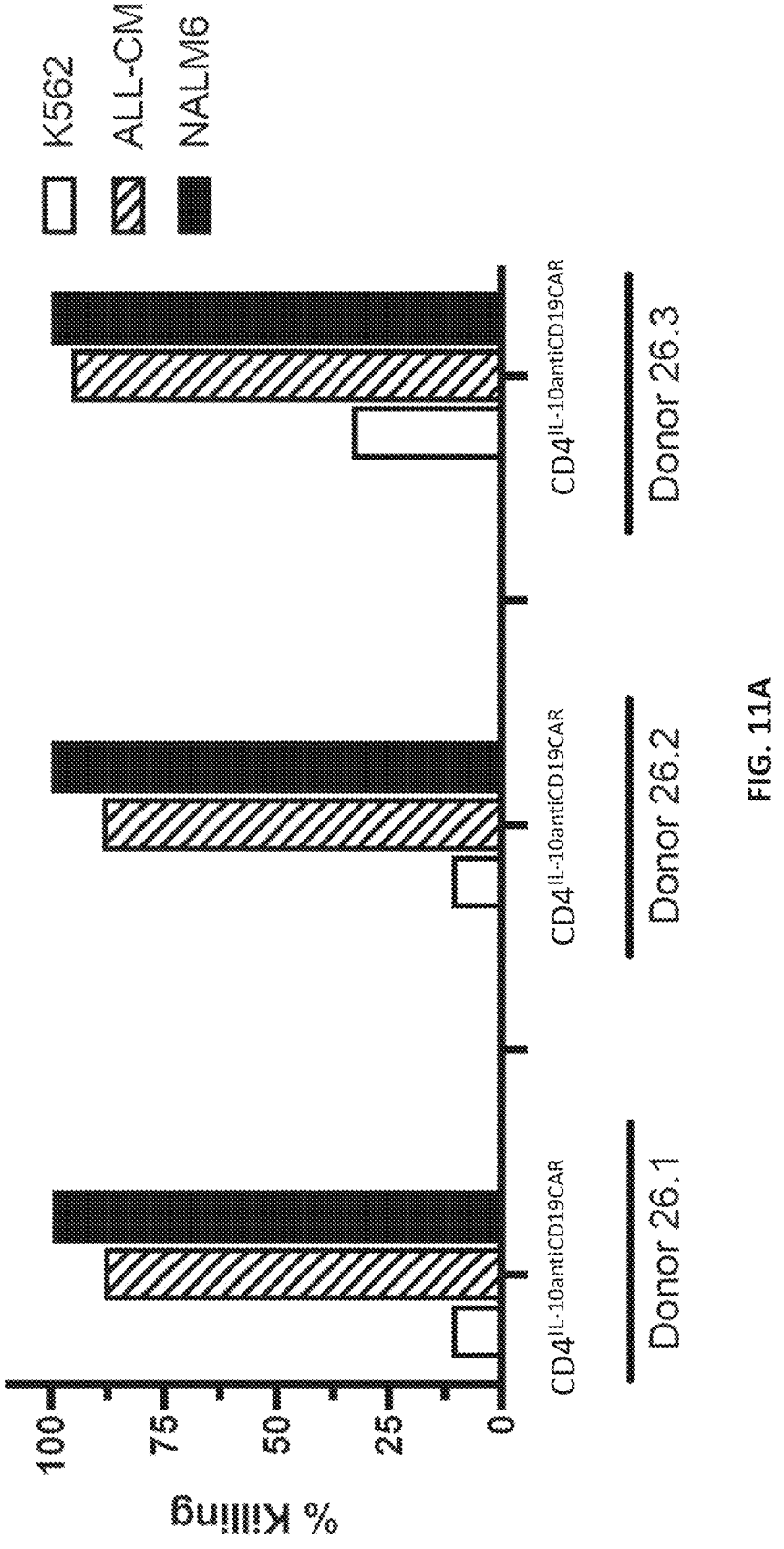

FIG. 11A shows that CD4$^{IL-10antiCD19CAR}$ cells generated from CD4+ T cells isolated from three different donors (26.1, 26.2, and 26.3) killed CD19+ NALM6 cells in vitro.

Figure 11B:
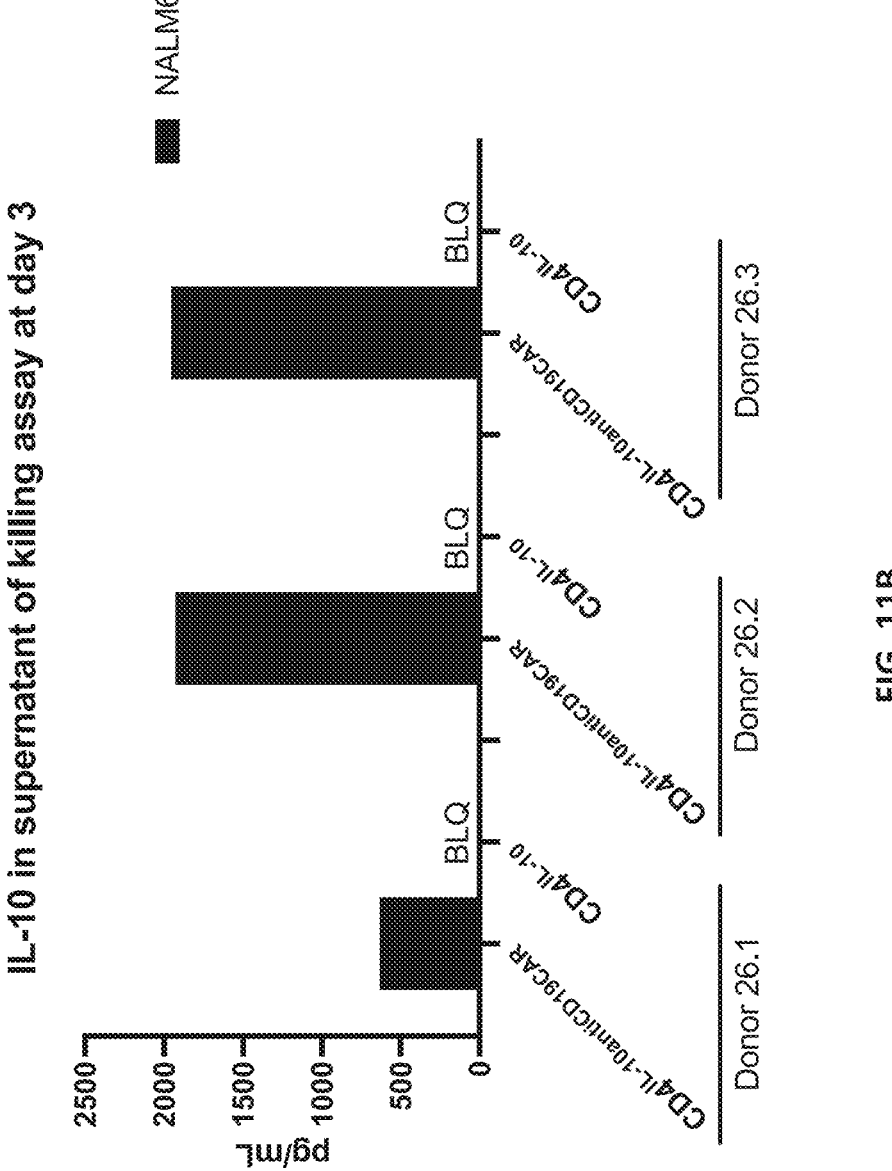

FIG. 11B shows IL-10 levels in the supernatant at day 3 of co-cultures of NALM6 cells and CD4$^{IL-10}$ T cells (control) or NALM6 cells and CD4$^{IL-10antiCD19CAR}$ cells. BLQ: below the level of quantification (31 pg/mL).

Figure 12:
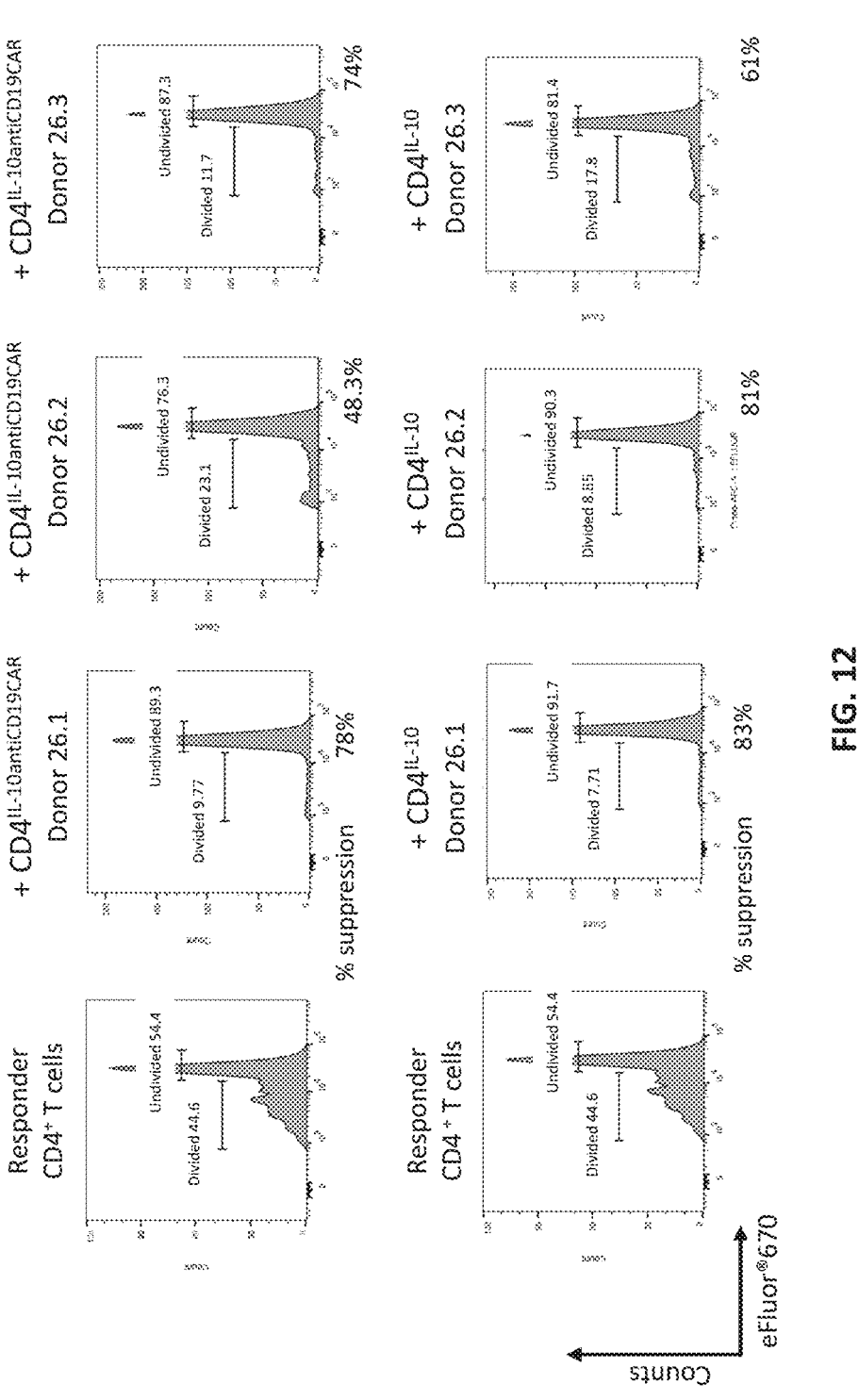

FIG. 12 shows flow cytometry plots (count versus eFluor®670) from a proliferation assay of allogeneic CD4+ T cells following co-culture with CD4$^{IL-10}$ T cells (control) and CD4$^{IL-10antiCD19CAR}$ cells isolated after a second restimulation (TF2) (see FIG. 5C). Top panel shows proliferation of CD4+ T cells following co culture with CD4$^{IL-10antiCD19CAR}$ cells. Bottom panel shows proliferation of CD4+ T cells following co-culture with CD4$^{IL-10}$ T cells (control). Flow cytometry plots show "undivided" cells and "divided" cells, where dividing cells include smaller and smaller amounts of the eFluor®670 because of dilution following each division. Suppression mediated by CD4$^{IL-10}$ T cells (control) and CD4$^{IL-10antiCD19CAR}$ cells was calculated as follows: 100−([proliferation of responders in the presence of CD4$^{1-10}$ T cells (control) or CD4$^{IL-10antiCD19CAR}$ cells/proliferation of responders]×100).

Figure 13:
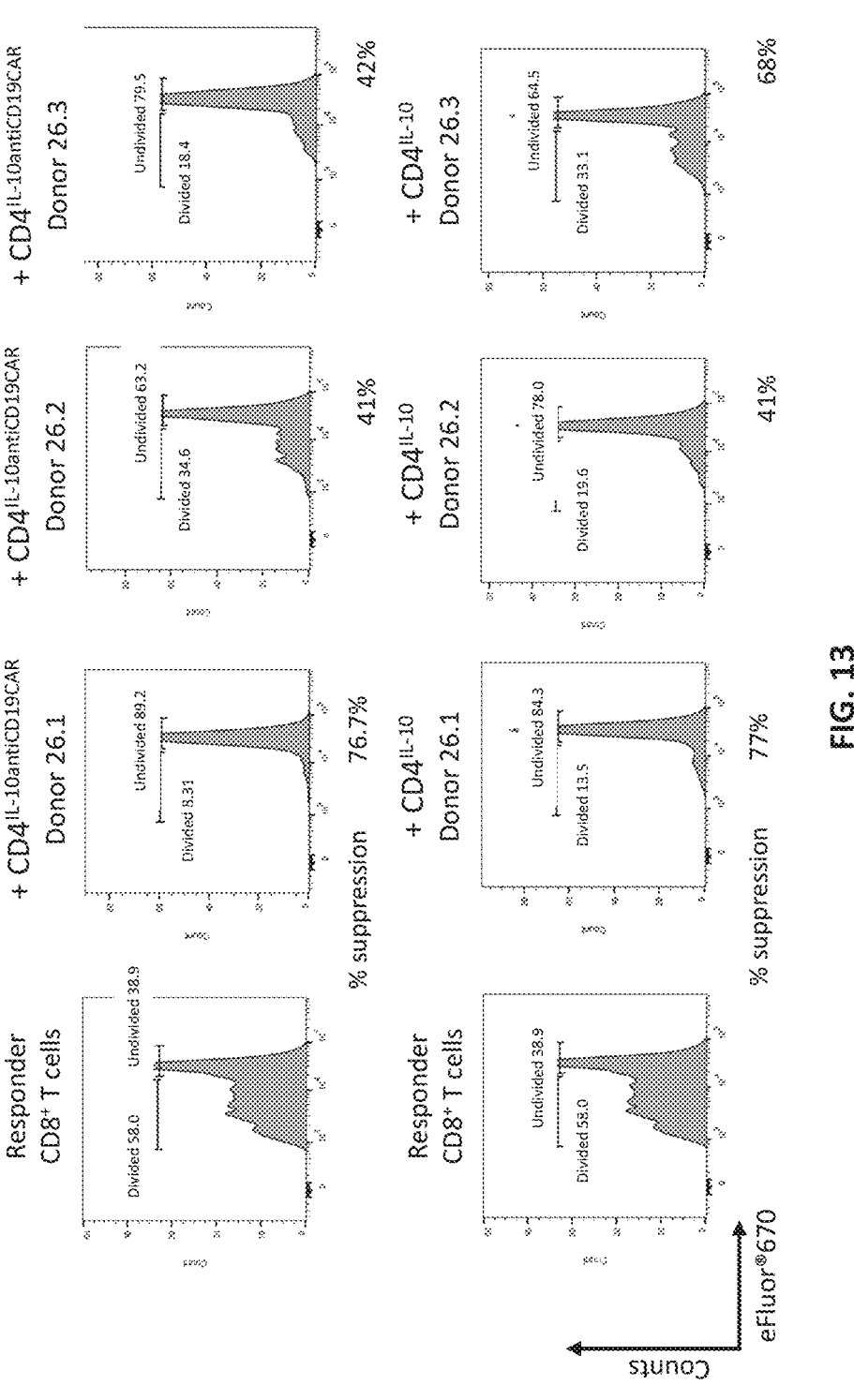

FIG. 13 shows flow cytometry plots (count versus eFluor®670) from a proliferation assay of allogeneic CD8+ T cells following co-culture with CD4$^{IL-10}$ T cells (control) and CD4$^{IL-10antiCD19CAR}$ cells isolated after a second restimulation (TF2) (see FIG. 5C). Top panel shows proliferation of CD8+ T cells following co culture with CD4$^{IL-10antiCD19CAR}$ cells. Bottom panel shows proliferation of CD8+ T cells following co-culture with CD4$^{IL-10}$ T cells (control). Flow cytometry plots show "undivided" cells and "divided" cells, where dividing cells include smaller and smaller amounts of the eFluor®670 because of dilution following each division. Suppression mediated by CD4$^{IL-10}$ T cells (control) and CD4$^{IL-10antiCD19CAR}$ cells was calculated as follows: 100−([proliferation of responders in the presence of CD4$^{IL-10}$ T cells (control) or CD4$^{IL-10antiCD19CAR}$ cells/proliferation of responders]×100).

Figure 14:
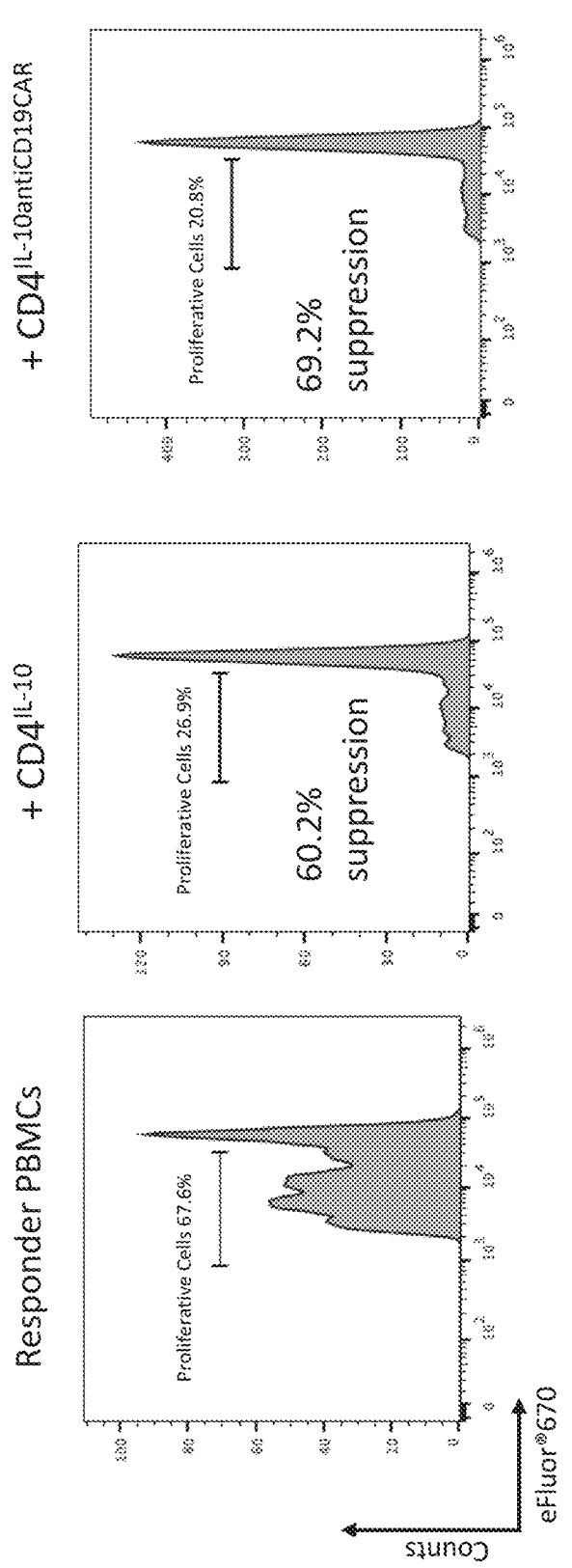

FIG. 14 shows flow cytometry plots (count versus eFluor®670) from a proliferation assay of allogeneic PBMC following co-culture with $CD4^{IL-10}$ T cells (control) and $CD4^{IL-10antiCD19CAR}$ cells isolated after a third restimulation (TF3) (see FIG. 5C). Flow cytometry plots show "proliferative" cells, where dividing cells include smaller and smaller amounts of the eFluor®670 because of dilution following each division. Suppression mediated by $CD4^{IL-10}$ T cells (control) and $CD4^{IL-10antiCD19CAR}$ cells was calculated as follows: 100–([proliferation of responders in the presence of $CD4^{IL-10}$ T cells (control) or $CD4^{IL-10antiCD19CAR}$ cells/proliferation of responders]×100).

Figure 15:
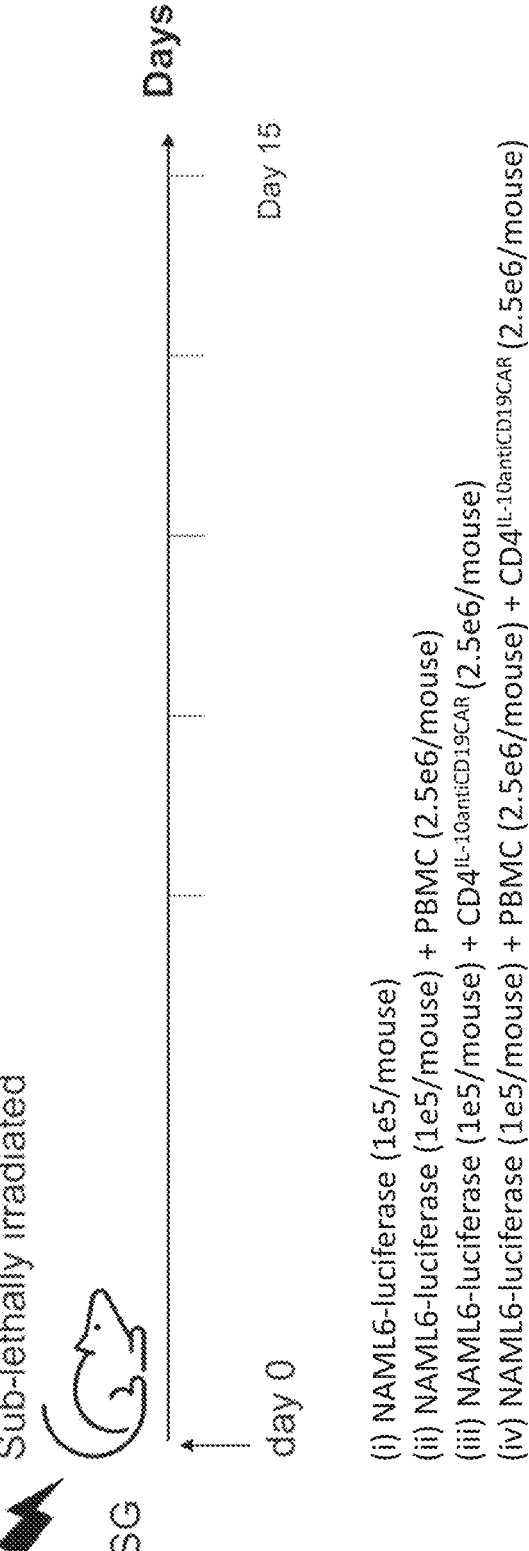

FIG. 15 shows a schematic of the experimental outline for assessing CD19+ tumor cell growth in vivo in Mice. At day 0, NSG mice were injected with (i) NALM6-luciferase ($1\times10^5$ per mouse), (ii) NALM6-luciferase ($1\times10^5$ per mouse)+PBMC ($2.5\times10^6$ per mouse), (iii) NALM6-luciferase ($1\times10^5$ per mouse)+$CD4^{IL-10antiCD19CAR}$ cells ($2.5\times10^6$ per mouse), or (iv) NALM6-luciferase ($1\times10^5$ per mouse)+PBMC ($2.5\times10^6$ per mouse)+$CD4^{IL-10antiCD19CAR}$ cells ($2.5\times10^6$ per mouse).

Figure 16A:
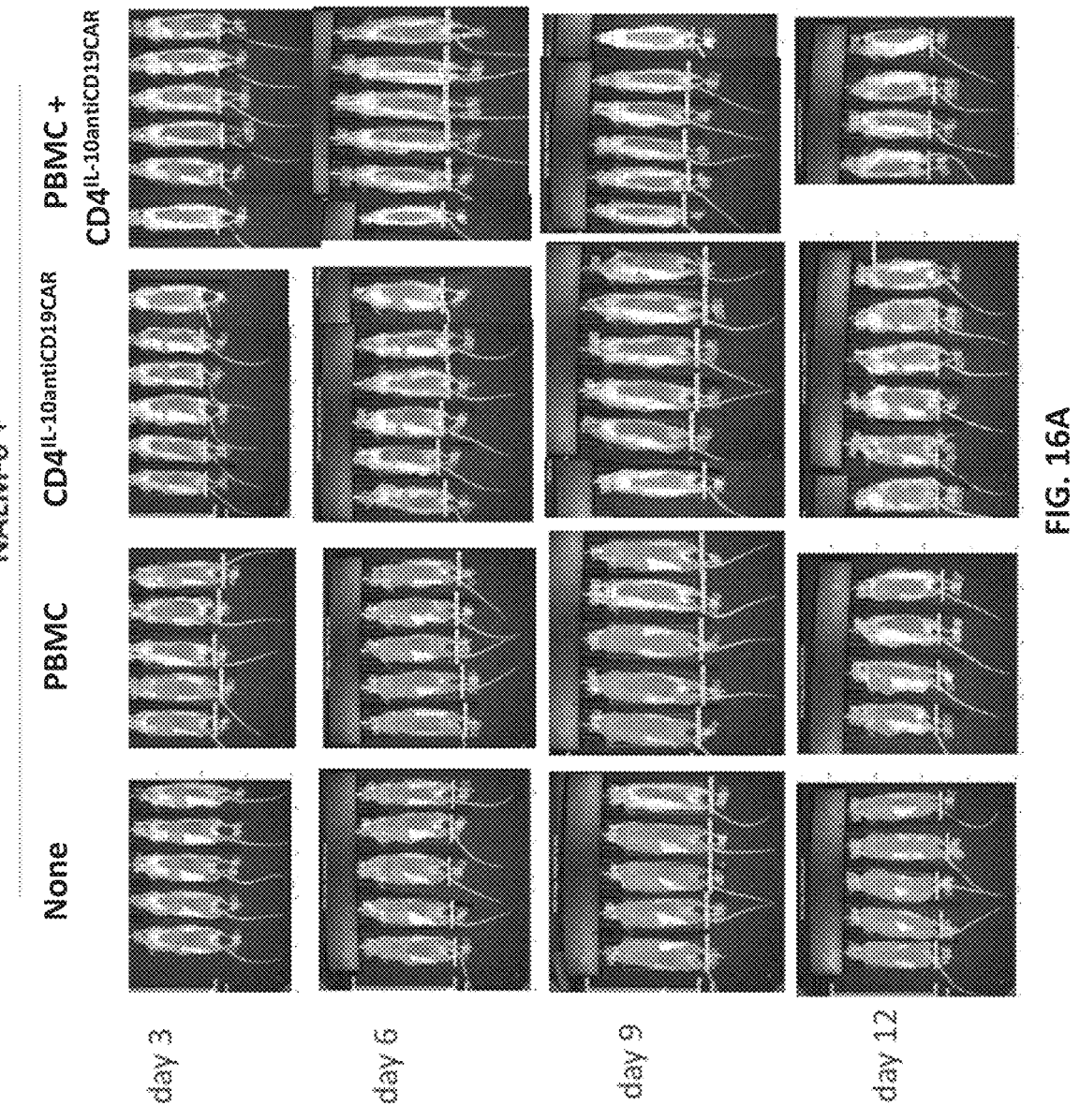

FIG. 16A shows bioluminescence from NALM6-luciferase cells in NSG mice at day 3, 6, 9, and 12 after injection with conditions (i) to (iv) described in FIG. 15.

Figure 16B:
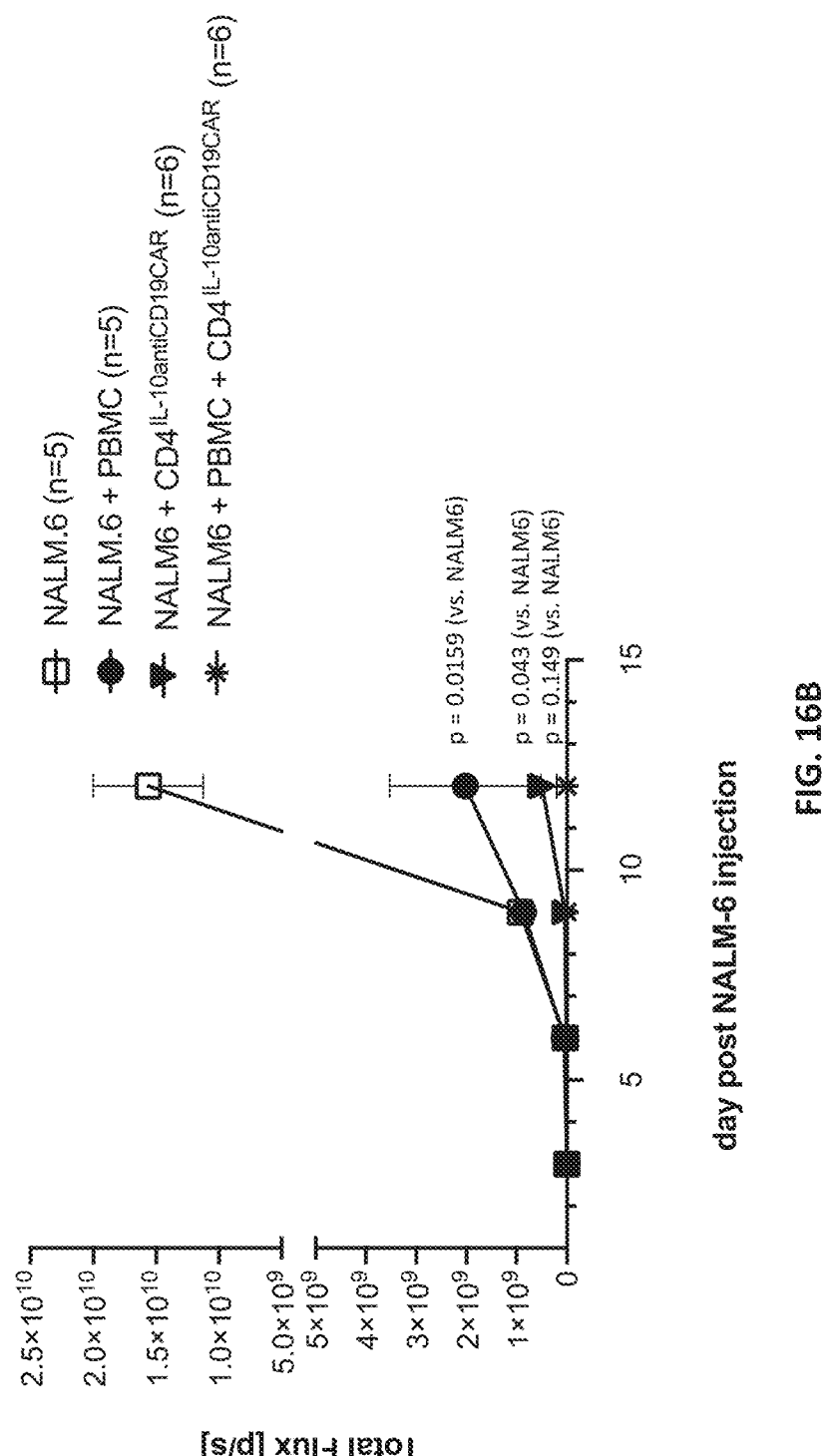

FIG. 16B shows a line graph that quantifies the bioluminescence from the images in FIG. 16A. Total flux [p/s] over time (day post NALM6-luciferase injection) for each of the conditions (i) to (iv) described in FIG. 15. P-values were measured at day 12 using a Mann-Whitney test comparing conditions (ii) to (iv) to condition (i) (NALM6-luciferase alone).

Figure 17:
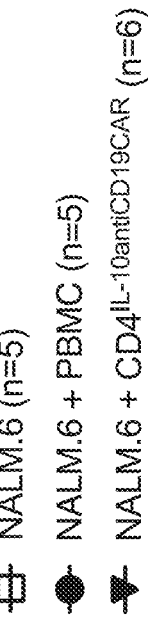
Figure 17:
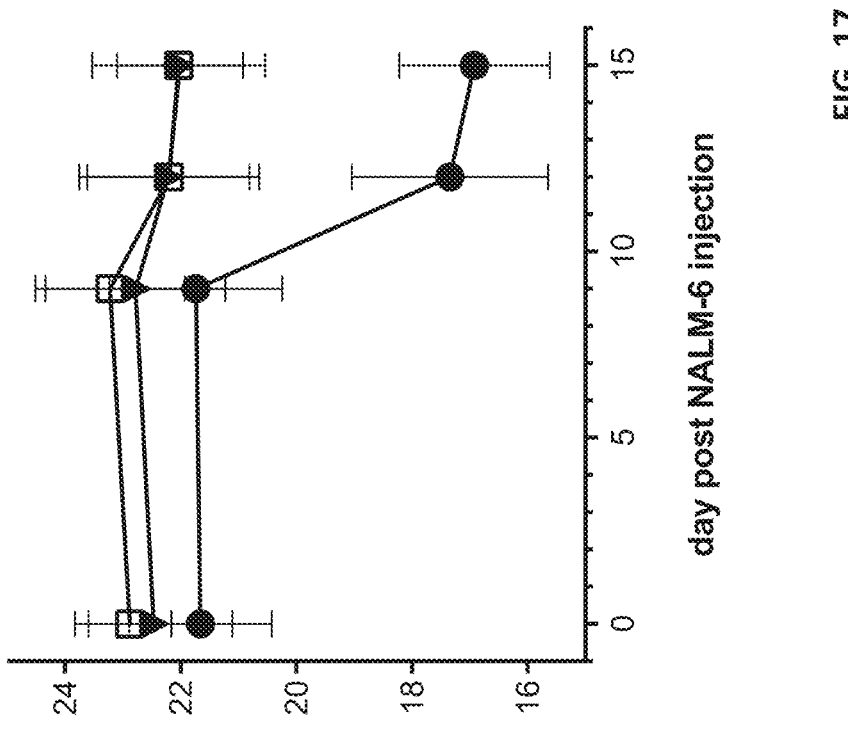

FIG. 17 shows a line graph for weight loss over time for the mice described in FIG. 15 with conditions (1), (ii), and (iii). Weight loss is used as an indicator of xeno-graft-versus host disease (GvHD).

Figure 18A:
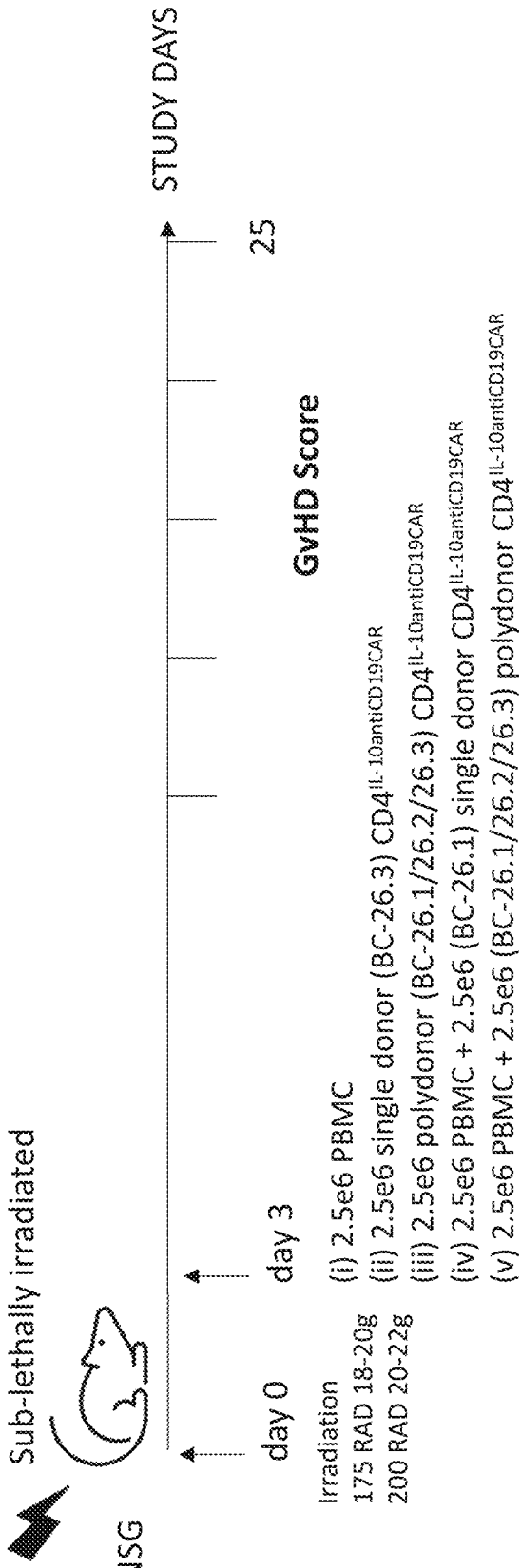
Figure 18B:
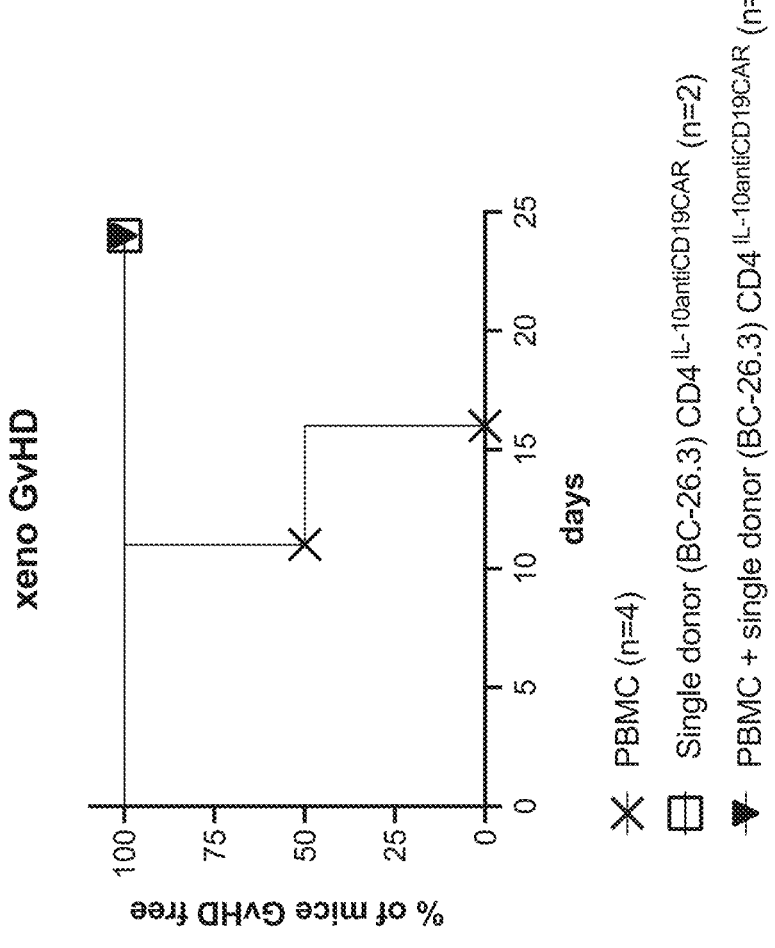
Figure 18C:
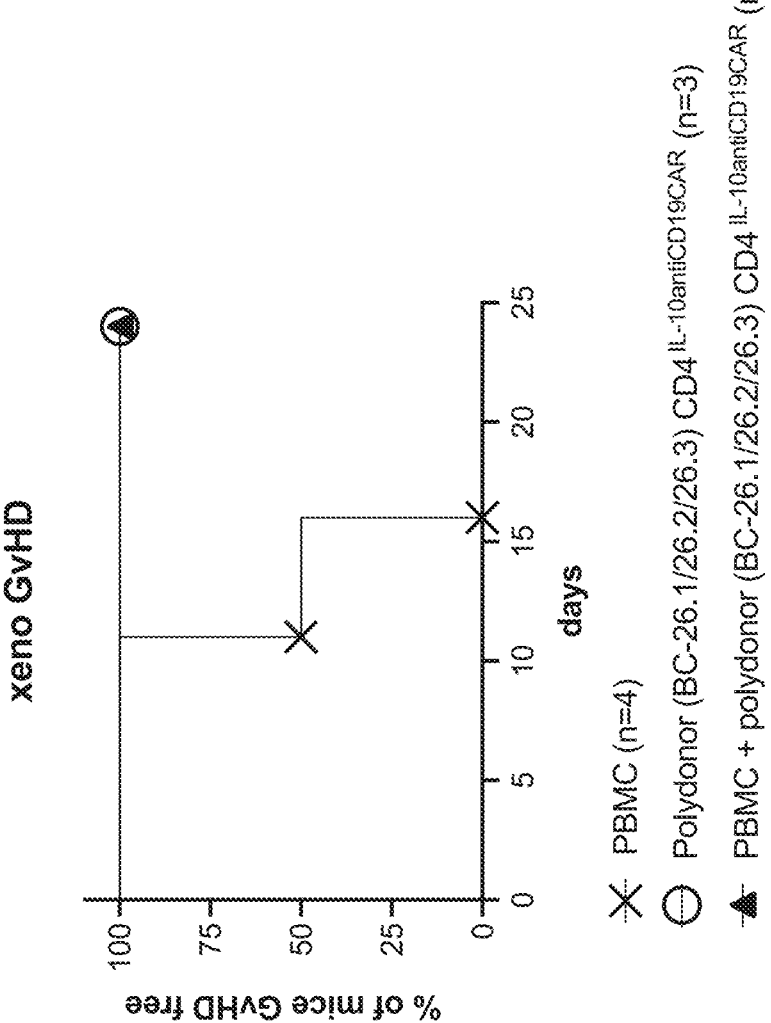

FIGS. 18A-18C show single donor $CD4^{IL-10antiCD19CAR}$ cells and polydonor $CD4^{IL-10antiCD19CAR}$ cells in humanized mouse model of xeno-GvHD. FIG. 18A shows single donor $CD4^{IL-10antiCD19CAR}$ cells tested in a humanized mouse model of xeno-GvHD induced by allogeneic PBMC in which irradiated NSG mice were injected intravenous (i.v.) with (i) allogeneic PBMC (2.5E6 cells/mouse), (ii) single donor $CD4^{IL-10antiCD19CAR}$ cells (2.5E6 cells/mouse), (iii) polydonor $CD4^{IL-10antiCD19CAR}$ cells (2.5E6 cells/mouse), (iv) PBMC+ single donor $CD4^{IL-10antiCD19CAR}$ cells, (v) or PBMC+ poly donor $CD4^{IL-10antiCD19CAR}$ cells (2.5E6 cells/ mouse) at Day 3. FIG. 18B shows $CD4^{IL-10antiCD19CAR}$ cells tested in a humanized mouse model of xeno-GvHD induced by allogeneic PBMC in which irradiated NSG mice were injected intravenous (i.v.) with allogeneic PBMC (2.5E6 cells/mouse) and/or single donor $CD4^{IL-10antiCD19CAR}$ cells at day 3. FIG. 18C shows $CD4^{IL-10antiCD19CAR}$ cells tested in a humanized mouse model of xeno-GvHD induced by allogeneic PBMC in which irradiated NSG mice were injected intravenous (i.v.) with allogeneic PBMC (2.5E6 cells/mouse) and/or polydonor $CD4^{IL-10antiCD19CAR}$ cells (2.5E6 cells/mouse) at Day 3. PBMC: peripheral mononuclear cells; GvHD: graft vs. host disease.

Figure 19:
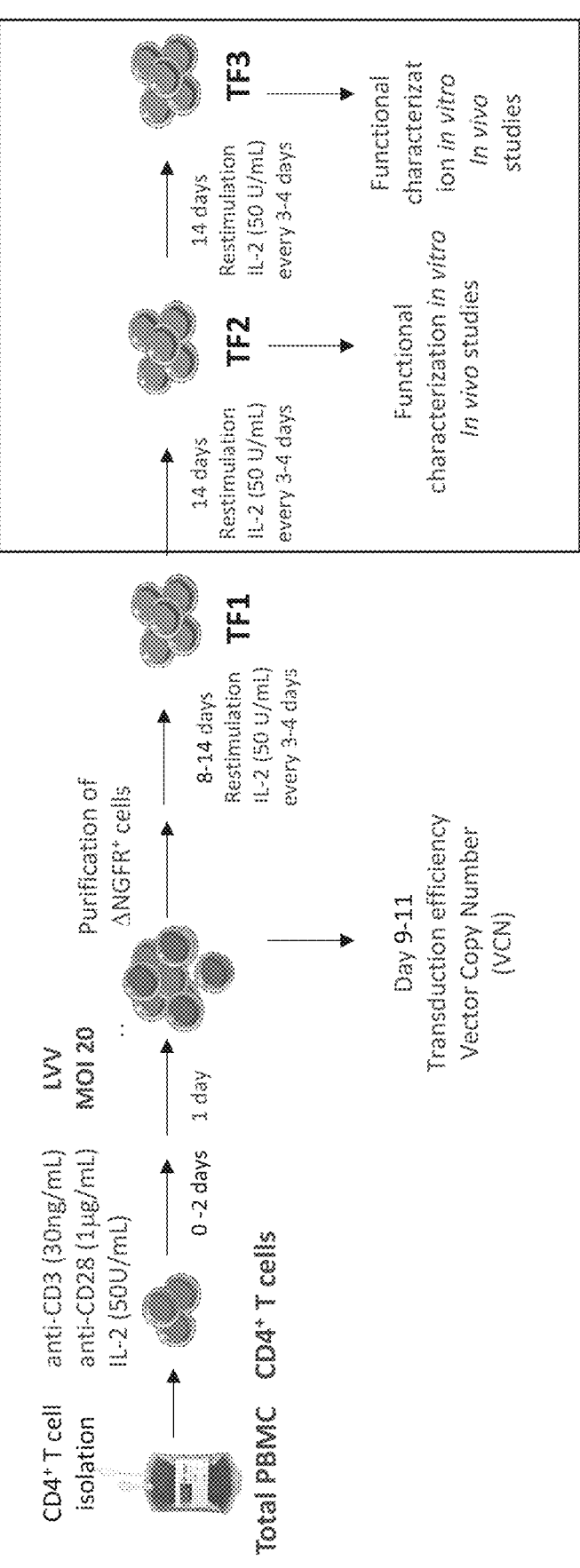

FIG. 19 illustrates an exemplary protocol for generating $CD4^{IL-10}$ cells.

Figure 20A:
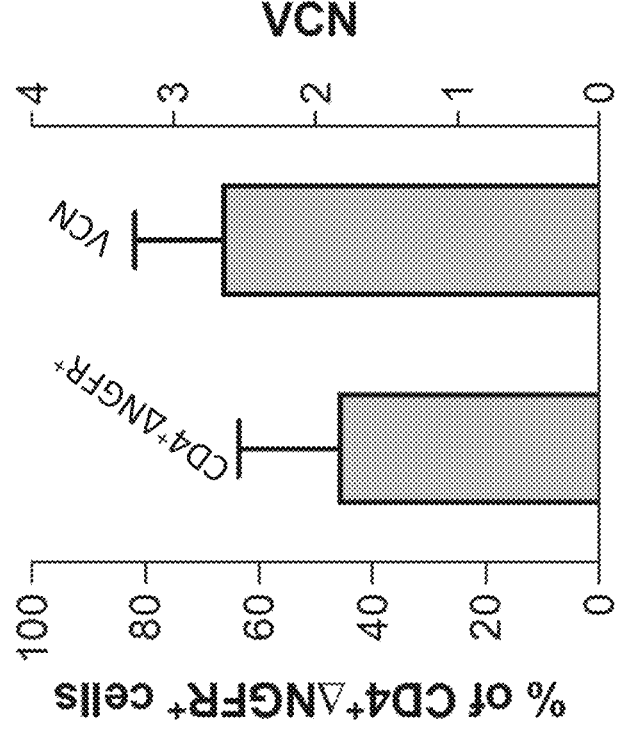
Figure 20B:
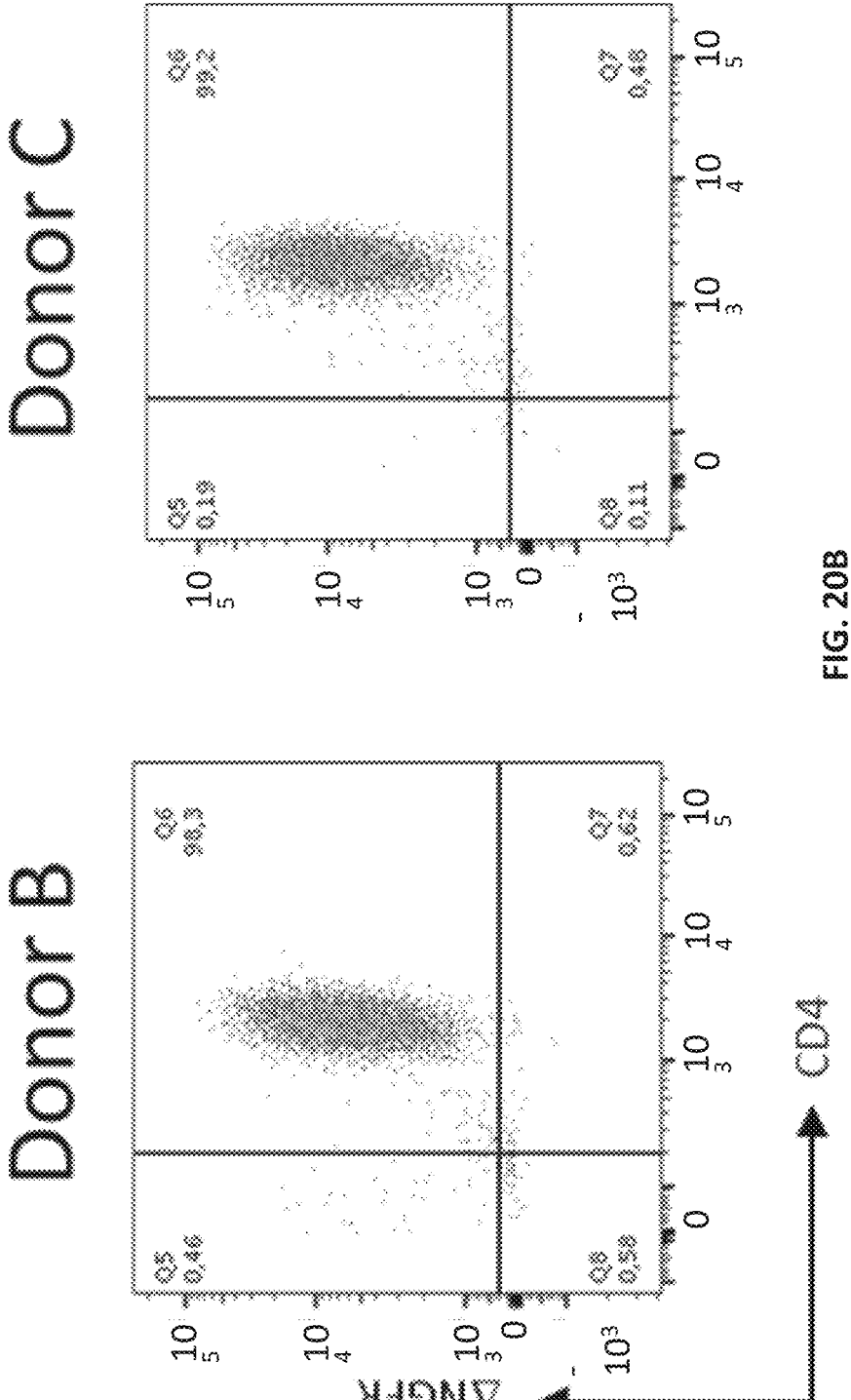

FIG. 20A shows percentages of CD4⁻ΔNGFR+ cells (mean+SD, n=10) and vector copy numbers (VCN, mean±SD, n=10) in human CD4⁺ T cells transduced with LV-IL-10/ΔNGFR (a bidirectional lentiviral vector encoding for human IL-10 and a truncated form the human NGF receptor). FIG. 20B shows FACS analysis of expression of CD4 and ΔNGER in human CD4⁺ T cells from two representative donors (Donor B and Donor C) transduced with LV-IL-10/ΔNGFR and purified using anti-CD271 Microbeads.

Figure 21:
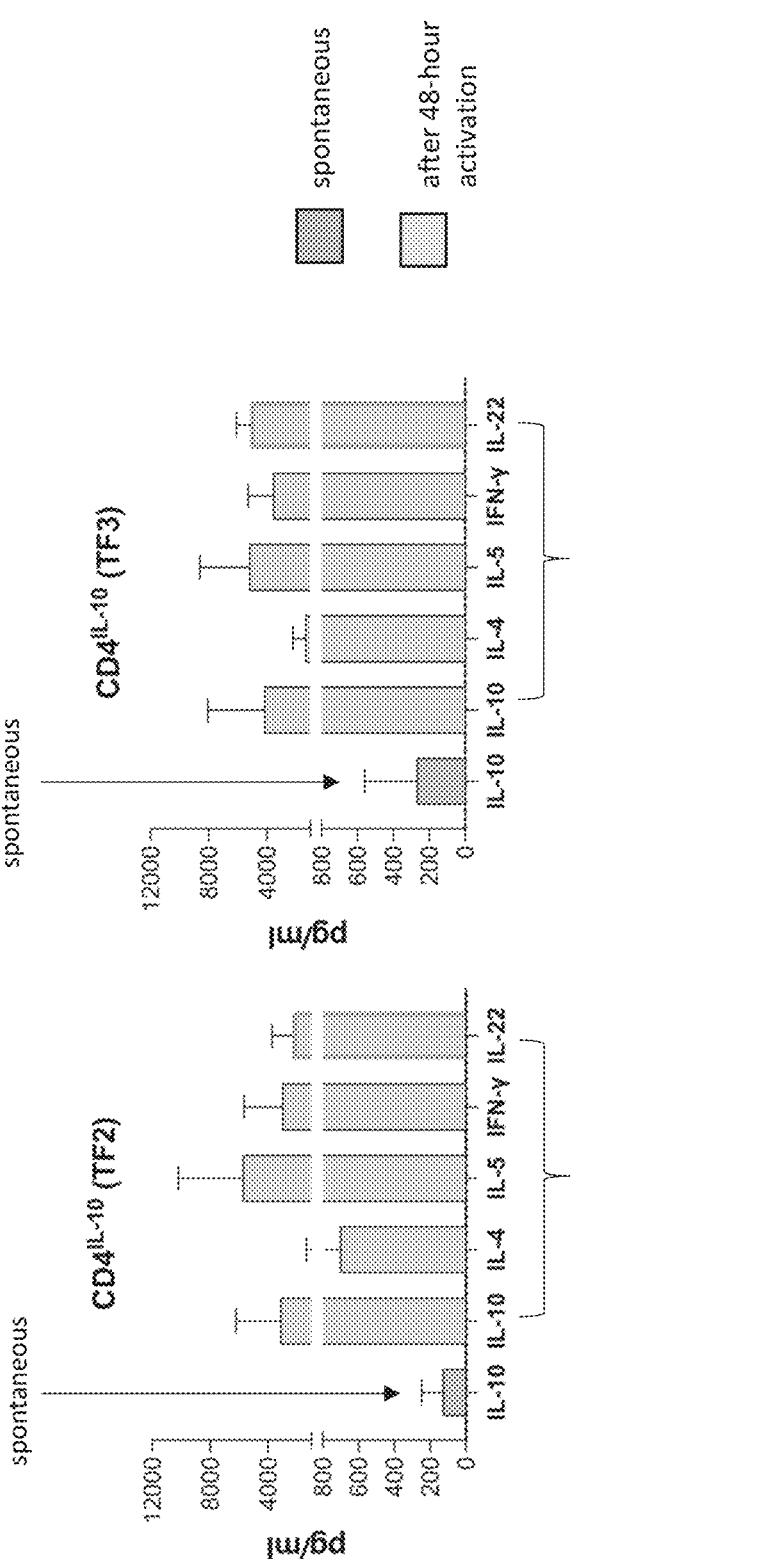

FIG. 21 shows cytokine production profile of single donor $CD4^{IL-10}$ cells after the second (TF2) and third (TF3) restimulation. The TF2 and TF3 $CD4^{IL-10}$ cells were left unstimulated (arrows indicate spontaneous/unstimulated sample) or stimulated with immobilized CD3 (10 µg/mL) and soluble CD28 mAb (1 µg/mL) for 48 hours. Culture supernatants were collected and levels of IL-10, IL-4, IL-5, IFN-γ and IL-22 were determined by ELISA. All samples were tested in triplicate. Mean±SD, n=8 donors tested are presented.

Figure 22B:
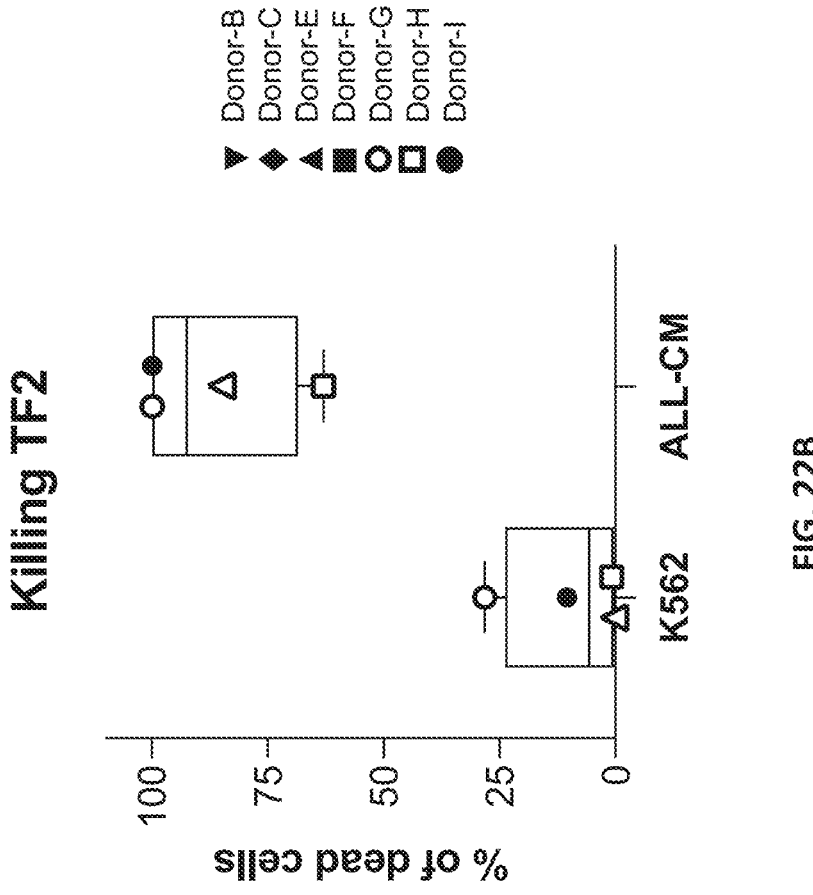
Figure 22A:
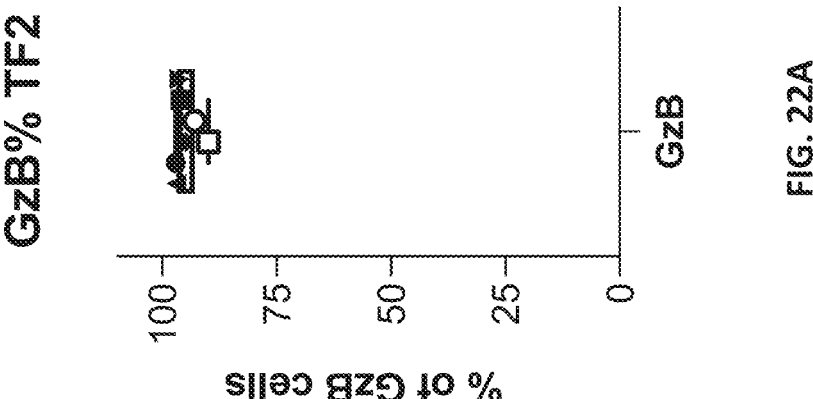

FIG. 22A shows the percentage of $CD4^{IL-10}$ cells expressing granzyme B (GzB) after $2^{nd}$ round of stimulation (TF2) analyzed by FACS. Box and whiskers of n=7 donors and single donors are presented. FIG. 22B shows % dead cells when $CD4^{IL-10}$ cells ($10^5$/well) were co-cultured with K562 and ALL-CM cells ($10^5$/well) at 1:1 ratio for 3 days. Box and whiskers represent data from n=4 donors and dots represent data from single donors.

Figure 23A:
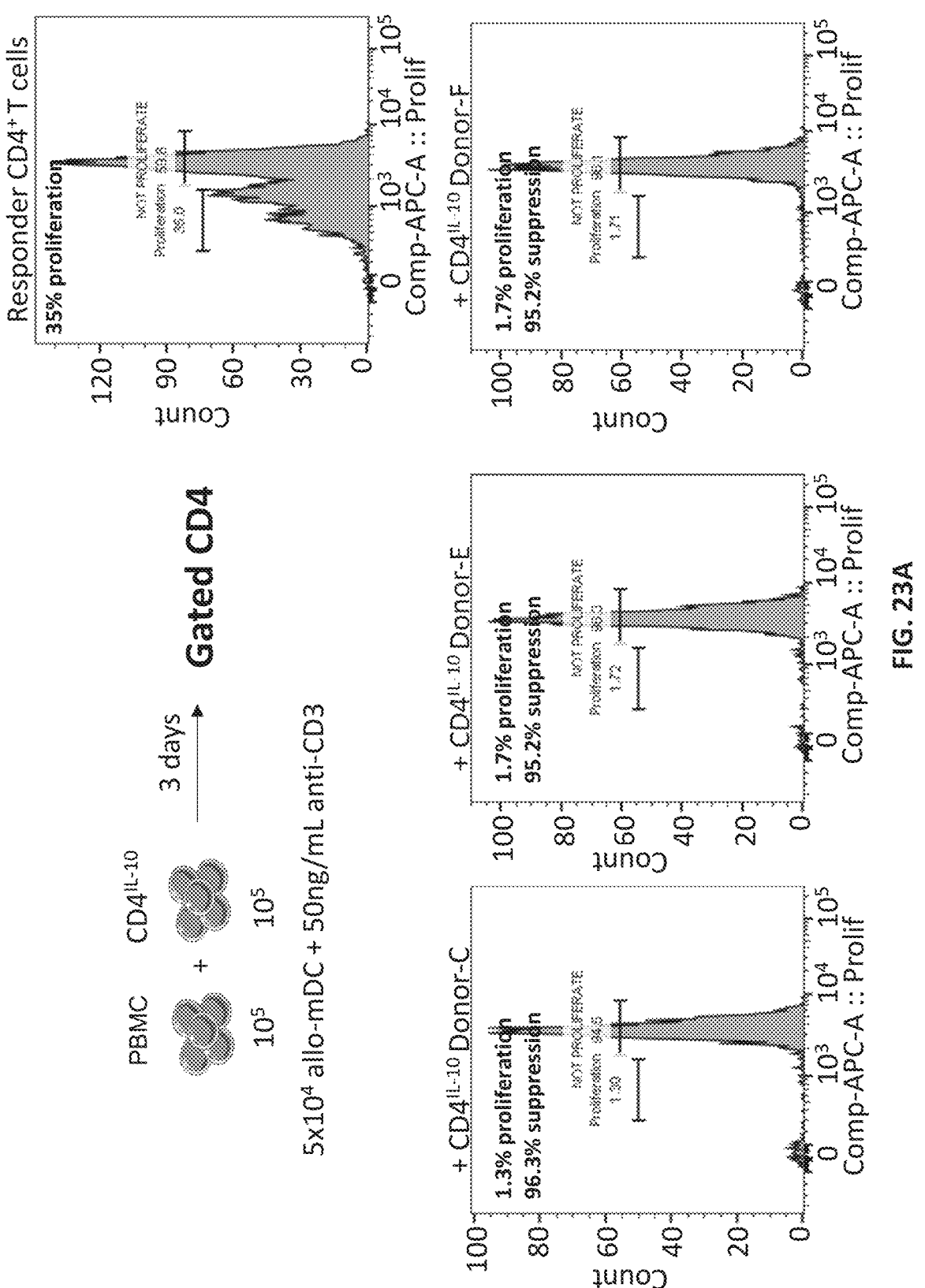
Figure 23B:
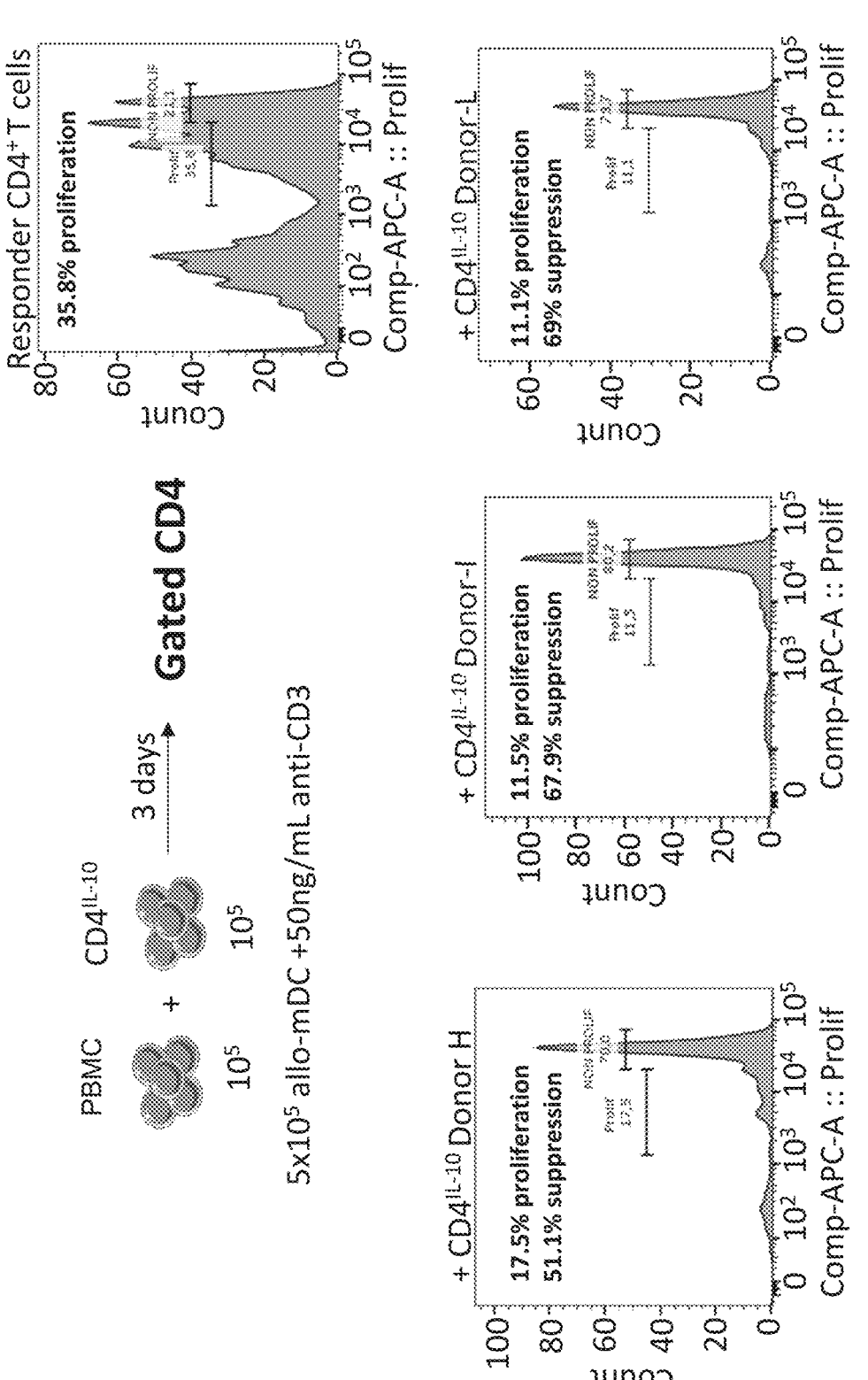

FIGS. 23A and 23B show that single donor $CD4^{IL-10}$ cells can suppress the proliferation of allogeneic CD4⁺ T cells. Allogeneic PBMC cells were labeled with eFluor® 670 ($10^5$ cells/well) and stimulated with allogeneic mature dendritic (DC) cells ($5\times10^4$ cells/well) and soluble anti-CD3 mAbs in the absence or presence of $CD4^{IL-10}$ cells ($10^5$ cells/well) at a 1:1 Responder:Suppressor ratio. After 4 days of culture, the percentages of proliferating responder cells were determined by eFluor® 670 dilution with flow cytometry after gating on CD4⁺ΔNGFR⁻ T cells. FIG. 23A show results from Donor-C, Donor-E, and Donor-F and FIG. 23B show results from Donor-H, Donor-I and Donor-L. Percentages of proliferation and suppression are indicated. The suppression mediated by $CD4^{IL-10}$ cells was calculated as follows: 100–([proliferation of responders in the presence of $CD4^{IL-10}$ cells/proliferation of responders alone]×100).

Figure 24A:
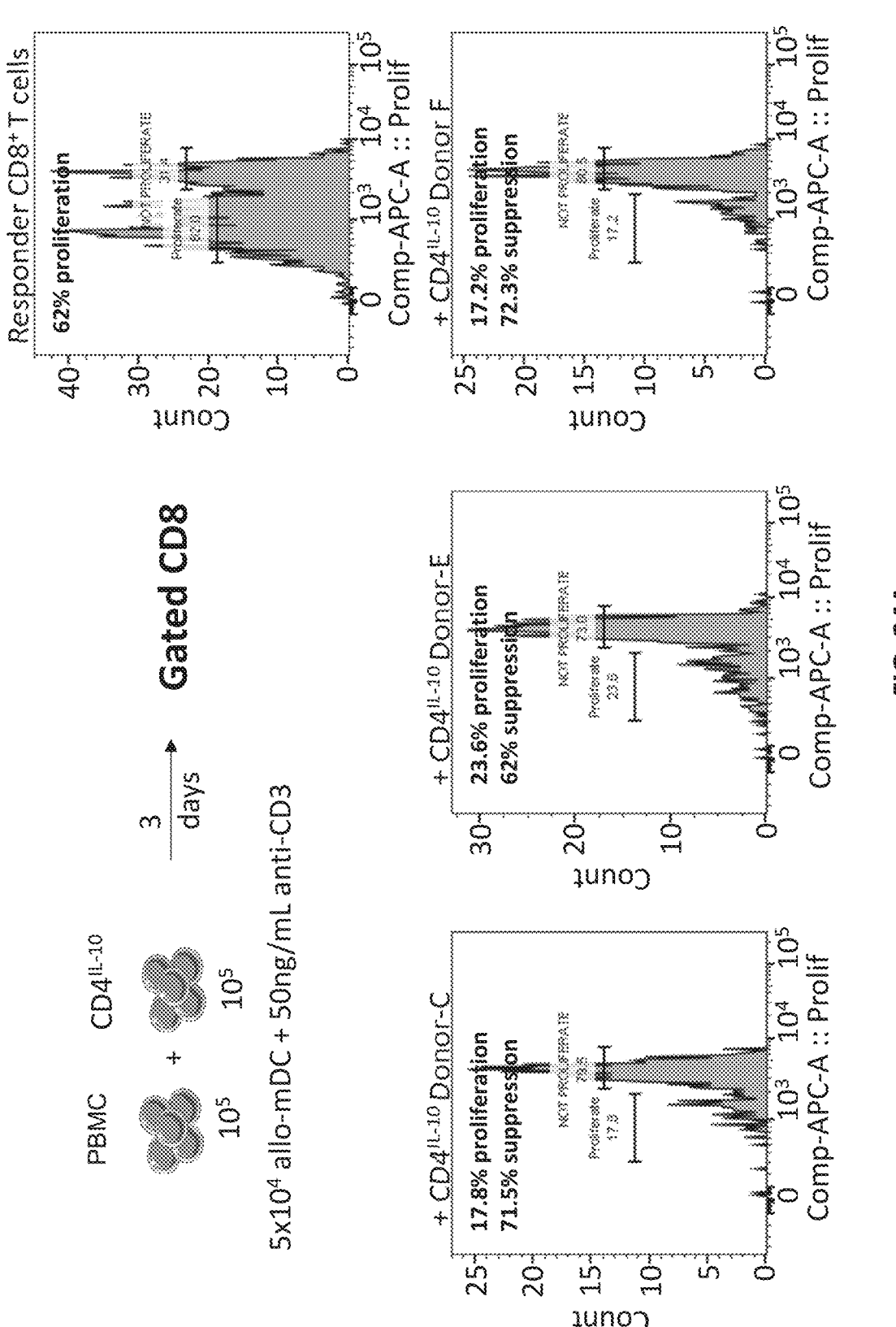
Figure 24B:
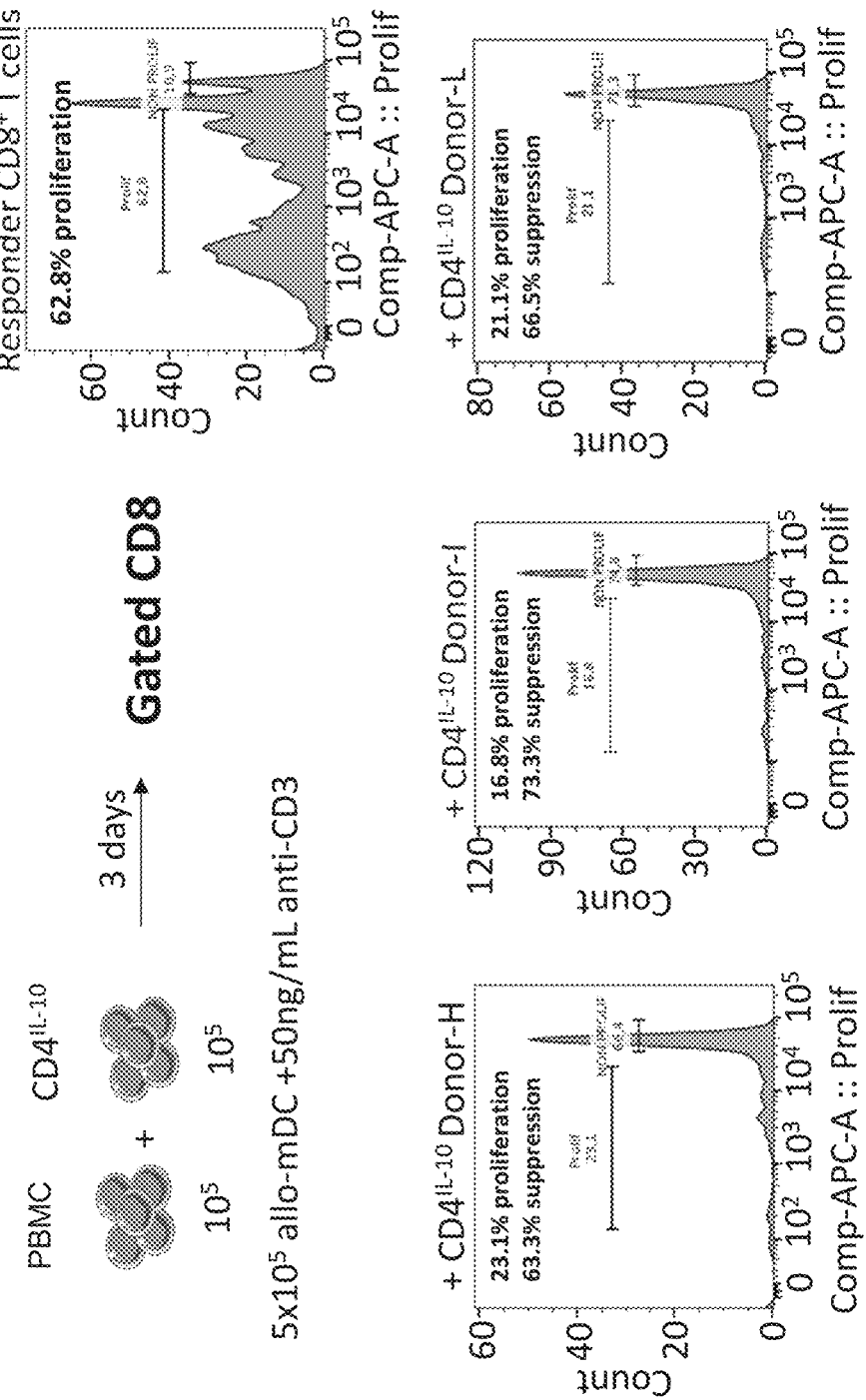

FIGS. 24A and 24B show that single donor $CD4^{IL-10}$ cells can suppress the proliferation of allogeneic CD8⁺ T cells. Allogeneic PBMC cells were labeled with eFluor® 670 ($10^5$ cells/well) and stimulated with allogeneic mature dendritic (DC) cells ($5\times10^4$ cells/well) and soluble anti-CD3 mAbs in the absence or presence of $CD4^{IL-10}$ cells ($10^5$ cells/well) at a 1:1 Responder:Suppressor ratio. After 4 days of culture, the percentages of proliferating responder cells were determined by eFluor® 670 dilution with flow cytometry after gating on CD4 ΔNGFR T cells. FIG. 24A show results from Donor-C, Donor-E, and Donor-F and FIG. 24B show results from Donor-H, Donor-I and Donor-L. Percentages of proliferation and suppression are indicated. The suppression mediated by $CD4^{IL-10}$ cells was calculated as follows: 100–([proliferation of responders in the presence of $CD4^{IL-10}$ cells/proliferation of responders alone]×100).

Figure 25:
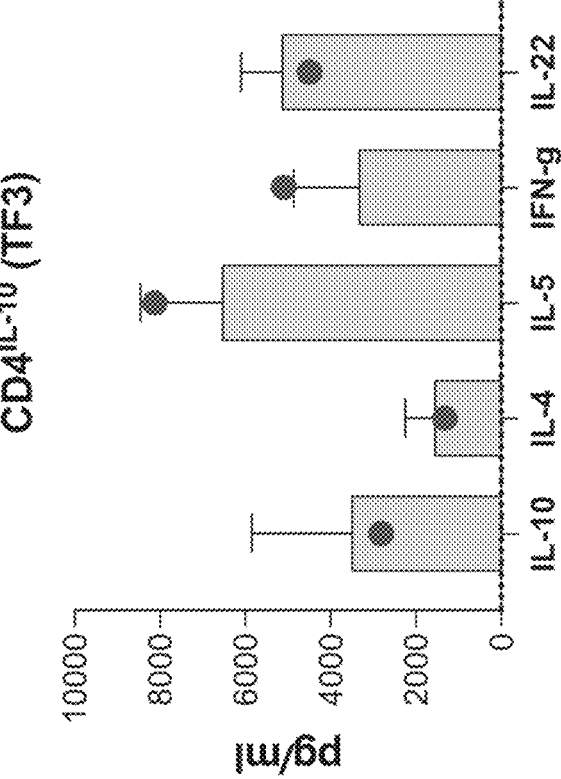

FIG. 25 shows cytokine production profile of polydonor $CD4^{IL-10}$ cells after third (TF3) restimulation, compared to mean levels (+/–SD) produced by $CD4^{IL-10}$ cells from 8 individual donors. The TF3 $CD4^{IL-10}$ cells from three donors were pooled at a 1:1:1 ratio and stimulated with immobilized CD3 (10 µg/mL) and soluble CD28 mAb (1 µg/mL) for 48 hours. Culture supernatants were collected and levels of IL-10, IL-4, IL-5, IFN-gamma and IL-22 were determined by ELISA. Dots are results of polydonor $CD4^{IL-10}$ cells; gray bars represent mean±SD, n=8 single donors.

Figure 26B:
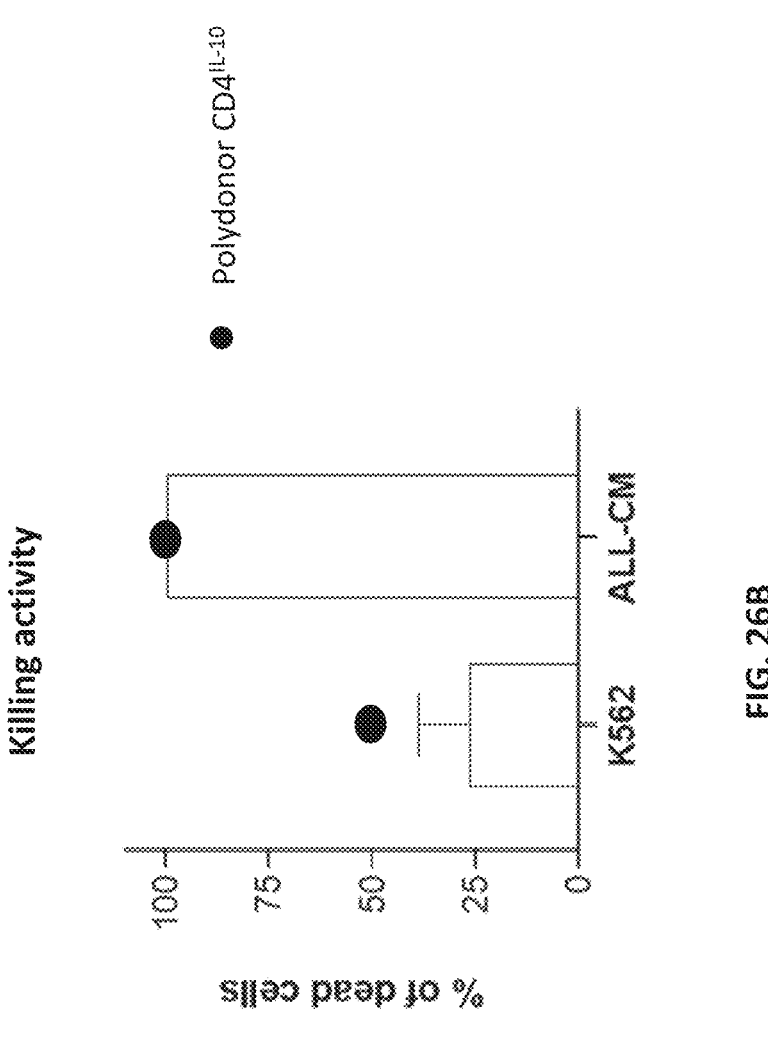
Figure 26A:
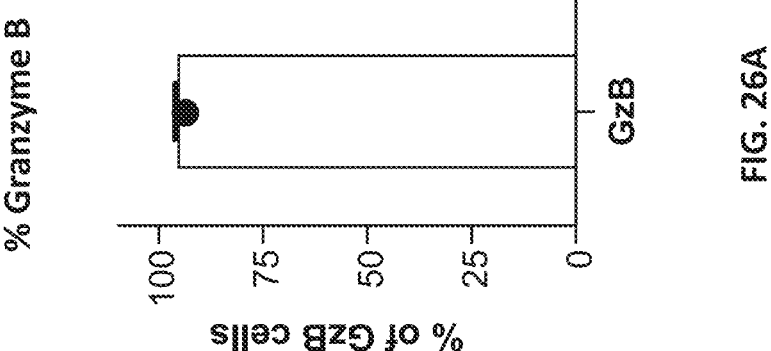

FIG. 26A shows the percentage of polydonor $CD4^{IL-10}$ cells expressing granzyme B (GzB) compared to mean % levels (+/–SD) of granzyme B expression by $CD4^{IL-10}$ cells of n=3 single donors used to generate the pool. Cells were analyzed by FACS after the $3^{rd}$ round of stimulation (TF3). FIG. 26B shows % dead cells when polydonor CD4$^{IL-10}$ cells ($10^5$/well) were co-cultured with K562 and ALL-CM cells ($10^5$/well) at 1:1 ratio for 3 days. Residual leukemic cells (CD45$^+$CD33$^+$) were counted by FACS for each target cell. Dots are results of polydonor CD4$^{IL-10}$ and gray bars represent mean±SD of n=3 single donors used to generate the pool.

Figure 27A:
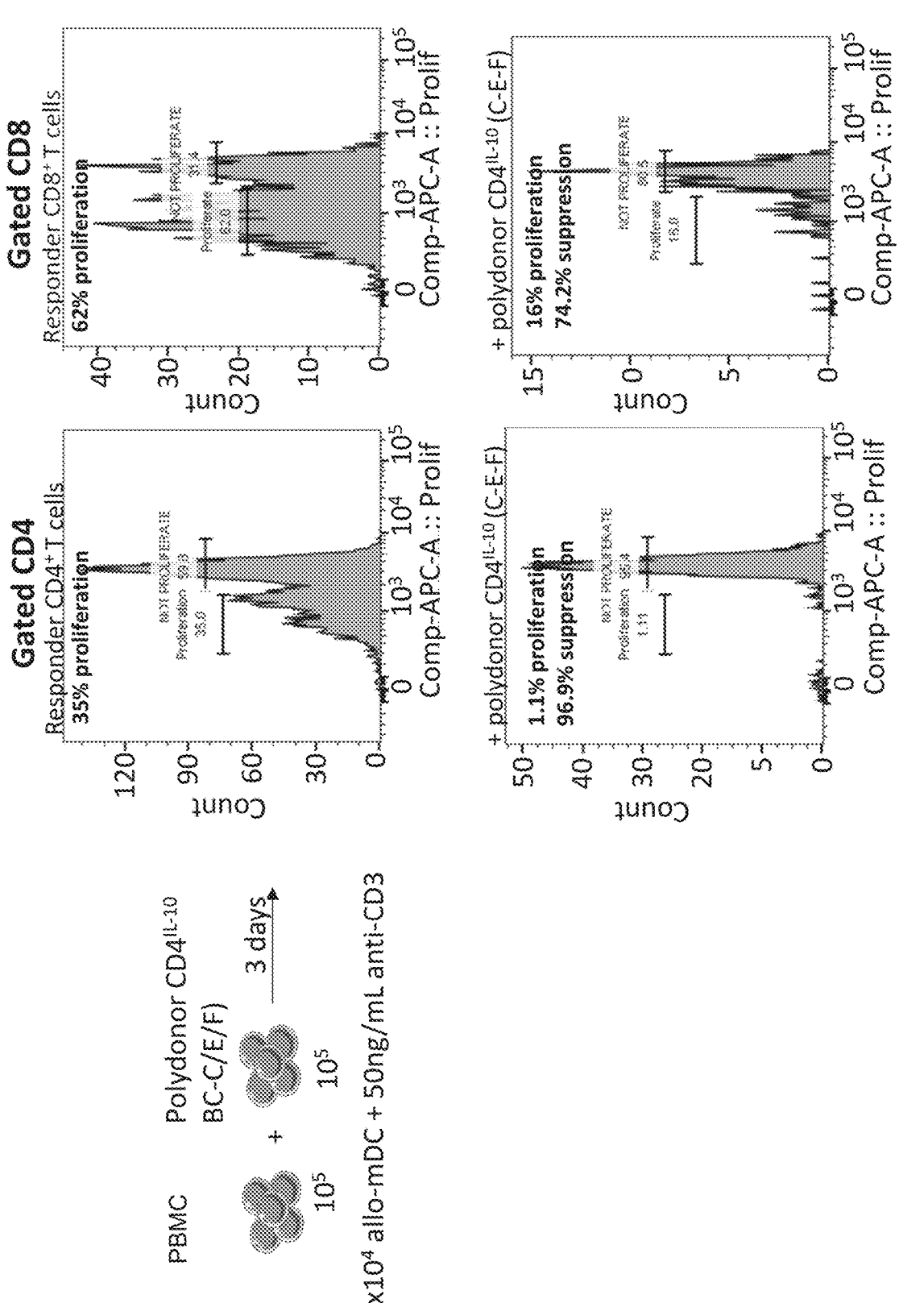
Figure 27B:
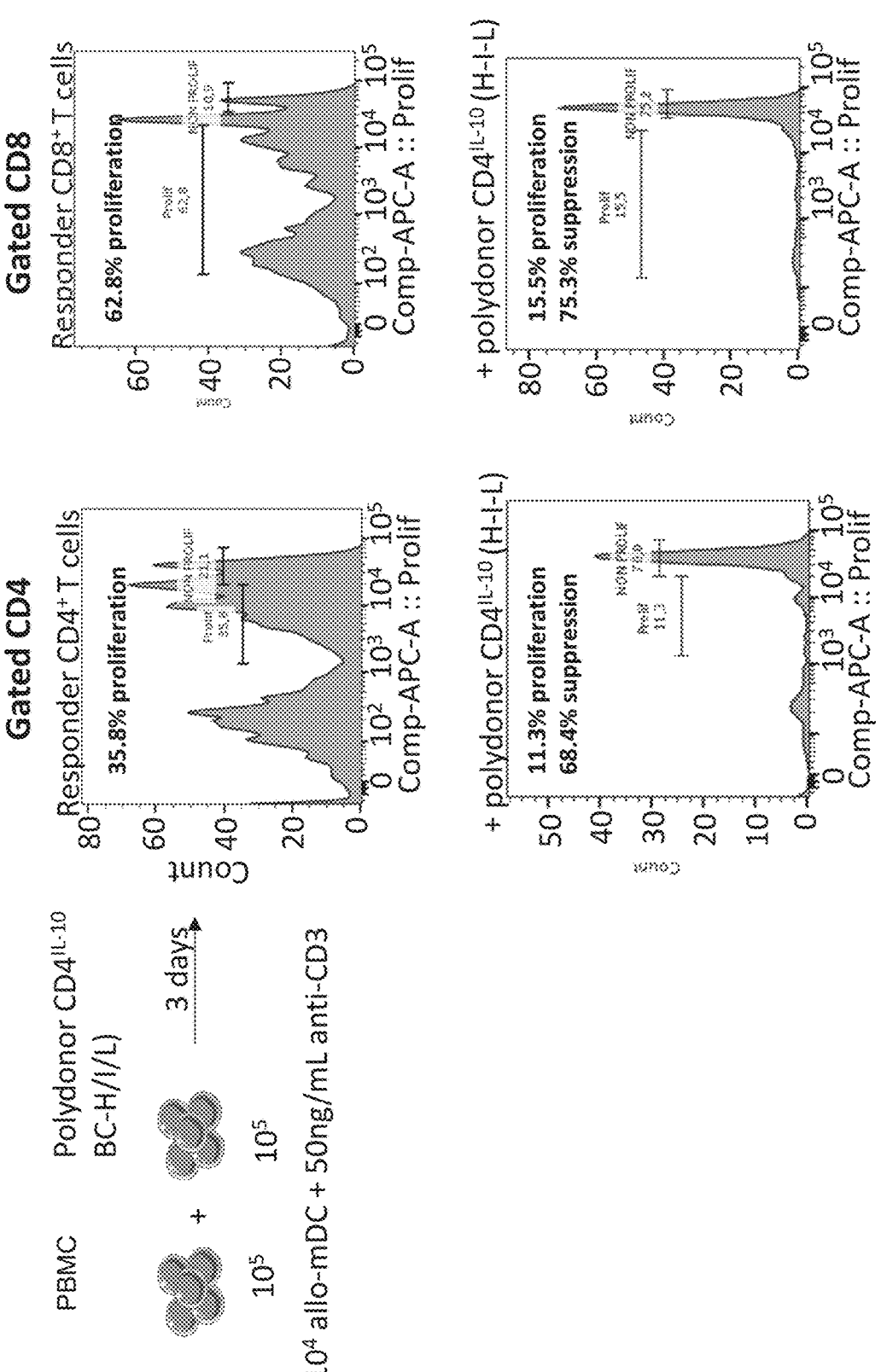

FIGS. 27A and 27B show that polydonor CD4$^{IL-10}$ cells can suppress the proliferation of allogeneic CD4$^+$ T cells and CD8$^+$ T cells. Allogeneic PBMC cells were labeled with eFluor® 670 ($10^5$ cells/well) and stimulated with allogeneic mature dendritic (DC) cells ($5×10^4$ cells/well) and soluble anti-CD3 mAbs in the absence or presence of polydonor CD4$^{IL-10}$ cells ($10^5$ cells/well) at a 1:1 Responder:Suppressor ratio. After 4 days of culture, the percentages of proliferating responder cells were determined by eFluor® 670 dilution with flow cytometry after gating on CD4 ΔNGFR$^-$ T cells and CD8$^+$ΔNGFR$^-$ T cells. FIG. 27A shows results from polydonor CD4$^{IL-10}$ cells containing CD4$^+$ cells pooled from Donor-C, Donor-E, and Donor-F. FIG. 27B shows results from polydonor CD4$^{IL-10}$ cells containing CD4$^+$ cells pooled from Donor-H, Donor-I, and Donor-L. The suppression mediated by CD4$^{IL-10}$ cells was calculated as follows: 100–([proliferation of responders in the presence of CD4$^{IL-10}$ cells/proliferation of responders alone]×100).

Figure 28:
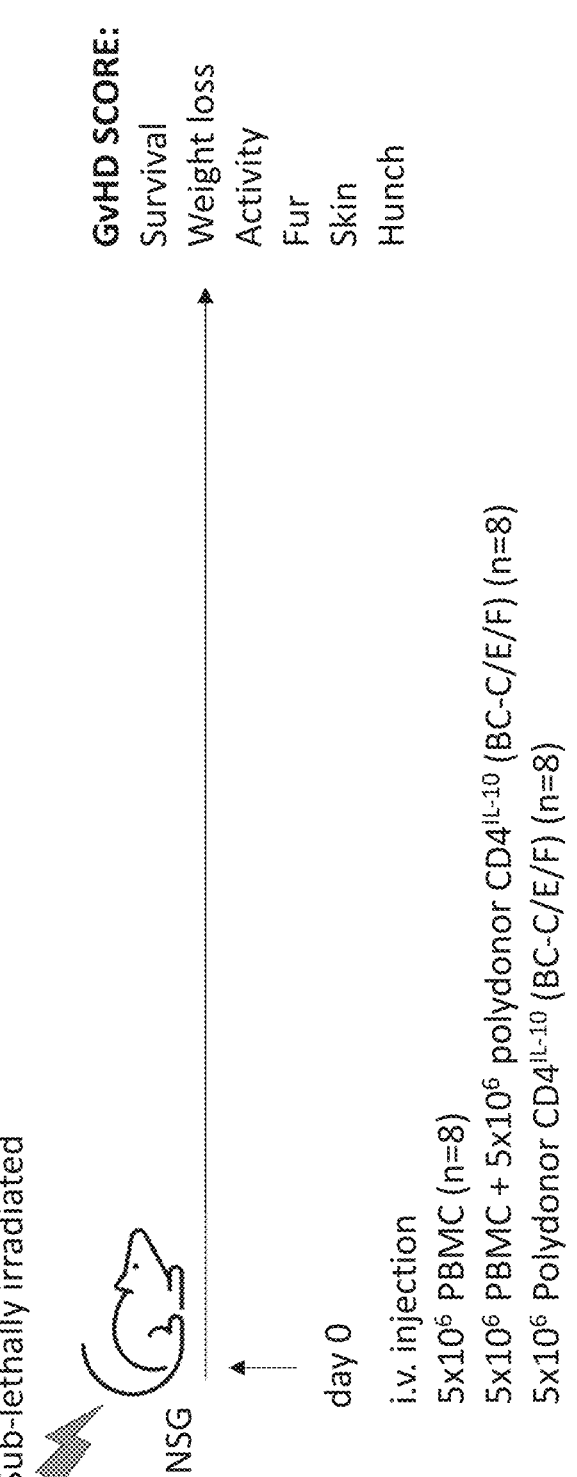

FIG. 28 illustrates a protocol for testing induction of GvHD by human PBMC and/or polydonor CD4$^{IL-10}$ cells injected on day 0 post-irradiation.

Figure 29:
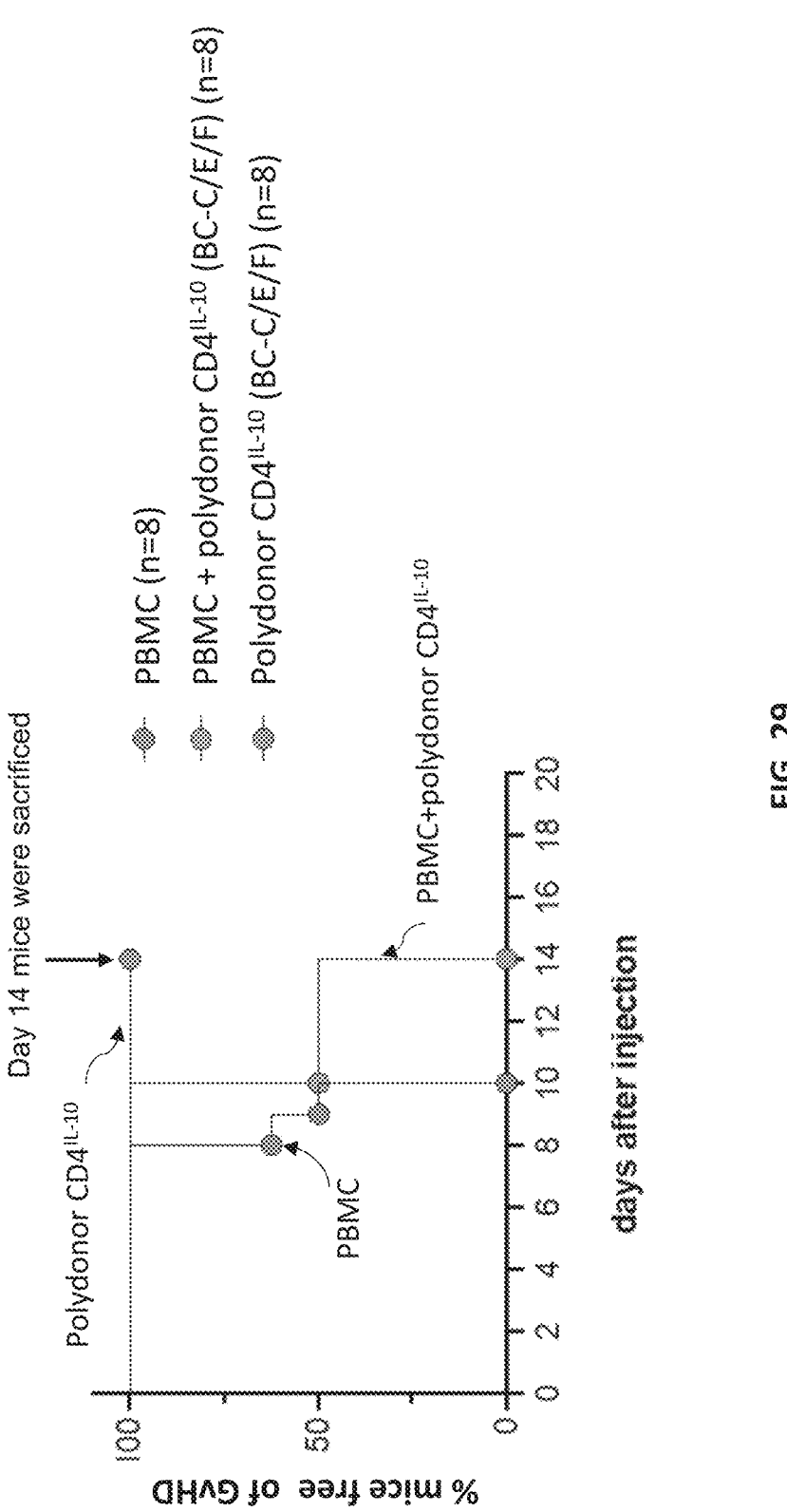

FIG. 29 shows % of NSG mice demonstrating GvHD in each day after injection of PBMC ($5×10^6$ cells/mouse), polydonor (three donors) CD4$^{IL-10}$ cells ($5×10^6$ cells/mouse), or PBMC ($5×10^6$ cells/mouse) in combination with polydonor CD4$^{IL-10}$ cells (three donors) ($5×10^6$ cells/mouse).

Figure 30:
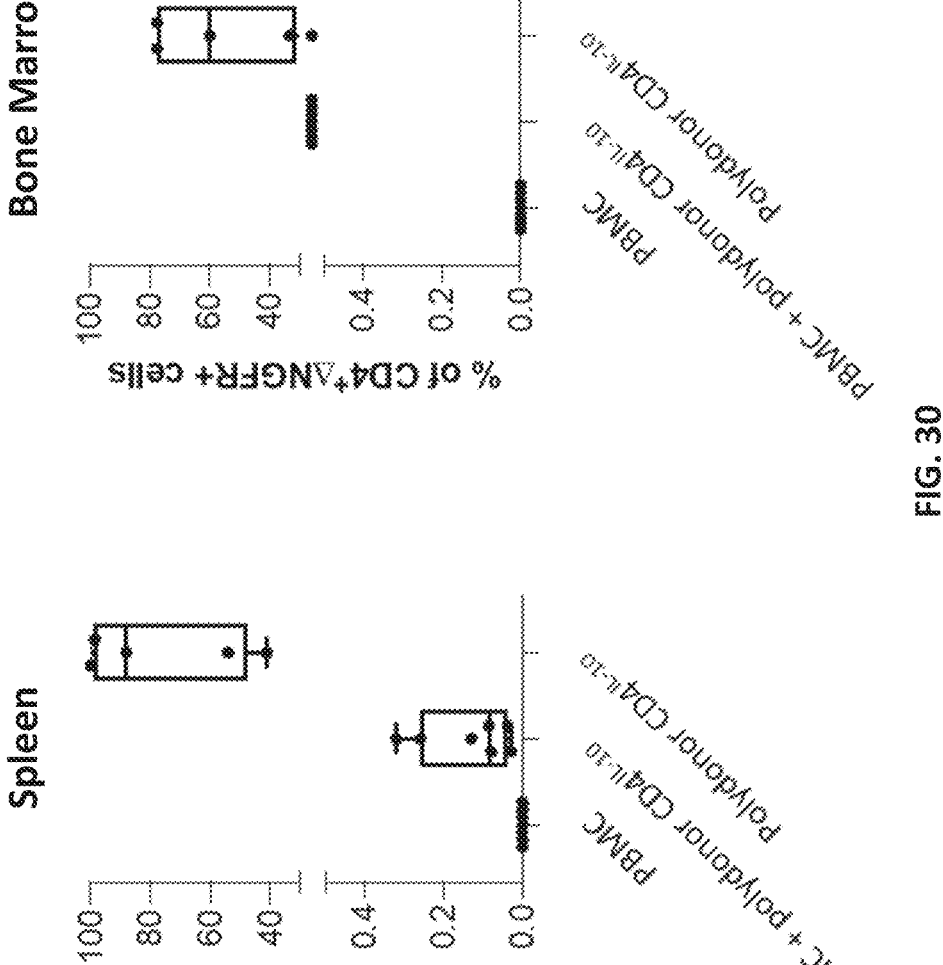

FIG. 30 shows migration of CD4$^{IL-10}$ cells to spleen (left panel) and bone marrow (right panel) in NSG mice injected with PBMC ($5×10^6$ cells/mouse), polydonor (three donors) CD4$^{IL-10}$ cells ($5×10^6$ cells/mouse), or PBMC ($5×10^6$ cells/mouse) in combination with polydonor CD4$^{IL-10}$ cells (three donors) ($5×10^6$ cells/mouse). Box and whiskers on n=8 donors and single donors are presented.

Figure 31:
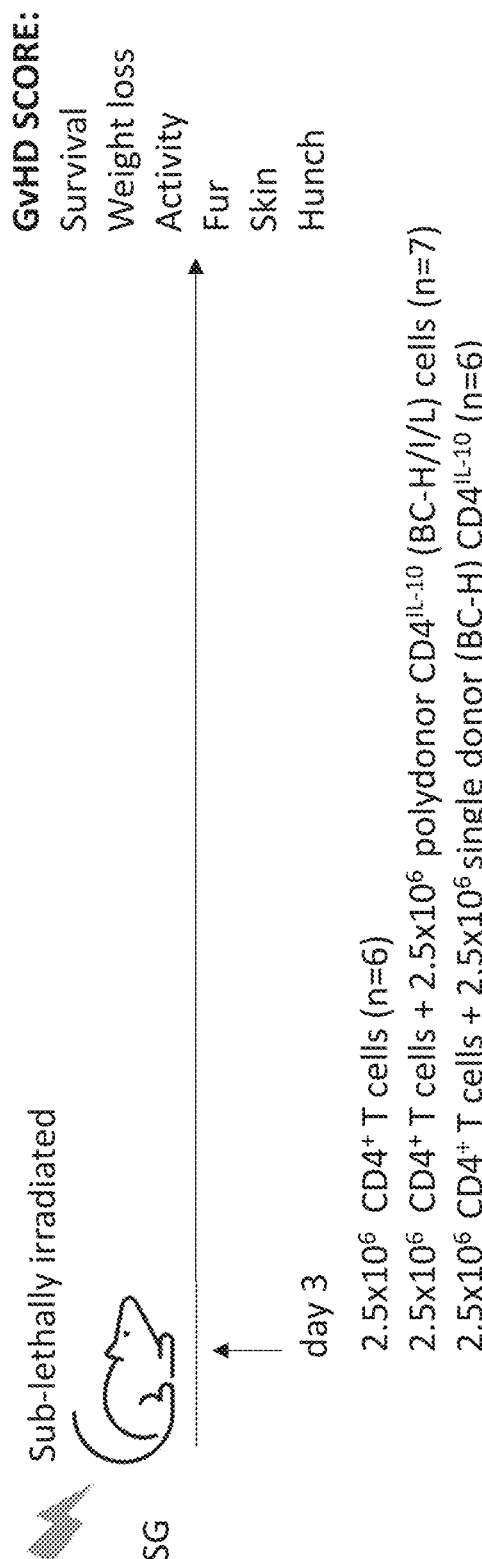

FIG. 31 illustrates a protocol for testing induction of GvHD by CD4$^+$ T cells and polydonor or single-donor (BC-H) CD4$^{IL-10}$ cells injected on day 0 post-irradiation.

Figure 32:
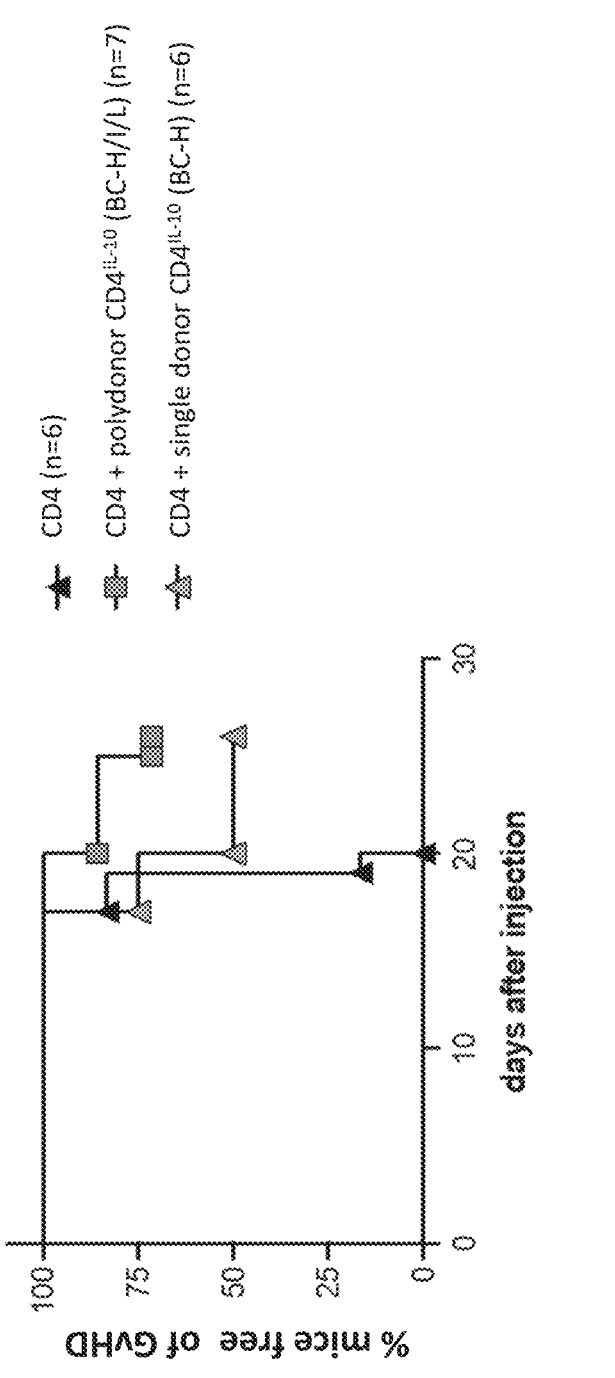

FIG. 32 shows % of NSG mice demonstrating GvHD on each day after injection.

Figure 33A:
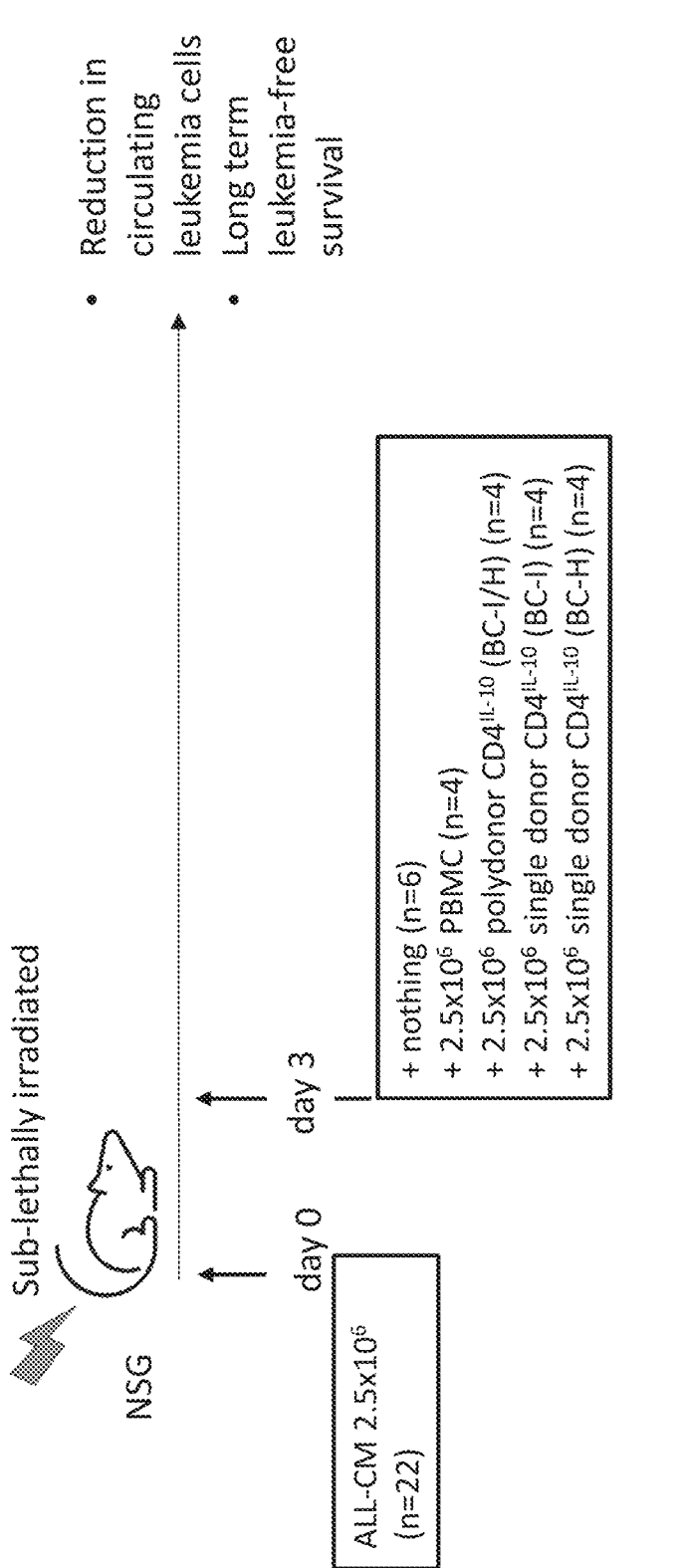
Figure 33B:
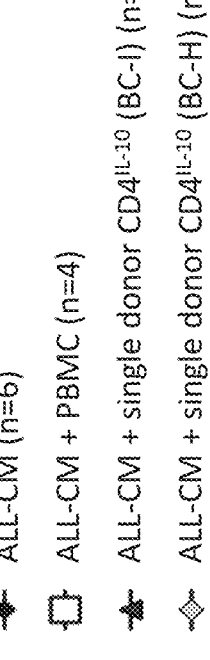
Figure 33C:
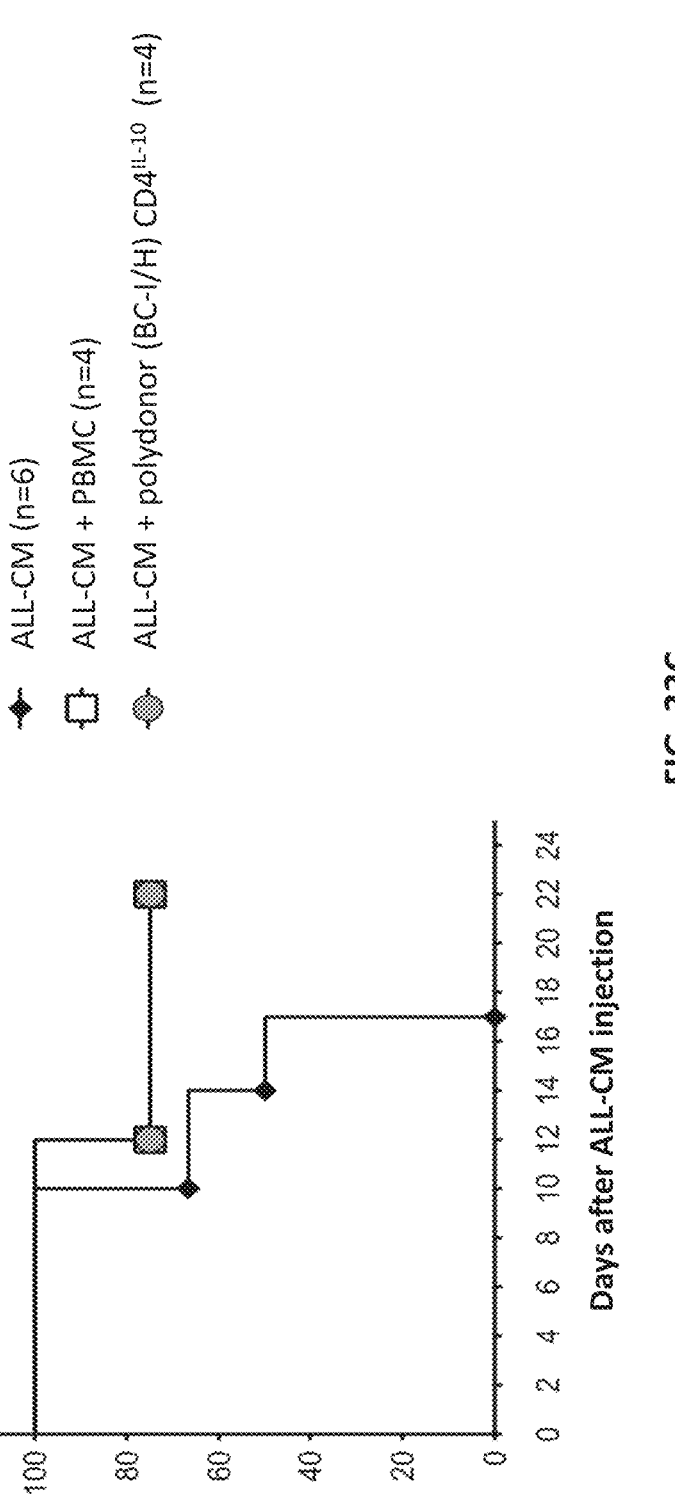

FIGS. 33A-33C shows graft-versus-leukemia (GvL) effect tested based on reduction of circulating leukemia cells and long-term leukemia free survival, Leukemia was measured as previously described (Locafaro G. et al Molecular Therapy 2017). NSG mice were sub-lethally irradiated and intravenously injected with myeloid leukemia cells (ALL-CM) ($5×10^6$) at day 0. FIG. 33A is an illustration of the experiment. FIG. 33B shows leukemia free survival rate in the animals injected with PBMC ($5×10^6$) or single donor (from donor BC-I and donor BC-H) CD4$^{IL-10}$ cells ($2.5×10^6$) at day 3. FIG. 33C.shows leukemia free survival rate in the animals injected with PBMC ($5×10^6$) or polydonor CD4$^{IL-10}$ cells (from donor BC-I and donor BC-H) ($2.5×10^6$) at day 3.

Figure 34A:
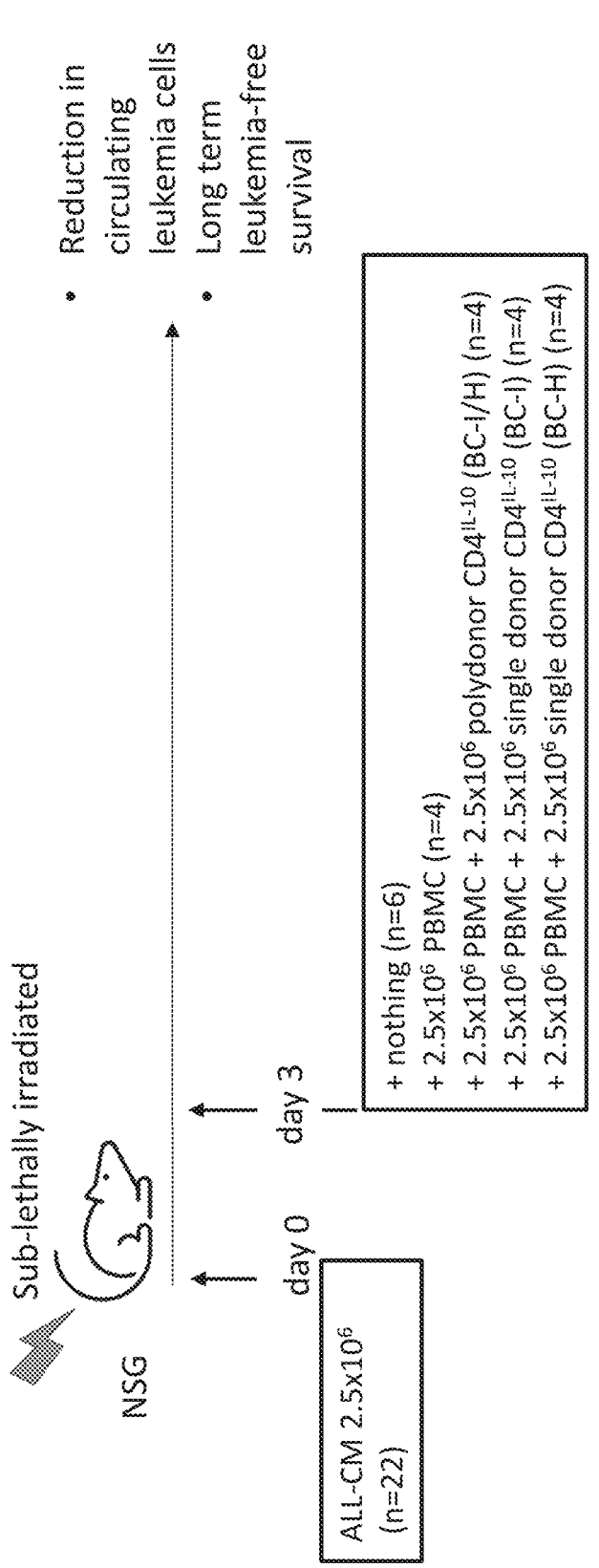
Figure 34B:
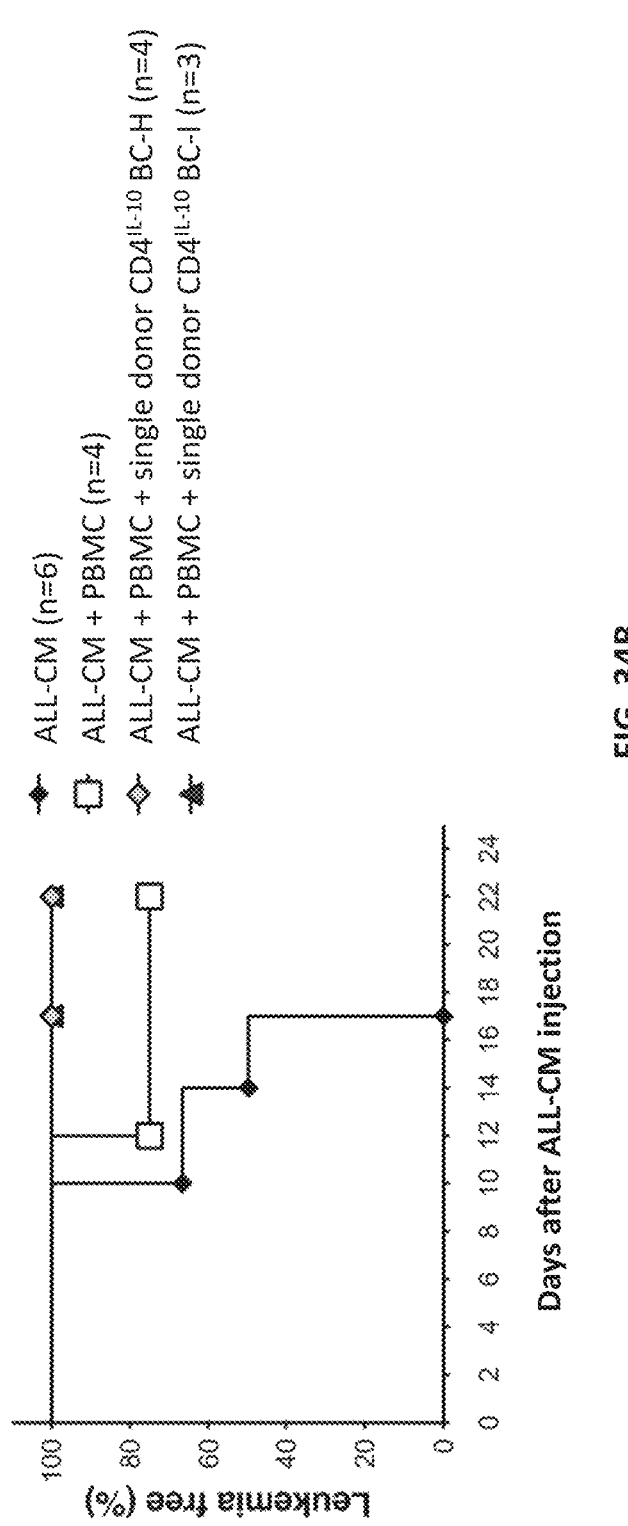
Figure 34C:
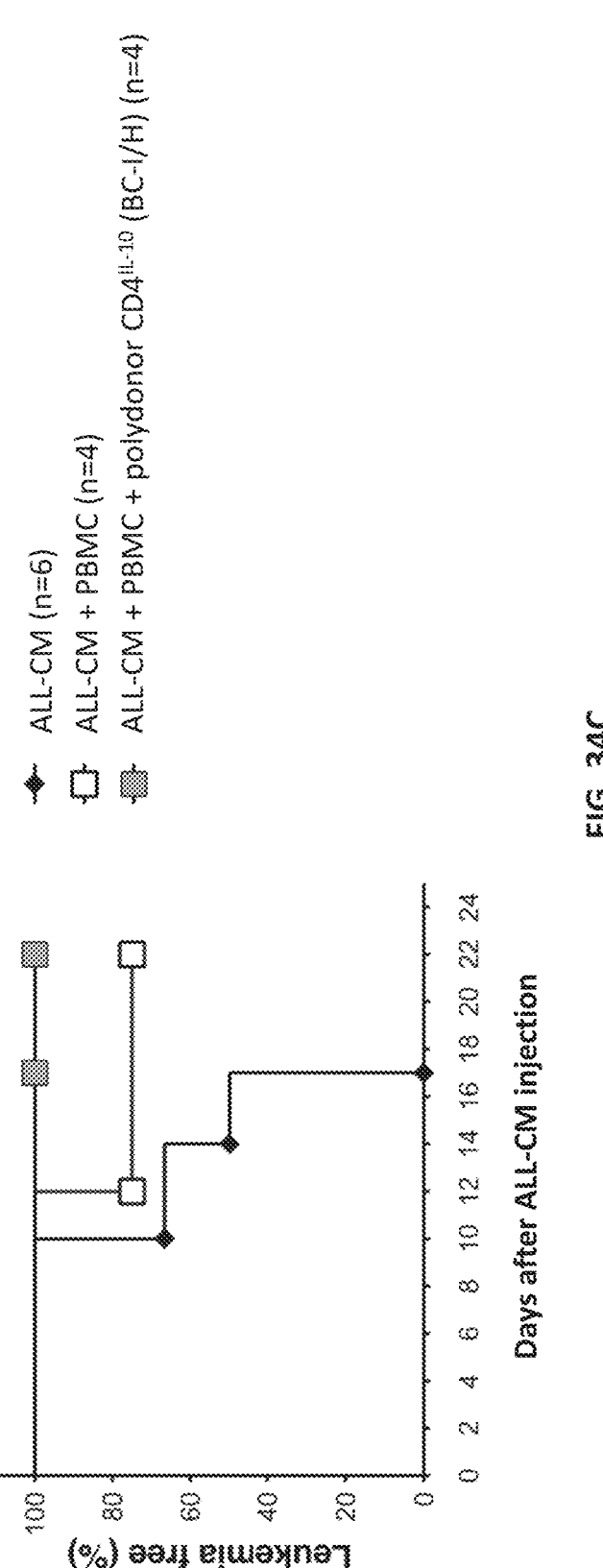

FIGS. 34A-34C show long-term leukemia free survival rate measured in NSG mice sub-lethally irradiated and intravenously injected with ALL-CM cells ($5×10^6$) at day 0. FIG. 34A shows an illustration of the experiment. FIG. 34B shows data from animals injected with mononuclear cells (PBMC) ($5×10^6$) alone or mononuclear cells (PBMC) ($5×10^6$)+single donor (from donor BC-H and donor BC-I)

CD4$^{IL-10}$ cells ($2.5×10^6$) at day 3. FIG. 34C shows data from animals injected with mononuclear cells (PBMC) ($5×10^6$) alone or mononuclear cells (PBMC) ($5×10^6$)+polydonor CD4$^{IL-10}$ cells (BC-I/H) ($2.5×10^6$) at day 3.

Figure 35A:
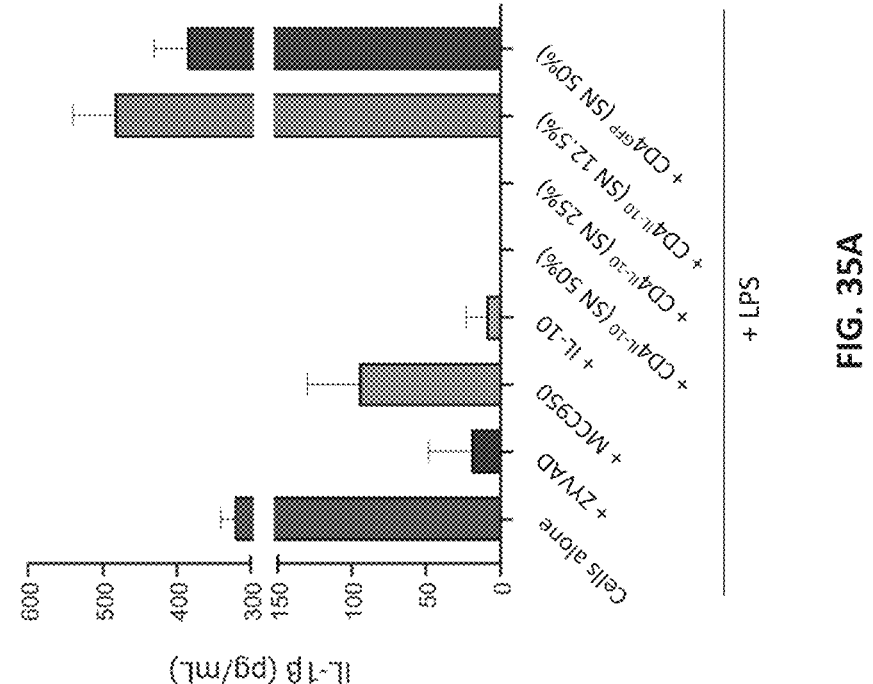
Figure 35B:
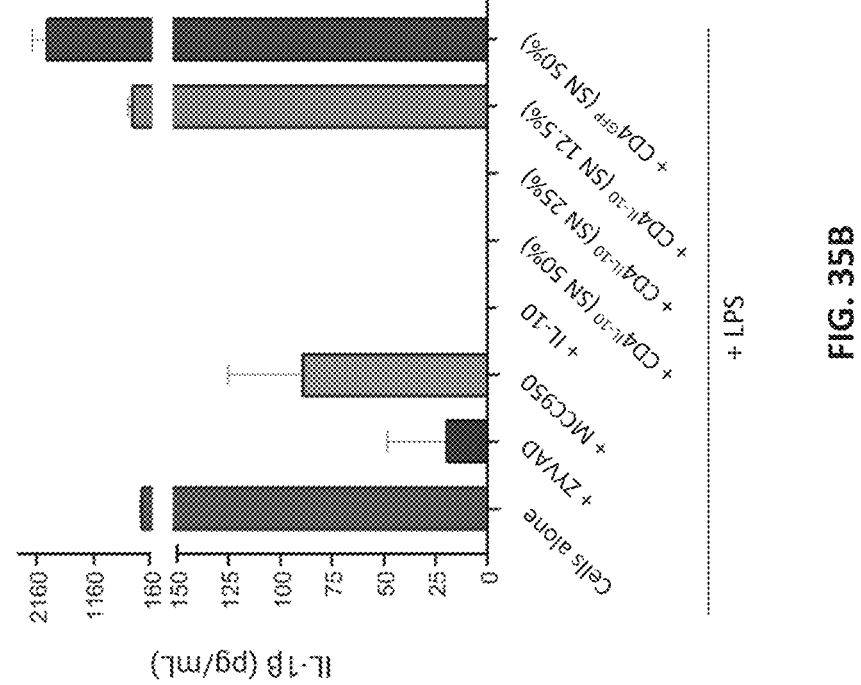
Figure 35C:
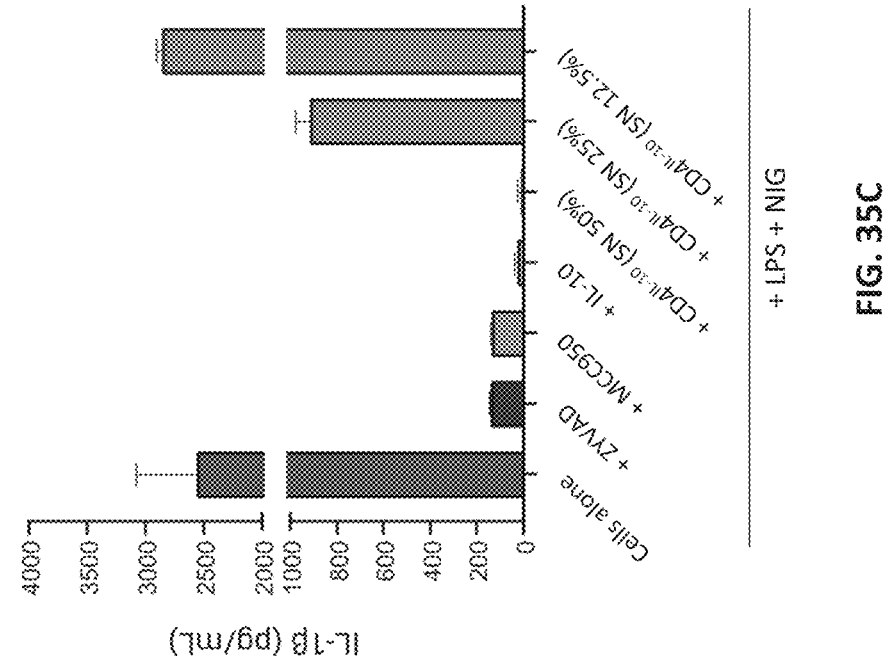
Figure 35D:
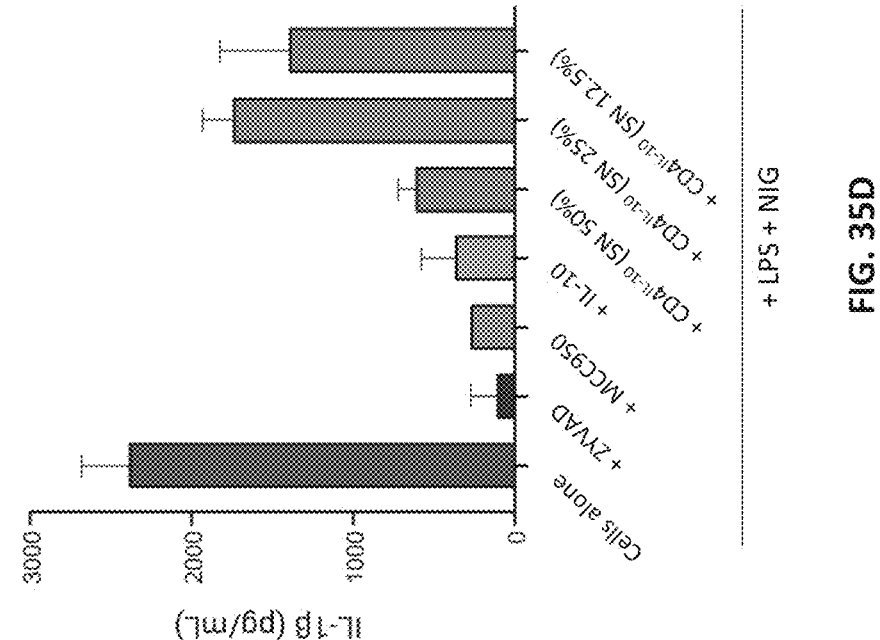
Figure 35E:
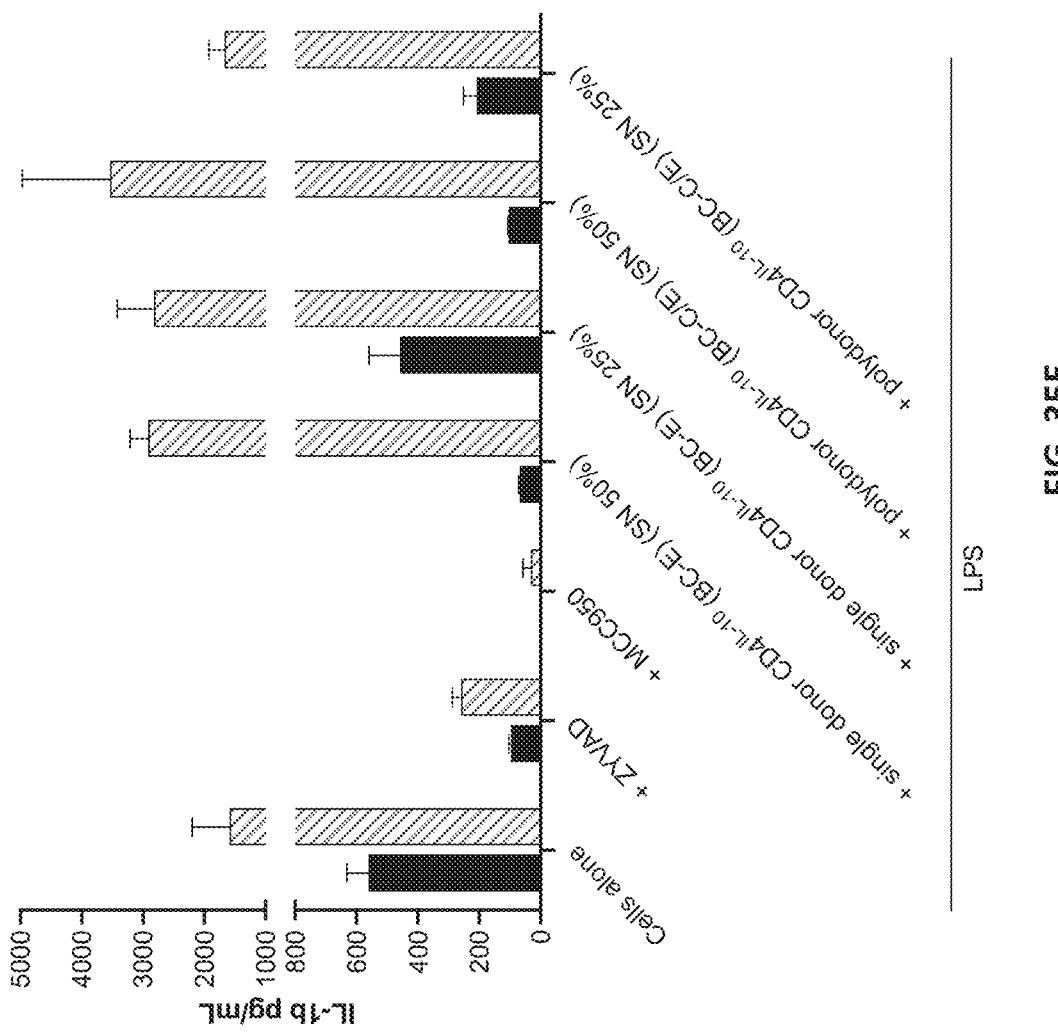
Figure 35F:
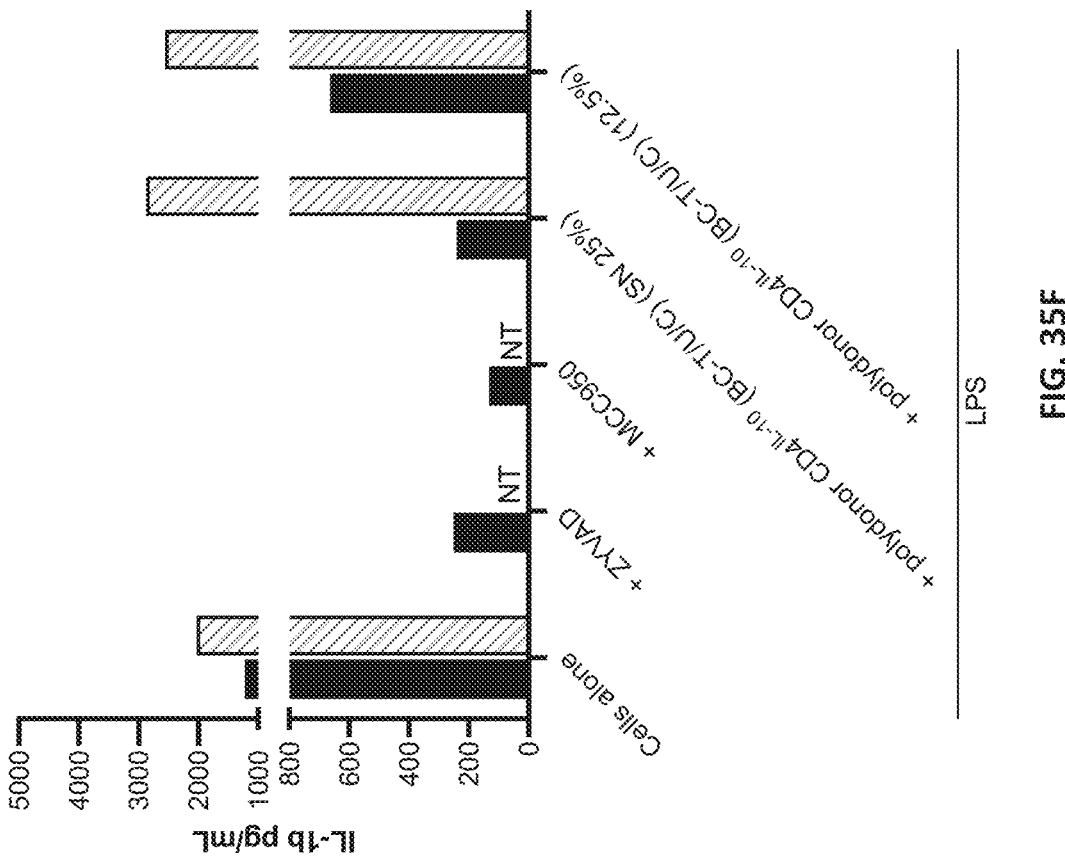
Figure 35G:
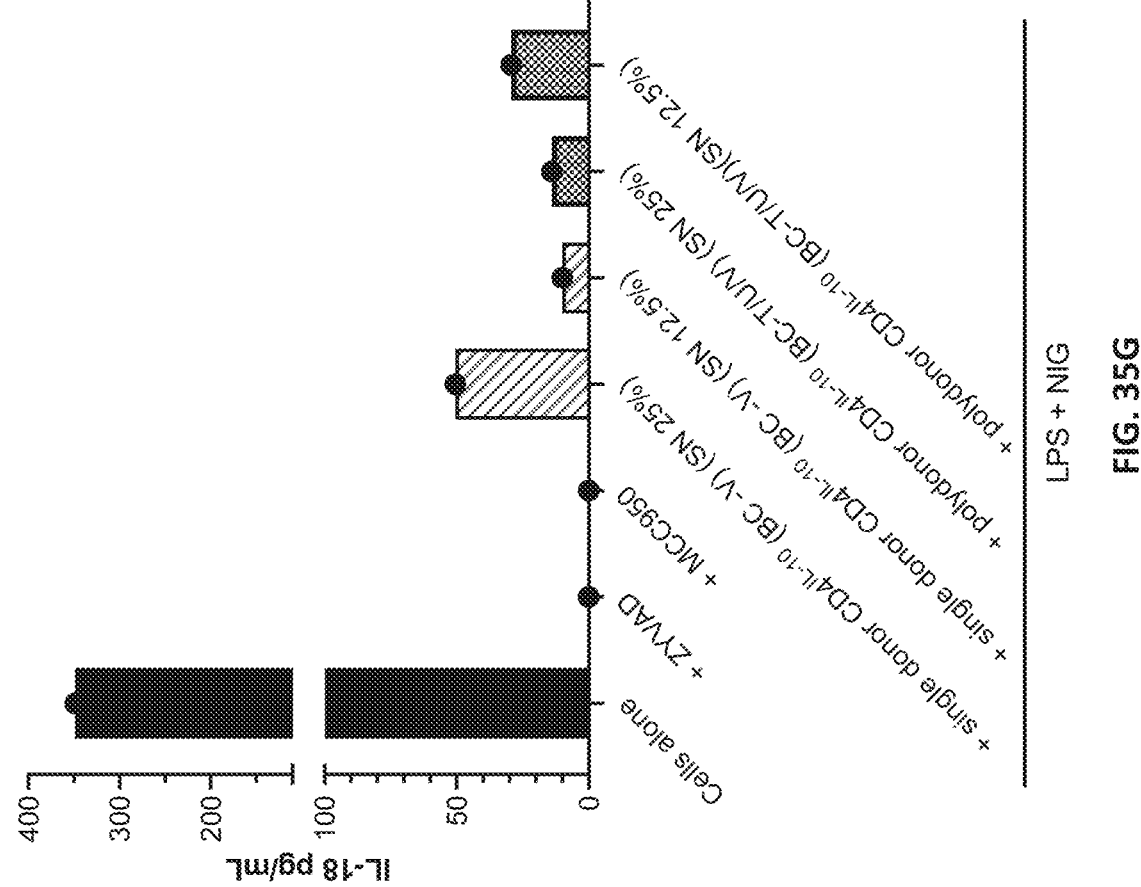

FIG. 35A-35G show inhibition of NLPR3 inflammasome activation by CD4$^{IL-10}$ cells. FIG. 35A shows the effect of CD4TL-10 cell supernatant from a single donor (#1) on the production of IL-1β by LPS activated monocytes. FIG. 35B shows the effect of CD4$^{IL-10}$ cell supernatant from another single donor (#2) on the production of IL-10 by LPS activated monocytes. FIG. 35C shows the effect of CD4$^{IL-10}$ cell supernatant from a single donor (#1) on the inhibition of LPS induced IL-1β production enhanced by NLPR3 inflammasome activator nigericine (NIG). FIG. 35D shows the effect of CD4$^{IL-10}$ cell supernatant from a single donor (#2) on the inhibition of LPS induced IL-1β production enhanced by NLPR3 inflammasome activator nigericine (NIG). FIG. 35E is a bar graph that shows the effect of CD4$^{IL-10}$ cell supernatant from a single donor and pooled cells from 2 different donors on LPS induced IL-1β production by monocytes in the presence or absence of anti-IL-10 receptor (anti-IL-10R) mAb. FIG. 35F shows the effect of polydonor CD4$^{IL-10}$ cell supernatants on IL-1β production by monocytes in the presence or absence of anti-IL-10 receptor (anti-IL-10R) mAb. FIG. 35G shows the effects of polydonor CD4$^{IL-10}$ cell supernatants on IL-18 production induced by LPS in combination with nigericin in the presence or absence of anti-IL-10R mAb.

Figure 36:
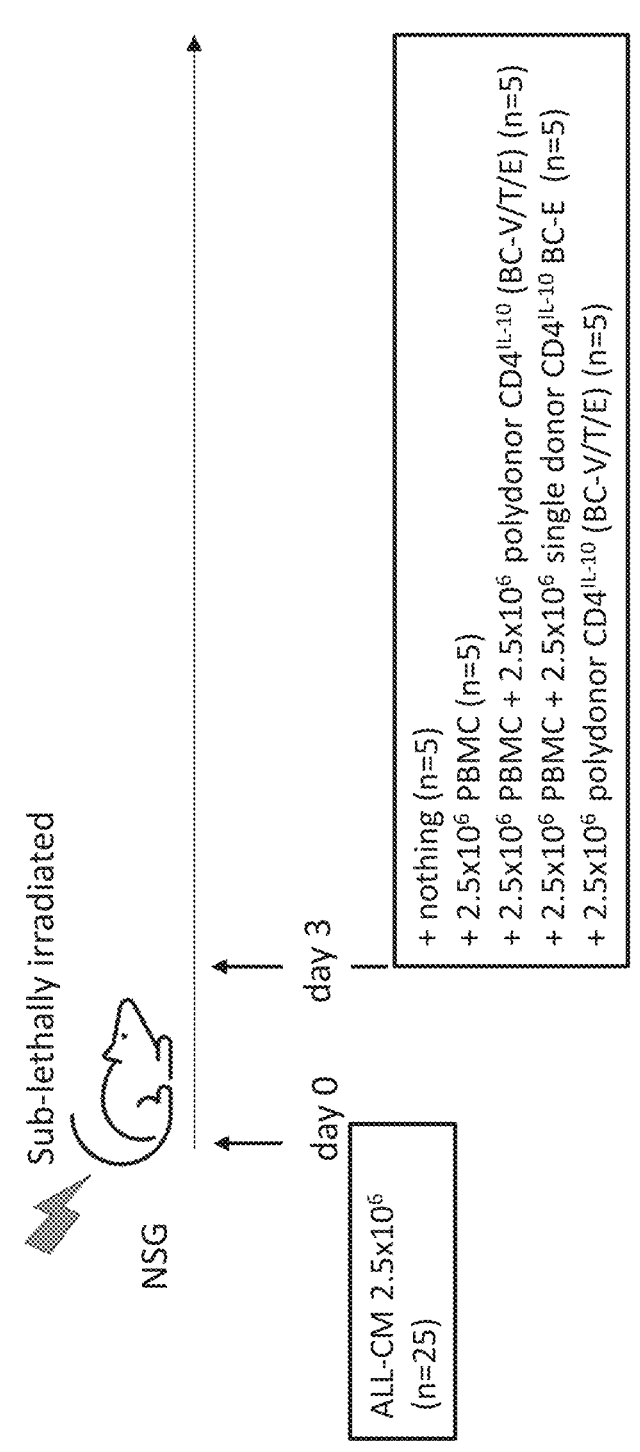

FIG. 36 illustrates an experimental protocol for testing graft versus myeloid leukemia and xeno-GvHD effects. NSG-mice were intravenously injected with ALL-CM cells) ($2.5×10°$ on day 0. At day 3 the mice were divided into five groups and each group was treated with (i) none as a control, (ii) allogeneic mononuclear cells (PBMC); (iii) allogeneic PBMC and polydonor CD4$^{IL-10}$ cells (BC-E, BC-V, BC-T, pooled 1:1:1); (iv) allogeneic PBMC and single-donor CD4$^{IL-10}$ cells (BC-E); or (v) polydonor CD4$^{IL-10}$ cells at concentrations as indicated in FIG. 36.

Figure 37:
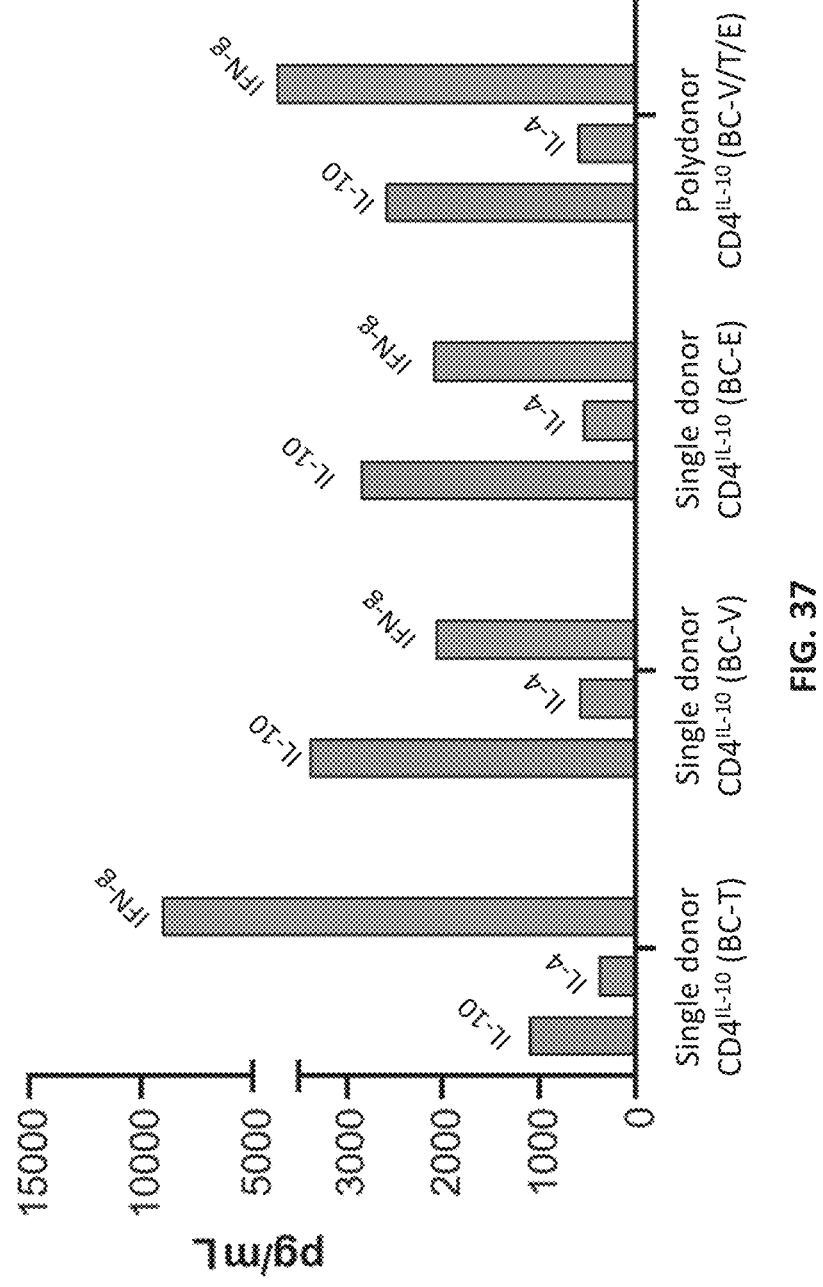

FIG. 37 is a bar graph depicting the cytokine secretion profiles of single-donor (BC-T, BC-V, and BC-E) and polydonor CD4$^{IL-10}$ cells (POOL: BC-E, BC-V and BC-T pooled 1:1:1).

Figure 38:
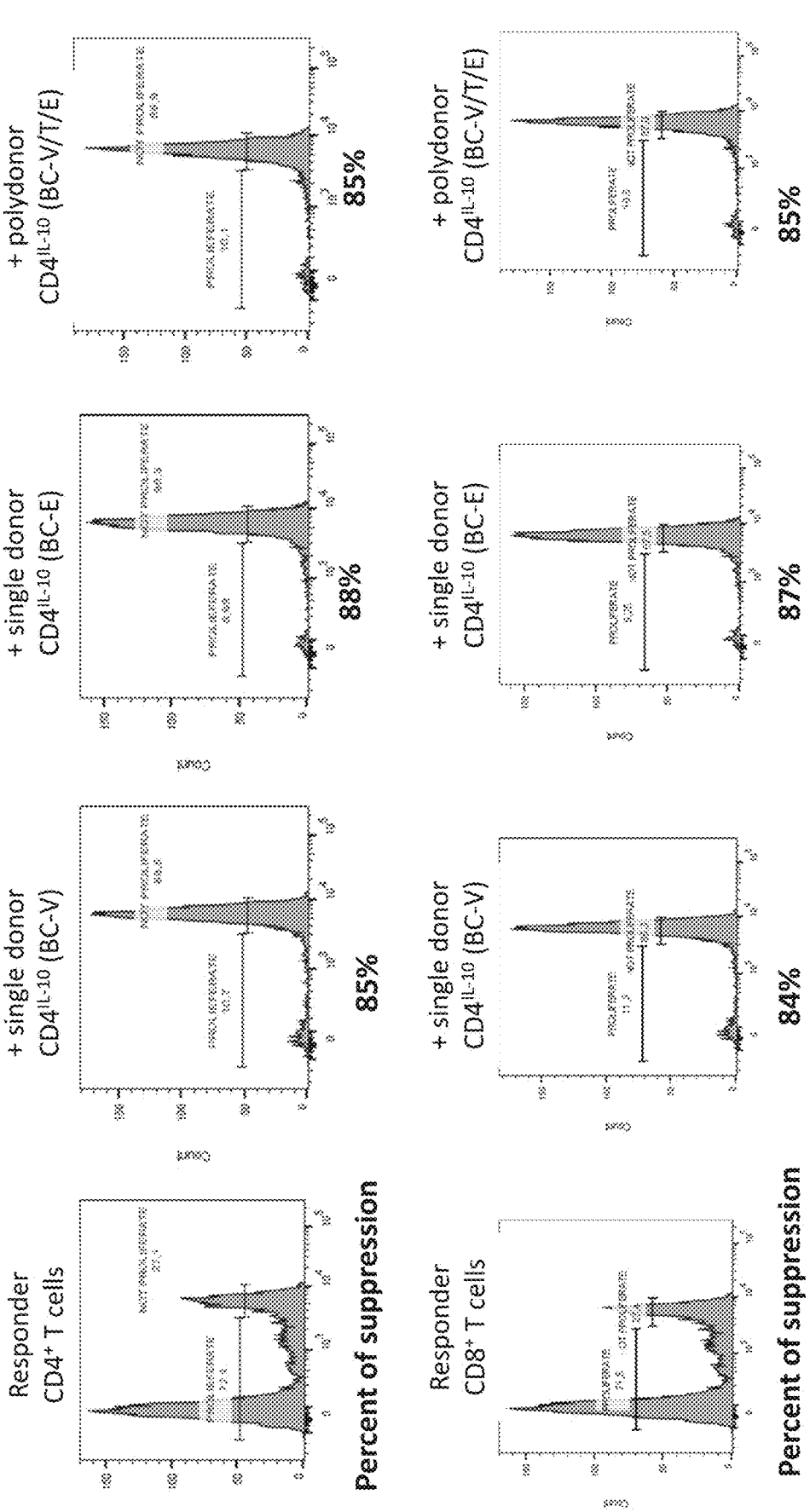

FIG. 38 show suppressive effects of single-donor (BC-V and BC-E) and polydonor CD4$^{IL-10}$ cells (pool of BC-V/E/T) on in vitro proliferation of allogeneic CD4+ and CD8+ T cells. Allogeneic PBMC cells were labeled with eFluor® 670 ($5×10^4$ cells/well) and stimulated with allogenic mature dendritic (DC) cells ($1×10^4$ cells/well) and soluble anti-CD3 mAbs in the absence or presence of CD4$^{IL-10}$ cells ($5×10^4$ cells/well) at a 1:1 Responder:Suppressor ratio. After 3 days of culture, the percentages of proliferating responder cells were determined by eFluor® 670 dilution with flow cytometry after gating on CD4$^+$-ΔNGFR (top) or CD8$^+$ ΔNGFR$^-$ (bottom) T cells. FIG. 38 shows results from single donors BC-V and BC-E and pooled cells from donors BC-V, BC-E and BC-T. Percentages of proliferation and suppression are indicated. The suppression mediated by CD4$^{IL-10}$ cells was calculated as follows: 100–([proliferation of responders in the presence of CD4$^{IL-10}$ cells/proliferation of responders alone]×100).

Figure 39:
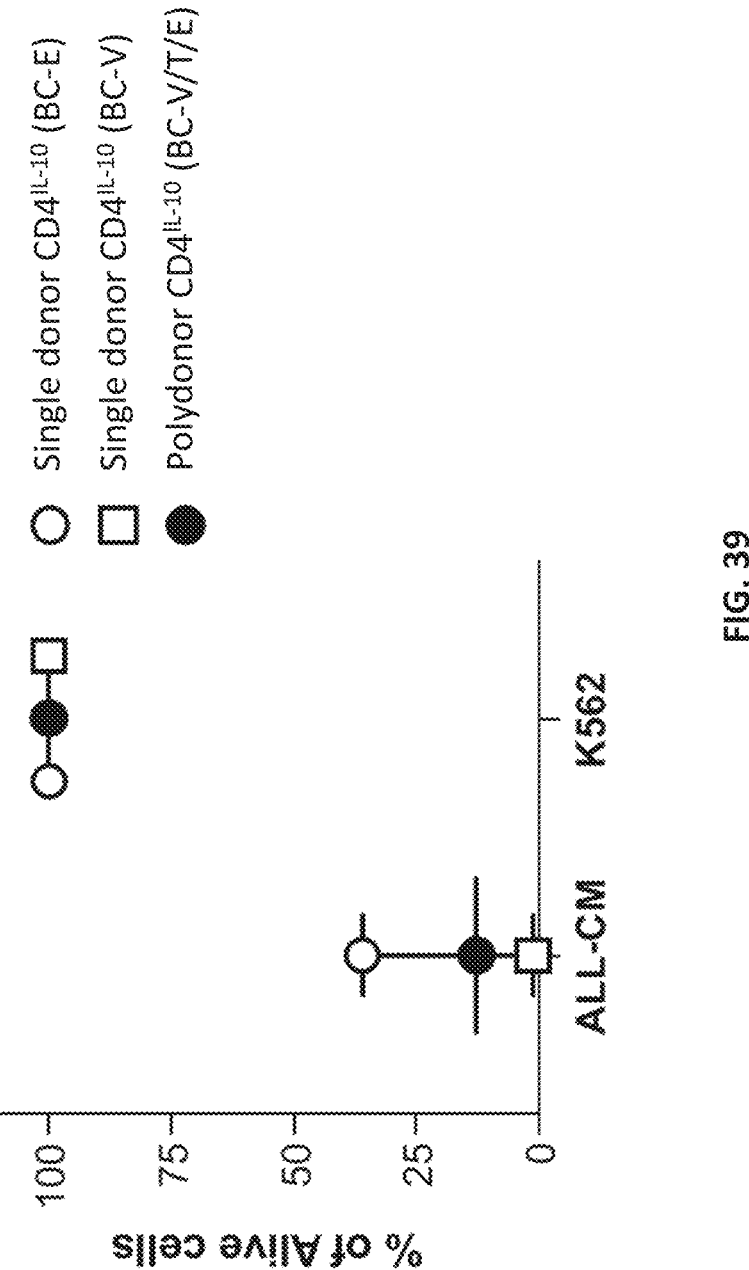

FIG. 39 shows % of alive cells in a co-culture of single (BC-E and BC-V) or polydonor CD4$^{IL-10}$ cells (BC-E+BC-V+BC-T) with ALL-CM myeloid tumor cells or K562 cells. The results show selective cytotoxic effect of single-donor and polydonor CD4$^{IL-10}$ cells on ALL-CM myeloid tumor cells, but not on K562 cells which lack Class I MHC expression.

Figure 40:
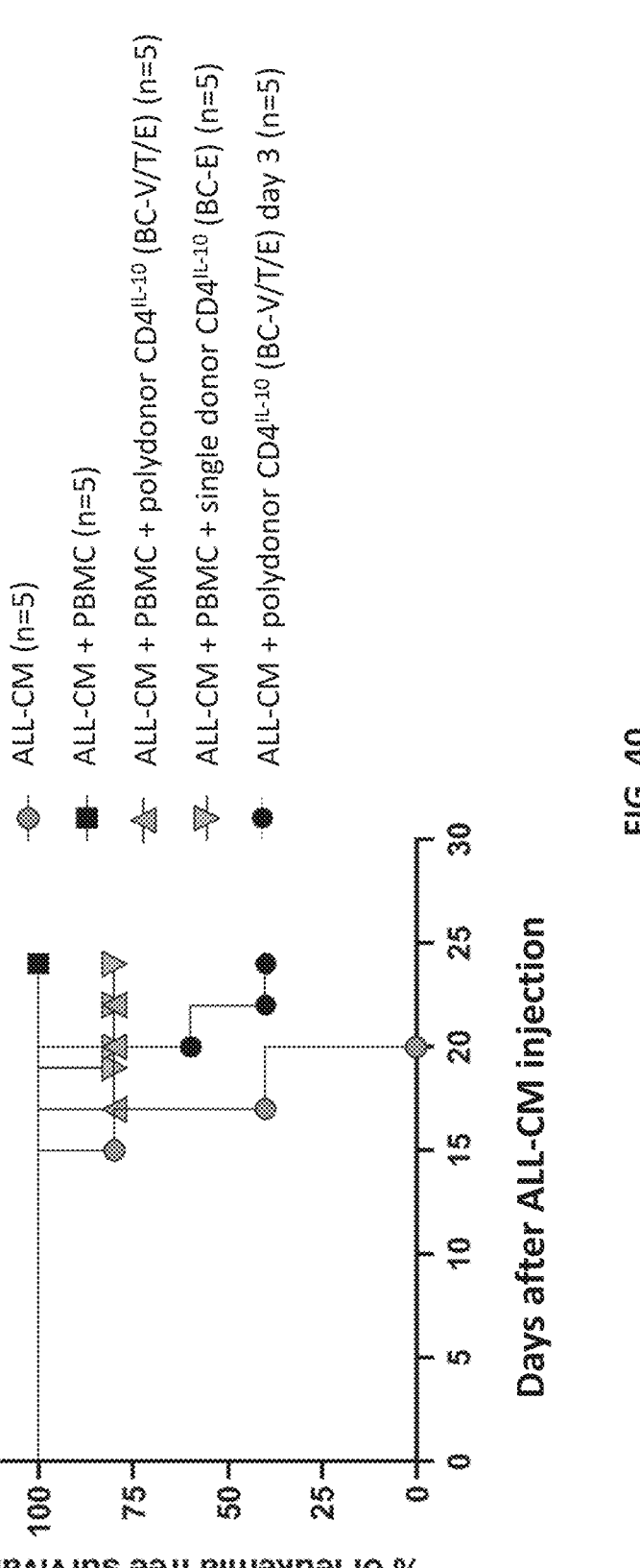

FIG. 40 shows leukemia-free survival rate measured in NSG-mice intravenously injected with ALL-CM cells (2.5× $10^6$) on day 0. At day 3 the mice were divided into five groups and each group was treated with (i) none as a control; (ii) allogeneic mononuclear cells (PBMC); (iii) allogeneic PBMC and polydonor CD4$^{IL-10}$ cells (B BC-V/T/ET); (iv) allogeneic PBMC and single-donor CD4$^{IL-10}$ cells (BC-E) or (v) polydonor CD4$^{IL-10}$ cells. The graph shows leukemia-free survival rate of animals in each group.

Figure 41:
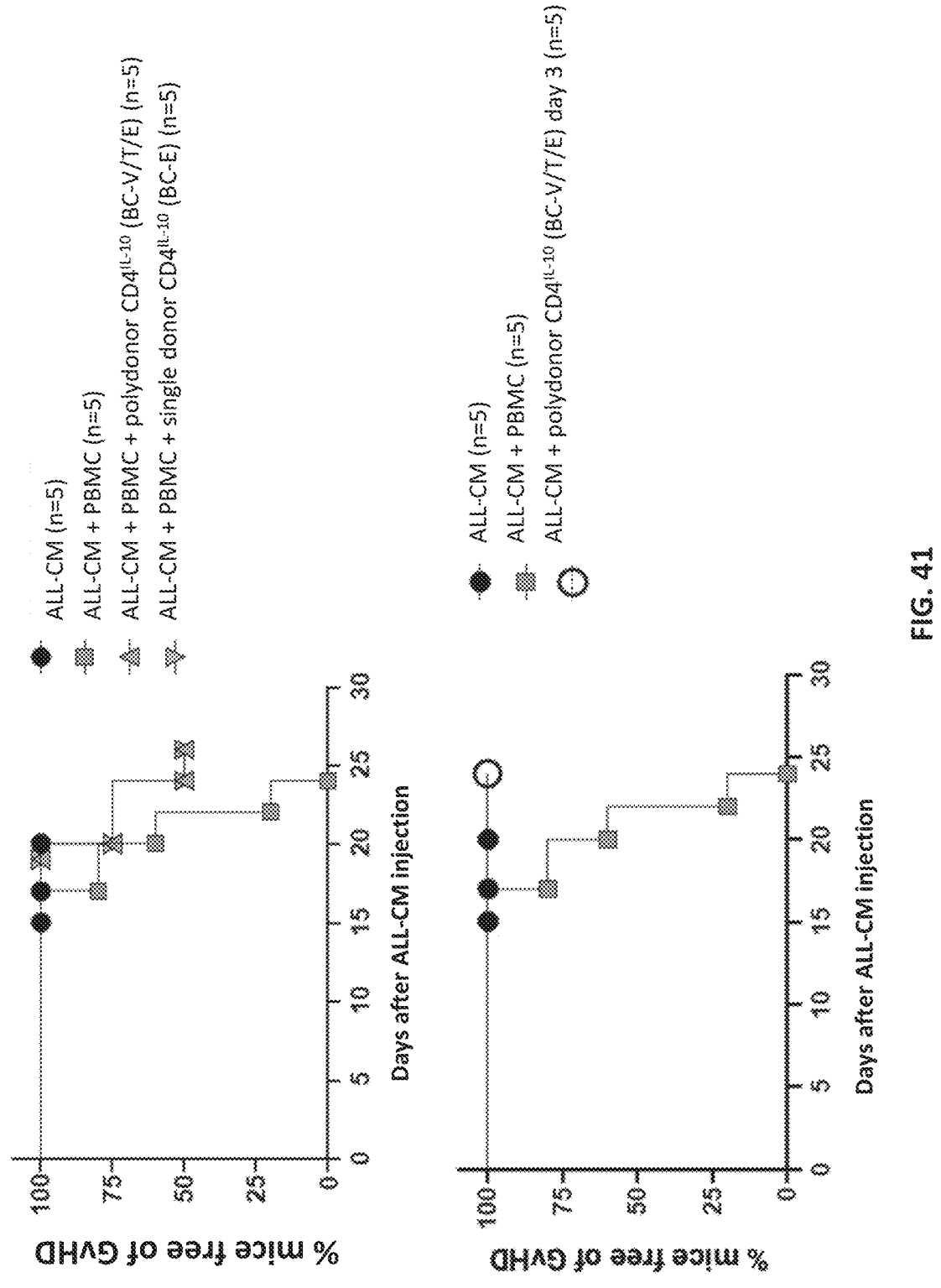

FIG. 41 shows % of NSG mice free of GvHD on each day following injection with ALL-CM cells (2.5×$10^6$) and subsequent administration of (i) none as a control; (ii) allogeneic mononuclear cells (PBMC); (iii) allogeneic PBMC and polydonor CD4$^{IL-10}$ cells (BC-E, BC-V, BC-T); (iv) allogeneic PBMC and single-donor CD4$^{IL-10}$ cells (BC-E) or (v) polydonor CD4$^{IL-}$10 cells were administered at day 3.

Figure 42:
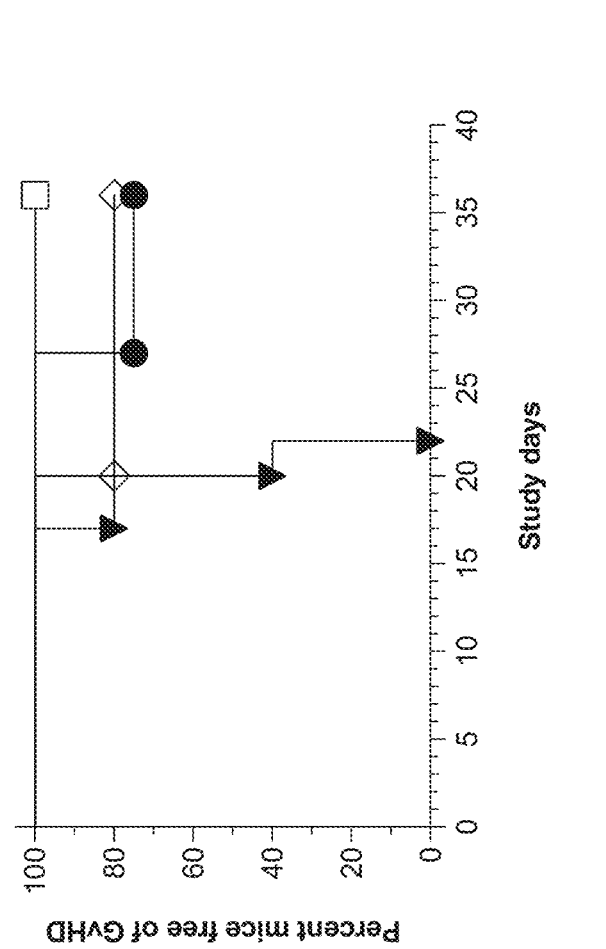

FIG. 42 shows that NSG mice dosed with 2.5E+06 of PBMC (allogeneic to the donors C, E, F and H) all succumbed to acute, and lethal xeno-GvHD at day 22. Administration of single-donor CD4$^{IL-10}$ cells (lot C) or polydonor CD4$^{IL-10}$ cells (lot CEFH) in combination with the PBMCs prevented the development of lethal xeno-GvHD in 75% (3/4 mice) and 80% (4/5 mice) of the mice, respectively. In contrast, transfer of 2.5E+06 polydonor CD4$^{IL-10}$ cells did not induce any sign of GvHD. Taken together these results indicate that polydonor CD4$^{IL-10}$ cells from 4 different donors suppress pathogenic human T cell responses as potently, or slightly more potently than single-donor CD4$^{IL-}$10 cells. PBMC: peripheral mononuclear cells; GvHD: graft vs. host disease.

FIG. 43A shows alignment of IL-10 protein sequences of various species, including human (SEQ ID NO: 1), *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66).

FIG. 43B provides sequences of IL-10 variants generated by substituting one or more amino acids of human IL-10 by amino acids of viral IL-10 (EBVB9) at the corresponding positions. Also provided are sequences of the exemplary variants, possible huIL-10 hybrid #1 (SEQ ID NO: 67) and possible huIL-10 hybrid #2 (SEQ ID NO: 68). "*" indicates the one or more amino acid positions that are substituted. "#" indicates the preferred 1105 to A10$^5$ amino acid substitution for IL-10 hybrid #2 (SEQ ID NO: 68).

FIG. 43C shows alignment of human IL-10 (SEQ ID NO: 1) with IL10 EBVB9 (SEQ ID NO: 66). "*" indicates the one or more amino acid positions that are substituted in IL-10 hybrid #1. "#" indicates the preferred 1105 to A10$^5$ amino acid substitution for IL-10 hybrid #2.

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

"Graft-versus-leukemia effect" or "GvL" refers to an effect that appears after allogeneic hematopoietic stem cell transplantation (HSCT) or bone marrow transplantation (BMT). T lymphocytes in the allogeneic graft eliminate malignant residual host leukemia cells.

"Graft versus tumor effect" or "GvT refers to an effect that appears after allogeneic hematopoietic stem cell transplantation (HSCT) or bone marrow transplantation (BMT). T lymphocytes in the allogeneic graft eliminate malignant residual host cancer cells, e.g., cells of myeloma and lymphoid and myeloid leukemias, lymphoma, multiple myeloma and possibly breast cancer. The term GvT is generic to GvL.

The terms "treatment", "treating", and the like are used herein in the broadest sense understood in the medical arts. In particular, the terms generally mean obtaining a desired pharmacologic and/or physiologic effect. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

"HLA-matched" as used herein refers to a pair of individuals having a matching HLA allele in the HLA class I (HLA-A, HLA-B, and HLA-C) and class II (HLA-DRB1 and HLA-DQB1) loci that allow the individuals to be immunologically compatible with each other. HLA compatibility can be determined using any of the methods available in the art, for example, as described in Tiervy, Haematologica 2016 Volume 101(6):680-687, which is incorporated by reference herein.

For a given locus, a pair of individuals have 2/2 match when each of two alleles of one individual match with the two alleles of the other individual. A pair of individuals have ½ match when only one of two alleles of one individual match with one of two alleles of the other individual. A pair of individuals have 10/10 match at the HLA-A, HLA-B, HLA-C, HLA-DRB1, and HLA-DQB1 loci when all of the ten alleles (two for each of the HLA-A, HLA-B, HLA-C, HLA-DRB1, and HLA-DQB1 loci) of one individual match with all ten alleles of the other individual.

In preferred embodiments, allele level typing is used for determination of HLA compatibility. Allele level typing corresponds to a unique nucleotide sequence for an HLA gene, as defined by using all digits in the first, second, third and fourth fields, e.g. A*02:01:01:01. Functionally, the third and fourth fields which characterize alleles that differ, respectively, by silent substitutions in the coding sequence and by substitutions in the non-coding sequence, are irrelevant, except when substitutions prevent the expression of HLA alleles (e.g., the null allele B*15:01:01:02N). Missing a null allele will lead to a mismatch that is very likely to be recognized by alloreactive T cells and have a deleterious clinical impact. Substitutions in non-coding sequences may influence the level of expression (e.g., the A24low allele A*24:02:01:02L). Such variability may also have an impact on anti-HLA allorecognition.

The term "HLA-mismatched" as used herein refers to a pair of individuals having a mis-matching HLA allele in the HLA class I (HLA-A, HLA-B, and HLA-C) and class II (HLA-DRB1 and HLA-DQB1) loci that make the individuals to be immunologically incompatible with each other.

The term "partially HLA-mismatched" as used herein refers to a pair of individuals having a mis-matching HLA allele in the HLA class I (HLA-A, HLA-B, and HLA-C) and class II (HLA-DRB1 and HLA-DQB1) loci that make the individuals to be immunologically incompatible with each other in a permissible degree. Some studies have identified permissive mismatches. Some HLA class I incompatibilities are considered to be more permissive.

"HLA haplotype" refers to a series of HLA loci-alleles by chromosome, one passed from the mother and one from the father. Genotypes for HLA class I (HLA-A, HLA-B, and HLA-C) and class II (HLA-DRB1 and HLA-DQB1) loci can be used to determine the HLA haplotype.

The term "therapeutically effective amount" is an amount that is effective to treat, and thus ameliorate a symptom of a disease.

The term "prophylactically effective amount" is an amount that is effect in terms of completely or partially preventing a disease, condition, or symptoms thereof.

The term "ameliorating" refers to any therapeutically beneficial result in the treatment of a disease state, e.g., a neurodegenerative disease state, including prophylaxis, lessening in the severity or progression, remission, or cure thereof.

The term "CD4$^{IL-10/CAR}$" refers to any CD4$^{IL-10}$ cell genetically modified to express a chimeric antigen receptor. In cases where CD4$^{IL-10/CAR}$ refers to a specific chimeric antigen receptor, nomenclature can include a designation of the specificity of the CAR, for example, "CD4$^{IL-10/anti-[antigen]\ CAR}$" cell. For example, CD4$^{IL-10/CAR}$ and CD4$^{IL-10/CD19\ CAR}$ can be used interchangeably.

The term "autologous" as used herein refers to cells derived from the same individual (e.g., patient) to whom the cells are re-introduced.

The term "allogeneic" as used herein refers to cells taken from two or more different individuals of the same species that are not genetically identical.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

6.3. CD4$^{IL-10/CAR}$ Cells

In a first aspect, a CD4$^+$ T cell or a population of CD4$^+$ T cells are described that have been genetically modified to express a chimeric antigen receptor (CAR) from a first exogenous polynucleotide encoding the CAR and to express IL-10 from a second exogenous polynucleotide encoding IL-10 (CD) 4$^{IL-10/CAR}$ cells).

6.3.1. CD4$^+$ T Cells and T Cell Donors

CD4$^+$ T cells used for generating CD4$^{IL-10/CAR}$ (autologous or allogeneic single-donor CD4$^{IL-10/CAR}$ or allogeneic polydonor CD4$^{IL-10/CAR}$) populations can be isolated from peripheral blood, cord blood, or other blood samples from a donor, preferably a human donor, using methods available in the art. In typical embodiments, CD4$^+$ T cells are isolated from peripheral blood. In certain embodiments, CD4$^+$ T cell are isolated using leukapheresis and buffy coats. In certain embodiments, CD4$^+$ T cells are isolated from peripheral blood obtained from third parties.

In some embodiments, CD4$^+$ T cells are isolated from a prior-frozen stock of blood or a prior-frozen stock of peripheral blood mononuclear cells (PBMCs) or a prior-frozen stock of CD4$^+$ T cells. In some embodiments, CD4$^+$ T cells are isolated from peripheral blood or from PBMCs that have not previously been frozen. In some embodiments, the CD4$^+$ T cells are separately isolated from blood or PBMCs obtained from individual donors, and then pooled. In some embodiments, the CD4$^+$ T cells are isolated from blood or PBMCs that have first been pooled from a plurality of donors.

In some embodiments, the CD4$^+$ T cells are obtained from a single T cell donor. In some embodiments, the CD4$^+$ T cells are obtained from two, three, four, five, six, seven, eight, nine, or ten different T cell donors.

In some embodiments, the CD4$^+$ T cells are obtained from the patient who will be treated with the CD4$^{IL-10/CAR}$ cells.

In some embodiments, the one or more T cell donors are selected without regard to genotype. In some embodiments, the one or more T cell donors are selected based on genotype.

In certain embodiments, the one or more T cell donors are selected based on their HLA haplotypes.

In some embodiments, some or all of the at least two different T cell donors have matching HLA haplotypes. In some embodiments, some or all of the at least two different T cell donors have a mis-matched HLA haplotype.

In some embodiments, all of the CD4$^+$ T cells in the population have at least 1/10, 2/10, 3/10, 4/10, 5/10, 6/10, 7/10, 8/10, or 9/10 match at the HLA-A, HLA-B, HLA-C, HLA-DRB1, and HLA-DQB1 loci to each other. In some embodiments, all of the CD4$^+$ T cells in the population have at least 1/8, 2/8, 3/8, 4/8, 5/8, 6/8, 7/8, or 8/8 match at the HLA-A, HLA-B, HLA-C, and HLA-DRB1 loci to each other. In some embodiments, all the CD4$^+$ T cells in the population have 2/2 match at the HLA-A locus to each other. In some embodiments, all the CD4$^+$ T cells in the population have 2/2 match at the HLA-B locus to each other. In some embodiments, all the CD4$^+$ T cells in the population have 2/2 match at the HLA-C locus to each other. In some embodiments, all the CD4$^+$ T cells in the population have at least 3/4 or 4/4 match at the HLA-DRB1 and HLA DQB1 loci with each other. In some embodiments, all the CD4$^+$ T cells in the population have an A*02 allele or A*24 allele.

In some embodiments, none of the one or more T cell donors is a host to be treated with the CD4$^{IL-10/CAR}$ cells. In some embodiments, none of the one or more T cell donors is a donor of stem cells (e.g., HSC), tissue or organ that will be used together with the CD4$^{IL-10/CAR}$ cells in the methods of treatment described herein. In some embodiments, one or more of the T cell donors is a host to be treated with the CD4$^{IL-10/CAR}$ cells.

In some embodiments, one or more of the T cell donors are HLA-mismatched or partially HLA-mismatched to the patient to be treated (host). In some embodiments, one or more of the T cell donors have less than 5/10, 6/10, 7/10, 8/10, 9/10 or 10/10 match at the HLA-A, HLA-B, HLA-C, HLA-DRB1, and HLA-DQB1 loci to the patient. In some embodiments, one or more of the T cell donors have less than 4/8, 5/8, 6/8, 7/8, or 8/8 match at the HLA-A, HLA-B, HLA-C. and HLA-DRB1 loci to the patient. In some embodiments, one or more of the T cell donors have less than 2/2 match at the HLA-A, HLA-B, or HLA-C locus to the patient. In some embodiments, one or more of the T cell donors have less than 2/4, 3/4 or 4/4 match at the HLA-DRB1 and HLA-DQB1 loci to the patient.

In some embodiments, one or more of the T cell donors are HLA-mismatched or partially HLA-mismatched with the HSC donor. In some embodiments, one or more of the T cell donors have less than 5/10, 6/10, 7/10, 8/10, 9/10 or 10/10 match at the HLA-A, HLA-B, HLA-C, HLA-DRB1, and HLA-DQB1 loci to the HSC donor. In some embodiments, one or more of the T cell donors have less than 4/8, 5/8, 6/8, 7/8, or 8/8 match at the HLA-A, HLA-B, HLA-C, and HLA-DRB1 loci to the HSC donor. In some embodiments, one or more of the T cell donors have less than 2/2 match at the HLA-A, HLA-B, or HLA-C locus to the HSC donor. In some embodiments, one or more of the T cell donors have less than ¾ or 4/4 match at the HLA-DRB1 and HLA-DQB1 loci to the HSC donor.

In the preferred embodiments, none of the CD4$^+$ T cells are immortalized.

6.3.2. Exogenous Polynucleotide Encoding CAR

CD4$^{IL10/CAR}$ cells of the present disclosure are CD4$^+$ T cells that have been genetically modified to express comprise a first exogenous polynucleotide segment encoding a chimeric antigen receptor (CAR) from a first exogenous polynucleotide segment encoding the CAR. CARs have a modular design with four major components: an antigen-binding domain, a hinge, a transmembrane domain and an intracellular signaling domain. Each of these elements has a distinct function and, optimal molecular design of the CAR can be achieved through many variations of the constituent protein domains, as described in Rafiq et al. (*Nat. Rev. Clin. Onco.*, 17:147-167 (2020), which is herein incorporated by reference in its entirety).

In some embodiments, the CAR encoding polynucleotide segment encodes a first-generation CAR, a second-generation CAR, or a third-generation CAR. In some embodiments, a first-generation CAR includes an antigen-binding domain, a hinge region, a transmembrane domain, and an intracellular signaling domain. In some embodiments, a second-generation CAR includes an antigen-binding domain, a hinge region, a transmembrane domain, a co-stimulatory domain, and an intracellular signaling domain. Non-limiting examples of second-generation CAR include those described in U.S. Patent Publication Nos. 2004/0043401, 2013/0287748, 2014/0227237, 2014/0099309, and 2014/0050708; WO 2012/079000; and WO 2015/157252, which are herein incorporated by reference in their entireties.

In some embodiments, a second-generation CAR is a pCAR. In some embodiments, a pCAR comprises a second generation CAR comprising: (i) (a) a signaling region; (b) a co-stimulatory signaling region; (c) a transmembrane domain; and (d) a first binding element that specifically interacts with a first epitope on a target antigen; and (ii) a chimeric co-stimulatory receptor (CCR) comprising (e) a co-stimulatory signaling region which is different from that of (b); (f) a transmembrane domain; and (g) a second binding element that specifically interacts with a second epitope on a second target antigen. Non-limiting examples of pCAR are as described in U.S. Pat. No. 10,703,794, which is herein incorporated by reference in its entirety.

In some embodiments, a third-generation CAR comprises an antigen-binding domain, a hinge region, a transmembrane domain, a first co-stimulatory domain and a second co-stimulatory domain, and an intracellular signaling domain. Non-limiting examples of a third-generation CAR include those described in U.S. Patent Publication Nos. 2014/0322275A1; 2019/0345217; 2019/0112380A1; and 2020/0031904A1; which are herein incorporated by reference in their entireties.

In some embodiments, the antigen binding domain comprises a single chain antibody fragment (e.g., an scFv), nanobody (e.g., camelid V$_H$H domains), cytokines, ligands, or a peptide (adenectins and DARPins).

6.3.2.1. Antigen-Binding Domain

In some embodiments, the antigen-binding domain of the CAR comprises a single chain antibody fragment. In some embodiments, the single chain antibody fragment comprises a single chain Fv (scFv).

In some embodiments, the antigen-binding domain targets an antigen associated with an autoimmune disease, inflammatory disorders, or cancer. In some embodiments, the antigen-binding domain targets an autoantigen.

In some embodiments, the antigen-binding domain targets an antigen associated with an autoimmune disease or inflammatory disorder. In some embodiments, an antigen associated with an autoimmune disease or inflammatory disorder is selected from the group consisting of but not limited to: anti-HLA-A*02, anti-HLA-A*24 or citrullinated peptides, insulin, MOG, GAD65, LA2, gliadin, and desmoglein in the context of relevant MHC molecules. In some embodiments, an antigen associated with an autoimmune disease or inflammatory disorder is selected from the group consisting of: CD19, CD20, CD22, CD27, BCMA and CD38.

In some embodiments, the antigen-binding domain targets a cancer-associated antigen. In some embodiments, a cancer-associated antigen is selected from the group consisting of: CD19, CD20, CD22, BCMA, B7-H3, CEA, BCMA, CD23, Lym1, Lym2, CLEC5A, CDH179b, FLT3, GCC, Muc, CSF2RA, GFRa4, CD32, CD33, IL1IRa, IL13Ra, NYBRI, SLea, CD200R, TGFBetaR2, CD276, TROP2, LAMP1, PTK7, DLL3, CDH1, CDH6, CDH17, CDH19, TSHR and tyrosinase.

In some embodiments, the antigen-binding domain targets a B cell antigen. In some embodiments, a B cell antigen is selected based in part on its expression during B-cell differentiation, for example, as shown in FIG. 4. Non-limiting examples of antigen-binding domains that target B cell antigens are described in WO 2020/010235, which is herein incorporated by reference in its entirety. In some embodiments, the antigen-binding domain targets CD19. In some embodiments, the antigen-binding domain targets CD20. In some embodiments, the antigen-binding domain targets CD22. In some embodiments, the antigen-binding domain targets BCMA. In some embodiments, the antigen-binding domain targets B7-H3. In some embodiments, the antigen-binding domain targets CD27. In some embodiments, the antigen-binding domain targets CD38. In some embodiments, the antigen-binding domain targets B cell maturation antigen (BCMA). In some embodiments, the antigen-binding domain targets carcinoembryonic antigen (CEA).

In some embodiments, the single chain antibody fragment comprises a single chain Fv (scFv) that binds to CD19 (e.g., cluster of differentiation 19 protein (CD19) (e.g., OMIM Acc. No. 107265)).

In some embodiments, the scFv that targets CD19 is derived from an anti-human CD19-specific mAb clone FMC63 (Nicholson et al., *Mol. Immunol.*, 34(16-17):1157-65 (1997), which is herein incorporated by reference in its entirety). In some embodiments, the scFv that targets CD19 is described in U.S. Patent Publication Nos. 2018/0355052 or 2020/0392200, or WO 2020/010235, each of which are herein incorporated by reference in their entireties.

In some embodiments, the anti-CD19 antigen binding domain comprises the sequence of SEQ ID NO: 11. In some embodiments, the anti-CD19 antigen-binding domain comprises a sequence having at least 80%, 85%, 90%, 95%, 98%, or 99% sequence identity to SEQ ID NO: 11. In some embodiments, the polynucleotide segment encoding an anti-CD19 antigen-binding domain comprises the SEQ ID NO: 12. In some embodiments, the polynucleotide segment encoding an anti-CD19 antigen-binding domain comprises a sequence having at least 80%, 85%, 90%, 95%, 98%, or 99% sequence identity to SEQ ID NO: 12.

In some embodiments, the anti-CD19 antigen-binding domain comprises a heavy chain variable domain comprising a sequence having at least 80%, 85%, 90%, 95%, 98%, or 99% sequence identity to SEQ ID NO: 13. In some embodiments, the anti-CD19 antigen-binding domain comprises a light chain variable domain comprising a sequence having at least 80%, 85%, 90%, 95%, 98%, or 99% sequence identity to SEQ ID NO: 14. In some embodiments, the anti-CD19 antigen-binding domain comprises a heavy chain variable domain comprising a sequence having at least 80%, 85%, 90%, 95%, 98%, or 99% sequence identity to SEQ ID NO: 13 and a light chain variable domain comprising a sequence having at least 80%, 85%, 90%, 95%, 98%, or 99% sequence identity to SEQ ID NO: 14.

In some embodiments, the single chain antibody fragment comprises a single chain Fv (scFv) that binds to CD20 (e.g., cluster of differentiation 20 protein (CD20) (e.g., OMIM Acc. No. 112210)). Non-limiting examples of scFvs that target CD20 include those described in WO 2020/010235 and U.S. Patent Publication No. 2020/0392200, which are herein incorporated by reference in their entireties.

In some embodiments, the anti-CD20 antigen binding domain comprises the sequence of SEQ ID NO: 18. In some embodiments, the anti-CD20 antigen-binding domain comprises a sequence having at least 90%, 95%, 98%, or 99% sequence identity to SEQ ID NO: 18. In some embodiments, the polynucleotide segment encoding an anti-CD20 antigen-binding domain comprises the SEQ ID NO: 19. In some embodiments, the polynucleotide segment encoding an anti-CD20 antigen-binding domain comprises a sequence having at least 80%, 85%, 90%, 95%, 98%, or 99% sequence identity to SEQ ID NO: 19.

In some embodiments, the anti-CD20 antigen-binding domain comprises a heavy chain variable domain comprising a sequence having at least 80%, 85%, 90%, 95%, 98%, or 99% sequence identity to SEQ ID NO: 20. In some embodiments, the anti-CD20 antigen-binding domain comprises a light chain variable domain comprising a sequence having at least 80%, 85%, 90%, 95%, 98%, or 99% sequence identity to SEQ ID NO: 21. In some embodiments, the anti-CD20 antigen-binding domain comprises a heavy chain variable domain comprising a sequence having at least 80%, 85%, 90%, 95%, 98%, or 99% sequence identity to SEQ ID NO: 20 and a light chain variable domain comprising a sequence having at least 80%, 85%, 90%, 95%, 98%, or 99% sequence identity to SEQ ID NO: 21.

In some embodiments, the single chain antibody fragment comprises a single chain Fv (scFv) that binds to CD22 (e.g., cluster of differentiation 22 protein (CD22) (e.g., OMIM Acc. No. 107266)). Non-limiting examples of scFvs that target CD22 include those described in WO 2020/010235 and U.S. Patent Publication No. 2020/0392200, which are herein incorporated by reference in their entireties.

In some embodiments, the anti-CD22 antigen binding domain comprises the sequence of SEQ ID NO: 24. In some embodiments, the anti-CD22 antigen-binding domain comprises a sequence having at least 80%, 85%, 90%, 95%, 98%, or 99% sequence identity to SEQ ID NO: 24. In some embodiments, the polynucleotide segment encoding an anti-CD22 antigen-binding domain comprises the SEQ ID NO: 25. In some embodiments, the polynucleotide segment encoding an anti-CD22 antigen-binding domain comprises a sequence having at least 80%, 85%, 90%, 95%, 98%, or 99% sequence identity to SEQ ID NO: 25.

In some embodiments, the anti-CD22 antigen-binding domain comprises a heavy chain variable domain comprising a sequence having at least 80%, 85%, 90%, 95%, 98%, or 99% sequence identity to SEQ ID NO: 26. In some embodiments, the anti-CD22 antigen-binding domain comprises a light chain variable domain comprising a sequence having at least 80%, 85%, 90%, 95%, 98%, or 99% sequence identity to SEQ ID NO: 27. In some embodiments, the anti-CD22 antigen-binding domain comprises a heavy chain variable domain comprising a sequence having at least 80%, 85%, 90%, 95%, 98%, or 99% sequence identity to SEQ ID NO: 26 and a light chain variable domain comprising a sequence having at least 80%, 85%, 90%, 95%, 98%, or 99% sequence identity to SEQ ID NO: 27.

In some embodiments, the single chain antibody fragment comprises a single chain Fv (scFv) that binds to B-cell maturation antigen (BCMA) also known as tumor necrosis factor receptor superfamily member 17 (TNFRSF17).

Non-limiting examples of scFvs that target BCMA include those described in U.S. Pat. No. 9,765,342B2 or WO 2010/104949 which are incorporated by reference in their entireties. For example, as described in WO 2010/104949, the anti-BCMA scFv can include the antigen binding domain of the A7D12.2, C11 D5.3, C12A3.2, or C13F12.1 antibody.

In some embodiments, the anti-BCMA antigen-binding domain comprises a heavy chain variable domain comprising a sequence having at least 80%, 85%, 90%, 95%, 98%, or 99% sequence identity to SEQ ID NO: 50 or 52. In some embodiments, the anti-BCMA antigen-binding domain comprises a light chain variable domain comprising a sequence having at least 80%, 85%, 90%, 95%, 98%, or 99% sequence identity to SEQ ID NO: 51 or 53. In some embodiments, the anti-BCMA antigen-binding domain comprises a heavy chain variable domain comprising a sequence having at least 80%, 85%, 90%, 95%, 98%, or 99% sequence identity to SEQ ID NO: 50 or 52 and a light chain variable domain comprising a sequence having at least 80%, 85%, 90%, 95%, 98%, or 99% sequence identity to SEQ ID NO: 51 or 53.

In some embodiments, the single chain antibody fragment comprises a single chain Fv (scFv) that binds to B7-H3, also known as CD276 (e.g., cluster of differentiation 276 protein (CD276) (e.g., OMIM Acc. No. 605715)).

Non-limiting examples of scFvs that target B7-H3 include those described in U.S. Patent Publication Nos. 2016/0053017 and 2018/0346544, which are herein incorporated by reference in their entireties. For example, as described in U.S. Patent Publication No. 2018/0346544, the anti-CD276 scFv can include the antigen binding domain of the MGA271 (CD276.MG), CD276.N1, CD276.N2, CD276.N3, CD276.N4, or CD276.N5 antibody.

In some embodiments, the anti-B7-H3 antigen binding domain comprises the sequence of SEQ ID NO: 36. In some embodiments, the anti-B7-H3 antigen-binding domain comprises a sequence having at least 80%, 85%, 90%, 95%, 98%, or 99% sequence identity to SEQ ID NO: 36. In some embodiments, the polynucleotide segment encoding an anti-B7-H3 antigen-binding domain comprises the SEQ ID NO: 37. In some embodiments, the polynucleotide segment encoding an anti-B7-H3 antigen-binding domain comprises a sequence having at least 80%, 85%, 90%, 95%, 98%, or 99% sequence identity to SEQ ID NO: 37.

In some embodiments, the anti-B7-H3 antigen-binding domain comprises a heavy chain variable domain comprising a sequence having at least 80%, 85%, 90%, 95%, 98%, or 99% sequence identity to SEQ ID NO: 38. In some embodiments, the anti-B7-H3 antigen-binding domain comprises a light chain variable domain comprising a sequence having at least 80%, 85%, 90%, 95%, 98%, or 99% sequence identity to SEQ ID NO: 39. In some embodiments, the anti-B7-H3 antigen-binding domain comprises a heavy chain variable domain comprising a sequence having at least 80%, 85%, 90%, 95%, 98%, or 99% sequence identity to SEQ ID NO: 38 and a light chain variable domain comprising a sequence having at least 80%, 85%, 90%, 95%, 98%, or 99% sequence identity to SEQ ID NO: 39.

In some embodiments, the single chain antibody fragment comprises a single chain Fv (scFv) that binds to CD27 (e.g., OMIM Acc. No. 186711).

In some embodiments, the single chain antibody fragment comprises a single chain Fv (scFv) that binds to CD38 (e.g., OMIM Acc. No. 107270)).

In some embodiments, the single chain antibody fragment comprises a single chain Fv (scFv) that binds to CEA (e.g., carcinoembryonic antigen protein (CEA) (e.g., OMIM Acc. No. 114890)).

In some embodiments, the single chain antibody fragment comprises a single chain Fv (scFv) that binds to BCMA (e.g., B cell maturation antigen (BCMA) (e.g., OMIM Acc. No. 109545)).

6.3.2.2. Hinge Region

The hinge region connects the extracellular antigen-binding domain to the intracellular signaling domains (e.g., one or more co-stimulatory domains and the intracellular signaling domains) through the transmembrane domain. The hinge provides sufficient flexibility to overcome steric hindrance and adequate length to facilitate access and binding of the antigen-binding domain to the target antigen. In some embodiments, differences in the length and composition of the hinge can affect antigen binding and signaling through the CAR. For example, spacer sequences in the hinge region, or a spacer sequences added to the hinge region, facilitate access and binding of the antigen-binding domain to the target antigen. In some embodiments, the hinge region influences cytokine production.

In some embodiments, the hinge region is selected from a human CD8 hinge region, a human CD28 hinge region, a IgG1 hinge region, or a IgG4 hinge region. In some embodiments, the hinge region is derived from a human CD8. In some embodiments, the hinge region derived from human CD8 comprises the sequence of SEQ ID NO: 28. In some embodiments, the hinge region derived from human CD8 comprises a sequence having at least at least 80%, 85%, 90%, 95%, 98%, or 99% sequence identity to SEQ ID NO: 28.

6.3.2.3. Transmembrane Domain

The transmembrane region anchors the CAR in the CD4$^{IL10/CAR}$ T cell. In some embodiments, the transmembrane domain influences stability and function of the CAR.

In some embodiments, the transmembrane domain is selected from a group consisting of: TNFRSF 19 transmembrane domain, a CD3zeta transmembrane domain, a CD8α transmembrane domain, a CD4 transmembrane domain, a CD28 transmembrane domain, or an B7-family inducible costimulatory (ICOS) transmembrane domain. In some embodiments, the transmembrane domain is derived from a TNFRSF 19. In some embodiments, the transmembrane domain derived from TNFRSF 19 comprises a sequence of SEQ ID NO: 29. In some embodiments, the transmembrane domain derived from TNFRSF 19 comprises a sequence having at least at least 80%, 85%, 90%, 95%, 98%, or 99% sequence identity to SEQ ID NO: 29.

6.3.2.4. Intracellular Signaling Domain and Co-Stimulatory Domains

The intracellular signaling domain activates the CD4$^{IL10/CAR}$ T cell. In some embodiments, the intracellular signaling domain participates in T cell function, metabolism and persistence.

In some embodiments, the intracellular signaling domain comprises an immunoreceptor tyrosine-based activation motif (ITAM). In some embodiments, the intracellular signaling domain comprises two or more immunoreceptor tyrosine-based activation motifs (ITAM). In some embodiments, the immunoreceptor tyrosine-based activation motif (ITAM) is derived from CD3zeta. In some embodiments, the intracellular signaling domain derived from CD3zeta comprises a sequence of SEQ ID NO: 30 In some embodiments, the intracellular signaling domain derived from CD3zeta comprises a sequence having at least at least 80%, 85%, 90%, 95%, 98%, or 99% sequence identity to SEQ ID NO: 30.

In some embodiments, the intracellular signaling domain further comprises one or more co-stimulatory domains. In such cases, the one or more co-stimulatory domains enhance T cell activation, function, metabolism, and persistence as compared to CD4$^+$ T cells comprising a CAR without one or more co-stimulatory domains. CD4$^+$ (e.g., CD4$^{IL10/CAR}$) T cells with CARs containing co-stimulatory domains in addition to activation domains produce IL-2 and can proliferate upon repeated antigen exposure.

In some embodiments, co-stimulatory domains derived from different sources (e.g., 4-1BB and CD28) induce different functional and metabolic profiles in CD4$^+$ (e.g., CD4$^{IL10/CAR}$) T cells. For example, CD4$^+$ (e.g., CD4$^{IL10/CAR}$) T cells having a CAR comprising a co-stimulatory domain derived from CD28 experience enhanced differentiation into effector memory T cells. In another example, CD4$^+$ (e.g., CD4$^{IL10/CAR}$) T cells having a CAR comprising a co-stimulatory domain derived from 4-1BB experience enhanced differentiation into central memory T cells.

In some embodiments, the one or more co-stimulatory domains is 4-1BB, CD28, OX40, ICOS, CD27, MYD88-CD40, and KIR2DS2.

In some embodiments, the one or more co-stimulatory domains is derived from 4-1BB. In some embodiments, the co-stimulatory domain derived from 4-1BB comprises a sequence of SEQ ID NO: 31. In some embodiments, the co-stimulatory domain derived from 4-1BB comprises a sequence having at least at least 80%, 85%, 90%, 95%, 98%, or 99% sequence identity to SEQ ID NO: 31.

In some embodiments, the one or more co-stimulatory domains is derived from CD28. In some embodiments, the one or more co-stimulatory domains comprises a CD28 co-stimulatory domain. In some embodiments, the co-stimulatory domain derived from CD28 comprises the sequence of SEQ ID NO: 32. In some embodiments, the co-stimulatory domain derived from CD28 comprises a sequence having at least at least 80%, 85%, 90%, 95%, 98%, or 99% sequence identity to SEQ ID NO: 32.

In some embodiments, a CAR comprises two co-stimulatory domains. In some embodiments, a CAR includes a first co-stimulatory domain comprising a co-stimulatory domain derived from 4-1BB and a second co-stimulatory domain comprising a co-stimulatory domain derived from a CD28 co-stimulatory domain.

6.3.2.5. Chimeric Antigen Receptors (CARs)

In some embodiments, the CAR encoding polynucleotide segment encodes a CAR comprising an antigen-binding domain that targets an antigen associated with an autoimmune disease, inflammatory disorders, or cancer.

In some embodiments, the CAR encoding polynucleotide segment encodes a CAR comprising an antigen-binding domain that targets an antigen associated with an autoimmune disease or inflammatory disorder. In some embodiments, an antigen associated with an autoimmune disease or inflammatory disorder is selected from the group consisting of but not limited to: anti-HLA-A*02, anti-HLA-A*24 or citrullinated peptides, insulin, MOG, GAD65, IA2, gliadin, and desmoglein in the context of relevant MHC molecules.

In some embodiments, the CAR encoding polynucleotide segment encodes a CAR comprising an antigen-binding domain that targets a cancer-associated antigen. In some embodiments, a cancer-associated antigen is selected from the group consisting of: CD19, CD20, CD22, B7-H3, CEA, BCMA, CD23, Lym1, Lym2, CLEC5A, CDH179b, FLT3, GCC, Muc, CSF2RA, GFRa4, CD32, CD33, IL1lRa, IL13Ra, NYBRI, SLea, CD200R, TGFBetaR2, CD276, TROP2, LAMP1, PTK7, DLL3, CDH1, CDH6, CDH17, CDH19, TSHR and tyrosinase.

In some embodiments, the CAR encoding polynucleotide segment encodes a CAR comprising an antigen-binding domain that targets a B cell antigen. In some embodiments, a B cell antigen is selected based in part on its expression during B-cell differentiation, for example, as shown in FIG. 4. Non-limiting examples of antigen-binding domains that target B cell antigens are described in WO 2020/010235, which is herein incorporated by reference in its entirety. In some embodiments, the antigen-binding domain targets CD19. In some embodiments, the antigen-binding domain targets CD20. In some embodiments, the antigen-binding domain targets CD22. In some embodiments, the antigen-binding domain targets B7-H3. In some embodiments, the antigen-binding domain targets CD27. In some embodiments, the antigen-binding domain targets CD38. In some embodiments, the antigen-binding domain targets B cell maturation antigen (BCMA). In some embodiments, the antigen-binding domain targets carcinoembryonic antigen (CEA).

In some embodiments, the CAR encoding polynucleotide segment encodes a CAR comprising an anti-CD19 antigen-binding domain. In some embodiments, the CAR encoding polynucleotide segment encodes a second-generation CAR comprising an anti-CD19 antigen-binding domain. In some embodiments, the CAR encoding polynucleotide segment encodes a third-generation CAR comprising an anti-CD19 antigen-binding domain.

In some embodiments, the CAR encoding polynucleotide segment encodes an anti-CD19 CAR including: an anti-CD19 antigen-binding domain, a binge region, a transmembrane domain, a co-stimulatory domain, and an intracellular signaling domain. In some embodiments, the CAR encoding polynucleotide segment encodes an anti-CD19 antigen-binding domain; a human CD8 hinge region; a TNFRSF 19 transmembrane region; a 4-1BB co stimulatory domain; and a CD3zeta chain intracellular signaling domain. In some embodiments, the anti-CD19 CAR comprises the sequence of SEQ ID NO: 9. In some embodiments, the anti-CD19 CAR comprises a sequence having at least at least 80%, 85%, 90%, 95%, 98%, or 99% sequence identity to SEQ ID NO: 9. In some embodiments, the first exogenous polynucleotide segment comprises the sequence of SEQ ID NO: 10. In some embodiments, the first exogenous polynucleotide segment comprises a sequence having at least at least 80%, 85%, 90%, 95%, 98%, or 99% sequence identity to SEQ ID NO: 10.

Non-limiting examples of CARs comprising an anti-CD19 antigen-binding domain include: U.S. Patent Publication No. 2020/0392200, WO 2020/010235 or WO 2012/079000, which are herein incorporated by reference in their entireties.

In some embodiments, the CAR encoding polynucleotide segment encodes a CAR comprising an anti-CD20 antigen-binding domain. In some embodiments, the CAR encoding polynucleotide segment encodes a second-generation CAR comprising an anti-CD20 antigen-binding domain. In some embodiments, the CAR encoding polynucleotide segment encodes a third-generation CAR comprising an anti-CD20 antigen-binding domain.

In some embodiments, the CAR encoding polynucleotide segment encodes an anti-CD20 CAR including: an anti-CD20 antigen-binding domain, a transmembrane domain, a co-stimulatory domain, and an intracellular signaling domain. In some embodiments, the CAR encoding polynucleotide segment encodes an anti-CD20 antigen-binding domain; a human CD8 transmembrane region; a 4-1BB co stimulatory domain; and a CD3zeta chain intracellular signaling domain. In some embodiments, the anti-CD20 CAR comprises the sequence of SEQ ID NO: 16. In some embodiments, the anti-CD20 CAR comprises a sequence having at least at least 80%, 85%, 90%, 95%, 98%, or 99% sequence identity to SEQ ID NO: 16. In some embodiments, the first exogenous polynucleotide segment comprises the sequence of SEQ ID NO: 17. In some embodiments, the first exogenous polynucleotide segment comprises a sequence having at least at least 80%, 85%, 90%, 95%, 98%, or 99% sequence identity to SEQ ID NO: 17.

Non-limiting examples of CARs comprising an anti-CD20 antigen-binding domain include: U.S. Patent Publication No. 2020/0392200 or WO 2020/010235, both of which are herein incorporated by reference in their entireties.

In some embodiments, the CAR encoding polynucleotide segment encodes a CAR comprising an anti-CD22 antigen-binding domain. In some embodiments, the CAR encoding polynucleotide segment encodes a second-generation CAR comprising an anti-CD22 antigen-binding domain. In some embodiments, the CAR encoding polynucleotide segment encodes a third-generation CAR comprising an anti-CD22 antigen-binding domain.

In some embodiments, the anti-CD22 CAR comprises the sequence of SEQ ID NO: 22. In some embodiments, the anti-CD22CAR comprises a sequence having at least at least 80%, 85%, 90%, 95%, 98%, or 99% sequence identity to SEQ ID NO: 22. In some embodiments, the first exogenous polynucleotide segment comprises the sequence of SEQ ID NO: 23. In some embodiments, the first exogenous polynucleotide segment comprises a sequence having at least at least 80%, 85%, 90%, 95%, 98%, or 99% sequence identity to SEQ ID NO: 23.

Non-limiting examples of CARs that include an anti-CD22 CAR include those described in WO 2020/010235 and U.S. Patent Publication No. 2020/0392200, which are herein incorporated by reference in their entireties.

Non-limiting examples of CARs that include an anti-B7-H3 CAR include those described in U.S. Patent Publication Nos. 2016/0053017, 2017/0369585, and 2018/0346544, which are herein incorporated by reference in their entireties.

In some embodiments, the CAR encoding polynucleotide segment encodes a CAR comprising an anti-B7-H3 antigen-binding domain. In some embodiments, the CAR encoding polynucleotide segment encodes a second-generation CAR comprising an anti-B7-H3 antigen-binding domain. In some embodiments, the CAR encoding polynucleotide segment encodes a third-generation CAR comprising an anti-B7-H3 antigen-binding domain.

In some embodiments, the anti-B7-H3 CAR comprises the sequence of SEQ ID NO: 34. In some embodiments, the anti-B7-H3 CAR comprises a sequence having at least at least 80%, 85%, 90%, 95%, 98%, or 99% sequence identity to SEQ ID NO: 34. In some embodiments, the first exogenous polynucleotide segment comprises the sequence of SEQ ID NO: 35. In some embodiments, the first exogenous polynucleotide segment comprises a sequence having at least at least 80%, 85%, 90%, 95%, 98%, or 99% sequence identity to SEQ ID NO: 35.

In some embodiments, the CAR encoding polynucleotide segment encodes a CAR comprising an anti-CD27 antigen-binding domain. In some embodiments, the CAR encoding polynucleotide segment encodes a second-generation CAR comprising an anti-CD27 antigen-binding domain. In some embodiments, the CAR encoding polynucleotide segment encodes a third-generation CAR comprising an anti-CD27 antigen-binding domain.

In some embodiments, the CAR encoding polynucleotide segment encodes a CAR comprising an anti-CD38 antigen-binding domain. In some embodiments, the CAR encoding polynucleotide segment encodes a second-generation CAR comprising an anti-CD38 antigen-binding domain. In some embodiments, the CAR encoding polynucleotide segment encodes a third-generation CAR comprising an anti-CD38antigen-binding domain.

In some embodiments, the CAR encoding polynucleotide segment encodes a CAR comprising an anti-CEA antigen-binding domain. In some embodiments, the CAR encoding polynucleotide segment encodes a second-generation CAR comprising an anti-CEA antigen-binding domain. In some embodiments, the CAR encoding polynucleotide segment encodes a third-generation CAR comprising an anti-CEA antigen-binding domain.

In some embodiments, the CAR encoding polynucleotide segment encodes a CAR comprising an anti-BCMA antigen-binding domain. In some embodiments, the CAR encoding polynucleotide segment encodes a second-generation CAR comprising an anti-BCMA antigen-binding domain. In some embodiments, the CAR encoding polynucleotide segment encodes a third-generation CAR comprising an anti-BCMA antigen-binding domain. In some embodiments, the anti-BCMA CAR comprises the sequence of SEQ ID NOs: 41-49 and 54. In some embodiments, the anti-BCMA CAR comprises a sequence having at least at least 80%, 85%, 90%, 95%, 98%, or 99% sequence identity to SEQ ID NOs: 41-49 and 54.

The first exogenous polynucleotide further comprises one or more regulatory elements (e.g., any of the regulatory elements described herein or known in the art) operably linked to a coding sequence of the CAR. In some embodiments, the regulatory element is a promoter.

In some embodiments, the regulatory element comprises a promoter capable of directing expression of the CAR in CD4$^+$ T cells. In some embodiments, the promoter drives constitutive expression of the CAR in CD4$^+$ T cells. In some embodiments, the promoter drives expression of the CAR in activated CD4$^+$ T cells.

In some embodiments, the first exogenous polynucleotide segment further comprises a segment encoding a selection marker (e.g., any of the selection markers described herein or known in the art) that permits selection of successfully transduced CD4$^+$ T cells.

In some embodiments, the first exogenous polynucleotide segment is delivered into CD4$^+$ T cells using a vector. In some embodiments, the vector is a plasmid vector. In some embodiments, the vector is a viral vector. In some embodiments, the vector is a retroviral vector (e.g., a gammaretroviral vector). In some embodiments, the vector is a lentiviral vector.

In some embodiments, the first exogenous polynucleotide segment is delivered into CD4$^+$ T cells using a lentiviral vector and the first exogenous polynucleotide segment comprises lentiviral vector sequences. In certain embodiments, a lentiviral vector disclosed in Mátrai et al., *Molecular Therapy* 18(3):477-490 (2010) ("Mátrai"), incorporated by reference herein, is used. In some embodiments, the first exogenous polynucleotide segment encoding a chimeric antigen receptor (CAR); and the second exogenous polynucleotide segment encoding interleukin-10 (IL-10) are present in a single lentiviral vector. In such cases, the first exogenous polynucleotide and second exogenous polynucleotide segment are operably linked to a first promoter. For example, the lentiviral vector includes a human PGK promoter, the first exogenous polynucleotide operably linked to the second exogenous polynucleotide segment via an internal ribosome entry site (IRES) or a self-cleaving peptide (e.g., a 2A self-cleaving peptide).

In some embodiments, the first exogenous polynucleotide segment is integrated in the T cell nuclear genome. In some embodiments, the first exogenous polynucleotide segment is not integrated in the nuclear genome. In some embodiments, the first exogenous segment polynucleotide exists in the T cell cytoplasm.

6.3.3. Exogenous Polynucleotide Encoding IL-10

The single donor CD4$^{IL-10/CAR}$ cells or polydonor CD4$^{IL-10/CAR}$ cells of the present disclosure have been further genetically modified to comprise a second exogenous polynucleotide segment encoding IL-10. The second exogenous polynucleotide segment comprises an IL-10-encoding polynucleotide segment operably linked to one or more regulatory elements (e.g., any of the one or more regulatory elements described herein or known in the art).

The IL-10-encoding polynucleotide segment can encode IL-10 of a human, bonobo or rhesus. In some embodiments, the IL-10-encoding polynucleotide segment encodes human IL-10 having the sequence of SEQ ID NO: 1. In some embodiments, the IL-10-encoding polynucleotide segment encodes a variant of human IL-10 having at least 90%, 95%, 98%, or 99% sequence identity to SEQ ID NO: 1. In some embodiments, the IL-10-encoding polynucleotide segment has the nucleotide sequence of SEQ ID NO: 2. In some embodiments, the IL-10-encoding polynucleotide segment has at least 90%, 95%, 98%, or 99% sequence identity to SEQ ID NO: 2.

In some embodiments, the exogenous polynucleotide encodes viral-IL-10. In various embodiments, the exogenous polypeptide encodes IL-10 from HCMV, GMCMV, RhCMV, BaCMV, MOCMV, SMCMV, EBV, Bonobo-HV, BaLCV, OvHV-2, EHV-2, CyHV-3, AngHV-1, ORFV, BPSV, PCPV, LSDV, SPV, GPV, or CNPV. In some embodiments, the exogenous polypeptide encodes viral IL-10 from EBV or ORFV.

In some embodiments, the viral-IL-10 comprises the sequence of SEQ ID NO: 6. In some embodiments, the viral IL-10 comprises a sequence having at least 80%, 85%, 90%, 95%, 97%, 98%, 98% or 99% sequence identity to SEQ ID NO: 6 or 18. In some embodiments, the exogenous polypeptide coding a viral IL-10 comprises the sequence of SEQ ID NO: 7. In some embodiments, the exogenous polypeptide coding a viral IL-10 comprises a sequence having at least 80%, 85%, 90%, 95%, 97%, 98%, 98% or 99% sequence identity to SEQ ID NO: 7.

In some embodiments, the IL-10 is a protein comprising human IL-10 with one, two, three, four, five, six, seven, eight, nine or ten amino acid modifications. In some embodiments, the one, two, three, four, five, six, seven, eight, nine or ten amino acid modifications are substituted with amino acids of viral IL-10 at corresponding amino acid positions.

In some embodiments, the IL-10-encoding polynucleotide segment encodes a variant of human IL-10 having one, two, three, four, five, six, seven, eight, nine, ten or more amino acid substitutions compared to human IL-10 (e.g., SEQ ID NO: 1). In some embodiments, the one, two, three, four, five, six, seven, eight, nine or ten amino acid substitution are substitution(s) with amino acid(s) of viral IL-10 at corresponding amino acid position(s). In some embodiments, the IL-10-encoding polynucleotide segment encodes a variant of human IL-10 having one, two, three, four, five, six, seven, eight, nine, ten or more amino acid insertion, deletion or modification compared to human IL-10 (e.g., SEQ ID NO: 1). In some embodiments, the variant of human IL-10 has the sequence of SEQ ID NO: 56 or 57.

In some embodiments, the IL-10-encoding polynucleotide segment encodes IL-10 of a *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID) NO: 63); *Pan paniscus*, "BONOBO" (SEQ ID NO: 64); *Pan troglodytes*, "CHIMP" (SEQ ID NO: 65); and EBVB9 (SEQ ID NO: 66). In some embodiments, the IL-10-encoding polynucleotide segment encodes a protein having at least 90%, 95%, 98%, or 99% sequence identity to IL-10 of a *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66).

In some embodiments, the IL-10-encoding polynucleotide segment encodes a variant of human IL-10 having one, two, three, four, five, six, seven, eight, nine, ten or more amino acid substitutions, insertions, and/or deletions compared to human IL-10 (e.g., SEQ ID NO: 1). In some embodiments, the modifications are substitutions, insertions, and/or deletions with amino acids of *Mus musculus*, "MOUSE" (SEQ ID NO: 58); *Rattus norvegicus*, "RAT" (SEQ ID NO: 59); *Macaca mulatta*, "MACMU" (SEQ ID NO: 60); *Gorilla gorilla*, "GORILLA" (SEQ ID NO: 61); *Macaca fascicularis*, "CYNO" (SEQ ID NO: 62); *Papio Anubis*, "OLIVE BABOON" (SEQ ID NO: 63); *Pan paniscus*, "BONOBO" (SEQ ID NO: 64); *Pan troglodytes*, "CHIMP" (SEQ ID NO: 65); and EBVB9 (SEQ ID NO: 66), at the corresponding positions. In some embodiments, the variant of human IL-10 has the sequence of SEQ ID NO: 67 or SEQ ID NO: 68.

In some embodiments, the IL-10-encoding polynucleotide segment encodes a variant of human IL-10 having reduced immunostimulatory activity compared to human IL-10. In some embodiments, the variant of human IL-10 includes 1105A substitution. In some embodiments, a variant of human IL-10 is made using the method described in A Single Amino Acid Determines the Immunostimulatory Activity of Interleukin 10, J Exp Med, 191, 2, 2000, p. 213-223.

The second exogenous polynucleotide segment further comprises one or more regulatory element operably linked to a coding sequence of IL-10 where the one or more regulatory element directs expression of the encoded IL-10 in transduced CD4$^+$ T cells.

In some embodiments, the regulatory element(s) comprise a promoter capable of directing expression of IL-10 in CD4$^+$ T cells. In some embodiments, the promoter drives constitutive expression of IL-10 in CD4$^+$ T cells. In some embodiments, the promoter drives expression of IL-10 in activated CD4$^+$ T cells.

In some embodiments, the second exogenous polynucleotide segment further comprises a segment encoding a selection marker (e.g., any of the selection markers described herein or known in the art) that permits selection of successfully transduced CD4$^+$ T cells.

In typical embodiments, the exogenous polynucleotide is delivered into CD4+ T cells using a vector. In some embodiments, the vector is a plasmid vector. In some embodiments, the vector is a viral vector.

In some embodiments, the first exogenous polynucleotide segment encoding CAR and the second exogenous polynucleotide segment encoding IL-10 are in the same vector. In some embodiments, the first exogenous polynucleotide segment encoding CAR and the second exogenous polynucleotide segment encoding IL-10 are in the same viral vector. In some embodiments, the first exogenous polynucleotide segment encoding CAR and the second exogenous polynucleotide segment encoding IL-10 are in the same lentiviral vector.

In certain embodiments, the exogenous polynucleotide is delivered into CD4+ T cells using a lentiviral vector and the exogenous polynucleotide comprises lentiviral vector sequences. In certain embodiments, a lentiviral vector disclosed in Mátrai et al., *Molecular Therapy* 18(3):477-490 (2010) ("Mátrai"), incorporated by reference herein, is used.

In some embodiments, the second exogenous polynucleotide segment is integrated in the T cell nuclear genome. In some embodiments, the second exogenous polynucleotide segment is not integrated in the nuclear genome. In some embodiments, the second exogenous polynucleotide segment exists in the T cell cytoplasm.

In particular embodiments, the second exogenous polynucleotide segment has the sequence of SEQ ID NO: 5. In some embodiments, the exogenous polynucleotide has at least 80%, 85%, 90%, 95%, 98%, or 99% sequence identity to SEQ ID NO: 5.

6.3.4. Regulatory Elements

In some embodiments, the first and/or second exogenous polynucleotide segments further comprise a regulatory element operably linked to a coding sequence of a CAR or IL-10, respectively. In some embodiments, the regulatory element comprises a promoter sequence, an enhancer sequence, a non-coding sequence, or any combination thereof.

In some embodiments, the first exogenous polynucleotide segment further comprises a regulatory element operably linked to a coding sequence of the CAR where the regulatory elements direct expression of the encoded CAR in transduced CD4$^+$ T cells. In some embodiments, an inducible promoter is used to induce expression of the CAR when therapeutically appropriate.

In some embodiments, the second exogenous polynucleotide segment further comprises a regulatory element operably linked to a coding sequence of IL-10 where the regulatory elements direct expression of the encoded IL-10 in transduced CD4$^+$ T cells. In some embodiments, an inducible promoter is used to induce expression of IL-10 when therapeutically appropriate. In some embodiments, the IL-10 promoter is used.

In some embodiments, the promoter is a tissue-specific promoter. In some embodiments, the promoter is a lineage-specific promoter. In some embodiments, the promoter is promoter that can be used to drive ubiquitous expression of the CAR or IL-10.

In some embodiments, the promoter is a native human promoter. In some embodiments, the promoter is a human elongation factor (EF)1α promoter. In some embodiments, the promoter is a human phosphoglycerate kinase promoter (PGK). In some embodiments, the promoter is a human ubiquitin C promoter (UBI-C).

In some embodiments, the promoter is a synthetic promoter. In certain embodiments, the promoter is a minimal CMV core promoter. In particular embodiments, the promoter is an inducible or constitutive bidirectional promoter. In specific embodiments, the synthetic bidirectional promoter disclosed in Amendola et al., *Nature Biotechnology,* 23(1):108-116 (2005) is used. This promoter can mediate coordinated transcription of two mRNAs in a ubiquitous or a tissue-specific manner. In certain embodiments, the bidirectional promoter induces expression of CAR and a selection marker or IL-10 and a selection marker.

In some embodiments, the promoter is a native human promoter. In some embodiments, the promoter is a human elongation factor (EF)1α promoter. In some embodiments, the promoter is a human phosphoglycerate kinase promoter (PGK). In some embodiments, the promoter is a human ubiquitin C promoter (UBI-C).

In some embodiments, the first and/or second exogenous polynucleotide segment further comprises one or more non-coding sequences 3' to the coding sequence. Non-limiting examples of non-coding sequences 3' to the coding sequence include 3' untranslated region (UTR), a poly(A) signal and a woodchuck hepatitis virus post-transcriptional regulatory element (WPRE).

In some embodiments, an exogenous polynucleotide comprises more than one coding sequence. For example, an exogenous polynucleotide includes the first exogenous polynucleotide segment and the second exogenous polynucleotide segment on a single contiguous polynucleotide sequence (e.g., a single polynucleotide construct). In some embodiments, the one or more coding sequences include a sequence encoding a CAR and a sequence encoding a selection marker. In some embodiments, the one or more coding sequences include a sequence encoding IL-10 and a sequence encoding a selection marker. In some embodiments, the one or more coding sequences include a sequence encoding a CAR, a sequence encoding IL-10, and one or more sequences encoding a selection marker. In some embodiments, the exogenous polynucleotide is free of a selection marker.

In some embodiments, the multiple coding sequences are separated by one or more internal ribosome entry site (IRES).

In some embodiments, the multiple coding sequences are separated by one or more self-cleaving peptides. In some embodiments, the self-cleaving peptides can be 2A self-cleaving peptides. Non-limiting examples of self-cleaving peptides include 2A peptides (18-22 amino acids), including a peptide from foot-and-mouth disease virus (F2A), porcine teschovirus-1 (P2A), Thosea asigna virus (T2A), or equine rhinitis A virus (E2A). In some embodiments, the first exogenous polynucleotide, the second exogenous polynucleotide, or both, comprise a sequence encoding a Furin P2A peptide. In some embodiments, the first exogenous polynucleotide, the second exogenous polynucleotide, or both, comprise a sequence encoding a T2A peptide. In some embodiments, the first exogenous polynucleotide, the second exogenous polynucleotide, or both, comprise a sequence encoding an E2A peptide.

In some embodiments, the coding sequence further comprises a self-cleaving peptide between the coding sequence of the heavy chain and the coding sequence of the light chain. In some embodiments, the self-cleaving peptide is selected from the group consisting of F2A, P2A, T2A and E2A.

6.3.5. Selection Markers

In some embodiments, the first exogenous polynucleotide segment, the second exogenous nucleotide segment, or both, further comprise a polynucleotide segment encoding a selection marker that permits selection of successfully transduced CD4$^+$ T cells. In some embodiments, the first exogenous polynucleotide segment, the second exogenous nucleotide segment, or both, are free of a selection marker.

In some embodiments, an exogenous polynucleotide comprises the first exogenous polynucleotide segment and the second exogenous polynucleotide segment are on a single contiguous polynucleotide sequence (e.g., a single polynucleotide construct). In such cases, the exogenous polynucleotide includes one or more selection makers that permits selection of successfully transduced CD4$^+$ T cells.

In some embodiments, the selection marker is ΔNGFR. In certain embodiments, the selection marker is a polypeptide having the sequence of SEQ ID NO: 3. In certain embodiments, the selection marker is a polypeptide having at least 90%, 95%, 98%, or 99% sequence identity to SEQ ID NO: 3. In particular embodiments, the nucleotide sequence encoding the ΔNGFR selection marker has the sequence of SEQ ID NO: 4. In some embodiments, the nucleotide sequence encoding the ΔNGER selection marker has at least 90%, 95%, 98%, or 99% sequence identity to SEQ ID NO: 4.

In some embodiments, expression of the selection marker correlates with expression of IL-10 from the exogenous polynucleotide. In some embodiments, expression of the selection marker linearly correlates with expression of IL-10 from the exogenous polynucleotide. Accordingly, in some embodiments, expression of the selection marker is measured to infer expression of IL-10 from the exogenous polynucleotide.

In some embodiments, the selection marker is a truncated form of EGFR polypeptide. In some embodiments, the selection marker is a truncated form of the human EGFR polypeptide, optionally huEGFR disclosed in Wang et al. "A transgene-encoded cell surface polypeptide for selection, in vivo tracking, and ablation of engineered cells", *Blood, v.* 118, n. 5 (2011), incorporated by reference in its entirety herein.

In some embodiments, the exogenous polynucleotide further comprises a sequence encoding an antibiotic resistance gene. In some embodiments, the exogenous polynucleotide comprises a sequence encoding an ampicillin resistance gene.

6.3.6. Gene Expression of CD4$^{IL\text{-}10/CAR}$ Cells or Polydonor CD4$^{IL\text{-}10/CAR}$ CD4$^{IL\text{-}10/CAR}$ cells express IL-10. In some embodiments, CD4$^{IL\text{-}10/CAR}$ cells constitutively express IL-10. In some embodiments, CD4$^{IL\text{-}10/CAR}$ cells express IL-10 when activated.

In some embodiments, CD4$^{IL\text{-}10/CAR}$ cells (e.g., autologous single-donor or allogeneic single-donor) or polydonor CD4$_{IL\text{-}10/CAR}$ cells constitutively express at least 100 pg of IL-10 per 10$^6$ of the CD4$^+$ T cells/mL of culture. In some embodiments, CD4$^{IL\text{-}10/CAR}$ cells or polydonor CD4$^{IL\text{-}10/CAR}$ cells constitutively express at least 200 pg, 500 pg, 1 ng, 5 ng, 10 ng, or 50 ng of IL-10 per 10$^6$ of the CD4$^+$ T cells/mL of culture.

In some embodiments, CD4$^{IL\text{-}10/CAR}$ cells (e.g., autologous single-donor or allogeneic single-donor) or polydonor CD4$^{IL\text{-}10/CAR}$ cells express at least 1 ng or 2 ng IL-10 per 10$^6$ of the CD4$^+$ T cells/mL of culture after activation with a combination of anti-CD3 and anti-CD28 antibodies, or anti-CD3 antibody and anti-CD28 antibody coated beads. In some embodiments, polydonor CD4$^{IL\text{-}10}$ T cells express at least 5 ng, 10 ng, 100 ng, 200 ng, or 500 ng IL-10 per 10$^6$ of the CD4$^+$ T cells/mL of culture after activation with anti-CD3 and anti-CD28 antibodies or CD3 antibody and CD28 antibody coated beads.

In various embodiments, the amount of IL-10 production is determined 12 hours, 24 hours, or 48 hours after activation using various methods for protein detection and measurement, such as ELISA, real-time polymerase chain reaction (PCR), spectroscopic procedures, colorimetry, amino acid analysis, radiolabeling, Edman degradation, HPLC, western blotting, etc. In preferred embodiments, the amount of IL-10 production is determined by ELISA 48 hours after activation with anti-CD3 and anti-CD28 antibodies.

In some embodiments, CD4$^{IL\text{-}10/CAR}$ cells (e.g., autologous single-donor or allogeneic single-donor) or polydonor CD4$^{IL\text{-}10/CAR}$ cells express IL-10 at a level at least 5-fold higher than unmodified CD4$^+$ T cells. In some embodiments, polydonor CD4$^{IL\text{-}10}$ T cells express IL-10 at a level at least 6, 7, 8, 9, 10, 11, 12, 13, 14, 15, 20, 30, 40, or 50-fold higher than unmodified CD4$^+$ T cells.

In some embodiments, CD4$^{IL\text{-}10/CAR}$ cells (e.g., autologous single-donor or allogeneic single-donor) or polydonor CD4$^{IL\text{-}10/CAR}$ cells express at least 100 pg IL-5 per 10$^6$ of the CD4$^+$ T cells/mL. In some embodiments, CD4$^{IL\text{-}10/CAR}$ cells (e.g., autologous single-donor or allogeneic single-donor) or polydonor CD4$^{IL\text{-}10/CAR}$ cells express at least 100 pg, 200 pg, 500 pg, 1 ng, 5 ng, 10 ng, or 50 ng IL-5 per 10$^6$ of the CD4$^+$ T cells/mL.

In some embodiments, CD4$^{IL\text{-}10/CAR}$ cells (e.g., autologous single-donor or allogeneic single-donor) or polydonor CD4$^{IL\text{-}10/CAR}$ cells express at least 1 ng IL-5 per 10$^6$ of the CD4$^+$ T cells/mL after activation with anti-CD3 and anti-CD28 antibodies. In some embodiments, CD4$^{IL\text{-}10/CAR}$ cells (e.g., autologous single-donor or allogeneic single-donor) or polydonor CD4$^{IL\text{-}10/CAR}$ cells express at least 2 ng, 5 ng, 10 ng, 100 ng, 200 ng, or 500 ng IL-5 per 10$^6$ of the CD4$^+$ T cells/mL after activation with anti-CD3 and anti-CD28 antibodies.

In various embodiments, the amount of IL-5 production is determined 12 hours, 24 hours, or 48 hours after activation using various methods for protein detection and measurement, such as ELISA, real-time polymerase chain reaction (PCR), spectroscopic procedures, colorimetry, amino acid analysis, radiolabeling, Edman degradation, HPLC, western blotting, etc. In preferred embodiments, the amount of IL-5 production is determined by ELISA 48 hours after activation with anti-CD3 and anti-CD28 antibodies.

In some embodiments, CD4$^{IL\text{-}10/CAR}$ cells (e.g., autologous single-donor or allogeneic single-donor) or polydonor CD4$^{IL\text{-}10/CAR}$ cells express at least 100 pg IFN-γ per 10$^6$ of the CD4$^+$ T cells/mL. In some embodiments, CD4$^{IL\text{-}10/CAR}$ cells (e.g., autologous single-donor or allogeneic single-donor) or polydonor CD4$^{IL\text{-}10/CAR}$ cells express at least 100 pg, 200 pg, 500 pg, 1 ng, 5 ng, 10 ng, or 50 ng IFN-γ per 10$^6$ of the CD4$^+$ T cells/mL.

In some embodiments, CD4$^{IL\text{-}10/CAR}$ cells (e.g., autologous single-donor or allogeneic single-donor) or polydonor CD4$^{IL\text{-}10/CAR}$ cells express at least 1 ng IFN-γ per 10$^6$ of the CD4$^+$ T cells/mL after activation with anti-CD3 and anti-CD28 antibodies. In some embodiments, CD4$^{IL\text{-}10/CAR}$ cells (e.g., autologous single-donor or allogeneic single-donor) or polydonor CD4$^{IL\text{-}10/CAR}$ cells express at least 2 ng, 5 ng, 10 ng, 100 ng, 200 ng, or 500 ng IFN-γ per 10$^6$ of the CD4$^+$ T cells/mL after activation with anti-CD3 and anti-CD28 antibodies.

In various embodiments, the amount of IFN-γ production is determined 12 hours, 24 hours, or 48 hours after activation using various methods for protein detection and measurement, such as ELISA, real-time polymerase chain reaction (PCR), spectroscopic procedures, colorimetry, amino acid analysis, radiolabeling, Edman degradation, HPLC, western blotting, etc. In preferred embodiments, the amount of IFN-γ production is determined by ELISA 48 hours after activation with anti-CD3 and anti-CD28 antibodies.

In some embodiments, CD4$^{IL\text{-}10/CAR}$ cells (e.g., autologous single-donor or allogeneic single-donor) or polydonor CD4$^{IL\text{-}10/CAR}$ cells express at least 25 pg IL-4 per 10$^6$ of the CD4$^+$ T cells/mL. In some embodiments, CD4$^{IL\text{-}10/CAR}$ cells (e.g., autologous single-donor or allogeneic single-donor) or polydonor CD4$^{IL\text{-}10/CAR}$ cells express at least 25 pg, 50 pg, 75 pg, 100 pg, 200 pg, 500 pg, 1 ng, 5 ng, 10 ng, or 50 ng IL-4 per 10$^6$ of the CD4$^+$ T cells/mL.

In some embodiments, CD4$^{IL\text{-}10/CAR}$ cells (e.g., autologous single-donor or allogeneic single-donor) or polydonor CD4TL-10/CAR cells express at least 100 pg IL-4 per 10$^6$ of the CD4$^+$ T cells/mL after activation with anti-CD3 and anti-CD28 antibodies. In some embodiments, CD4$^{IL\text{-}10/CAR}$ cells (e.g., autologous single-donor or allogeneic single-donor) or polydonor CD4$^{IL-10/CAR}$ cells express at least 100 pg, 200 pg, 300 pg, 400 pg, 500 pg, 600 pg, 700 pg, 800 pg, 900 pg, 1000 pg, 2 ng, 5 ng, 10 ng, 100 ng, 200 ng, or 500 ng IL-4 per 10$^6$ of the CD4$^+$ T cells/mL after activation with anti-CD3 and anti-CD28 antibodies.

In various embodiments, the amount of IL-4 production is determined 12 hours, 24 hours, or 48 hours after activation using various methods for protein detection and measurement, such as ELISA, real-time polymerase chain reaction (PCR), spectroscopic procedures, colorimetry, amino acid analysis, radiolabeling, Edman degradation, HPLC, western blotting, etc. In preferred embodiments, the amount of IL-4 production is determined by ELISA 48 hours after activation with anti-CD3 and anti-CD28 antibodies.

In some embodiments, the expression one or more of IL-10, IL-4, IFN-γ, IL-22, and IL-5 is stable after one or more re-stimulations.

In some embodiments, CD4$^{IL-10/CAR}$ cells (e.g., autologous single-donor or allogeneic single-donor) or polydonor CD4$^{IL-10/CAR}$ cells further express a selection marker. In some embodiments, CD4$^{IL-10/CAR}$ cells or polydonor CD4$^{IL-10/CAR}$ cells express a protein typically expressed in Tr1 cells. In some embodiments, CD4$^{IL-10/CAR}$ cells or polydonor CD4$^{IL-10/CAR}$ cells express a marker protein characteristic of Tr1 cells.

In some embodiments, CD4$^{IL-10/CAR}$ cells (e.g., autologous single-donor or allogeneic single-donor) or polydonor CD4$^{IL-10/CAR}$ cells express CD49b. In some embodiments, CD4$^{IL-10/CAR}$ cells or polydonor CD4$^{IL-10/CAR}$ cells express LAG-3. In some embodiments, CD4$^{IL-10/CAR}$ cells or polydonor CD4$^{IL-10/CAR}$ cells express TGF-β. In some embodiments, CD4$^{IL-10/CAR}$ cells or polydonor CD4$^{IL-10/CAR}$ cells express IFN-γ. In some embodiments, CD4$^{IL-10/CAR}$ cells or polydonor CD4$^{IL-10/CAR}$ cells express GzB. In some embodiments, polydonor CD4$^{IL-10}$ cells release GzB when activated with myeloid antigen-presenting cells. In some embodiments. CD4$^{IL-10/CAR}$ cells or polydonor CD4$^{IL-10/CAR}$ cells express perforin. In some embodiments, CD4$^{IL-10/CAR}$ cells or polydonor CD4$^{IL-10/CAR}$ cells release perforin when activated with myeloid antigen-presenting cells. In some embodiments, CD4$^{IL-10/CAR}$ cells or polydonor CD4$^{IL-10/CAR}$ cells express CD18. In some embodiments, CD4$^{IL-10/CAR}$ cells or polydonor CD4$^{IL-10/CAR}$ cells express CD2. In some embodiments, CD4$^{IL-10/CAR}$ cells or polydonor CD4$^{IL-10/CAR}$ cells express CD226. In some embodiments, polydonor CD4$^{IL-10}$ cells express IL-22. In some embodiments, CD4$^{IL-10/CAR}$ cells or polydonor CD4$^{IL-10/CAR}$ cells express IL-10.

In some embodiments, CD4$^{IL-10/CAR}$ cells (e.g., autologous single-donor or allogeneic single-donor) or polydonor CD4$^{IL-10/CAR}$ cells exhibit at least one function of Tr1 cells. In various embodiments, the function is secretion of IL-10, secretion of TGF-β, and by the specific killing of myeloid antigen-presenting cells through the release of Granzyme B (GzB) and perforin.

6.3.7. Additional Properties of CD4$^{IL-10/CAR}$ Cells

In some embodiments, a CD4$^{IL-10/CAR}$ cell comprises an anti-CD19 CAR. In some embodiments, the CD4$^{IL-10/CAR}$ cell is capable of in vitro cytotoxicity to a CD19$^+$ target cell. In some embodiments, the CD4$^{IL-10/CAR}$ cell is capable of in vivo cytotoxicity to a CD19$^+$ target cell. In some embodiments, the CD19$^+$ target cell is an autoantibody-producing B cell. In some embodiments, the CD19$^+$ target cell is a CD19$^+$ cancer cell. In some embodiments, the cytotoxicity to a CD19$^+$ target cell is maintained after one or more restimulations (see, e.g., production methods described in FIGS. 5A-5C).

In some embodiments, the CD4$^{IL-10/CAR}$ cell is capable of in vitro cytotoxicity to a myeloid target cell. In some embodiments, the CD4$^{IL-10/CAR}$ cell is capable of in vivo cytotoxicity to a myeloid target cell. In some embodiments, the CD4$^{IL-10/CAR}$ cell is capable of cytotoxicity to a CD19$^+$ target cell and a myeloid target cell. In some embodiments, the myeloid target cell expressing one or more of Class I MHC, CD13, CD54 and CD112. In some embodiments, the cytotoxicity to a myeloid target cell is maintained after one or more restimulations (see, e.g., production methods described in FIGS. 5A-5C).

In some embodiments, the CD4TL-10/CAR cell is capable of suppressing allogeneic CD4$^+$ T cell proliferation. In some embodiments, the CD4$^{IL-10/CAR}$ cell is capable of suppressing allogeneic CD4$^+$ T cell proliferation by at least 10%, at least 20%, at least 30%, at least 40%, at least 50%, at least 60%, at least 70%, at least 80%, or at least 90%.

In some embodiments, the CD4$^{IL-10/CAR}$ cell is capable of suppressing allogeneic CD8$^+$ T cell proliferation. In some embodiments, the CD4$^{IL-10/CAR}$ cell is capable of suppressing allogeneic CD8$^+$ T cell proliferation by at least 10%, at least 20%, at least 30%, at least 40%, at least 50%, at least 60%, at least 70%, at least 80%, or at least 90%.

In some embodiments, the CD4$^{IL-10/CAR}$ cell is capable of suppressing allogeneic CD4$^+$ T cell proliferation and allogenic CD8$^+$ T cell proliferation. In some embodiments, the CD4$^{IL-10/CAR}$ cell is capable of suppressing allogeneic CD4$^+$ T cell proliferation by at least 10%, at least 20%, at least 30%, at least 40%, at least 50%, at least 60%, at least 70%, at least 80%, or at least 90% and suppressing allogeneic CD8$^+$ T cell proliferation by at least 10%, at least 20%, at least 30%, at least 40%, at least 50%, at least 60%, at least 70%, at least 80%, or at least 90%.

In some embodiments, suppression mediated by CD4$^{IL-10/CAR}$ cells is calculated as follows: 100−([proliferation of responders in the presence of CD4$^{IL-10}$ T cells (control) and CD4$^{IL-10/CAR}$ T cells/proliferation of responders]×100).

In some embodiments, the suppressive property is stable after one or more restimulations.

6.3.8. Product by Process

In some embodiments CD4$^{IL-10/CAR}$ T cells (autologous or allogeneic single-donor or allogeneic polydonor CD4$^{IL-10/CAR}$ cells) are obtained by modifying CD4$^+$ T cells with an exogenous polynucleotide segment encoding a CAR and an exogenous polynucleotide segment encoding IL-10. In some embodiments, modifying CD4$^+$ T cells with a first exogenous polynucleotide segment encoding a CAR and a second exogenous polynucleotide segment encoding IL-10 comprises: (1) a first transduction with the polynucleotide segment encoding IL-10 followed by a second transduction with the exogenous polynucleotide segment encoding the CAR; (ii) a first transduction with the polynucleotide segment encoding the CAR followed by a second transduction with the exogenous polynucleotide segment encoding IL-10; (iii) simultaneous transduction (i.e., co-transduction) of the polynucleotide segment encoding IL-10 and the exogenous polynucleotide segment encoding the CAR; or (iv) transduction of a single polynucleotide construct comprising both the polynucleotide segment encoding IL-10 and the polynucleotide segment encoding the CAR. In some embodiments, the polynucleotide encoding IL-10 further comprises a coding sequence of a marker protein (e.g., deltaNGFR).

In some embodiments, CD4$^{IL-10/CAR}$ cells (single-donor or polydonor CD4$^{IL-10/CAR}$ cells) are obtained by modifying CD4$^+$ T cells with (i) a first polynucleotide construct comprising a polynucleotide segment encoding a CAR and second polynucleotide construct comprising a polynucleotide segment encoding IL-10 or (ii) a single polynucleotide construct comprising a polynucleotide segment encoding a CAR and a polynucleotide segment encoding IL-10.

In some embodiments, the first exogenous polynucleotide segment encoding a CAR, the second exogenous polynucleotide segment encoding IL-10, or a polynucleotide construct comprising the first and second exogenous polynucleotide segments is introduced to CD4$^+$ T cells by a viral vector or a plasmid vector. In some embodiments, CD4$^+$ T cells are transduced with a first viral vector (e.g., any of the viral vectors described herein) containing the polynucleotide segment encoding IL-10 followed by a second transduction with a second viral vector (e.g., any of the viral vectors described herein) containing the polynucleotide segment encoding a CAR. In another embodiment, CD4$^+$ T cells are co-transduced with a first viral vector (e.g., any of the viral vectors described herein) containing the first exogenous polynucleotide segment and a second viral vector containing the second exogenous polynucleotide segment. In yet another embodiment, CD4$^+$ T cells are transduced with a viral vector (e.g., any of the viral vectors described herein) containing both the first and second exogenous polynucleotide segments.

In some embodiments, polydonor CD4$^{IL-10/CAR}$ are generated by (i) pooling primary CD4$^+$ T cells obtained from at least two different T cell donors; and (ii) modifying the pooled CD4$^+$ T cells according to the methods described herein. In some embodiments, poly donor CD4$^{IL-10/CAR}$ T cells are generated by (i) obtaining primary CD4$^+$ T cells from at least two different T cell donors; (ii) separately modifying each donor's CD4$^+$ T cells according to the methods described herein, and then (iii) pooling the genetically modified CD4$^+$ T cells.

In some embodiments, CD4$^{IL-10/CAR}$ T cells have been cultured in the presence of proteins capable of activating CD4$^+$ T cells. In some embodiments, CD4$^{IL-10/CAR}$ T cells have been cultured in the presence of anti-CD3 antibody and anti-CD28 antibody, or anti-CD3 antibody and anti-CD28 antibody coated beads. In some embodiments, CD4$^{IL-10/CAR}$ T cells have been cultured in the presence of anti-CD3 antibodies, anti-CD28 antibodies, and IL-2, or anti-CD3 antibody and anti-CD28 antibody coated beads and IL-2. In some embodiments, CD4$^{IL-10/CAR}$ T cells have been cultured in the presence of a polymeric nanomatrix reagent to activate and expand human T cells via CD3 and CD28. In some embodiments, CD4$^{IL-10/CAR}$ T cells have been cultured in the presence of other T-cell specific immune cell culture media, activators, and supplements.

In some embodiments, CD4$^{IL-10/CAR}$ (single-donor or polydonor CD4$^{IL-10/CAR}$ T cells) are in a frozen stock (e.g., frozen suspension). In some embodiments, CD4$^{IL-10/CAR}$ (single-donor or polydonor CD4$^{IL-10/CAR}$ T cells) are in a liquid suspension.

6.4. Population of CD4$^{IL10/CAR}$ T Cells

In another aspect, the disclosure features a population of CD4$^{IL10/CAR}$ T cells as described herein above. In some embodiments, the population further comprises CD4$^+$ T cells (e.g., primary CD4$^+$ T cells).

In some embodiments, the population of CD4$^+$ T cells comprise CD4$^+$ T cells obtained from an autologous or allogeneic single T cell donor (single-donor CD4$^{IL-10/CAR}$ cells). In some embodiments, the primary CD4$^+$ T cells are from a single T cell donor. In some embodiments, the primary CD4$^+$ T cells are from the same individual (i.e., the same patient). In some embodiments, the population of CD4$^+$ T cells comprise CD4$^+$ T cells obtained from at least two different T cell donors (polydonor CD4$^{IL-10/CAR}$ cells). In some embodiments, the primary CD4$^+$ T cells are from the donor of the allo-HSCT.

In some embodiments, the CD4$^+$ T cells were obtained from two, three, four, five, six, seven, eight, nine, or ten different T cell donors and pooled. Polydonor CD40-10 T cells and methods of making and using the same are described in PCT/US2021/039464, which is herein incorporated by reference in its entirety. Methods and/or compositions described therein can be adopted to generate polydonor CD4$^{IL-10/CAR}$ cells.

In some embodiments, the primary CD4$^+$ T cells are from donors selected from donors after analyzing a donors' genetic information. In some embodiments, genetic information of a donor (i.e., the donor of the primary CD4$^+$ T cells) is not analyzed. In some embodiments, the primary CD4$^+$ T cells are from donors selected based on their HLA haplotypes. In some embodiments, the CD4$^+$ T cells in the population collectively have six, seven, eight, nine, ten, eleven, twelve, or more different HLA haplotypes. In some embodiments, all the CD4$^+$ T cells in the population have at least 1/10, 2/10, 3/10, 4/10, 5/10, 6/10, 7/10, 8/10, or 9/10 match at the HLA-A, HLA-B, HLA-C, HLA-DRB1, and HLA-DQB1 loci to each other. In some embodiments, all the CD4$^+$ T cells in the population have at least 1/8, 2/8, 3/8, 4/8, 5/8, 6/8, 7/8, or 8/8 match at the HLA-A, HLA-B, HLA-C, and HLA-DRB1 loci to each other.

In some embodiments, all the CD4$^+$ T cells in the population have 2/2 match at the HLA-A locus to each other. In some embodiments, all the CD4$^+$ T cell in the population have 2/2 match at the HLA-B locus to each other. In some embodiments, all the CD4$^+$ T cell in the population have 2/2 match at the HLA-C locus to each other. In some embodiments, all the CD4$^+$ T cells in the population have at least 3/4 or 4/4 match at the HLA-DRB1 and HLA-DQB1 loci with each other. In some embodiments, all the CD4$^+$ T cells in the population have an A*02 or an A*24 allele. In some embodiments, all the CD4$^+$ T cells are A*02 or A*24 negative.

In some embodiments, all of the CD4$^+$ T cells in the population have less than 5/10, 6/10, 7/10, 8/10, or 9/10 match at the HLA-A, HLA-B, HLA-C, HLA-DRB1, and HLA-DQB1 loci to each other. In some embodiments, all of the CD4$^+$ T cells in the population have less than 4/8, 5/8, 6/8, 7/8, or 8/8 match at the HLA-A, HLA-B, HLA-C, and HLA-DRB1 loci to each other. In some embodiments, all the CD4$^+$ T cells in the population have less than 2/2 match at the HLA-A locus to each other. In some embodiments, all the CD4$^+$ T cells in the population have less than 2/2 match at the HLA-B locus to each other. In some embodiments, all the CD4$^+$ T cells in the population have less than 2/2 match at the HLA-C locus to each other. In some embodiments, all the CD4$^+$ T cells in the population have less than 3/4 or 4/4 match at the HLA-DRB1 and HLA DQB1 loci with each other.

In some embodiments, at least 30% (e.g., at least 30%, at least 35%, at least 40%, at least 45%, at least 50%, at least 55%, at least 60%, at least 65%, at least 70%, at least 80%, at least 90%, at least 95%, or at least 98%) of the CD4$^+$ T cells within the population express the CAR and IL-10 as inferred by the expression of ΔNGFR.

In some embodiments, the CD4$^+$ T cells are in a frozen suspension. In some embodiments, the CD4$^+$ T cells are in a liquid suspension. In some embodiments, the liquid suspension has previously been frozen.

6.5. Pharmaceutical Compositions

In another aspect, pharmaceutical compositions are provided. In some embodiments, the pharmaceutical composition comprises any of the single donor CD4$^{IL-10/CAR}$ T cells provided herein, any of the polydonor CD4$^{IL-10/CAR}$ T cells provided herein, or any of the populations of polydonor CD4$^{IL-10/CAR}$ T cells provided herein, and a pharmaceutically acceptable carrier or diluent.

The pharmaceutical composition can be formulated for administration by any route of administration appropriate for human or veterinary medicine. In typical embodiments, the composition is formulated for intravenous (IV) administration. In some embodiments, the composition is formulated for intravenous (IV) infusion. In embodiments formulated for IV administration, the pharmaceutical composition will be in the form of a parenterally acceptable aqueous solution which is pyrogen-free and has suitable pH, isotonicity and stability.

In some embodiments, the pharmaceutically acceptable carrier or diluent is saline, lactated Ringer's solution, or other physiologically compatible solution. In various embodiments, the pharmaceutical composition solution comprises 2-20%, preferably 5%, human serum albumin.

In some embodiments, unit dosage forms of the pharmaceutical composition are provided that are adapted for administration of the pharmaceutical composition by systemic administration, in particular, for intravenous administration.

In some embodiments, the unit dosage form contains 10$^4$ to 10$^{11}$ CD4$^{IL-10/CAR}$ cells or polydonor CD4$^{IL-10/CAR}$ cells, 10$^4$ to 10$^{10}$ CD4$^{IL-10/CAR}$ cells or polydonor CD4$^{IL-10/CAR}$ cells, 10$^4$ to 10$^9$ CD4$^{IL-10/CAR}$ T cells or polydonor CD4$^{IL-10/CAR}$ cells, 10$^5$ to 10$^{10}$ CD4$^{IL-10/CAR}$ cells or polydonor CD4$^{IL-10/CAR}$ cells, 10$^5$ to 10$^9$ CD4$^{IL-10/CAR}$ cells or polydonor CD4$^{IL-10/CAR}$ cells, 10$^5$ to 10$^8$ CD4$^{IL-10/CAR}$ cells or polydonor CD4$^{IL-10/CAR}$ cells, or 10$^5$ to 10$^7$ CD4$^{IL-10/CAR}$ cells or polydonor CD4$^{IL-10/CAR}$ cells.

In typical embodiments, the pharmaceutical composition in the unit dosage form is in liquid form.

6.6. Methods of Making Single Donor CD4$^{IL10/CAR}$ Cells or Polydonor CD4$^{IL10/CAR}$ cells In another aspect, the present disclosure provides a method of making CD4$^{IL10/CAR}$ cells or polydonor CD4$^{IL10/CAR}$ cells.

In some embodiments, the methods provided herein include modifying the CD4$^+$ T cells or pooled CD4$^+$ T cells by introducing an exogenous polynucleotide segment encoding a CAR and an exogenous polynucleotide segment encoding IL-10. In some embodiments, modifying the CD4$^+$ T cells or pooled CD4$^+$ T cells with a exogenous polynucleotide segment encoding a CAR and a exogenous polynucleotide segment encoding IL-10 comprises: (i) a first transduction with the polynucleotide segment encoding IL-10 followed by a second transduction with the exogenous polynucleotide segment encoding the CAR; (ii) a first transduction with the polynucleotide segment encoding the CAR followed by a second transduction with the exogenous polynucleotide segment encoding IL-10; (iii) simultaneous transduction (i.e., co-transduction) of the polynucleotide segment encoding IL-10 and the exogenous polynucleotide segment encoding the CAR; or (iv) transduction of a single polynucleotide construct comprising both the polynucleotide segment encoding IL-10 and the polynucleotide segment encoding the CAR.

In some embodiments, the single polynucleotide construct comprising the polynucleotide segment encoding IL-10 and the polynucleotide segment encoding the CAR is a bidirectional vector in which IL-10 is under one promoter (e.g., PGK or EF1a) and the CAR is under a second promoter (for example CMV). In such cases, if the construct includes a polynucleotide sequence encoding a selection marker, the polynucleotide sequence can be downstream of a either the IL-10 or the CAR.

In some embodiments, the single polynucleotide construct comprising the polynucleotide segment encoding IL-10 and the polynucleotide segment encoding the CAR comprises from 5' to 3' the sequence encoding IL-10 and the sequence encoding the CAR. In such embodiments, the sequence encoding IL-10 and the sequence encoding the CAR are operably linked to a single promoter (e.g., constitutive or inducible). In such embodiments, a sequence encoding an internal ribosome entry site (IRES) or a sequence encoding a 2A-peptide is located between the sequence encoding IL-10 and the sequence encoding the CAR.

In some embodiments, the single polynucleotide construct comprising the polynucleotide segment encoding IL-10 and the polynucleotide segment encoding the CAR comprises from 5' to 3' the sequence encoding the CAR and the sequence encoding IL-10. In such embodiments, the sequence encoding the CAR and the sequence encoding IL-10 are operably linked to a single promoter (e.g., constitutive or inducible). In such embodiments, a sequence encoding an internal ribosome entry site (IRES) or a sequence encoding a 2A-peptide is located between the sequence encoding the CAR and the sequence encoding IL-10.

In some embodiments, the method comprises the steps of: (a) pooling primary CD4$^+$ T cells obtained from one or more T cell donors; and (b) modifying the pooled CD4$^+$ T cells by introducing a first exogenous polynucleotide segment encoding a CAR and a second exogenous polynucleotide segment encoding IL-10 according to the methods provided herein. In other embodiments, the method comprises the steps of: (a) obtaining primary CD4$^+$ T cells from one or more T cell donors; (b) separately modifying each donor's CD4$^+$ T cells by introducing a first exogenous polynucleotide segment encoding a CAR and a second exogenous polynucleotide segment encoding IL-10 (e.g., according to the methods provided herein); and then pooling the genetically modified CD4$^+$ T cells, thereby obtaining the CD4$^{IL-10/CAR}$ cells. Various methods known in the art can be used to introduce a first exogenous polynucleotide segment encoding a CAR, a second exogenous polynucleotide segment encoding IL-10, or both, to primary CD4$^+$ T cells.

In some embodiments, the method further comprises the step of incubating the primary CD4$^+$ T cells or genetically-modified CD4$^+$ T cells in the presence of an anti-CD3 antibody and anti-CD28 antibody, or anti-CD3 antibody and anti-CD28 antibody coated beads. In some embodiments, the method further comprises the step of incubating the primary CD4$^+$ T cells or genetically-modified CD4$^+$ T cells in the presence of anti-CD3 antibody, anti-CD28 antibody and IL-2 or anti-CD3 antibody and anti-CD28 antibody coated beads and IL-2. In some embodiments, the method further comprises the step of incubating the primary CD4$^+$ T cells or genetically-modified CD4$^+$ T cells in the presence of a mixture of feeder cells. In some embodiments, the method further comprises the step of incubating the primary CD4$^+$ T cells or genetically-modified CD4$^+$ T cells in the presence of nanopreparations of anti-CD3 antibody and anti-CD28 antibody. In some embodiments, the incubation is done in the presence of a polymeric nanomatrix reagent to activate and expand human T cells via CD3 and CD28. In some embodiments, CD4$^{IL-10/CAR}$ T cells have been cultured in the presence of other T-cell specific immune cell culture media, activators, and supplements.

In some embodiments, the incubation step is performed before introducing a first exogenous polynucleotide segment encoding a CAR and a second exogenous polynucleotide segment encoding IL-10 according to the methods provided herein. In some embodiments, the incubation step is performed after (a) pooling primary CD4$^+$ T cells obtained from one or more different T cell donors; but before (b) modifying the pooled CD4$^+$ T cells by introducing a first exogenous polynucleotide segment encoding a CAR, and a second exogenous polynucleotide segment encoding IL-10 according to the methods provided herein. In some embodiments, the incubation step is performed after (a) obtaining primary CD4$^+$ T cells from one or more different T cell donors; but before (b) separately modifying each donor's CD4$^+$ T cells by introducing a first exogenous polynucleotide segment encoding a CAR and a second exogenous polynucleotide segment encoding IL-10 according to the methods provided herein.

In some embodiments, the incubation step is performed after step (b). In other words, in some embodiments, the incubation step is performed after (b) modifying the pooled CD4$^+$ T cells by introducing a first exogenous polynucleotide segment encoding a CAR and a second exogenous polynucleotide segment encoding IL-10 according to the methods provided herein. In some embodiments, the incubation step is performed after (b) separately modifying each donor's CD4$^+$ T cells by introducing a first exogenous polynucleotide segment encoding a CAR and a second exogenous polynucleotide segment encoding IL-10 according to the methods provided herein, but before pooling the genetically modified CD4$^+$ T cells, thereby obtaining the genetically-modified CD4$^+$ T cells. In some embodiments, the incubation step is performed after pooling the genetically modified CD4$^+$ T cells, thereby obtaining the CD4$^{IL-10/CAR}$ cells.

In some embodiments, the incubation step is performed more than once. In some embodiments, the incubation step is performed both before and after genetic modification of CD4$^+$ T cells.

In some embodiments, the first exogenous polynucleotide segment, the second exogenous polynucleotide segment, or both, is introduced into the primary CD4$^+$ T cells using a viral vector. In some embodiments, the first and second exogenous polynucleotide segments are located on the same viral vector. In some embodiments, the viral vector is a lentiviral vector.

In some embodiments, the first exogenous polynucleotide comprises a segment encoding a CAR having the sequence of SEQ ID NOs: 9, 16, 22, 34, 41-49, and 54 and the second exogenous polynucleotide segment encoding IL-10 having the sequence of SEQ ID NO: 1. In some embodiments, the first exogenous polynucleotide comprises a segment encoding a CAR having at least 80%, 85%, 90%, 95%, 98%, or 99% sequence identity to SEQ ID NOs: 9, 16, 22, 34, 41-49, and 54 and the second exogenous polynucleotide comprises a segment encoding IL-10 having at least 80%, 85%, 90%, 95%, 98%, or 99% sequence identity to SEQ ID NO: 1.

In some embodiments, the CAR-encoding polynucleotide segment has the sequence of SEQ ID NOs: 10, 17, 23, 35, or 55 and the IL-10-encoding polynucleotide segment has the sequence of SEQ ID NO: 2. In some embodiments, the CAR-encoding polynucleotide segment has at least 80%, 85%, 90%, 95%, 98%, or 99% sequence identity to SEQ ID NOs: 10, 17, 22, 35, or 55 and the IL-10-encoding polynucleotide segment has at least 80%, 85%, 90%, 95%, 98%, or 99% sequence identity to SEQ ID NO: 2. In some embodiments, the first exogenous polynucleotide segment, the second exogenous polynucleotide segment, or both, further comprise a segment encoding a marker permitting selection of successfully transduced CD4$^+$ T cells. In some embodiments, the encoded selection marker is ΔNGFR. In certain embodiments, the encoded selection marker has the sequence of SEQ ID NO: 4. In some embodiments, the encoded selection marker is a truncated form of human EGFR polypeptide.

In some embodiments, the method further comprises the step of isolating the genetically-modified CD4$^+$ T cells expressing one or more selection markers, thereby generating an enriched population of genetically-modified CD4$^{IL-10/CAR}$ cells.

In some embodiments, at least 40% (e.g., at least 50%, at least 60%, at least 70%, at least 80%, at least 90%, at least 95%, or at least 98%) of the genetically-modified CD4$^+$ T cells in the enriched population express a selection marker, wherein the selection marker is a proxy for IL-10 expression. In some embodiments, at least 75% (e.g., at least 80%, at least 90%, at least 95%, or at least 98%) of the genetically-modified CD4$^+$ T cells in the enriched population express a selection marker, wherein the selection marker is a proxy for IL-10 expression. In some embodiments, at least 75% of the genetically-modified CD4$^+$ T cells in the enriched population express a selection marker. In some embodiments, at least 95% of the genetically-modified CD4$^+$ T cells in the enriched population express a selection marker. In some embodiments, at least 96, 97, 98, or 99% of the genetically-modified CD4$^+$ T cells in the enriched population express a selection marker.

In some embodiments, at least 75% (e.g., at least 80%, at least 90%, at least 95%, or at least 98%) of the genetically-modified CD4$^+$ T cells in the enriched population express IL-10. In some embodiments, at least 75% of the genetically-modified CD4$^+$ T cells in the enriched population express IL-10. In some embodiments, at least 95% of the genetically-modified CD4+ T cells in the enriched population express IL-10. In some embodiments, at least 96, 97, 98, or 99% of the genetically-modified CD4$^+$ T cells in the enriched population express IL-10.

In some embodiments, at least 30% (e.g., at least 30%, at least 35%, at least 40%, at least 45%, at least 50%, at least 55%, at least 60%, at least 65%, at least 70%, at least 80%, at least 90%, at least 95%, or at least 98%) of the genetically-modified CD4$^+$ T cells in the enriched population express a CAR. In some embodiments, at least 50% of the genetically-modified CD4$^+$ T cells in the enriched population express a CAR. In some embodiments, at least 75% of the genetically-modified CD4$^+$ T cells in the enriched population express a CAR. In some embodiments, at least 95% of the genetically-modified CD4$^+$ T cells in the enriched population express a CAR. In some embodiments, at least 96, 97, 98, or 99% of the genetically-modified CD4$^+$ T cells in the enriched population express a CAR.

In some embodiments, at least 30% (e.g., at least 30%, at least 35%, at least 40%, at least 45%, at least 50%, at least 55%, at least 60%, at least 65%, at least 70%, at least 80%, at least 90%, at least 95%, or at least 98%) of the genetically-modified CD4$^+$ T cells in the enriched population express IL-10 and a CAR. In some embodiments, at least 50% of the genetically-modified CD4$^+$ T cells in the enriched population express IL-10 and a CAR. In some embodiments, at least 75% of the genetically-modified CD4$^+$ T cells in the enriched population express IL-10 and a CAR. In some embodiments, at least 95% of the genetically-modified CD4$^+$ T cells in the enriched population express IL-10 and a CAR. In some embodiments, at least 96, 97, 98, or 99% of the genetically-modified CD4$^+$ T cells in the enriched population express IL-10 and a CAR.

In some embodiments, the method further comprises the step of incubating the enriched population of the genetically-modified CD4$^+$ T cells. In some embodiments, the incubation is performed in the presence of anti-CD3 antibody and anti-CD28 antibody, or anti-CD3 antibody and anti-CD28 antibody coated beads. In some embodiments, the incubation is performed further in presence of IL-2. In some embodiments, the incubation is performed in the presence of feeder cells. In some embodiments, the incubation is performed in the presence of nanopreparations of anti-CD3 antibody and anti-CD28 antibody. In some embodiments, the incubation is performed in the presence of a polymeric nanomatrix reagent to activate and expand human T cells via CD3 and CD28. In some embodiments, CD4$^{IL-10/CAR}$ T cells have been cultured in the presence of other T-cell specific immune cell culture media, activators, and supplements.

In some embodiments, the method further comprises the step of freezing the genetically-modified CD4$^+$ T cells.

In some embodiments, the primary CD4$^+$ T cells are from donors selected based on their HLA haplotypes. In some embodiments, the method further comprises the step of selecting T cell donors by analyzing their genetic information. In some embodiments, the method comprises the step of analyzing genetic information or HLA haplotype of potential T cell donors.

In some embodiments, the primary CD4$^+$ T cells are from donors having at least a partial HLA match with a host to be treated with the primary CD4$^+$ T cells or a modification thereof. In some embodiments, the primary CD4$^+$ T cells are from donors having at least a partial HLA match with a stem cell (HSC), tissue or organ donor. In some embodiments, the CD4$^+$ T cells are from donors HLA matched with a stem cell (HSC), tissue, or organ donor. In some embodiments, the primary CD4$^+$ T cells are obtained from third party donors who are not biologically related with a host. In some embodiments, the primary CD4$^+$ T cells are obtained from third party donors who are not biologically related with a stem cell, tissue or organ donor.

In some embodiments, in step (a), the primary CD4$^+$ T cells are obtained from two, three, four, five, six, seven, eight, nine, or ten different T cell donors. In some embodiments, the at least two T cell donors have at least 1/10, 2/10, 3/10, 4/10, 5/10, 6/10, 7/10, 8/10, or 9/10 match at the HLA-A, HLA-B, HLA-C, HLA-DRB1, and HLA-DQB1 loci to each other. In some embodiments, the at least two T cell donors have at least 1/8, 2/8, 3/8, 4/8, 5/8, 6/8, 7/8, or 8/8 match at the HLA-A, HLA-B, HLA-C, and HLA-DRB1 loci to each other. In some embodiments, the at least two T cell donors have 2/2 match at the HLA-A locus to each other. In some embodiments, the at least two T cell donors have 2/2 match at the HLA-B locus to each other. In some embodiments, the at least two T cell donors have 2/2 match at the HLA-C locus to each other. In some embodiments, the at least two T cell donors have at least 3/4 or 4/4 match at the HLA-DRB1 and HLA-DQB1 loci to each other. In some embodiments, each of the at least two T cell donors has an A*02 or A*24 allele. In some embodiments, the T-cell donor is HLA-A*02 negative. In some embodiments, each of the at least two T cell donors is HLA-A*02 or HLA-A*24 negative.

In some embodiments, the at least two T cell donors have less than 5/10, 6/10, 7/10, 8/10, or 9/10 match at the HLA-A, HLA-B, HLA-C, HLA-DRB1, and HLA-DQB1 loci to each other. In some embodiments, the at least two T cell donors have less than 4/8, 5/8, 6/8, 7/8, or 8/8 match at the HLA-A, HLA-B, HLA-C, and HLA-DRB1 loci to each other. In some embodiments, the at least two T cell donors have less than 2/2 match at the HLA-A locus to each other. In some embodiments, the at least two T cell donors have less than 2/2 match at the HLA-B locus to each other. In some embodiments, the at least two T cell donors have less than 2/2 match at the HLA-C locus to each other. In some embodiments, the at least two T cell donors have less than ¾ or 4/4 match at the HLA-DRB1 and HLA-DQB1 loci to each other.

In some embodiments, in step (a), the primary CD4$^+$ T cells are obtained from one or more frozen stocks. In some embodiments, in step (a), the primary CD4$^+$ T cells are obtained from unfrozen peripheral blood mononuclear cells of the at least two different T cell donors. In some embodiments, the method further comprises the step of isolating CD4$^+$ T cells from the peripheral blood mononuclear cells. In some embodiments, in step (a), the primary CD4$^+$ T cells are obtained from a liquid suspension. In some embodiments, the liquid suspension is obtained from a previously frozen stock.

In some embodiments, the method does not comprise the step of anergizing the CD4$^+$ T cells in the presence of peripheral blood mononuclear cells (PBMCs) from a host. In some embodiments, the method does not comprise the step of anergizing the CD4$^+$ T cells in the presence of recombinant IL-10 protein, wherein the recombinant IL-10 protein is not expressed from the CD4$^+$ T cells. In some embodiments, the method does not comprise the step of anergizing the CD4$^+$ T cells in the presence of DC10 cells from a host.

In some embodiments, the methods provided herein include modifying the CD4$^+$ T cells or pooled CD4$^+$ T cells by introducing an exogenous polynucleotide segment encoding a CAR and an exogenous polynucleotide segment encoding IL-10 after one or more of the pooling, purification, restimulation, and expansion steps.

6.7. Methods of Using CD4$^{IL-10/CAR}$ Cells or Polydonor CD4$^{IL-10/CAR}$ In another aspect, the present disclosure provides a method of treating a patient, comprising the step of administering any of the CD4$^{IL-10/CAR}$ cells (e.g., autologous single-donor or allogeneic single-donor) provided herein, any of the allogeneic polydonor CD4$^{IL-10/CAR}$ T cells provided herein, any of the populations of polydonor CD4$^{IL-10/CAR}$ cells provided herein, or any of the pharmaceutical composition provided herein to a patient in need thereof.

In some embodiments, the method further comprises the preceding step of thawing a frozen suspension of CD4$^{IL-10/CAR}$ cells.

In some embodiments, the autologous single-donor or allogeneic single-donor CD4$^{IL-10/CAR}$ cells or allogeneic polydonor CD4$^{IL-10/CAR}$ cells or the pharmaceutical composition prevents or reduces severity of pathogenic T cell response in the patient.

In some embodiments, the polydonor CD4$^{IL-10}$ cells or the pharmaceutical composition prevents or reduces the severity of an inflammatory or autoimmune response.

In some embodiments, the polydonor CD4$^{IL-10/CAR}$ cells or the pharmaceutical composition prevents or reduces severity of pathogenic T cell response in the patient. In some embodiments, the polydonor CD4$^{IL-10/CAR}$ cells or the pharmaceutical composition reduces inflammation. In some embodiments, the polydonor CD4$^{IL-10/CAR}$ cells or the pharmaceutical composition enhances tissue repair. In some embodiments, the polydonor CD4$^{IL-10/CAR}$ cells or the pharmaceutical composition enhances immunological tolerance to self and non-pathogenic antigens and maintain immune homeostasis. In some embodiments, the polydonor CD4$^{IL-10/CAR}$ cells or the pharmaceutical composition downregulates pathogenic T-cell responses associated with organ transplantation, GvHD and various autoimmune and inflammatory diseases. In some embodiments, the polydonor CD4$^{IL-10/CAR}$ cells or the pharmaceutical composition treats autoimmune disease. In some embodiments, the polydonor CD4$^{IL-10/CAR}$ cells or the pharmaceutical composition reduces hyperactivity of NLPR3 inflammasome or reduces symptoms associated with hyperactivity of NLPR3 inflammasome. In some embodiments, the polydonor CD4$^{IL-10/CAR}$ cells or the pharmaceutical composition induces death of tumor cells or reduces tumor growth. In some embodiments, the polydonor CD4$^{IL-10/CAR}$ cells or the pharmaceutical composition increases disease free survival (e.g., absence of minimal residual disease). In some embodiments, the polydonor CD4$^{IL-10/CAR}$ cells or the pharmaceutical composition induces wound healing or tissue repair.

In some embodiments, the polydonor CD4$^{IL-10}$ cells or the pharmaceutical composition are administered at an amount effective to prevent or reduce severity of pathogenic T cell response in the patient. In some embodiments, the polydonor CD4$^{IL-10}$ cells or the pharmaceutical composition are administered at an amount effective to reduce inflammation. In some embodiments, the polydonor CD4$^{IL-10}$ cells or the pharmaceutical composition are administered at an amount effective to enhance tissue repair. In some embodiments, the polydonor CD4$^{IL-10}$ cells or the pharmaceutical composition are administered at an amount effective to enhance immunological tolerance to self and non-pathogenic antigens and maintain immune homeostasis. In some embodiments, the polydonor CD4$^{IL-10}$ cells or the pharmaceutical composition are administered at an amount effective to downregulate pathogenic T-cell responses associated with organ transplantation, GvHD and various autoimmune or inflammatory diseases. In some embodiments, the polydonor CD4$^{IL-10}$ cells or the pharmaceutical composition are administered at an amount effective to treat autoimmune disease. In some embodiments, the polydonor CD4$^{IL-10}$ cells or the pharmaceutical composition are administered at an amount effective to reduce hyperactivity of NLPR3 inflammasome or reduces symptoms associated with hyperactivity of NLPR3 inflammasome. In some embodiments, the polydonor CD4$^{IL-10}$ cells or the pharmaceutical composition are administered at an amount effective to induce death of tumor cells or reduces tumor growth. In some embodiments, the polydonor CD4-10 cells or the pharmaceutical composition are administered at an amount effective to increase disease free survival (e.g., absence of minimal residual disease).

In some embodiments, the single donor CD4$^{IL-10/CAR}$ cells (e.g., autologous or allogeneic) or the pharmaceutical composition prevents or reduces severity of pathogenic T cell response in the patient. In some embodiments, the single donor CD4$^{IL-10/CAR}$ cells or the pharmaceutical composition reduces inflammation. In some embodiments, the single donor CD4$^{IL-10/CAR}$ cells or the pharmaceutical composition enhances tissue repair. In some embodiments, the single donor CD4$^{IL-10/CAR}$ cells or the pharmaceutical composition enhances immunological tolerance to self and non-pathogenic antigens and maintain immune homeostasis. In some embodiments, the single donor CD4$^{IL-10/CAR}$ cells or the pharmaceutical composition downregulates pathogenic T-cell responses associated with organ transplantation, GvHD and various autoimmune and inflammatory diseases. In some embodiments, the single donor CD4$^{IL-10/CAR}$ cells or the pharmaceutical composition treats autoimmune disease. In some embodiments, the single donor CD4$^{IL-10/CAR}$ cells or the pharmaceutical composition reduces hyperactivity of NLPR3 inflammasome or reduces symptoms associated with hyperactivity of NLPR3 inflammasome. In some embodiments, the single donor CD4$^{IL-10/CAR}$ cells or the pharmaceutical composition induces death of tumor cells or reduces tumor growth. In some embodiments, the single donor CD4$^{IL-10/CAR}$ cells or the pharmaceutical composition increases disease free survival (e.g., absence of minimal residual disease). In some embodiments, the single donor CD4$^{IL-10/CAR}$ cells or the pharmaceutical composition induces wound healing or tissue repair.

In some embodiments, the treatment method further comprises monitoring CD4$^{IL-10/CAR}$ cells in a patient after administration. In some embodiments, the method comprises the step of detecting a selection marker in a biological sample obtained from the patient, thereby detecting presence or absence of CD4$^{IL-10/CAR}$ cells or polydonor CD4$^{IL-10/CAR}$ cells. In some embodiments, the method comprises the step of detecting a selection marker in a patient, and using detection of the selection marker to track and/or monitor CD4$^{IL-10/CAR}$ cells following administration to a patient. In some embodiments, the selection marker is detected at multiple time points to trace changes in presence of CD4$^{IL-10/CAR}$ cells in a patient. In some embodiments, the biological sample is a biopsy or blood sample from the patient.

The CD4$^{IL-10/CAR}$ cells (autologous single-donor, allogeneic single-donor or allogeneic polydonor CD4$^{IL-10/CAR}$ cells) are administered in a therapeutically effective amount. The amount can be determined based on the body weight and other clinical factors. In some embodiments, $10^3$ to $10^{11}$ cells/kg are administered. In some embodiments, $10^3$ to $10^{10}$ cells/kg are administered. In some embodiments, $10^3$ to $10^9$ cells/kg are administered. In some embodiments, $10^3$ to $10^8$ cells/kg are administered. In some embodiments, $10^3$ to $10^7$ cells/kg are administered. In some embodiments, $10^3$ to $10^6$ cells/kg are administered. In some embodiments, $10^3$ to $10^5$ cells/kg are administered. In some embodiments, $10^3$ to $10^4$ cells/kg are administered.

In various embodiments, CD4$^{IL-10/CAR}$ cells (autologous single-donor, allogeneic single-donor, or allogeneic polydonor CD4$^{IL-10/CAR}$ cells) are administered on a therapeutically effective schedule. In some embodiments, CD4$^{IL-10/CAR}$ cells (autologous single-donor, allogeneic single-donor, or allogeneic polydonor CD4$^{IL-10/CAR}$ cells) are administered once. In some embodiments, CD4$^{IL-10/CAR}$ cells (autologous single-donor, allogeneic single-donor, or allogeneic polydonor CD4$^{IL-10/CAR}$ cells) are administered every day, every 3 days, every 7 days, every 14 days, every 21 days, or every month.

The CD4$^{IL-10/CAR}$ AR cells (autologous single-donor, allogeneic single-donor, or allogeneic polydonor CD4$^{IL-10/CAR}$ cells) can be administered according to different administration routes, such as systemically, subcutaneously, or intraperitoneally. In some embodiments, the cells are administered within a saline or physiological solution which may contain 2-20%, preferably 5% human serum albumin.

6.7.1. Methods of Reducing or Preventing GvHD

In some embodiments, CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein is used to treat a patient before a hematopoietic stem cell (HSC) transplant (HSCT), concurrently with an HSCT, or following an HSCT.

In various embodiments, the HSCT is a matched related HSCT, or a matched unrelated HSCT. In various embodiments, the HSCT is a haploidentical HSCT, a mismatched related HSCT, or a mismatched unrelated HSCT.

In some embodiments, the patient has a hematological malignancy which requires treatment with allo-HSCT. In some embodiments, the hematological malignancy is mediated by aberrant myeloid cells. In some embodiments, the malignancy or hematological cancer is a myeloid leukemia. In some embodiments, the malignancy or hematological cancer is a CD19$^+$, CD20$^+$, CD22$^+$, BCMA$^+$, or B7-H3$^+$ hematological cancer. In some embodiments, the CD19$^+$, CD20$^+$, CD22$^+$, or B7-H3$^+$ hematological cancer is selected from chronic lymphocytic leukemia, acute lymphoblastic leukemia (ALL), and non-Hodgkin's lymphomas.

In some embodiments, T cell donors are selected based on genetic information of a patient to be treated with CD4$^{IL-10/CAR}$ (autologous single-donor or allogeneic single-donor) or allogeneic polydonor CD4$^{IL-10/CAR}$ cells and HSC, and/or genetic information of the HSC donor. In some embodiments, T cell donors are selected based on HLA haplotype of a patient to be treated with polydonor CD4$^{IL-10}$ cells and HSC, and/or HLA haplotype of the HSC donor. In some embodiments, the method further comprises the step, prior to administering CD4$^{IL-10}$ cells, of analyzing genetic information or HLA haplotype of T cell donors. In some embodiments, the method further comprises the step of analyzing genetic information or HLA haplotype of a host. In some embodiments, the method further comprises the step of analyzing genetic information or HLA haplotype of an HSC donor.

In some embodiments, T cell donors, a host and an HSC donor are not biologically related. In some embodiments, T cell donors, a host and an HSC donor have different HLA haplotypes. In some embodiments, T cell donors, a host and an HSC donor have at least partial mismatch in HLA haplotype. In some embodiments, T cell donors are selected when they have HLA haplotype with an HLA match over a threshold value.

In some embodiments, the HSC donor is partially HLA mismatched to the patient. In some embodiments, the HSC donor has less than 5/10, 6/10, 7/10, 8/10, 9/10 or 10/10 match at the HLA-A, HLA-B, HLA-C, HLA-DRB1, and HLA-DQB1 loci to the patient. In some embodiments, the HSC donor has less than 4/8, 5/8, 6/8, 7/8, or 8/8 match at the HLA-A, HLA-B, HLA-C, and HLA-DRB1 loci to the patient. In some embodiments, the HSC donor has less than 2/2 match at the HLA-A, HLA-B, or HLA-C locus to the patient. In some embodiments, the HSC donor has less than 3/4 or 4/4 match at the HLA-DRB1 and HLA-DQB1 loci to the patient.

In some embodiments, one or more of the T cell donors are HLA-mismatched or partially HLA-mismatched to the patient. In some embodiments, one or more of the T cell donors have less than 5/10, 6/10, 7/10, 8/10, 9/10 or 10/10 match at the HLA-A, HLA-B, HLA-C, HLA-DRB1, and HLA-DQB1 loci to the patient. In some embodiments, one or more of the T cell donors have less than 4/8, 5/8, 6/8, 7/8, or 8/8 match at the HLA-A, HLA-B, HLA-C, and HLA-DRB1 loci to the patient. In some embodiments, one or more of the T cell donors have less than 2/2 match at the HLA-A, HLA-B, or HLA-C locus to the patient. In some embodiments, one or more of the T cell donors have less than 2/4, 3/4 or 4/4 match at the HLA-DRB1 and HLA-DQB1 loci to the patient.

In some embodiments, one or more of the T cell donors are HLA-mismatched or partially HLA-mismatched with the HSC donor. In some embodiments, one or more of the T cell donors have less than 5/10, 6/10, 7/10, 8/10, 9/10 or 10/10 match at the HLA-A, HLA-B, HLA-C, HLA-DRB1, and HLA-DQB1 loci to the HSC donor. In some embodiments, one or more of the T cell donors have less than 4/8, 5/8, 6/8, 7/8, or 8/8 match at the HLA-A, HLA-B, HLA-C, and HLA-DRB1 loci to the HSC donor. In some embodiments, one or more of the T cell donors have less than 2/2 match at the HLA-A, HLA-B, or HLA-C locus to the HSC donor. In some embodiments, one or more of the T cell donors have less than 3/4 or 4/4 match at the HLA-DRB1 and HLA-DQB1 loci to the HSC donor.

In some embodiments, when administered to a patient, CD4$^{IL-10/CAR}$ cells (single donor or polydonor CD4DL-10/CAR cells), the population of single-donor or polydonor CD4$^{IL-10/CAR}$ cells, or any of the pharmaceutical compositions provided herein prevents or reduces severity of GvHD by the transplanted hematopoietic stem cells.

In some embodiments, when administered to a patient, CD4$^{IL-10/CAR}$ cells (single donor or polydonor CD4$^{IL-10/CAR}$ cells), the population of single-donor or polydonor CD4$^{IL-10/CAR}$ cells, or any of the pharmaceutical compositions provided herein prevents or reduces severity of pathological T cell response by the transplanted hematopoietic cells. In specific embodiments, the CD4$^{IL-10/CAR}$ or polydonor CD4$^{IL-10/CAR}$ cells prevents or reduces GvHD.

In some embodiments, the polydonor CD4$^{IL-10}$ cells or the pharmaceutical composition prevents or reduces severity of tissue damage induced by the pathogenic T cells or the inflammation.

6.7.2. Methods of Treating Cancer

In some embodiments, CD4$^{IL-10/CAR}$ cells (autologous single-donor, allogeneic single-donor or allogeneic polydonor CD4$^{IL-10/CAR}$ cells), the population of single-donor or polydonor CD4$^{IL-10/CAR}$ cells, or any of the pharmaceutical compositions provided herein are used for treatment of cancer. In some embodiments, CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are used for treating a malignancy.

In preferred embodiments, the CD4$^{IL-10/CAR}$ cells (autologous single-donor, allogeneic single-donor, or allogeneic polydonor $CD4^{IL-10/CAR}$ cells) directly mediate anti-tumor effects and in particular embodiments, an anti-leukemic effect.

In some embodiments, $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein and allogeneic are administered prior or after hematopoietic stem cell transplantation (HSCT), peripheral blood stem cells (PBSC), cord blood (CB), or bone marrow (BM) transplantation.

In some embodiments, the neoplastic cells express CD19. In some embodiments, the neoplastic cells express CD20. In some embodiments, the neoplastic cells express CD22. In some embodiments the neoplastic cells express BCMA. In some embodiments, the neoplastic cells express B7-H3. In some embodiments, the neoplastic cells express CD13. In some embodiments, the neoplastic cells express HLA-class I. In some embodiments, the neoplastic cells express CD54. In some embodiments, the neoplastic cells express CD13, HLA-class I and CD54. In some embodiments, the neoplastic cells express CD112. In some embodiments, the neoplastic cells express CD58. In some embodiments, the neoplastic cells express CD155. In some embodiments, the tumor expresses CD112, CD58, or CD155. In various embodiments, the tumor is a solid or hematological tumor. In some embodiments, the tumor is a solid tumor. In some embodiments, the solid tumor expresses B7-H3. In some embodiment, the solid tumor is selected from the group consisting of: breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

In some embodiments, the patient has a cancer selected from the group consisting of: Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Acute Lymphocytic (ALL), Acute Myeloid (AML, including myeloid sarcoma and leukemia cutis), Chronic Lymphocytic (CLL), Chronic Myeloid (CML) Leukemia, Chronic Myelomonocytic (CMML), Leukemia in Children, Liver Cancer, Lung Cancer, Lung Cancer with Non-Small Cell, Lung Cancer with Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma-Adult Soft Tissue Cancer, Skin Cancer, Skin Cancer-Basal and Squamous Cell, Skin Cancer-Melanoma, Skin Cancer-Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

In some embodiments, the cancer is a myeloid tumor. In particular embodiments, the cancer is AML or CML. In some embodiments, the cancer is a myeloid tumor. In some embodiments, the cancer is ALL.

In some embodiments, the method is used to treat a hematological cancer affecting blood, bone marrow, and lymph nodes. In various embodiments, the hematological cancer is a lymphoma (e.g., Hodgkin's Lymphoma), lymphocytic leukemias, myeloma. In various embodiments, the hematological cancer is acute or chronic myelogenous (myeloid) leukemia (AML, CML), or a myelodysplastic syndrome.

In some embodiments, the malignancy or hematological cancer is a $CD19^+$, $CD20^+$, $CD22^+$, $BCMA^+$, or $B7-H3^+$ hematological cancer. In some embodiments, the $CD19^+$, $CD20^+$, $CD22^+$, $BCMA^+$, or $B7-H3^+$ hematological cancer is chronic lymphocytic leukemia, acute lymphoblastic leukemia (ALL), and non-Hodgkin's lymphomas.

In some embodiments, the $CD4^{IL-10/CAR}$ cells (autologous single-donor, allogeneic single-donor, or allogeneic polydonor $CD4^{IL-10/CAR}$ cells) are used for treating a patient with a hematological cancer where the method includes administering a therapeutically effective amount of the $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein to the patient.

In some embodiments, the $CD4^{IL-10/CAR}$ cells are used for treating a patient with a $CD19^+$ hematological cancer where the method includes administering a therapeutically effective amount of $CD4^{IL}$-10/anti-CD19 CAR cells (autologous single-donor, allogeneic single-donor, or allogeneic polydonor $CD4^{IL-10/anti-CD19\ CAR}$), populations of single-donor or polydonor $CD4^{IL-10/anti-CD19\ CAR}$ cells, or any of the pharmaceutical compositions provided herein to the patient.

In some embodiments, the CD4TL-10/CAR cells are used for treating a patient with a $CD20^+$ hematological cancer where the method includes administering a therapeutically effective amount of $CD4^{IL-10/anti-CD20\ CAR}$ cells (autologous single-donor, allogeneic single-donor, or allogeneic polydonor $CD4^{IL-10/anti-CD20\ CAR}$), populations of single-donor or polydonor $CD4^{IL-10/anti-CD20\ CAR}$ cells, or any of the pharmaceutical compositions provided herein to the patient.

In some embodiments, the $CD4^{IL-10/CAR}$ cells are used for treating a patient with a $CD22^+$ hematological cancer where the method includes administering a therapeutically effective amount of $CD4^{IL-10/anti-CD22\ CAR}$ cells (autologous single-donor, allogeneic single-donor, or allogeneic polydonor $CD4^{IL-10/anti-CD22\ CAR}$), populations of single-donor or polydonor $CD4^{IL-10/anti-CD22\ CAR}$ cells, or any of the pharmaceutical compositions provided herein to the patient.

In some embodiments, the $CD4^{IL-10/CAR}$ cells are used for treating a patient with a $B7-H3^+$ cancer (e.g., a solid cancer) where the method includes administering a therapeutically effective amount of $CD4^{IL-10/anti-B7-H3\ CAR}$ cells (autologous single-donor, allogeneic single-donor, or allogeneic polydonor $CD4^{IL-10/anti-B7-H3\ CAR}$), populations of single-donor or polydonor $CD4^{IL-10/anti-B7-H3\ CAR}$ cells, or any of the pharmaceutical compositions provided herein to the patient.

In some embodiments, the $CD4^{IL-10/CAR}$ cells are used for treating a patient with a $BCMA^+$ cancer (e.g., a solid cancer) where the method includes administering a therapeutically effective amount of $CD4^{IL-10/anti-BCMA\ CAR}$ cells (autologous single-donor, allogeneic single-donor, or allogeneic polydonor $CD4^{IL-10/anti-BCMA\ CAR}$), populations of single-donor or polydonor $CD4^{IL-10/anti-BCMA\ CAR}$ cells, or any of the pharmaceutical compositions provided herein to the patient.

In some embodiments, the cancer is refractory or resistant to a therapeutic intervention.

In some embodiments, the methods provided herein are used for preventing relapse of a CD19$^+$, CD20$^+$, CD22$^+$, BCMA$^+$, or B7-H3$^+$ hematological and solid cancers in a patient, comprising: administering to a patient, identified as having a CD19$^+$, CD20$^+$, CD22$^+$ BCMA$^+$, or B7-H3$^+$ hematological or solid cancers or at risk of having a relapse of a CD19$^+$, CD20$^+$, CD22$^+$, BCMA$^+$, or B7-H3$^+$ hematological or solid cancers, a therapeutically effective amount of the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are sufficient to induce an anti-cancer effect.

In some embodiments, the CD4$^{IL-10/CAR}$ cells (autologous single-donor, allogeneic single-donor, or allogeneic polydonor CD4$^{IL-10/CAR}$ cells) are used in combination with a therapeutic intervention. The combination may be simultaneous or performed at different times. Preferably the therapeutic intervention is selected from the group consisting of: chemotherapy, radiotherapy, allo-HSCT, immune suppression, blood transfusion, bone marrow transplant, growth factors, biologicals.

In some embodiments, the CD4$^{IL-10/CAR}$ cells (autologous single-donor, allogeneic single-donor, or allogeneic polydonor CD4$^{IL-10/CAR}$ cells) are used in treating a patient with a malignancy, where the method includes administering an allo-HSCT graft to the patient, and administering a therapeutically effective amount of the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein to the patient.

In some embodiments, the CD4$^{IL-10/CAR}$ cells (autologous single-donor, allogeneic single-donor, or allogeneic polydonor CD4$^{IL-10/CAR}$ cells) are used to treat cancer patients receiving allogeneic HSCT (allo-HSCT) in order to prevent GvHD and to induce long term tolerance (in addition to direct anti-tumor effects). The amount of CD4$^{IL-10/CAR}$ cells is sufficient to suppress or prevent graft versus host disease (GvHD) without suppressing graft versus leukemia (GvL) or graft versus tumor (GvT) efficacy of the allo-HSCT (mediated by donor T-cells present in stem cell preparation).

Also provided herein are methods for treating a patient with minimal residual disease, comprising: administering to a patient, identified as having minimal residual disease or at risk of having minimal residual disease, a therapeutically effective amount the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein sufficient to induce an anti-cancer effect.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein induce cell death of tumor infiltrating tumor growth promoting myeloid lineage cells (e.g., monocytes, macrophages, neutrophils).

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein induce cell death of B cells (e.g., CD19$^+$ B cells, CD20$^+$ B cells, CD22$^+$ B cell, BCMA$^+$, B7-H3$^+$ B cells, or B7-H3$^+$ solid tumor cells).

6.7.3. Methods of Treating Inflammatory or Autoimmune Disease

In some embodiments, single donor or polydonor CD4$^{IL-10/CAR}$ cells are administered to treat inflammatory or autoimmune disease. In some embodiments, single donor or polydonor CD4$^{IL-10/CAR}$ cells are administered to treat a disease or disorder involving hyperactivity of NLPR3 inflammasome.

The NOD-like receptor family (NLR) protein NLRP3 is an intracellular signaling molecule that senses danger signals from pathogenic, environmental or endogenous source. Following activation, NLPR3 interacts with caspase-1, forming a complex termed the inflammasome. This results in the activation of caspase-1, which cleaves the pro-inflammatory cytokines IL-1β and IL-18 to their active forms and mediates a type of inflammatory cell death known as pyroptosis.

In some embodiments, single donor or polydonor CD4$^{IL-10/CAR}$ cells are administered to treat an inflammatory disease selected from Muckle-Wells syndrome (MWS), familial cold auto-inflammatory syndrome (FCAS) and neonatal onset multi-system inflammatory disease (NOMID). In some embodiments, single donor or polydonor CD4$^{IL-10/CAR}$ cells are administered to treat a chronic disease selected from metabolic syndrome, type 2 diabetes, atherosclerosis, Alzheimer, Parkinson, ALS, non-alcoholic steatohepatitis, osteoarthritis, silicosis, asbestosis, gout, and lung fibrosis. In some embodiments, single donor or polydonor CD4$^{IL-10/CAR}$ cells are administered to treat Crohn's disease, Ulcerative colitis, Multiple sclerosis and systemic lupus erythromytosis or inflammatory eye diseases such as diabetic retinopathy, acute glaucoma and age related macular degeneration.

In some embodiments, single donor or polydonor CD4$^{IL-10/CAR}$ cells are administered to treat a disease associated with NLRP3. The disease can be selected from the group consisting of: CAPS, NASH, Alzheimer, Parkinson, cardiovascular disease, osteoarthritis, gout, pseudogout, nephrocalcitosis, type II diabetes, Sjogren syndrome, sickle cell disease (SCD), AMD, infections, cerebral malaria, asbestosis, contact hypersensitivity, sunburn, silicosis, cystic fibrosis, inflammatory bowel disease, ALS, myelodysplastic syndrome, and uveitis.

In some embodiments, the disease is a brain disorder selected from Parkinson, Alzheimer, age-related cognitive impairment, frontotemporal dementia, traumatic brain injury, intracerebral hemorrhage, sepsis-associated encephalopathy, cerebral ischemia, subarachnoid hemorrhage, epilepsy, acrylamide poisoning, opioid-induced neuroinflammation, chronic migraine, perioperative neurocognitive disorder, poststroke cognitive impairment, post-cardiac arrest cognitive impairment, social isolation-induced cognitive impairment, anxiety and post-traumatic stress disorder.

In some embodiments, the disease is a lung disorder selected from asthma, IR lung injury, ARDS/COPD, particulate matter-induced lung injury, radiation pneumonitis, pulmonary hypertension, sarcoidosis, cystic fibrosis, and allergic rhinitis.

In some embodiments, the disease is a heart disorder selected from atherosclerosis, heart failure, hypertension, myocardial infarction, atrial fibrillation, cardiac injury induced by metabolic dysfunction, heart failure, and endothelial dysfunction.

In some embodiments, the disease is a gastrointestinal disease, such as colitis. In some embodiments, the disease is a liver disorder selected from acute liver failure, circadian regulation of immunity, NASH, cognitive dysfunction in diabetes, IR liver injury, idiosyncratic drug-induced liver injury and liver fibrosis. In some embodiments, the disease is a pancreas or kidney disorder selected from diabetic encephalopathy, diabetes-associated atherosclerosis, insulin resistance, islet transplantation rejection, chronic crystal nephropathy, renal fibrosis, I/R kidney injury, obesity-associated renal disease, and renal hypertension. In some embodiments, the disease is a skin or eye disorder selected from psoriasis and retinal neovascularization. In some embodiments, the disease is a reproductive disorder such as preterm birth. In some embodiments, the disease is an immune disorder selected from primary dysmenorrhea, innate immunity, innate to adaptive immunity, systemic lupus erythematosus-lupus nephritis, and multiple sclerosis. In some embodiments, the disease is an inheritable disorder selected from Muckle-Wells syndrome, rheumatoid arthritis, sickle cell disease and VCP-associated disease. In some embodiments, the disease is a pain disorder selected from multiple sclerosis-associated neuropathic pain, chronic prostatitis/chronic pelvic pain, cancer-induced bone pain, and hyperalgesia. In some embodiments, the disease is cancer, such as human squamous cell carcinoma of head and neck cancer. In some embodiments, the disease is an infective disorder, such as bacterial, viral or parasitic infection.

In some embodiments, single donor or polydonor $CD4^{IL-10/CAR}$ cells are used in combination with a currently available treatments for NLRP3 related diseases, such as a biologic agent that target IL-1. The biologic agent includes the recombinant IL-1 receptor antagonist Anakinra, the neutralizing IL-1β antibody Canakinumab and the soluble decoy IL-1 receptor Rilonacept.

In some embodiments, single donor or polydonor $CD4^{IL-10/CAR}$ cells are administered to treat a disease selected from Type 2 diabetes, metabolic syndrome, cardiovascular diseases, SLE, MS, CD, Ulcerative colitis (UC), osteoarthritis, Nonalcoholic steatohepatitis (Nash), Parkinson, ALS, lung fibrosis, silicosis, asbestosis, diabetic retinopathy, and age-related macular degeneration.

In some embodiments, single donor or polydonor $CD4^{IL-10/CAR}$ cells are administered to treat inflammation. The inflammation can be related to coronary artery disease (CAD), Type 2 diabetes, neurodegenerative diseases, or inflammatory bowel disease, but is not limited thereto.

In some embodiments, single donor or polydonor $CD4^{IL-10/CAR}$ cells are administered to treat a disease or disorder involving increased IL-1β production by activated monocytes, macrophages or dendritic cells. In some embodiments, single donor or polydonor $CD4^{IL-10/CAR}$ cells are administered to treat a disease or disorder involving increased IL-18 production by activated monocytes, macrophages or dendritic cells. In some embodiments, single donor or polydonor $CD4^{IL-10/CAR}$ cells are administered to treat a disease or disorder involving increased mature caspase 1 production by activated monocytes, macrophages or dendritic cells.

In some embodiments, single donor or polydonor $CD4^{IL-10/CAR}$ cells are administered to reduce IL-1β production by activated monocytes, macrophages or dendritic cells. In some embodiments, single donor or polydonor $CD4^{IL-10/CAR}$ cells are administered to reduce IL-18 production by activated monocytes, macrophages or dendritic cells. In some embodiments, single donor or polydonor $CD4^{IL-10/CAR}$ cells are administered to reduce mature caspase 1 production by activated monocytes, macrophages or dendritic cells.

6.7.4. Methods of Treating Other Disorders

In some embodiments, $CD4^{IL-10/CAR}$ cells (autologous single-donor, allogeneic single-donor, or allogeneic polydonor $CD4^{IL-10/CAR}$ cells) are administered to a patient in need of immune tolerization. In some embodiments, a method provided herein includes administering a therapeutically effective amount the $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein, to a patient in need of immune tolerization.

In some embodiments, the $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein are administered to a patient to treat autoimmune disease.

In some embodiments, the autoimmune disease is selected from the group consisting of: autoimmune uveitis, psoriasis, vitiligo, alopecia areata, psoriatic arthritis, inflammatory bowel disease, Hashimoto's thyroiditis, autoimmune vasculitis, ulcerative colitis, bullous diseases, scleroderma, celiac disease, graves disease, systemic sclerosis, myasthenia gravis, anti-NMDA encephalitis, pemphigoid diseases (vulgaris and foliaceus), epidermolysis bullosa acquisita, thrombotic thrombocytopenia purpura, ididopathic thrombocytic purpora, autoantibody induced vascular inflammation, autoantibody induced carditis, rheumatoid arthritis, autoantibody induced rheumatoid arthritis, neuromyelitis optica spectrum disorders, systemic lupus erythematosus (SLE), multiple sclerosis (MS), sjögren's syndrome, autoimmune myopathies, type I diabetes, addison disease, pernicious anemia, autoimmune hepatitis, primary biliary cholangitis (PBC), autoimmune pancreatitis, goodpasture's disease, primary membranous nephropathy, ovarian insufficiency, autoimmune orchitis, dry eye disease, and idiopathic interstitial pneumonias. In some embodiments, the autoimmune disease is Crohn's disease, ulcerative colitis, celiac disease, type-1 diabetes, lupus, psoriasis, psoriatic arthritis, or rheumatoid arthritis. In some embodiments, the patient has an allergic or atopic disease. The allergic or atopic disease can be selected from the group consisting of: asthma, atopic dermatitis, and rhinitis. In some embodiments, the patient has a food allergy.

In some embodiments, the $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein are administered to prevent or reduce severity of pathogenic T cell response to cell and organ transplantation other than HSCT. In some embodiments, the method comprises the step of organ transplantation to the patient, either prior to or subsequent to administration of the $CD4^{IL-10/CAR}$ cells (autologous single-donor, allogeneic single-donor, or allogeneic polydonor $CD4^{IL-10/CAR}$ cells), the population of single-donor or polydonor $CD4^{IL-10/CAR}$ cells, or any of the pharmaceutical compositions provided herein. In certain embodiments, the organ is a kidney, a heart, a lung, a liver, or pancreatic islet cells. In preferred embodiments, the $CD4^{IL-10/CAR}$ cells (autologous single-donor, allogeneic single-donor, or allogeneic polydonor $CD4^{IL-10/CAR}$ cells), the population of single-donor or polydonor CD4$^{IL-10/CAR}$ cells, or any of the pharmaceutical compositions provided herein prevents or reduces severity of host rejection of the organ transplantation.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to prevent or reduce immune response associated with gene therapy, e.g., administration of recombinant Adenovirus, Adeno-Associated Virus (AAV), Herpes simplex virus (HSV), Retrovirus, Lentivirus, a non-integration Lentivirus, Alphavirus, Flavivirus, Rhabdovirus, Measles virus, Newcastle disease Virus, Poxvirus, or Picornavirus. In these embodiments, the method further comprises the step of administering a recombinant Adenovirus, Adeno-Associated Virus (AAV), Herpes simplex virus (HSV), Retrovirus, Lentivirus, a non-integrating lentivirus, Alphavirus, Flavivirus, Rhabdovirus, Measles virus, Newcastle disease Virus, Poxvirus, or Picornavirus to the patient, either prior to or subsequent to administration of the CD4$^{IL-10/CAR}$ cells or the pharmaceutical composition.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to prevent or reduce immune response against a recombinant viral vector other than AAV. In these embodiments, the method further comprises the step of administering a recombinant viral vector other than AAV to the patient, either prior to or subsequent to administration of the CD4$^{IL-10/CAR}$ cells, the population of CD4$^{IL-10/CAR}$ cells, or the pharmaceutical composition. Non-limiting examples of viral vectors other than AAV include: Herpes simplex virus (HSV), Retrovirus, Lentivirus, Alphavirus, Flavivirus, Rhabdovirus, Measles virus, Newcastle disease Virus, Poxvirus, or Picornavirus.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to prevent or reduce immune response associated with transplantation of iPS-derived tissues or cells. The iPS-derived tissues and cells include, but are not limited to cardiomyocytes, hepatocytes, epithelial cells, cartilage, bone and muscle cells, neurons.

In some embodiments, the method further comprises the step of administering an immunogenic therapeutic protein to the patient, either prior to or subsequent to administration of the CD4$^{IL-10/CAR}$ cells, the population of CD4$^{IL-10/CAR}$ cells, or the pharmaceutical composition. In some embodiments, the CD4$^{IL-10/CAR}$ cells, the population of CD4$^{IL-10/CAR}$ cells, or the pharmaceutical composition reduces immune responses against the immunogenic therapeutic protein. In some embodiments, the immunogenic therapeutic protein is selected from a therapeutic antibody, a factor VIII replacement, a cytokine, and a cytokine mutein.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to treat inflammation. The inflammation can be related to coronary artery disease (CAD), Type 2 diabetes, neurodegenerative diseases, non-alcohol steatohepatitis (NASH), or inflammatory bowel disease, but is not limited thereto.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to treat a disease or disorder involving hyperactivity of NLPR3 inflammasome. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to treat a disease or disorder involving increased IL-1β production by activated monocytes, macrophages or dendritic cells. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to treat a disease or disorder involving increased IL-18 production by activated monocytes, macrophages or dendritic cells. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to treat a disease or disorder involving increased mature caspase 1 production by activated monocytes, macrophages or dendritic cells.

In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to reduce IL-18 production by activated monocytes, macrophages or dendritic cells. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to reduce IL-18 production by activated monocytes, macrophages or dendritic cells. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to reduce mature caspase 1 production by activated monocytes, macrophages or dendritic cells.

In some embodiments, the CD4$^{IL-10/CAR}$ cells (s autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to reduce patient hyperactive immune response to viral infection. In some embodiments, the virus is SARS-coV-2. In some embodiments, the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein are administered to reduce hyperactive immune responses to bacterial infections, such as toxic shock, cytokine storm, a therapeutic antibody, a factor VIII replacement, a cytokine, and a cytokine mutein.

In another aspect, the present disclosure provides a method for treating or inhibiting autoimmune disease, allergic disease, or inflammatory disease in a patient, comprising the step of administering to a patient, identified as having autoimmune disease, allergic disease, or inflammatory disease, a therapeutically effective amount of the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein sufficient to treat or inhibit the autoimmune disease, allergic disease, or inflammatory disease.

In another aspect, the present disclosure provides a method for reducing transplant rejection in a patient transplanted with hematopoietic stem cells, bone marrow cells, or a solid organ, comprising the step of administering to a patient, identified as having rejection of transplanted hematopoietic stem cells, bone marrow cells, or a solid organ, a therapeutically effective amount of the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein sufficient to reduce transplant rejection.

In another aspect, the present disclosure provides a method for treating graft-versus-host disease (GvHD) in a patient, comprising: administering to a patient, identified as having graft-versus-host disease (GvHD) or at risk of having graft-versus-host disease (GvHD), a therapeutically effective amount of the CD4$^{IL-10/CAR}$ cells (autologous single-donor, allogeneic single-donor, or allogeneic polydonor CD4$^{IL-10/CAR}$ cells), the population of single-donor or polydonor CD4$^{IL-10/CAR}$ cells, or any of the pharmaceutical compositions provided herein sufficient to suppress or prevent GvHD. In some embodiments, the GvHD is acute GvHD. In some embodiments, the GvHD is chronic GvHD.

In another aspect, the present disclosure features a method for treating tissue or organ damage (e.g., wound healing) in a patient, comprising: administering to a patient, identified as having tissue or organ damage or at risk of having tissue or organ damage, a therapeutically effective amount of any of the CD4$^{IL-10/CAR}$ AR cells provided herein, any of the populations of CD4$^{IL-10/CAR}$ cells provided herein, or the pharmaceutical composition provided herein sufficient to induce repair of tissue or organ damage.

6.8. Polynucleotides and Vectors

This disclosure also features one or more polynucleotide constructs comprising (a) a first polynucleotide segment encoding a chimeric antigen receptor (CAR) (e.g., any of the CARs provided herein); and (b) a second polynucleotide segment encoding interleukin-10 (IL-10) and (c) a third polynucleotides segment encoding the truncated form of the NGFR. In some embodiments, the first polynucleotide segment and the second and third polynucleotide are in the same construct. In some embodiments, the first polynucleotide is in the first polynucleotide construct, and the second and third polynucleotide segment is in the second polynucleotide construct. In some embodiments, the third polynucleotide segment is optional.

In some embodiments, the first polynucleotide segment comprises a regulatory element (e.g., any of the exemplary regulatory elements (e.g., any of the promoters) described herein) operably linked to the coding sequence of the CAR. In some embodiments, the regulatory element drives expression of the CAR.

In some embodiments, the second polynucleotide segment comprises a regulatory element (e.g., any of the exemplary regulatory elements (e.g., any of the promoters) described herein) operably linked to a coding sequence of the IL-10. In some embodiments, the regulatory element drives constitutive expression of the IL-10.

In some embodiments, the third polynucleotide segment comprises a regulatory element (e.g., any of the exemplary regulatory elements (e.g., any of the promoters) described herein) operably linked to a coding sequence of the selection marker (e.g., ΔNGFR). In some embodiments, the regulatory element drives constitutive expression of the ΔNGER.

In some embodiments, the polynucleotide construct includes an internal ribosome entry site (IRES) or a self-cleaving peptide between the first polynucleotide segment and the second polynucleotide segment. In some embodiments, the polynucleotide construct includes an internal ribosome entry site (IRES) or a self-cleaving peptide between the second polynucleotide segment and the first polynucleotide segment. In some embodiments, the self-cleaving peptide is selected from the group consisting of F2A, P2A, T2A and E2A.

In some embodiments, the polynucleotide construct includes from 5' to 3': a promoter operably linked to the first polynucleotide segment, a self-cleaving peptide or IRES, and a second polynucleotide segment. In some embodiments, the polynucleotide construct includes from 5' to 3': a promoter operably linked to the first polynucleotide segment, a self-cleaving peptide or IRES, and a second polynucleotide segment, and a second promoter operably linked to the third polynucleotide segment.

In some embodiments, the polynucleotide construct includes from 5' to 3': a promoter operably linked to the second polynucleotide segment, a self-cleaving peptide or IRES, and a first polynucleotide segment.

In some embodiments, the polynucleotide construct includes a first promoter operably linked to the first polynucleotide segment and a second promoter operably linked to the second polynucleotide segment. In some embodiments, the polynucleotide construct includes a first promoter operably linked to the first polynucleotide segment, a second promoter operably linked to the second polynucleotide segment, and a third promoter operably linked to the third polynucleotide segment.

In some embodiments, the polynucleotide construct encodes an antigen-binding domain that targets an antigen associated with an autoimmune disease, inflammatory disorder, or cancer. In some embodiments, the antigen is selected from the group consisting of: CD19, CD20, CD22, CD27, BCMA, CD38, HLA*A2, HLA*A24 or citrullinated peptides, insulin, MOG, GAD65, IA2, gliadin, and desmoglein in the context of relevant MHC molecules.

In some embodiments, the polynucleotide construct includes a sequence encoding an antigen-binding domain that targets a cancer-associated antigen. In some embodiments, a cancer-associated antigen is selected from the group consisting of: CD19, CD20, CD22, CD23, CD27, CD38, CEA, BCMA, Lym1, Lym2, CLEC5A, CDH179b, FLT3, GCC, Muc, CSF2RA, GFRa4, CD32, CD33, IL11Ra, IL13Ra, NYBRI, SLea, CD200R, TGFBetaR2, CEA, CD276, TROP2, LAMP1, PTK7, DLL3, CDH1, CDH6, CDH17, CDH19, TSHR, B7-H3 and tyrosinase.

In some embodiments, the first polynucleotide segment comprises the sequence of SEQ ID NOs: 10, 17, 23, 35, or 55.

In some embodiments, the second polynucleotide segment comprises the sequence of SEQ ID NO: 2.

In some embodiments, the polynucleotide construct further comprises one or more selection markers (e.g., any of the selection markers provided herein). In some embodiments, the first polynucleotide segment, second polynucleotide segment, or both, further comprising a sequence encoding a selection marker.

In some embodiments, the polynucleotide construct includes a $\Delta$NGFR as a selection marker.

In some embodiments, the polynucleotide construct includes a $\Delta$NGFR comprising the sequence of SEQ ID NO: 4.

In some embodiments, the polynucleotide construct includes a truncated form of EGFR as a selection marker.

In some embodiments, the one or more polynucleotide constructs are one or more vectors. In some embodiments, the vector is a viral vector. Non-limiting examples of viral vectors include: lentivirus, retrovirus, gammaretroviruses, adeno-associated virus, adenovirus, helper-dependent adenovirus, sendai virus, or a baculovirus. In some embodiments, the polynucleotide construct is a lentiviral vector.

In some embodiments, the first polynucleotide is in the first lentiviral vector, and the second polynucleotide segment is in the second lentiviral vector.

In some embodiments, the lentiviral vector is capable of integrating into the T cell nuclear genome. In some embodiments, the lentiviral vector is not capable of integrating into T cell nuclear genome. In some embodiments, an integration-deficient lentiviral vector is used. For example, in some embodiments, an integration-deficient or other lentiviral vector disclosed in Mátrai is used. In some embodiments, an integrase-defective lentivirus is used. For example, an integrase-defective lentivirus containing an inactivating mutation in the integrase (D64V) can be used as described in Mátrai et al., *Hepatology* 53:1696-1707 (2011), which is incorporated by reference herein, is used.

6.9. Examples

The following examples are provided by way of illustration not limitation.

6.9.1. Summary of Experimental Observations

Overall, the data in the experiments described below demonstrated that human CD4+ T cells can be transduced with two different lentiviral vectors: 1) a LVV encoding a synthetic CAR comprising a human B cell surface antigen binding domain, a CD8a hinge, and a CD8α transmembrane domain, a CD28 costimulatory domain, and a CD3zeta activation domain and 2) a bidirectional vector encoding the human IL-10 gene, plus a truncated form of the NGFR gene. The resulting transduced CD4$^+$ T cells expressed both the CD19 CAR (as measured by CD19 expression) and IL-10/NGFR as measured by NGER expression. No differences in transduction efficiencies were found, when the double transduced CD4$^+$ T cells (designated generically as CD4$^{IL-10/CAR}$ cells or as CD4$^{IL-10antiCD19CAR}$ cells when expressing the anti-CD19 CAR described in FIGS. 2A-2B) were generated following sequential or simultaneous transduction with the two different lentiviral vectors.

Following activation through CD3 and CD28, the CD4$^{IL-10/CAR}$ cells displayed cytokine production profiles similar to those of CD4$^{IL-10}$ cells and those described for Tr1 cells. For example, the CD4$^{IL-10/CAR}$ cells produced high levels of IL-10, and no or low levels of IL-4, IFN-γ, and IL-5. Notably, this cytokine production profile was stable after prolonged culture periods.

Interestingly, co-culture of CD19$^+$ target cells and CD4$^{IL-10antiCD19CAR}$ cells resulted in specific activation of the CD4$^{IL-10anti-CD19 CAR}$ cells and induction of IL-10 production.

CD4$^{IL-10antiCD19CAR}$ cells suppressed PBMC proliferation, allogeneic CD4$^+$ T cell proliferation, and allogeneic CD8$^+$ T cell proliferation in vitro, as also seen with CD4$^{IL-10}$ cells.

CD4$^{IL-10antiCD19CAR}$ cells specifically killed CD19$^+$ target cells in vitro, but like CD4$^{IL-10}$ cells, they maintained their ability to kill myeloid target cells, which depend on the expression of one or more of Class I MHC, CD13, CD54 and CD112. In addition, the CD4$^{IL-10anti-CD19 CAR}$ T cells strongly inhibited CD19$^+$ target cell growth vivo. Importantly, single donor and polydonor CD4$^{IL-10antiCD19 CAR}$ cells, similarly as described for single donor and polydonor CD4$^{IL-10}$ cells, did not induce xeno-GvHD, whereas PBMC's induced severe xeno-GvHD. Finally, the CD4$^{IL-10antiCD19 CAR}$ cells synergized with the PBMC in their antitumor effect, indicating that they do not interfere with protective GvL responses, as described for CD4$^{IL-10}$ cells (Locafaro et al. Mol Ther. 2017; 25(10):2254-2269). In addition, the single donor and poly donor CD4$^{IL-10antiCD19 CAR}$ cells protected mice from xeno-GvHD in a humanized mouse model of GvHD induced by allogeneic PBMC (see FIGS. 18A-18C).

This data showed that specific interactions between the CD4$^{IL-10anti-CD19 CAR}$ and CD19 expressed on the target cells induce activation of these cells resulting in specific killing of CD19$^+$ target cells and IL-10 production.

Taken together, the data showed CD4$^{IL-10/CAR}$ T cells have unique clinical utility for the treatment of all B-cell and T-cell mediated auto immune diseases because they will not only eliminate autoantibody producing B cells but also simultaneously suppress pathogenic autoimmune CD4$^+$ T cell and CD8$^+$ T cell responses through the production of IL-10. The data also showed that single donor or polydonor CD4$^{IL-10antiCD19 CAR}$ cells have unique clinical utility for the treatment/elimination of CD19$^+$ tumor cells and prevention of tumor relapses, particularly in patients undergoing allogeneic HSCT, as the CD4$^{IL-10antiCD19 CAR}$ cells did not induce GvHD by themselves and did not interfere with protective anti-tumor effects (GvL effects) of the PBMC.

Importantly, even at high concentrations, CD4$^{IL-10antiCD19 CAR}$ cells (either autologous or allogeneic) did not induce GvHD by themselves. These results demonstrate that CD4$^{IL-10/CAR}$ cells can be used for treatment of i) leukemias and other malignancies expressing the target antigen, ii) leukemias and other malignancies in patients undergoing allogeneic HSCT or BM transplantation to reduce GvHD while preserving GvL or GvT therapeutic effects of the HSCT, iii) auto immune diseases through the removal of auto immune B-cells, and down regulation of pathogenic T cell responses and the NLPR3 inflammasome, iv) inflammatory diseases through down regulation of pathogenic T cell responses and the NLPR3 inflammasome, v) cell and organ transplant rejection, vi) solid tumors expressing tumor associated antigens including but not limited to B7-H3 and vii) immune-mediated diseases through tissue repair and wound healing.

6.9.2. Example 1: Generation of CD4$^{IL-10/Anti-CD19 CAR}$ Cells

6.9.2.1. Vector Production for IL-10/$\Delta$NGER and Anti-CD19 CAR

Figure 1:
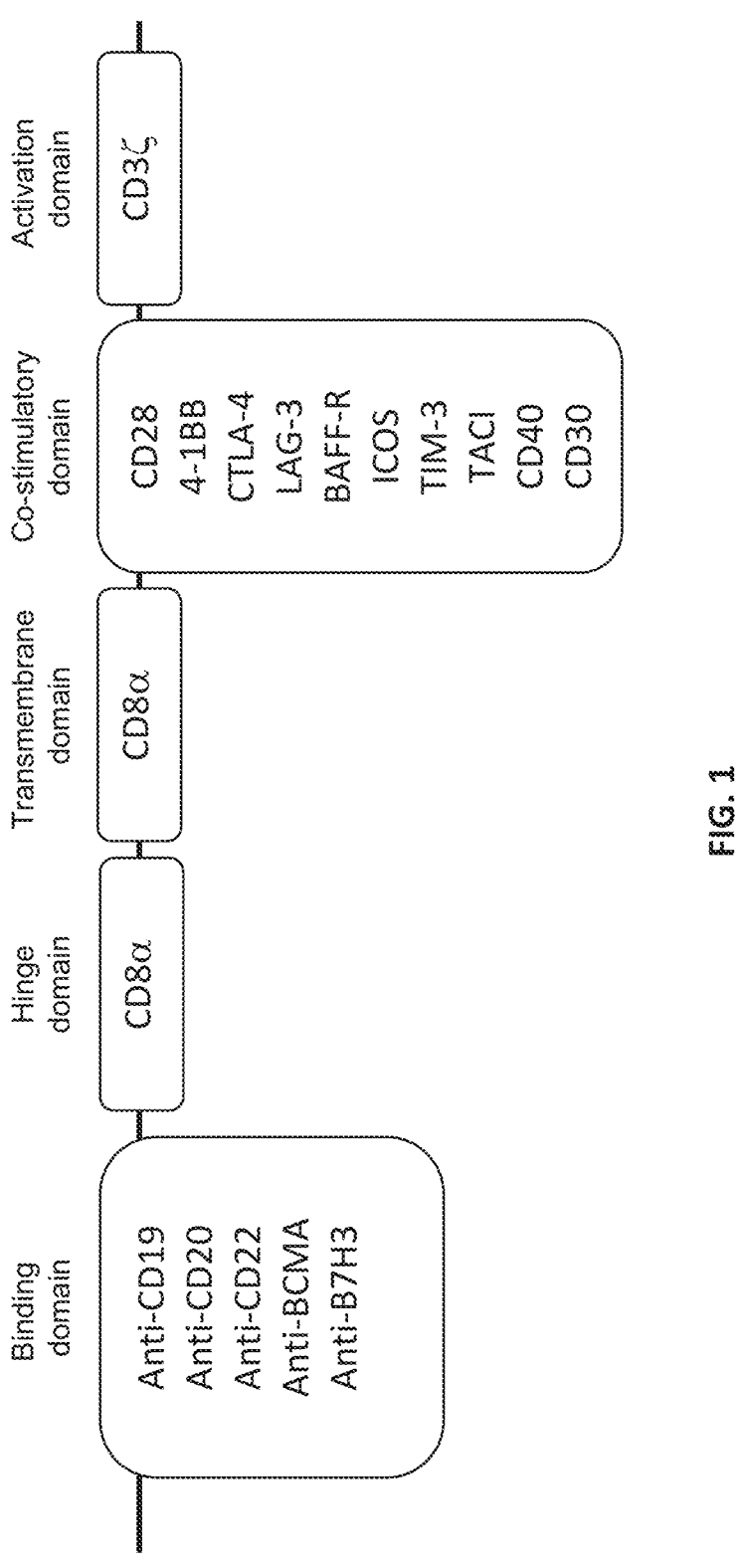
FIG. 1 is a non-limiting illustration of structure for various chimeric antigen receptors (CARs) provided herein.
Figure 2A:
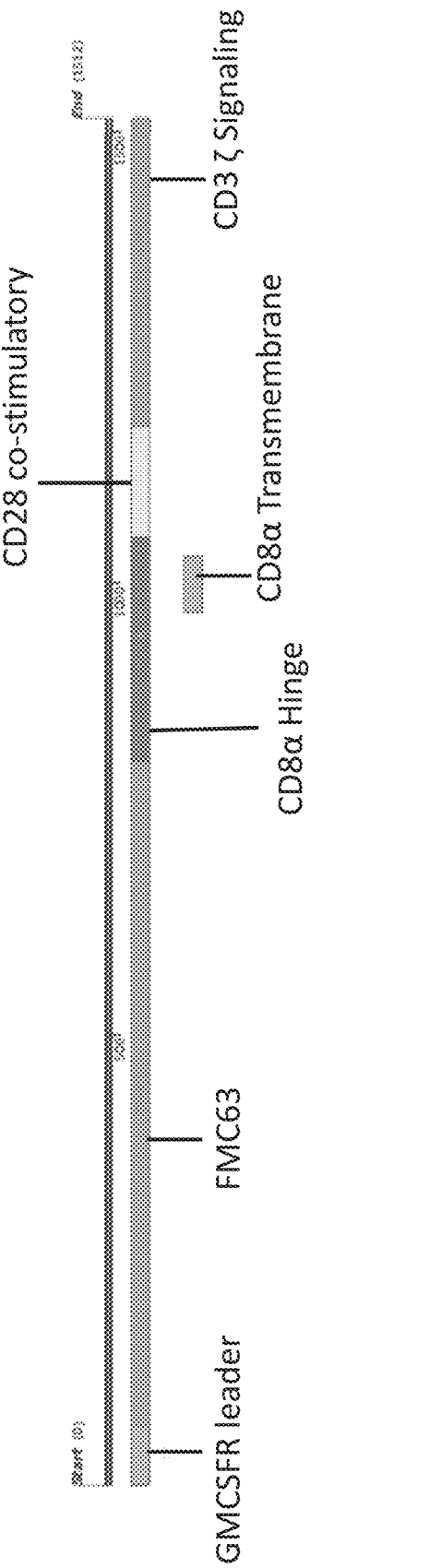
FIG. 2A illustrates the partial structure of an anti-CD19 CAR coding sequence that includes a scFv from a fully-human anti-CD19 monoclonal antibody FMC63, a CD8a hinge, a CD8a transmembrane domain, a CD28 costimulatory domain, and a CD36 activation domain, that is used in the lentiviral vector for delivering the anti-CD19 CAR into CD4+ T cells to produce CD4$^{IL-10anti-CD19\ CAR}$ cells.
Figure 2B:
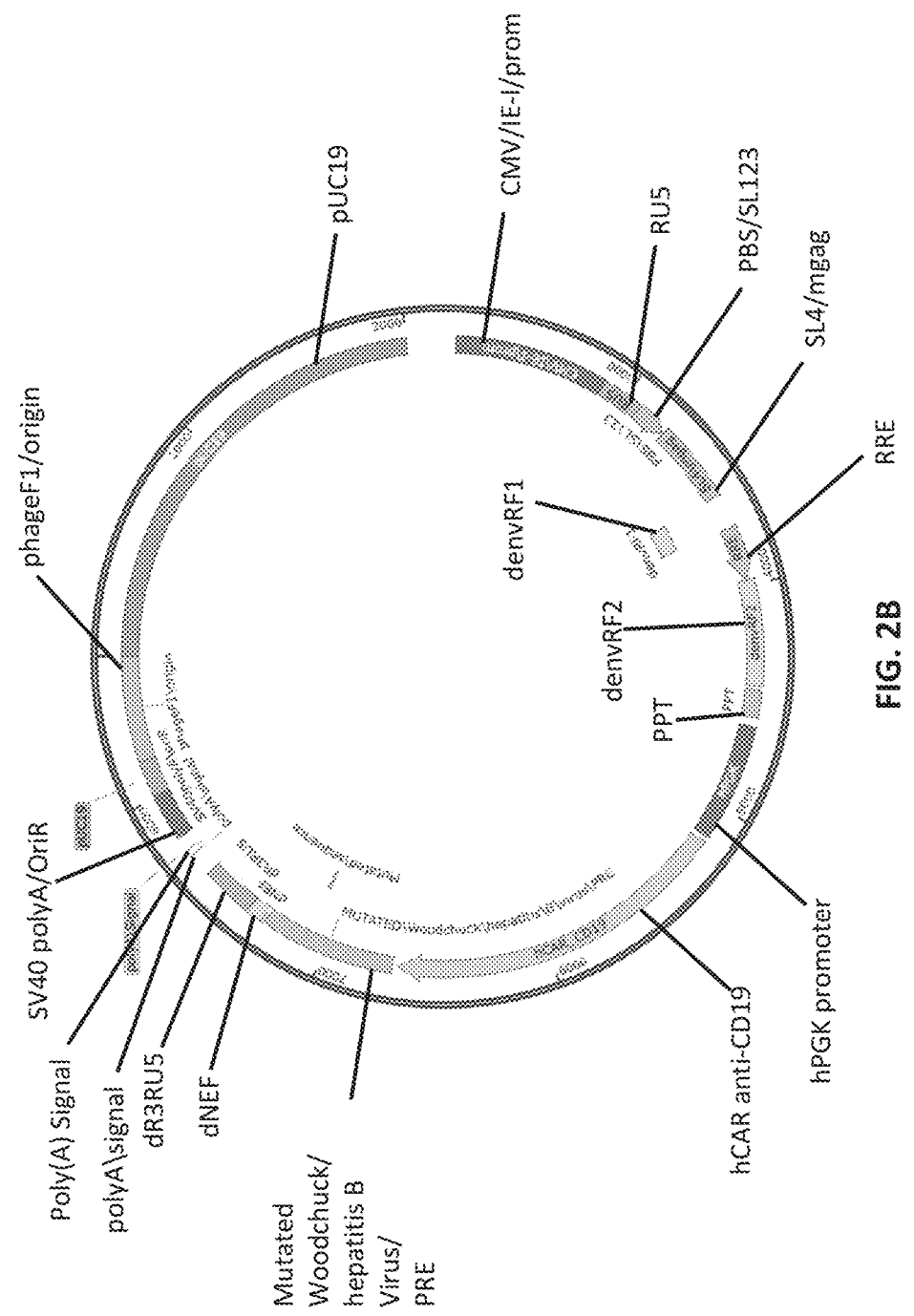
FIG. 2B illustrates a lentiviral vector (pLV anti-CD19 CAR) used for delivering the anti-CD19 CAR into CD4+ T cells to produce CD4$^{IL-10antiCD19CAR}$ cells.

A second generation CD19 CAR was used for the production of CD4$^{IL-10anti-CD19 CAR}$ cells. The CD19 CAR included a scFv from a fully-human anti-CD19 monoclonal antibody (SEQ ID NO: 12), a CD8a hinge, and a CD8α transmembrane domain, a CD28 costimulatory domain, and a CD3ξ (CD3 zeta) activation domain (FIG. 2A). The CD19 CAR as shown in FIG. 2A was inserted into a lentiviral vector (LVV) (see FIG. 2B). See FIG. 1 for illustration of exemplary CARs targeting CD19, CD20, CD22, BCMA or B7H3. The lentiviral vector was generated by ligating the coding sequence of the anti-CD19 scFv (FMC63) into the lentiviral backbone including the human CD8g hinge region, and CD8α trans membrane region, the CD28 co stimulatory domain and the CD35 intracellular signaling domain. Surface expression of the anti-CD19 CAR was monitored with an anti-CD19-CAR detection agent (Miltenyi).

To introduce a polynucleotide encoding IL-10 into the CD4$^+$ T cells to produce the CD4$^{IL-10anti-CD19\ CAR}$ cells a lentiviral vector (LVV) containing coding sequences of both the human IL-10 (SEQ ID NO: 2) and a truncated form of the NGFR (also known as CD271) (ΔNGFR) (SEQ ID NO: 4) (FIG. 4) was used. The LVV containing IL-10 and ΔNGFR coding sequence is further described in WO2016/146542, which is hereby incorporated by reference in its entirety.

The lentiviral vector was generated by ligating the coding sequence of human IL-10 from 549 bp fragment of pH15C (ATCC 68192)) into plasmid pLVIL-10. The presence of the bidirectional promoter (human PGK promoter plus minimal core element of the CMV promoter in the opposite direction) allowed co-expression of the two transgenes. The plasmid further contained a coding sequence of an antibiotic resistance gene (e.g., ampicillin or kanamycin). See FIG. 3A and FIG. 3B for exemplary illustration of the IL-10 construct.

The lentiviral vectors were produced by Ca$_3$PO$_4$ transient four-plasmid co-transfection into 293T cells and concentrated by ultracentrifugation: 1 μM sodium butyrate was added to the cultures for vector collection. Titer was estimated on 293T cells by limiting dilution, and vector particles are measured by HIV-1 Gag p24 antigen immune capture (NEN Life Science Products; Waltham, MA). Vector infectivity was calculated as the ratio between titer and particle. For concentrated vectors, titers ranged from 1×10$^8$ to 6×10$^9$ transducing units/mL, and infectivity from 5×10$^4$ to 5×10$^5$ transducing units/ng.

6.9.2.2. Production of CD4$^{IL-10/CAR}$ Cells

As shown in FIGS. 5A-5C, three different methods were used to generate CD4$^{IL-10antiCD19}$ CAR cells. For each of the different methods, CD4$^+$ T cells were purified from healthy human donors. The purified human CD4$^+$ T cells were activated with anti-CD3/anti-CD28 beads (Miltenyi) (3:1 cells:beads ratio), in complete culture medium (X-vivo supplemented with 5% human AB serum and rhIL-2 (50 U/mL).

FIG. 5A shows that the activated CD4$^+$ T cells were transduced with a lentiviral vector encoding an anti-CD19 CAR (LVV$^{CD19-CAR}$) 48 hours after activation and transduced 24 hours later (i.e., 72 hours after activation) with a bidirectional lentiviral vector encoding human IL-10 and a truncated form of the human NGF receptor (LVV$^{IL-10-NGFR}$). Both LVVs were used at a multiplicity of infection (MOI) of 20.

FIG. 5B shows that activated CD4$^+$ T cells were transduced with the LVV$^{IL-10-NGFR}$ 48 hours after activation and transduced 24 hours later (i.e., 27 hours after activation) with LVV$^{CD19-CAR}$.

FIG. 5C shows the activated CD4$^+$ T cells were transduced simultaneously with LVV$^{IL-10-NGFR}$ and LVV$^{CD19-CAR}$ 48 hours after activation. Controls CD4$^{IL10}$ cells were generated by transducing activated CD4$^+$ T cells 48 hours after activation with LVV$^{IL-10-NGFR}$ only. For each of FIGS. 5A-5C, the transductions were conducted in the presence of polybrene (8 μg/mL). Additionally, for each of FIGS. 5A-5C, 10-28 days after transduction, transduced cells (i.e., ΔNGER$^+$ cells) were purified using anti-CD271 microbeads (Miltenyi) and anti-CD19 CAR microbeads (Miltenyi). Purified cells were re-stimulated every 14 days as previously described (Andolfi et al. Mol. Ther. 20(9): 1778-1790 (2012) and Locafaro et al. Mol. Ther. 25(10): 2254-2269 (2017)). After the second (TF2) and third (TF3) re-stimulation the resulting cells (CD4$^{IL-10antiCD19\ CAR}$) were characterized in vitro and in vivo. Culture medium was refreshed every 2-3 days, as needed through the entire culture period.

CD4$^{IL-10antiCD19\ CAR}$ cells were analyzed at TF3 (i.e., after the third re-stimulation) by staining with an anti-CD271 mAb (Biolegend) and an anti-CD19 CAR detection reagent (Miltenyi) and analyzed by flow cytometry. Staining indicated that identity and the purity of the CD4$^{IL-10antiCD19\ CAR}$ cells determine as co-expression of NGFR and the anti-CD19 CAR for the three different transduction methods was 88.6% (FIG. 6A from method described in FIG. 5A), 64.1% (FIG. 6B from method described in FIG. 5B) and 52.6% (FIG. 6C from method described in FIG. 5C), respectively. As expected, CD4$^{IL-10}$ cells generated respectively from the same donors (donor 26.1 and 26.2) using the method described in FIG. 5C and used as controls did not express the CD19 CAR (FIG. 7).

As shown in FIG. 7, CD4$^{IL-10antiCD19\ CAR}$ cells expressed both IL-10 (as measured by the expression of NGFR) and the anti-CD19 CAR. In this experiment, CD4$^+$ T cells from two different donors (26.1 and 26.2) were transduced simultaneously with LVV$^{IL-}$10-NGFR and LVV anti-CD19 CAR 48 hours after bead activation (method SC). To generate the CD4$^{IL-10}$ T cells (control), CD4$^+$ T cells from donors 26.1 and 26.2 were transduced solely with LVV$^{IL-10-NGFR}$ 48 hours after bead activation. For this analysis, CD4$^{IL-10}$ cells (control) and CD4$^{IL-10antiCD19\ CAR}$ cells were analyzed following a second round of restimulation (i.e., TF2) with feeder cells. Both CD4$^{IL-10}$ cells (control) and CD4$^{IL-10anti-CD19\ CAR}$ T cells were stained with anti-CD271 mAb (Biolegends) and a CD19-CAR detection reagent (Miltenyi) and analyzed by flow cytometry. As shown in FIG. 7, the majority of the cells transduced with LVV$^{IL-10-}$NGER and LVV$^{CD19-CAR}$ expressed CD271 and the CD19-CAR (FIG. 7, right panels) whereas the majority of the cells that were only transduced with LVV$^{IL-10-NGFR}$ expressed CD271, but not the CD19-CAR (FIG. 7, left panels).

These results indicate that CD4$^{IL-10antiCD19\ CAR}$ cells can be successfully generated independent of timing and sequence of transduction with the two different LVVs. In addition, this suggest that CD4$^{IL-10/CAR}$ can be generated using a single LVV encoding both the IL-10 and the CAR.

6.9.2.3. CD4$^{IL-10antiCD19\ CAR}$ Cells have a Cytokine Production Profile which is Comparable to that of Naturally Derived Tr1 Cells and CD4$^{IL-10}$ Cells CD4$^{IL-10antiCD19\ CAR}$ cells from 3 different healthy donors (26.1, 26.2 and 26.3) were generated by simultaneous transduction with (i) LVV containing anti-CD19-CAR and (ii) LVV containing IL-10 and ΔNGER according to the methods described in FIG. 5C. In particular, to generate the CD4$^{IL-10antiCD19\ CAR}$ cells, CD4$^+$ T cells from the three different donors (26.1, 26.2, and 26.3) were transduced simultaneously with LVV$^{IL-10-NGFR}$ and LVV$^{CD19-CAR}$ 48 hours after bead activation. To generate the CD4$^{IL-10}$ T cells (control), CD4$^+$ T cells from the three different donors (26.1, 26.2, and 26.3) were transduced with LVV$^{IL\text{-}10\text{-}NGFR}$ 48 hours after bead activation.

For this analysis, $2 \times 10^5$ cells (in 200 µL) for each CD4$^{IL\text{-}10}$ cells (control) and CD4$^{IL\text{-}10/CAR}$ T cells were restimulated as previously described in Andolfi et al. Mol. Ther. 20(9): 1778-1790 (2012) and Locafaro et al. Mol. Ther. 25(10): 2254-2269 (2017). At day 14 after the second round (TF2) of restimulation, cells were stimulated with immobilized anti-CD3 and soluble anti-CD28 mAbs for 48 hours. Culture supernatants were collected and levels of IL-10, IL-4, IL-5, and IFN-γ were determined by ELISA.

As shown in FIGS. 8A-8D, although some individual differences in cytokine production levels were observed, the CD4$^{IL\text{-}10/CAR}$ cells, like CD4$^{IL\text{-}10}$ cells and Tr1 cells (not shown), produced high levels of IL-10, low levels of IL-4, and variable levels of IFN-γ, and IL-5.

Similar results were obtained with CD4$^{IL\text{-}10antiCD19\ CAR}$ cells derived from donor 24.2, which were collected at TF 3 (FIG. 9). To generate the CD4$^{IL\text{-}10antiCD19\ CAR}$ cells for this experiment, CD4$^+$ T cells from donor 24.2 were transduced simultaneously with LVV$^{IL\text{-}10\text{-}NGFR}$ and LVV$^{CD19\text{-}CAR}$ 48 hours after bead activation (see FIG. 5C). To generate the CD4$^{IL\text{-}10}$ T cells (control), CD4$^+$ T cells from donor 24.2 were transduced solely with LVV$^{IL\text{-}10\text{-}NGFR}$ 48 hours after bead activation. For this analysis, $2 \times 10^5$ cells (in 200 µL) for each CD4$^{IL\text{-}10}$ T cells (control) and CD4$^{IL\text{-}10/CAR}$ T cells were restimulated as previously described in Andolfi et al. Mol. Ther. 20(9): 1778-1790 (2012) and Locafaro et al. Mol. Ther. 25(10): 2254-2269 (2017). Briefly, at day 14 after the third round (TF3) of restimulation, cells were stimulated with immobilized anti-CD3 and soluble anti-CD28 mAbs for 48 hours. Culture supernatants were collected, and levels of IL-10, IL-4, IL-5, and IFN-γ were determined by ELISA.

As shown in FIG. 9, even after prolonged culture these cells still produce high levels of IL-10, low levels of IL-4, and variable levels of IL-5 and IFN-γ.

Collectively, the data in FIGS. 8A-8D and FIG. 9 indicate that simultaneous transduction of purified CD4$^{IL\text{-}10}$ cells with LVV$^{IL\text{-}10\text{-}NGFR}$ and LVV$_{CD19\text{-}CAR}$ is feasible and results in the generation of CD4$^{IL\text{-}10\text{-}CAR}$ T cells with the same unique and characteristic cytokine production profile as CD4$^{IL\text{-}10}$ T cells and Tr1 cells. In addition, no differences in the cytokine production profiles were observed when CD4$^{IL\text{-}10\text{-}CAR}$ T were harvested at TF2 or TF3, indicating that these cytokine production profiles are stable over prolonged periods of time.

6.9.3. Example 2: Cytotoxicity of CD4$^{IL\text{-}10antiCD19}$ CAR Cells and Activation Following Engagement with CD$^{19+}$ Target Cells It was known that CD4"1-10 cells are able to kill myeloid tumor cells such as ALL-CM under defined conditions (Andolfi et al. Mol Ther. 2012; 20(9):1778-1790). This experiment was designed to assess whether co-expression of an anti-CD19 CAR produces cells (CD4$^{IL\text{-}10antiCD\ 19\ CAR}$) that can kill CD19$^+$ cells when co-cultured with a cell line expressing CD19 (e.g., NALM6).

In particular, CD4$^{IL\text{-}10}$ cells (control) and CD4$^{IL\text{-}10antiCD19\ CAR}$ cells, both generated from CD4$^+$ T cells isolated from donor 24.2 were collected following a third restimulation (TF3) (see FIG. 5C) and were co-cultured with K562, NALM6 (CD19$^+$), or ALL-CM target cells ($10^5$ cells/well) at a 1:1 ratio for three days. Following the three day co-culture, flow cytometry was used to determine the presence of residual target cells in each co-culture.

The data showed that CD4$^{IL\text{-}10antiCD19\ CAR}$ cells, through engagement of the CD19-CAR with CD19$^+$ target cells, kill CD19$^+$ NALM6 cells. In contrast, CD4$^{IL\text{-}10}$ cells used as controls were ineffective and did not kill CD19$^+$ NALM6 cells (FIG. 10). Furthermore, CD4$^{IL\text{-}10antiCD19\ CAR}$ cells, like CD4$^{IL\text{-}10}$ cells, killed the myeloid tumor cell line ALL CM. Both the CD4$^{IL\text{-}10antiCD19}$ cells and the CD4$^{IL\text{-}10}$ cells had no, or very low cytotoxic effect on K562 cells, which are highly susceptible to non-specific cytotoxicity and to killing by NK cells (FIG. 10).

These results indicate that engagement of the CD19-CAR expressed on the CD4$^{IL\text{-}10antiCD19\ CAR}$ cells with CD19 expressed on the NALM6 lymphoma cells triggers the cytotoxic machinery of the CD4$^{IL\text{-}10antiCD19\ CAR}$ cells, resulting in selective and efficient killing of CD19$^+$ target cells. In addition, CD4$^{IL\text{-}10antiCD19\ CAR}$ cells, like CD4$^{IL\text{-}10}$ cells, maintain the ability to kill myeloid target cells that express one or more of CD13, Class I MHC antigens, CD54 and CD112 as previously described (Andolfi et al. Mol Ther. 2012; 20(9):1778-1790).

In addition to inducing selective cytotoxic activity, engagement of the CD4$^{IL\text{-}10antiCD19\ CAR}$ with CD19$^+$ NALM6 target cells resulted in selective activation and IL-10 production by the CD4$^{IL\text{-}10antiCD19\ CAR}$ cells.

For these experiments, CD4$^{IL\text{-}10}$ cells (control) and CD4$^{IL\text{-}10antiCD19\ CAR}$ cells were generated from CD4$^+$ T cells isolated from three different donors (26.1, 26.2, and 26.3). Prior to assessing IL-10 production, selective killing of CD19$^+$ cells was confirmed for CD4$^{IL\text{-}10antiCD19}$ CAR cells generated from each of the three different donors.

In particular, CD4$^{IL\text{-}10}$ cells (control) and CD4$^{IL\text{-}10antiCD19\ CAR}$ cells generated from CD4$^+$ T cells isolated from three different donors (26.1, 26.2, and 26.3) were collected following a second restimulation (TF2) (see FIG. 5C) and were co-cultured with K562 cells, NALM6 (CD19$^+$) cells, or ALL-CM target cells ($10^5$ cells/well) at a 1:1 ratio for three days. Following the three day co-culture, flow cytometry was used to determine the presence of residual leukemic target cells in each co-culture. The K562 cell line, which is highly susceptible to non-specific cytotoxicity and to killing by NK cells, served as a control. The data are shown in FIG. 11A.

As shown in FIG. 11A, CD4$^{IL\text{-}10antiCD19\ CAR}$ cells generated from 3 different donors (26.1, 26.2 and 26.3) efficiently killed CD19$^+$ NALM6 cells. CD4$^{IL\text{-}10antiCD\ 19\ CAR}$ cells maintained their capacity to kill the myeloid tumor cell line ALL-CM, whereas they were not, or were only weakly cytotoxic for K562 cells, which do not express CD19, but are known to be sensitive to non-specific cytotoxicity and killing by NK cells (FIG. 11A). CD4$^{IL\text{-}10antiCD19\ CAR}$ also killed ALL-CM, a myeloid leukemia cell line. Significant amounts of IL-10 were measured in the supernatants of the cytotoxicity assays after only 3 days of co-culture with NALM6 cells (FIG. 11B). In contrast, no IL-10 (limit of quantification: 31 pg/mL) could be detected in co-cultures of NALM6 cells with the CD4$^{IL\text{-}10}$ cells from the same donor (FIG. 11B).

Taken together, the data showed that CD4$^{IL\text{-}10antiCD19\ CAR}$ cells are selectively activated by engagement of the CD19-CAR with CD19 expressed on relevant target cells. This activation led to (i) cytotoxic/cytolytic activity of the cells resulting in killing of the CD19$^+$ target cells and (ii) induction of IL-10 production, which is required for the CD4$^{IL\text{-}10antiCD19\ CAR}$ cells immune regulatory and suppressor functions. Furthermore, the CD4$^{IL\text{-}10antiCD19\ CAR}$ cells maintain the same cytotoxic capabilities towards myeloid tumor target cells that was previously observed with $CD4^{IL-10}$ cells. Lastly, the failure of $CD4^{IL-10}$ cells to kill $CD19^+$ NALM6 cells (FIG. 11B), demonstrated that the cytotoxic activities of the $CD4^{IL-10antiCD19\ CAR}$ cells was due to anti-CD19 CAR-engagement with $CD19^+$ target cells.

6.9.4. Example 3: $CD4^{IL-10antiCD19\ CAR}$ Cells Suppress the Proliferative Responses of Both Allogeneic $CD4^+$ and $CD8^+$ T Cells As $CD4^{IL-10antiCD19\ CAR}$ cells and $CD4^{IL-10}$ cells harvested at TF2 or TF3 each produce high levels of IL-10, both were tested for their ability to suppress the proliferation of allogeneic CD4+ and $CD8^+$ T cells taken from healthy donors.

To assess proliferation of allogeneic $CD4^+$ T cells, allogeneic PBMC cells were labeled with eFluor® 670 ($1\times10^5$ cells per well) and stimulated with mature allogeneic dendritic cell (DCs) ($5\times10^4$ cells per well) and soluble anti-CD3 mAbs in the presence or absence of $CD4^{IL-}10$ cells (control) or $CD4^{IL-10antiCD19\ CAR}$ cells ($1\times10^5$ cells per well) isolated after a second restimulation (see FIG. 5C) at a 1:1 Responder:Suppressor ratio. After 4 days of culture, the percentage of $CD4^+$ proliferating responder T cells was determined by eFluor®670 dilution with flow cytometry. For flow cytometry, cells were gated on $CD4^+\Delta NGFR^-$ T cells.

To assess proliferation of allogeneic $CD8^+$ T cells, allogeneic PBMC cells were labeled with eFluor® 670 ($1\times10^5$ cells per well) and stimulated with allogeneic mature dendritic cell (DCs) ($5\times10^4$ cells per well) and soluble anti-CD3 mAbs in the presence or absence of $CD4^{IL-10}$ cells (control) or $CD4^{IL-10antiCD19\ CAR}$ cells ($1\times10^5$ cells per well) isolated after a second restimulation (see FIG. 5C) at a 1:1 Responder:Suppressor ratio. After 4 days of culture, the percentage of $CD8^+$ proliferating responder T cells was determined by eFluor®670 dilution with flow cytometry. For flow cytometry, cells were gated on $CD8^+\Delta NGFR^-$ T cells.

To assess proliferation of allogeneic PBMC, allogeneic PBMC cells were labeled with eFluor® 670 ($1\times10^5$ cells per well) and stimulated with allogeneic mature dendritic cell (DCs) ($5\times10^4$ cells per well) and soluble anti-CD3 mAbs in the presence or absence of $CD4^{IL-10}$ (control) or $CD4^{IL-10antiCD19CAR}$ cells ($1\times10^5$ cells per well) isolated after a second restimulation (see FIG. 5C) at a 1:1 Responder:Suppressor ratio. After 4 days of culture, the percentage of $CD8^+$ proliferating responder T cells was determined by eFluor®670 dilution with flow cytometry. For flow cytometry, cells were gated on $CD3^+\Delta NGFR^-$ T cells.

As shown in FIG. 12, $CD4^{IL-10antiCD19\ CAR}$ cells derived from 3 different healthy donors 26.1, 26.2, and 26.3 harvested at TF2, suppress the proliferation of allogeneic $CD4^+$ T cells by 78%, 48%, and 74%, respectively. They also suppress the proliferation of allogeneic $CD8^+$ T cells by 77%, 41%, and 42%, respectively (FIG. 13). Comparable results were obtained with $CD4^{IL-10}$ cells generated from the same 3 donors (i.e., 26.1, 26.2, and 26.3), which inhibited the proliferation of allogeneic $CD4^+$ T cells by 83%, 81%, and 61%, respectively, and $CD8^+$ T cells by 77%, 41%, and 68%, respectively (FIG. 12 and FIG. 13). Finally, $CD4^{IL-10antiCD19\ CAR}$ cells and $CD4^{IL-10}$ cells were also effective in suppressing the proliferation of allogeneic T cells when harvested at TF3. In particular, the $CD4^{IL-10antiCD19\ CAR}$ cells, like $CD4^{IL-10}$ cells, suppressed the proliferation of the PBMC by 69% and 60%, respectively (FIG. 14).

Taken together, these results showed that $CD4^{IL-10/CAR}$ cells have immunosuppressive effects on both allogeneic $CD4^+$ T cells and allogeneic $CD8^+$ T cells, and the immunosuppressive effects are comparable to those of $CD4^{IL-10}$ cells; co-expression of the CAR did not abrogate or alter the immunosuppressive effects of $CD4^{IL-10}$ cells. The results also showed that the immune suppressive function is stable after a prolonged culture period (i.e., in $CD4^{IL-10antiCD19\ CAR}$ T cells isolated after TF3).

6.9.5. Example 4: Treatment or Prevention of GvHD and Cancer Using $CD4^{IL-10antiCD19\ CAR}$ Cells Effects of $CD4^{IL-10antiCD19\ CAR}$ Cells In Vivo A population of $CD4^{IL-10antiCD\ 19\ CAR}$ cells were tested in a humanized xeno-GvHD disease and tumor transplant NSG mouse model for their effect on $CD19^+$ tumor growth, GvL effects, and induction of GvHD.

According to their body weight, NSG mice were sublethally irradiated with 175-200 Gr. At day 0, NSG mice were injected with (1) NALM6-luciferase ($1\times10^5$ per mouse), (ii) NALM6-luciferase ($1\times10^5$ per mouse)+PBMC ($2.5\times10^6$ per mouse), (iii) NALM6-luciferase ($1\times10^5$ per mouse)+$CD4^{IL-10antiCD19\ CAR}$ cells ($2.5\times10^6$ per mouse), or (iv) NALM6-luciferase ($1\times10^5$ per mouse)+PBMC ($2.5\times10^6$ per mouse)+$CD4^{IL-10antiCD19\ CAR}$ cells ($2.5\times10^6$ per mouse) (see FIG. 15).

Effects on leukemia cell growth were determined by a standard bioluminescence measurements (see FIGS. 16A-16B). In addition, the mice were monitored for development of GvHD by measuring weight at days 0, 9, 12, and 15, after administration of PBMC and/or the $CD4^{IL-10antiCD19\ CAR}$ cells (see FIG. 17).

As shown in FIGS. 16A-16B, although the PBMC inhibited NALM6 cell growth (FIGS. 16A-16B), modeling the graft-versus-leukemia effect of an allo-HSCT in human patients, they induced xeno-GvHD in the mice (FIG. 17), analogous to the GvHD seen in human allo-HSCT therapy. In contrast, the $CD4^{IL-10antiCD\ 19\ CAR}$ cells inhibited NALM6 cell growth (FIGS. 16A-16B) and did not cause any signs of xeno-GvHD (FIG. 17) as determined by weight loss. Treatment with PBMC+$CD4^{IL-10/CAR}$ T cells had greatest anti-leukemia effect (FIG. 16A-16B) and greatest anti-tumor effect (FIG. 17).

These data indicate that $CD4^{IL-10antiCD19\ CAR}$ T cells are strongly cytotoxic and selectively kill $CD19^+$ target cells in vivo. In addition, they do not interfere with the protective GvL effects of the PBMC; indeed, they work synergistically. In contrast to the PBMC, treatment with the $CD4^{IL-10antiCD19\ CAR}$ T cells alone, or in conjunction with PBMC, did not induce xeno-GvHD.

6.9.6. Example 5: $CD4^{IL-10antiCD19\ CAR}$ Cells Suppressive Activity In Vivo and Effectively Prevent Severe Xeno-GvHD An additional study described in FIG. 18A was used to assess whether single donor or polydonor $CD4^{IL-10antiCD19\ CAR}$ cells induced GvHD and whether they protected from GvHD induced by PBMC. In particular, humanized NSG mice were sub-lethally irradiated and GvHD was induced by allogeneic PBMC. Mice were treated according to FIG. 18A. On day 3 mice were dosed intravenously with (i) PBMC (2.5E6 cells/mouse), (ii) single donor (BC26.3) $CD4^{IL-10antiCD19\ CAR}$ cells (2.5E6 cells/mouse), (iii) polydonor (BC-26.1, BC26.2, and BC26.3) $CD4^{IL-10antiCD19\ CAR}$ cells (2.5E6 cells/mouse), (iv) PBMC (2.5E6 cells/mouse) and single donor (BC26.3) $CD4^{IL-10antiCD19\ CAR}$ cells (2.5E6 cells/mouse), or (v) PBMC (2.5E6 cells/mouse) and polydonor (BC-26.1, BC26.2, and BC26.3) CD4$^{IL-10antiCD19\ CAR}$ cells (2.5e6 cells/mouse) (see FIG. 18A). GvHD was determined using a composite score of weight loss, fur appearance, skin appearance, hunch, and activity (Bondanza et al. 2006). Mice with a combined score ≥6 and/or a weight loss ≥20% were euthanized for humane reasons. The donor of the PBMC was unrelated to the donors used to generate the single donor CD4$^{IL-10anti-CD19CAR}$ and polydonor CD4$^{IL-10antiCD19\ CAR}$.

As shown in FIG. 18B and FIG. 18C, the injection of 2.5E6 PBMC cells induced fulminant and rapidly lethal xeno-GvHD by day 16, whereas mice that received 2.5E6 single donor CD4$^{IL-10antiCD19\ CAR}$ cells (FIG. 18B) or 2.5E6 polydonor CD4$^{IL-10antiCD19\ CAR}$ cells (FIG. 18C) did not develop any signs of xeno-GvHD. Furthermore, when mice received both 2.5E6 PBMC and 2.5E6 single donor CD4$^{IL-10antiCD19\ CAR}$ cells (FIG. 18B) or 2.5E6 PBMC and 2.5E6 polydonor CD4$^{IL-10antiCD19\ CAR}$ cells (FIG. 18C), the co-administration of PBMC and single donor CD4$^{IL-10antiCD19\ CAR}$ cells or polydonor CD4$^{IL-10antiCD19\ CAR}$ protected the mice against PBMC-induced xeno-GvHD.

These results indicate that single donor CD4$^{IL-10antiCD19\ CAR}$ cells and polydonor CD4$^{IL-10antiCD19\ CAR}$ do not induce xeno-GvHD in vivo. In addition, single donor CD4$^{IL-10antiCD19\ CAR}$ cells and polydonor CD4$^{IL-10antiCD19\ CAR}$ effectively prevent severe xeno-GvHD induced by PBMC, demonstrating that they have suppressive activity in vivo.

Other Experiments

The mice in the treatment groups are monitored for additional periods to determine effects of the CD4$^{IL-10/CAR}$ cells on long term survival.

The amount and localization of the CD4$^{IL-10/CAR}$ cells are also monitored in peripheral blood and tissues after administration. Specifically, presence of CD4$^{IL-10/CAR}$ cells are monitored in peripheral blood and at sites of inflammation:

lymph nodes, spleen, gut, and bone marrow. The mice in the treatment group(s) are monitored for an additional 3 weeks to determine long-term survival.

The results demonstrate reduction and prevention of xeno-GvHD persists.

6.9.7. Example 6: Treatment of Chronic Inflammatory and Autoimmune Diseases Using CD4$^{IL-10/CAR}$ Cells Activation of the NLPR3 inflammasome has been implicated in many chronic inflammatory and autoimmune diseases. The NLPR3 inflammasome can be activated by "danger signals" which lead to caspase1-mediated production of the pro-inflammatory cytokines IL-1β and IL-18 by monocytes/macrophages. A series of in vitro experiments are performed to investigate the effects of CD4$^{IL-10/anti-CD19\ CAR}$ cells on the NLPR3 inflammasome and IL-1 β/IL-18 production by human monocytes.

First, human PBMC are isolated from peripheral blood by standard density centrifugation on Ficoll/Paque (Sigma-Aldrich). Monocytes are isolated from the human PBMC by negative selection using monocyte isolation kit II (Miltenyi) according to the manufacturer's instructions. Negative selection is preferred because positive selection or adherence can lead to undesired activation of the cells. Isolated monocytes are plated at 5×10$^4$ cells/200 μl in the presence of various dilutions of supernatants from CD4$^{IL-10/anti-CD19\ CAR}$ cells/200 μl per well in 96-well microtiter plates in culture medium containing 3% toxin free human AB serum.

Table 1 summarizes treatment conditions applied to different sets of monocytes, each set including 6 wells of cells. Monocytes are activated by LPS in combination with the NLPR3 inflammasome activator nigericin. The caspase 1 inhibitor Z-YVADfmk and the specific NLPR3 inhibitor MC950 are added as indicated as controls.

TABLE 1

| Group # | Monocytes | CD4 cells/supernatant | YVADfmk* | LPS** plus nigericin | Other |
|---|---|---|---|---|---|
| | | Medium control Incubation time: 1 hour; followed by activation by LPS for 4 hours | | | |
| 1 | Monocytes | No | No | No | |
| 2 | Monocytes | No | No | LPS + Nig | |
| 3 | Monocytes | No | Z-YVADfmk | LPS + Nig | |
| 4 | Monocytes | No | MCC950 | LPS + Nig | |
| | | Culture of monocytes in the presence of supernatants*** obtained from single donor or polydonor CD4$^{IL-10/CAR}$ cell- or from CD4$^{GFP}$ cell-culture | | | |
| 5 | Monocytes | 50% supernatant of single donor CD4$^{IL-10/CAR}$ cells | No | LPS + Nig | |
| 6 | Monocytes | 25% supernatant of single donor CD4$^{IL-10/CAR}$ cells | No | LPS + Nig | |
| 7 | Monocytes | 12.5% supernatant of single donor CD4$^{IL-10/CAR}$ cells | No | LPS + Nig | |
| 8 | Monocytes | 50% supernatant of single donor CD4$^{IL-10/CAR}$ cells | No | LPS + Nig | Anti-IL-10 receptor antibody |
| 9 | Monocytes | 50% supernatant of poly donor CD4$^{IL-10/CAR}$ cells | No | LPS + Nig | |
| 10 | Monocytes | 25% supernatant of poly donor CD4$^{IL-10/CAR}$ cells | No | LPS + Nig | |
| 11 | Monocytes | 12.5% supernatant of poly donor CD4$^{IL-10/CAR}$ cells | No | LPS + Nig | |

TABLE 1-continued

| Group # | Monocytes | CD4 cells/supernatant | YVADfmk* | LPS** plus nigericin | Other |
|---------|-----------|------------------------|----------|----------------------|-------|
| 12 | Monocytes | 50% supernatant of poly donor CD4$^{IL-10/CAR}$ cells | No | LPS + Nig | Anti-IL-10 receptor antibody |
| 13 | Monocytes | 50% supernatant of CD4$^{GFP}$ cells | No | LPS + Nig | |

*Z-YVADfmk is an inhibitor specific to caspase 1. 20 µM Z-YVADfmk (Biovision, Enzo Life Sciences, or Axxora Life Sciences) dissolved in DMSO is used.
**LPS (Sigma-Aldrich) 100 ng/mL plus nigericin (Nig, Invivogen) 10 µM added during the last 30 min of LPS incubation, MCC950 (Invivogen) 10 µM.
***Supernatants of CD4$^{IL-10}$ and CD4 GFP or NGFR cultures are obtained by incubating CD4$^{IL-10}$ or CD4 GFP cells at 1 × 10$^6$/mL for 3 days and collecting the supernatants. IL-10 production levels are measured by IL-10 specific ELISA. Anti-IL-10R antibody (Biolegend) 30 µg/mL.

After treatments outlined in Table 1, supernatants are collected from 6 wells for each group and IL-1 β/IL-18 production is measured by ELISA specific for mature IL-1β or IL-18 (Biolegend). Cells collected from selected groups are analyzed by Western Blot to determine levels of activated caspase 1.

Data from the experiments show that autologous single-donor, allogeneic single-donor, and allogeneic polydonor CD4$^{IL-10/anti-CD19 CAR}$ cells down-regulate IL-1β and IL-18 production by activated monocytes. They further show that autologous single-donor, allogeneic single-donor, and allogeneic polydonor CD4$^{IL-10/anti-CD19 CAR}$ cells down-regulate mature caspase-1 production in activated monocytes. Additionally, autologous single-donor, allogeneic single-donor, and allogeneic polydonor CD4$^{IL-10/anti-CD19 CAR}$ and IL-10 produced by the polydonor CD4$^{IL-10}$ down-regulate inflammasome.

Similar experiments are performed with human macrophages or dendritic cells instead of monocytes. Results from the experiments demonstrate that CD4$^{IL-10/anti-CD19 CAR}$ cells further down-regulate IL-1β, IL-18, and mature caspase-1 production from activated macrophages and dendritic cells.

These data indicate that autologous single-donor, allogeneic single-donor, and allogeneic polydonor CD4$^{IL-10/anti-CD19 CAR}$ cells can be used to treat diseases or disorders involving hyperactivation of NLPR3 inflammasome. In particular, autologous single-donor, allogeneic single-donor, and allogeneic polydonor CD4$^{IL-10/anti-CD19 CAR}$ cells can be used to treat chronic inflammatory and autoimmune diseases. The NLPR3 inflammasome can be activated by exogenous or endogenous "danger signals", such as Pathogen Associated Molecular Patterns (PAMPs), silica, asbestos, Danger Associated Molecular Patterns (DAMPs) like products from damaged mitochondria, necrotic and stressed cells, and uremic acid crystals.

6.9.8. Example 7: Generation of Polydonor CD4$^{IL-10}$ Cells

Vector Production

Polydonor CD4$^{IL-10}$ cells were produced by transduction with a lentiviral vector containing coding sequences of both the human IL-10 and a truncated form of the NGFR (ΔNGFR) (FIGS. 3A-3B), as described in WO2016/146542, incorporated by reference in its entirety herein. The sequence of the vector is provided as SEQ ID NO:5. In short, the lentiviral vector was generating by ligating the coding sequence of human IL-10 from 549 bp fragment of pH15C (ATCC 68192)) into plasmid #1074.1071.hPGK. GFP.WPRE.mhCMV.dNGFR.SV40PA. The presence of the bidirectional promoter (human PGK promoter plus minimal core element of the CMV promoter in the opposite direction) allows co-expression of the two transgenes. The plasmid further contains a coding sequence of an antibiotic resistance gene (e.g., ampicillin or kanamycin).

The lentiviral vectors were produced by Ca$_3$PO$_4$ transient four-plasmid co-transfection into 293T cells and concentrated by ultracentrifugation: 1 µM sodium butyrate was added to the cultures for vector collection. Titer was estimated on 293T cells by limiting dilution, and vector particles were measured by HIV-1 Gag p24 antigen immune capture (NEN Life Science Products; Waltham, MA). Vector infectivity was calculated as the ratio between titer and particle. For concentrated vectors, titers ranged from 5×10$^8$ to 6×10$^9$ transducing units/mL, and infectivity from 5×10$^4$ to 5×10$^5$ transducing units/ng.

Production of CD4$^{IL-10}$ Cells

FIG. 19 is a schematic representation of the production process of CD4$^{IL-10}$ cells. CD4$^+$ T cells from healthy donors were purified. Human CD4$^+$ T cells were activated with soluble anti-CD3, soluble anti-CD28 mAbs, and rhIL-2 (50 U/mL) for 48 hours before transduction with a bidirectional lentiviral vector encoding for human IL-10 and a truncated form the human NGF receptor (LV-IL-10/ΔNGFR) at multiplicity of infection (MOI) of 20.

After 11 days, transduced cells were analyzed by FACS for the expression of ΔNGER, and the vector copy number (VCN) was quantified by digital droplet PCR (ddPCR).

The mean transduction efficiency of CD4$^+$ T cells from 10 different donors was 45±17% with VCN of 2.7±0.6%. FIG. 20A shows percentages of CD4$^+$ΔNGFR$^+$ cells (mean±SD, n=10 left bar) and vector copy numbers (VCN, mean±SD, n=10 right bar) in human CD4$^+$ T cells transduced with LV-IL-10/ΔNGER (a bidirectional lentiviral vector encoding for human IL-10 and a truncated form the human NGF receptor). The frequency of CD4$^+$ΔNGER$^+$ cells and the vector copy numbers were quantified by digital droplet PCR (ddPCR) in CD4$^{IL-10}$ cells.

ΔNGFR$^+$ T cells were purified using anti-CD271 mAb-coated microbeads and resulted in >95% pure CD4$^{IL-10}$ cells populations. After purification, cells were stained with markers for CD4 and ΔNGER and analyzed by FACS. The data showed purity resulting from the purification step was over 98%. FIG. 20B shows FACS data from two representative donors (Donor B and Donor C) out of 10 donors tested. The purified CD4$^{IL-10}$ cells were restimulated 3 times at 14 day intervals and their in vitro and in vivo functions were tested after the second (TF2) and or third restimulation (TF3) functions.

Resting CD4$^{IL-10}$ cells produced IL-10 constitutively. Upon activation, the level of IL-10 produced was strongly enhanced.

$CD4^{IL-10}$ Cells have a Cytokine Production Profile which is Comparable to that of Naturally Derived Tr1 Cells.

Cytokine production profiles of single donor $CD4^{IL-10}$ cells were analyzed after the second (TF2) and third (TF3) restimulation and the results are provided in FIG. 21. Specifically, $CD4^{IL-10}$ cells ($2\times10^5$ cells in 200 μl) were restimulated as previously described (Andolfi et al. Mol Ther. 2012; 20(9):1778-1790 and Locafaro et al. Mol Ther. 2017; 25(10):2254-2269). At day 14, after the $2^{nd}$ round (TF2) and $3^{rd}$ round (TF3) of restimulation, $CD4^{IL-10}$ cells were left unstimulated (orange bar) or stimulated with immobilized anti-CD3 and soluble anti-CD28 mAbs (grey bars) for 48 hrs. Culture superatants were collected and levels of IL-10, IL-4, IL-5, IFN-γ, and IL-22 were determined by ELISA. All samples were tested in triplicate. Mean±SD, n=8 donors tested are presented. The results provided in FIG. 21 show that $CD4^{IL-10}$ cells stimulated with immobilized anti-CD3 and soluble anti-CD28 mAbs show a Tr1 cell cytokine production profile.

Although considerable variations between the different donors were observed, the overall cytokine production profiles after the second (TF2) or the third (TF3) restimulation were comparable and reflected those of Tr1 cells (Roncarolo et al., Immunity, 2018). Like Tr1 cells, the $CD4^{IL-10}$ cells produced high levels of IL-10, IL-5, IFN-γ, and IL-22, but low levels of IL-4 and undetectable levels of IL-2.

$CD4^{IL-10}$ Cells Express High Levels of Granzyme B and Selectively Kill Myeloid Leukemia Cells The $CD4^{IL-10}$ cells were further analyzed after the $2^{nd}$ round (TF2) of restimulation for expression of granzyme B (GzB). The data in FIG. 22A show that most of the $CD4^{IL-10}$ cells expressed GzB. More than 95% of all $CD4^{IL-10}$ cells derived from 7 different donors expressed high levels of Granzyme B.

The $CD4^{IL-10}$ cells from the $2^{nd}$ round (TF2) of restimulation were further analyzed for their cytotoxic effects against myeloid leukemia cells (ALL-CM) and an erythroid leukemia cell line (K562). $CD4^{IL-10}$ cells ($10^5$/well) were co-cultured with K562 and ALL-CM cells ($10^5$/well) at 1:1 ratio for 3 days. Residual leukemic cell lines ($CD45^{low}CD33^+$) were counted by FACS for each target cell.

The $CD4^{IL-10}$ cells selectively killed the myeloid leukemia cells (ALL-CM) as shown in FIG. 22B. The % of killed ALL-CM cells varied between 62% and 100%, whereas the killing of the erythroid leukemia cell line K562 (which are highly sensitive for nonspecific cytotoxic activities) varied between 0 and 27% (4 different donors tested). Taken together, these data confirm that $CD4^{IL-10}$ cells express Granzyme B and efficiently kill myeloid leukemia cells. As expected, some variations in the killing capacity of the $CD4^{IL-10}$ cells from individual donors was observed.

$CD4^{IL-10}$ Cells Suppress the Proliferative Responses of Both Allogeneic CD4+ and CD8+ T Cells The $CD4^{IL-10}$ cells were also analyzed for their effects on allogeneic CD4+ T cells or CD8+ T cells. Specifically, allogeneic PBMC cells were labeled with eFluor® 670 ($10^5$ cells/well) and stimulated with allogeneic mature dendritic (DC) cells ($5\times10^4$ cells/well) and soluble anti-CD3 mAbs in the absence or presence of $CD4^{IL-10}$ cells ($10^5$ cells/well) at a 1:1 Responder:Suppressor ratio. After 4 days of culture, the percentages of proliferating responder cells were determined by eFluor® 670 dilution with flow cytometry after gating on CD4+ΔNGFR T cells or CD8+ΔNGFR-T cells. FIGS. 23A and 23B show effects of $CD4^{IL-10}$ cells from six different, unpooled, donors (Donor-C, Donor-E, and Donor-F in FIG. 23A and Donor-H, Donor-I, and Donor-L in FIG. 23B) on CD4+ T cells with percentages of proliferation and suppression. FIGS. 24A and 24B show effects of $CD4^{IL-10}$ cells from six different, unpooled, donors (Donor-C, Donor-E, and Donor-F in FIG. 24A and Donor-H, Donor-I, and Donor-L in FIG. 24B) on CD8+ T cells.

The results demonstrated that $CD4^{IL-10}$ cells from 6 different donors, unpooled and tested separately, downregulated the proliferative responses of both allogeneic CD4+ and CD8+ T cells.

The suppressive effects on the CD4+ T-cells varied between 51% and 96%, while the suppressive effects on the CD8+ T-cells varied between 62% and 73%.

Production and Characterization of Polydonor $CD4^{IL-10}$ Cells $CD4^{IL-10}$ cells were generated as described above and FIG. 19 using CD4+ cells from multiple donors. $CD4^{IL-10}$ cells from each donor were stimulated by the second (TF2) and third (TF3) restimulation. After the third stimulation, $CD4^{IL-10}$ cells from the three donors were pooled at a 1:1:1 ratio and stimulated with immobilized anti-CD3 and soluble anti-CD28 mAbs for 48 hrs.

Polydonor $CD4^{IL-10}$ Cells have a Cytokine Production Profile which is Comparable to that of $CD4^{IL-10}$ Cells of Individual Donors and Tr1 Cells.

Culture supernatants were collected and levels of IL-10, IL-4, IL-5, IFN-γ and IL-22 were determined by ELISA. The results provided in FIG. 25 show that the cytokine production of polydonor $CD4^{IL-10}$ cells pooled from 3 different allogeneic donors (pooled 1:1:1) (red dot) was comparable to that of $CD4^{IL-10}$ cells from individual donor (n=8) derived $CD4^{IL-10}$ cells (gray bars). The polydonor CD4-10 cells produced high levels of IL-10, IL-5, IFN-γ and IL-22 and low levels of IL-4 and undetectable levels of IL-2 (not shown). These data indicate that it is feasible to pool $CD4^{IL-10}$ cells and that these polydonor $CD4^{IL-10}$ cells maintain the cytokine production signature of single donor derived $CD4^{IL-10}$ cells and Tr1 cells. Importantly, the pooled allogeneic cell populations contained >95% viable cells indicating that they did not kill each other.

Polydonor $CD4^{IL-10}$ Cells Express High Levels of Granzyme B and Kill Myeloid Leukemia Cell Lines.

The polydonor $CD4^{IL-10}$ cells were further analyzed after $3^{rd}$ round (TF3) of restimulation for expression of granzyme B (GzB). The data in FIG. 26A show that most of the polydonor $CD4^{IL-10}$ cells express GzB. Over 95% of the polydonor $CD4^{IL-10}$ cells expressed Granzyme B, comparable to the GzB expression of single donor derived $CD4^{IL-10}$ cells.

The $CD4^{IL-10}$ cells from $3^{rd}$ round (TF3) of restimulation were further analyzed for their cytotoxic effects on myeloid leukemia cells (ALL-CM cell line) or K562. The polydonor $CD4^{IL-10}$ cells ($10^5$/well) were co-cultured with K562 and ALL-CM cells ($10^5$/well) at 1:1 ratio for 3 days. Residual leukemic cell lines ($CD45^{low}CD33^+$) were counted by FACS for each target cell. The results provided in FIG. 26B show that some level of cytotoxicity against K562 cells, which are highly sensitive for nonspecific cytotoxicity and NK cell cytotoxicity. Nevertheless, a level of selectivity towards myeloid leukemia cells (ALL-CM) was obtained which is comparable to that of single donor derived $CD4^{IL-10}$ cells.

Polydonor $CD4^{IL-10}$ cells suppress the proliferative responses of both allogeneic CD4+ and CD8+ T Cells.

The polydonor $CD4^{IL-10}$ cells were also analyzed for their effects on allogeneic CD4+ T cells or CD8+ T cells. Specifically, allogeneic PBMC cells were labeled with eFluor® 670 ($10^5$ cells/well) and stimulated with allogeneic mature dendritic (DC) cells ($5\times10^4$ cells/well) and soluble anti-CD3 mAbs in the absence or presence of polydonor CD4$^{IL-10}$ cells ($10^5$ cells/well) at a 1:1 Responder:Suppressor ratio. After 4 days of culture, the percentages of proliferating responder cells were determined by eFluor® 670 dilution with flow cytometry after gating on CD4$^+$ΔNGFR$^-$ T cells and CD8+ΔNGFR-T cells. FIG. 27A shows results from polydonor CD4$^{IL-10}$ cells containing CD4$^{IL-10}$ cells from Donor-C, Donor-E, and Donor-F. FIG. 27B shows results from polydonor CD4$^{IL-10}$ cells containing CD4$^{IL-10}$ cells from Donor-H, Donor-I, and Donor-L, which had been frozen, stored and thawed prior to testing.

FIG. 27A shows that the polydonor CD4$^{IL-10}$ cells (from 3 different donors) suppress CD4$^+$ and CD8$^+$ T-cell responses by 96% and 74%, respectively. Comparable results were obtained with a second, different batch of polydonor CD4$^{IL-10}$ cells which was tested after the cells had been frozen, stored and thawed prior to testing (FIG. 27B). Suppression of CD4$^+$ and CD8$^+$ T cell proliferation was 68% and 75%, respectively. These data indicate that polydonor CD4$^{IL-10}$ cells can be frozen and stored without loss of function.

Collectively the data obtained with polydonor CD4$^{IL10}$ cells indicate that these cell preparations can be pooled without any problems. They contain >95% viable cells and maintain all the relevant functions (cytokine production, cytotoxic capacity, and suppression of allogeneic T cell responses) of single donor CD4$^{IL-10}$ cells. The use of larger pools of polydonor CD4$^{IL-10}$ cells should reduce the natural variations observed between CD4$^{IL-10}$ cell lots originating from different individual donors, and should provide a large quantity of off-the-shelf CD4$^{IL-10}$ cells for human therapy.

A polydonor CD4$^{IL-10}$ cell product will have significant advantages in terms of a more homogeneous product which will allow the determination of well defined, less lot-to-lot variation, potency, and release criteria. In addition, it will enable the development of a continuous large-scale cell production process.

Other Methods for Production of Polydonor CD4$^{IL-10}$ Cells

Before the lentiviral transduction, buffy coats from minimally 3-5 different donors were pooled. CD4$^+$ cells were isolated from buffy coats by positive selection using anti-CD4 antibody. Purity of the pooled CD4$^+$ cells was checked by FACS. Alternatively, frozen human CD4$^+$ cells were obtained from minimally 3-5 normal healthy donors. The frozen human CD4$^+$ cells were thawed before use. CD4$^+$ cells from buffy coats or frozen stocks were activated for 24-48 hours by a combination of CD3 and CD28 antibodies or CD3– and CD28 antibody coated beads in the presence of IL-2. In some cases, CD4$^+$ cells from buffy coats or frozen stocks were activated with soluble anti-CD3, soluble anti-CD28 mAbs, and rhIL-2 (50 U/mL) for 48 hours and transduced with a bidirectional lentiviral vector encoding for human IL-10 as described above for production of CD4$^{IL-10}$ cells.

In some cases, the HLA haplotype of the T cell donors (or CD4$^+$ cells isolated from the donors) were first determined and CD4$^+$ cells having desired HLA haplotypes are selectively pooled and used.

Polydonor CD4$^{IL-10}$ cells were generated by transducing the activated CD4$^+$ cells described above with the lentiviral vector containing human IL-10 and ΔNGER coding sequences described above. On Day 7-11, which is 5-9 days after the transduction, the cells were harvested and successfully transduced T cells purified utilizing an anti-NGFR antibody. This process generally results in 95% pure populations of polydonor CD4$^{IL-10}$ cells.

The purified polydonor CD4$^{IL-10}$ cells were counted and re-stimulated by a mixture of CD3– and CD28 antibodies, CD3– and CD28 antibody coated beads, optionally in the presence of feeder cells for another 8-10 days in the presence of IL-2. In some cases, the purified polydonor CD4$^{IL-10}$ cells were re-stimulated in the presence of feeder cells.

After a total culture period of 14-18 days, CD4$^{IL-10}$ cells were harvested, counted and tested for their capacity to produce IL-10 spontaneously or following activation with CD3 and CD28 antibodies or CD3 and CD28 antibody coated beads. Additionally, the levels of GrzB and perforin were measured. Their capacity to suppress human T cell (PBMC) and purified CD4$^+$ and CD8$^+$ T cell proliferation are also tested.

In addition, the production of IL-22 is measured both constitutively and following activation of 200,000 CD4$^{IL-10}$ cells in a volume of 200 microliter using a combination of CD3 and CD28 antibodies as described previously for the production of other cytokines such as IFN-γ, IL-10, IL-4 and IL-5. The pooled CD4$^{IL-10}$ cells were frozen before storage.

6.9.9. Example 8: Treatment or Prevention of GvHD Using Polydonor CD4$^{IL-18}$ Cells Effects of Polydonor CD4$^{IL-10}$ Cells In Vivo.

A population of polydonor CD4$^{IL-10}$ cells were tested in a humanized xeno GvHD disease model, an NSG mouse model, for their effect on xeno-GvHD induced by human PBMC as illustrated in FIG. 28. NSG mice were sub-lethally irradiated and intravenously injected with human PBMC ($5 \times 10^6$ cells/mouse), with polydonor (three donors) CD4$^{IL-10}$ cells ($5 \times 10^6$ cells/mouse), or with human PBMC ($5 \times 10^6$ cells/mouse) in combination with polydonor CD4$^{IL-10}$ cells (BC-C/E/F) ($5 \times 10^6$ cells/mouse). Xeno-GvHD was evaluated as previously described (Bondanza et al. Blood 2006) based on weight loss (>20% weight loss), skin lesions, fur condition, activity, and hunch.

FIG. 29 shows % of NSG mice demonstrating xeno-GvHD on each day after injection. Administration of $5 \times 10^6$ human PBMC to irradiated NSG mice resulted unexpectedly in an unusually fulminant GvHD. All mice died at day 10 which reflects very lethal xeno-GvHD. Co-administration of $5 \times 10^6$ polydonor CD4$^{IL-10}$ cells delayed this fulminant GvHD, but the mice were sacrificed at day 14 because they reached the prespecified humane 20% body weight loss criterion for sacrifice (FIG. 29). Nevertheless, these results indicate that polydonor CD4$^{IL-10}$ can delay very severe xeno-GvHD. Importantly, polydonor CD4$^{IL-10}$ cells administered alone at the same dose as the PBMC ($5 \times 10^6$ cells) failed to induce any sign of xeno-GvHD.

The presence of human CD4$^{IL-10}$ cells were also tested in the spleen (FIG. 30, left panels) and bone marrow (FIG. 30, right panels) of the NSG mice injected with human PBMC ($5 \times 10^6$ cells/mouse), polydonor (three donors; BC-C/E/F) CD4$^{IL-10}$ cells ($5 \times 10^6$ cells/mouse), or human PBMC ($5 \times 10^6$ cells/mouse) in combination with polydonor CD4$^{IL-10}$ cells (three donors; BC-C/E/F) ($5 \times 10^6$ cells/mouse) at 14 days post injection. The results provided in FIG. 30 show that polydonor CD4-10 cells migrated to spleen and bone marrow. Low percentages of these cells were found to be present 14 days after infusion of the cells. These results indicate that polydonor CD4$^{IL-10}$ cells delayed fulminant xeno-GvHD induced by human PBMC and that they do not themselves induce any xeno GvHD.

Polydonor CD4$^{IL-10}$ Cells Inhibit Severe Xeno GvHD by Purified CD4$^{+}$ Cells.

Polydonor CD4$^{IL-10}$ cells were tested in a humanized xeno GvHD model in which GvHD disease was induced by administration of $2.5 \times 10^6$ purified human CD4$^{+}$ T cells as illustrated in FIG. 31. NSG mice were sub-lethally irradiated at day 0 and on day 3 were intravenously injected with human CD4$^{+}$ T cells ($2.5 \times 10^6$ cells/mouse) alone or in combination with polydonor CD4$^{IL-10}$ cells (three different donors; BC-H/I/L) ($2.5 \times 10^6$ cells/mouse) or with CD4$^{IL-10}$ cells from a single donor (BC-H) from the pool ($2.5 \times 10^6$ cells/mouse). Xeno-GvHD was evaluated as previously described (Bondanza et al. Blood 2006) based on weight loss (>20% weight loss), skin lesions, fur condition, activity, and hunch.

FIG. 32 shows % of NSG mice demonstrating GvHD on each day after injection. The results show that polydonor CD4$^{IL-10}$ (BC-H/I/L) cells can inhibit the xeno-GvHD mediated by human allogeneic CD4$^{+}$ T cells. In this experiment, xeno GvHD was very severe, because all mice in the control group which received CD4$^{+}$ T cells were dead at day 20. In contrast, co-administration of $2.5 \times 10^6$ polydonor CD4$^{IL-10}$ inhibited GvHD by 75%. Single-donor CD4RL-10 cells were also protective but the effects were less potent. Other Experiments Therapeutic effects of the polydonor CD4$^{IL-10}$ cells are tested in four different groups of mice: (i) mice receiving human PBMC from a donor unrelated to the CD4$^{IL-10}$ cells (xeno-GvHD positive control); (ii) mice receiving the polydonor CD4$^{IL-10}$ cells (negative control); (iii) mice receiving a combination of PBMC and the polydonor CD4$^{IL-10}$ cells at 1:1 ratio; and (iv) mice receiving a combination of PBMC and the polydonor CD4$^{IL-10}$ cells at 2:1 ratio or at different ratios. Among animals receiving combination of PBMC and the polydonor CD4$^{IL-10}$ cells, some animals receive PBMC and the polydonor CD4$^{IL-10}$ cells concurrently, some animals receive polydonor CD4$^{IL-10}$ cells several days (e.g., 5 days) after receiving PBMC, and some animals receive polydonor CD4$^{IL-10}$ cells several days (e.g., 5 days) before receiving PBMC.

The mice are monitored for development of GvHD by measuring weight at weeks 1, 2, 3, 4, and if necessary week 5, after administration of PBMC and/or the polydonor CD4$^{IL-10}$ cells. In addition to weight loss, the mice will be inspected for skin lesions, fur condition and activity. The mice in the treatment groups are monitored for additional periods to determine effects of the polydonor CD4$^{IL-10}$ cells on long term survival.

The amount and localization of the polydonor CD4$^{IL-10}$ cells are also monitored in peripheral blood and tissues after administration. Specifically, presence of polydonor CD4$^{IL-10}$ cells are monitored in peripheral blood and at sites of inflammation: lymph nodes, spleen, gut, and bone marrow. The mice in the treatment group(s) are monitored for an additional 3 weeks to determine long-term survival.

The results demonstrate that polydonor CD4RL-10 cells are effective in reducing and preventing xeno-GvHD.

6.9.10. Example 9: Inhibition of GvHD and Treatment of Cancer

A population of polydonor CD4$^{IL-10}$ cells are tested in an NSG mouse model transplanted with human PBMC and AML tumor cells for their effect on xeno-GvHD induced by human PBMC and anti-tumor effects. AML cells (ALL-CM) are administered i.v. as described previously in WO 2016/

146542, PBMC or polydonor CD4$^{IL-10}$ cells or combinations thereof are administered 3 days later.

Polydonor CD4$^{IL-10}$ cells are obtained as described in Example 1. Therapeutic effects of the polydonor CD4$^{IL-10}$ cells are tested in four different groups of mice, each having received irradiation and $5 \times 10^6$ ALL-CM cells (AML mice) at day 0: (i) AML mice without additional treatment; (ii) AML mice receiving $5 \times 10^6$ human PBMC from a donor unrelated to the polydonor CD4$^{IL-10}$ cells—the PBMCs cause severe xeno-GvHD; (iii) AML mice receiving $2.5 \times 10^6$ polydonor CD4$^{IL-10}$ cells; and (iv) AML mice receiving combinations of PBMC and the polydonor CD4$^{IL-10}$ cells at 1:1 or 2:1 ratio or at different ratios. One additional group of mice do not receive ALL-CML cells but receive $5 \times 10^6$ human PBMC at day 3 after irradiation.

Effects of the polydonor CD4$^{IL-10}$ cells on xeno-GvHD induced by human PBMC are tested based on weight loss, skin lesions, fur condition, activity, death rate and long-term survival. Anti-tumor or graft versus leukemia (GvL) effects of the polydonor CD4$^{IL-10}$ cells are tested based on reduction of tumor cells in the circulation and long-term tumor free survival.

Some mice are monitored for up to 7 weeks in order to monitor long-term survival and complete tumor remissions.

Results demonstrate that polydonor CD4$^{IL-10}$ cells are effective in both inhibition of xeno-GvHD and treatment of cancer.

6.9.11. Example 10: Treatment of Cancer Using Polydonor CD4$^{IL-10}$ Cells

A population of polydonor CD4$^{IL-10}$ cells are tested in an ALL-CM leukemia model of T cell therapy in NSG mice.

NSG mice were sub-lethally irradiated and intravenously injected with myeloid leukemia cells (ALL-CM) ($5 \times 10^6$) at day 0 (See FIG. 33A). In the first group of animals, PBMC ($5 \times 10^6$) or single donor (from donor BC-I and donor BC-H) CD4$^{IL-10}$ cells ($2.5 \times 10^6$) were injected at day 3. In the second group of animals, PBMC ($5 \times 10^6$) or polydonor CD4$^{IL-10}$ cells ($2.5 \times 10^6$) were injected at day 3. Graft-versus-leukemia (GvL) effect was tested in the animals based on reduction of circulating leukemia cells and long-term leukemia free survival. Leukemia was measured as previously described (Locafaro G. et al Molecular Therapy 2017).

As provided in FIG. 33B and FIG. 33C, all of the mice injected with ALL-CM myeloid leukemia cells had extensive leukemia progression at day 17. Administration of $5 \times 10^6$ PBMC resulted in a strong inhibition of leukemia progression. Interestingly, a comparable level of inhibition of leukemia progression was obtained by lower number ($2.5 \times 10^6$) of single-donor CD4$^{IL10}$ (FIG. 33B) or polydonor CD4$^{IL10}$ (FIG. 33C). These data indicate that single donor and polydonor CD4$^{IL10}$ have strong direct anti myeloid leukemia effects.

Graft-versus-leukemia (GvL) effects of single-donor CD4$^{IL10}$ and polydonor CD4$^{IL10}$ were further tested in combination with PBMC in mice injected with ALL-CM myeloid leukemia cells (see FIG. 34A). Administration of $5 \times 10^6$ PBMC resulted in a strong inhibition of leukemia progression and administration of $5 \times 10^6$ PBMC combined with single donors CD4$^{IL10}$ ($2.5 \times 10^6$) had synergistic effect (FIG. 34B). Interestingly, administration of $5 \times 10^6$ PBMC combined with $2.5 \times 10^6$ polydonor CD4$^{IL10}$ had a comparable synergistic GvL effect (FIG. 34C). These data indicate that polydonor CD4$^{IL10}$ act in synergy with PBMC to mediate strong GvL effects.

6.9.12. Example 11: Treatment of Chronic Inflammatory and Autoimmune Diseases Using Polydonor CD4$^{IL-10}$ Cells Activation of the NLPR3 inflammasome has been implicated in many chronic inflammatory and autoimmune diseases. The NLPR3 inflammasome can be activated by "danger signals" which lead to caspase1-mediated production of the pro-inflammatory cytokines IL-1β and IL-18 by monocytes/macrophages. A series of in vitro experiments are performed to investigate the effects of polydonor CD4$^{IL-10}$ cells on the NLPR3 inflammasome and IL-1 β/IL-18 production by human monocytes.

First, human PBMC are isolated from peripheral blood by standard density centrifugation on Ficoll/Paque (Sigma-Aldrich). Monocytes are isolated from the human PBMC by negative selection using monocyte isolation kit II (Miltenyi) according to the manufacturer's instructions. Negative selection is preferred because positive selection or adherence can lead to undesired activation of the cells. Isolated monocytes are plated at $5 \times 10^4$ cells/200 µl in the presence of $2 \times 10^5$ or $1 \times 10^5$ polydonor CD4$^{IL-10}$ cells/200 µl per well in 96-well microtiter plates in culture medium containing 3% toxin free human AB serum.

Table 2 summarizes treatment conditions applied to 17 sets of monocytes, each set including 6 wells of cells. It is known that LPS alone can activate human monocytes without a second signal provided by ATP.

TABLE 2

| Group # | Monocytes | CD4 cells/supernatant | YVADfmk* | LPS** | Other |
|---|---|---|---|---|---|
| | | Medium control Incubation time: 1.5 hour; followed by activation by LPS for 4 hours | | | |
| 1 | Monocytes | No | No | No | |
| 2 | Monocytes | No | No | LPS | |
| 3 | Monocytes | No | YVADfmk | LPS | |
| | | Co cultivation of monocytes and polydonor CD4$^{IL-10}$ cells | | | |
| 4 | Monocytes | CD4$^{IL-10}$ cells | No | No | |
| 5 | Monocytes | CD4$^{IL-10}$ cells | No | LPS | |
| 6 | Monocytes | CD4$^{IL-10}$ cells | YVADfmk | LPS | |
| | | Co cultivation of monocytes and control CD4 GFP+ cells | | | |
| 7 | Monocytes | CD4 GFP cells | No | No | |
| 8 | Monocytes | CD4 GFP cells | No | LPS | |
| 9 | Monocytes | CD4 GFP cells | YVADfmk | LPS | |
| | | Cultivation of monocytes in the presence of supernatants*** of polydonor CD4$^{IL-10}$ cell or CD4 GFP+ cell culture | | | |
| 10 | Monocytes | 50% supernatant of CD4$^{IL-10}$ cells | No | LPS | |
| 11 | Monocytes | 25% supernatant of CD4$^{IL-10}$ cells | No | LPS | |
| 12 | Monocytes | 12.5% supernatant of CD4$^{IL-10}$ cells | No | LPS | |
| 13 | Monocytes | 50% supernatant of CD4$^{IL-10}$ cells | No | LPS | Anti-IL-10 antibody |
| 14 | Monocytes | 50% supernatant of CD4 GFP cells | No | LPS | |
| 15 | Monocytes | 25% supernatant of CD4 GFP cells | No | LPS | |
| 16 | Monocytes | 12.5% supernatant of CD4 GFP cells | No | LPS | |
| 17 | Monocytes | 50% supernatant of CD4 GFP cells | No | LPS | Anti-IL-10 antibody |

*YVADfmk is an inhibitor specific to caspase 1. 20 mM Z-YVADfmk (Biovision, Enzo Life Sciences, or Axxora Life Sciences) dissolved in DMSO is used.
**LPS (Signa-Aldrich) 100 ng/mL
***Supernatants of CD4$^{IL-10}$ and CD4 GFP or NGFR cultures are obtained by incubating CD4$^{IL-10}$ or CD4 GFP cells at $1 \times 10^6$/mL for 3 days and collecting the supernatants. IL-10 production levels are measured by IL-10 specific ELISA.

After treatments outlined in Table 2, supernatants are collected from 6 wells for each group and IL-1 β/IL-18 production is measured by ELISA specific for mature IL-1β or IL-18 (Biolegend). Cells collected from 6 wells for Group #3, 10, 13, 14, and 17 are analyzed by Western Blot to determine levels of activated caspase 1.

Data from the experiments show that polydonor CD4$^{IL-10}$ cells down-regulate IL-1β and IL-18 production by activated monocytes. They further show that polydonor CD4$^{IL-10}$ cells down-regulate mature caspase-1 production in activated monocytes. Additionally, polydonor CD4$^{IL-10}$ and IL-10 produced by the polydonor CD4$^{IL-10}$ down-regulate inflammasome.

Similar experiments are performed with human macrophages or dendritic cells instead of monocytes. Results from the experiments demonstrate that polydonor CD4$^{IL-10}$ cells further down-regulate IL-1β, IL-18, and mature caspase-1 production from activated macrophages and dendritic cells.

These suggest that polydonor CD4$^{IL-10}$ cells can be used to treat diseases or disorders involving hyperactivation of NLPR3 inflammasome. In particular, polydonor CD4$^{IL-10}$ cells can be used to treat chronic inflammatory and autoimmune diseases. The NLPR3 inflammasome can be activated by exogenous or endogenous "danger signals", such as Pathogen Associated Molecular Patterns (PAMPs), silica, asbestos, Danger Associated Molecular Patterns (DAMPs) like products from damaged mitochondria, necrotic and stressed cells, and uremic acid crystals.

6.9.13. Example 12: Supernatant of Polydonor CD4$^{IL-10}$ Cells Inhibit NLPR3 Inflammasome Activation and IL-1β and IL-18 Production by Human Monocytes CD14$^+$ monocytes were isolated from PBMC using a pan monocyte isolation kit (Miltenyi Biotec, Bergisch Gladbach, Germany) and plated in 96 flat microtiter wells at 2×10$^5$/200 μL per well and cultured in the presence of LPS. The cells were cultured further in the presence of Z-YVADfmk (20 μM), MMC950 (10 μM), IL-10 (10 ng/ml) or various concentrations of single- or pooled donor CD40-10 cell supernatants as summarized in Table 1.

The supernatants were obtained from single- or pooled donor CD4$^{IL-10}$ cells activated for 72 hours with a combination of CD3 and CD28 antibodies as described previously. (Andolfi et al. 2012, Mol. Therapy Vol. 20, 1778-1790, Locafaro et al. Mol Ther 2017, 25, 2254) In some cases (FIGS. 35C and 35D), the monocytes were incubated with LPS in combination with the NLPR3 inflammasome activator nigericin ("NIG") which was added during the last 30 minutes of the LPS activation.

The NLPR3 inflammasome was activated by LPS, resulting in the production of mature caspase 1 and the biologically active forms of IL-1β and IL-18. Monocytes plated in the absence of LPS activation did not produce detectable levels of IL-10 during the incubation period (not shown).

Addition of the supernatant of single donor derived CD4$^{IL-10}$ cells (containing 1769 pg IL-10/mL) inhibited IL-1β production by LPS activated monocytes from donor #1 and #2 at concentrations of 50%, 25% and 12.5% respectively, in a dose dependent fashion (FIG. 35A and FIG. 35B). Supernatant of CD4+ cells transduced with GFP was used as a control. Complete inhibition of IL-Iβ production is observed at concentrations of 50% and 25%, whereas supernatants of GFP transduced control CD4+ cells at concentrations of 50% were ineffective.

Various concentrations of CD$^{IL-10}$ T cell supernatant (50%, 25% or 12.5%), Z-YVADfmk or MCC950 were further tested on monocytes activated with LPS and nigericin ("NIG"). Supernatants from single donor (BC-E) or pooled donor CD4$^{IL-10}$ cells contained 5295 or 3532 pg IL-10/mL respectively. Supernatants of single donor CD4$^{IL-10}$ cells were also very effective in inhibiting LPS induced IL-1β production enhanced by the NLPR3 inflammasome activator nigericin (FIG. 35C and FIG. 35D).

The data demonstrate that the supernatants from CD4$^{IL-10}$ cells at concentrations of 50% were as effective as the irreversible caspase 1 inhibitor Z-YVADfmk (Guo et al. 2015, Nature Med 21, 677), the selective NLPR3 inflammasome inhibitor MCC950 (Coll et al. 2019, Nature Chem. Biol 15,556) and recombinant IL-10, indicating that IL-10 containing supernatants inhibit NLPR3 inflammasome activation and mature caspase1 production resulting in strong inhibition of the production of the proinflammatory cytokine IL-1β (FIG. 35A-35D).

Comparable results were obtained in second series of experiments with supernatants of single donor (BC-E) and pooled CD4$^{IL-10}$ cells from 2 different donors (BC-C/E). The CD4$^{IL-10}$ cells were activated by a combination of CD3 and CD28 antibodies as described (Andolfi et al. 2012). After 3 days the supernatants from the CD4$^{IL-10}$ cells were collected. These supernatants contained 5295 and 3532 pg IL-10/mL respectively, and inhibited LPS induced IL-1β production by monocytes from donor #3 in a dose dependent fashion (FIG. 35E). Supernatants at concentrations of 50% were as effective as Z-YVADfmk and MCC950. The inhibitory effects of the superatants of the pooled CD4$^{IL-10}$ cells were completely neutralized by an anti-IL-10 receptor antibody. Similarly, supernatants pooled from 3 different donors containing 2589 pg IL-10/mL, dose dependently inhibited IL-1β production by monocytes from donor #4 (FIG. 35F). The inhibitory effects of the supernatants are completely neutralized by an IL-10 receptor antibody demonstrating that NLPR3 activation is mediated by IL-10. The results indicate that production of the pro inflammatory cytokine IL-1β is strongly inhibited by IL-10 produced by the polydonor CD4$^{IL-10}$ T cells. As expected, the anti-IL-10 receptor antibody had no effect of the inhibition of IL-1β production mediated by Z-VADfmk and MCC950 (FIG. 35E).

CD4$^{IL-10}$ T cells were further tested on monocytes from donor #4 activated by LPS and nigericin. Various concentrations of single donor (BC-V) or polydonor (three donors; BC-T/U/V) CD4$^{IL-10}$ cell superatants containing 2583 or 2589 pg IL-10/mL respectively, ZYVADfmk or MCC950 were tested. Data provided in FIG. 35G show that pooled supernatants of 3 different donors (BC T-U-V) down regulate IL-18 production induced by LPS in combination with nigericin.

Collectively, these data indicate that IL-10 produced by single- and poly donor CD4$^{IL-10}$ cells strongly down regulates the NLPR3 inflammasome resulting in strong inhibition of the pro inflammatory cytokines IL-1β and IL-18.

6.9.14. Example 13: Single-Donor and Polydonor CD4$^{IL-10}$ Cells Inhibit Xeno GvHD and Myeloid Tumor Growth In Vivo Functional properties and quality of the single donor (BC-T, BC-V, and BC-E) or polydonor (BC-V/T/E) CD4$^{IL-10}$ cells were tested as described in Andolfi et al. Mol Ther 2012, 20, 177 and Locafaro et al. Mol Ther 2017, 25, 2254. Both single donor- and polydonor CD4$^{IL-10}$ cells produced high levels of IL-10, variable levels of IFN-gamma, very low levels of IL-4 and no detectable IL-2 (the latter not shown), reflecting the characteristic cytokine production profile of Tr1 cells (FIG. 37).

Further, the suppressive capacity of the single donor (BC-T, BC-V, and BC-E) or polydonor (BC-V/T/E) $CD4^{IL-10}$ cells on CD4+ and CD8+ T cell proliferation was measured in vitro on allogeneic PBMC. PBMC were labeled with eFLuor670 (Invitrogen). Labeled PBMC ($1\times10^5$) were activated with immobilized CD3 (10 mg/mL) and soluble CD28 antibodies (1mg/mL). Single and polydonor $CD4^{IL-10}$ cells were added at a 1:1 ratio in a final volume of 0.2 mL in 96 well round bottom plates. After 4 days of co-culture, their suppressive effects on the proliferation of eFluor670 labeled responder cells was determined by eFluor670 dilution using flow cytometry as described (Locafaro et al. Mol Ther 2017, 25, 2254). FIG. 38 provides results from the flow cytometry. Single- and polydonor $CD4^{IL-10}$ cells strongly inhibited in vitro proliferation of both allogeneic CD4+ and CD8+ T cells by more than 80% (FIG. 38).

The $CD4^{IL-10}$ cells were further analyzed for their cytotoxic effects against myeloid leukemia cells (ALL-CM) and an erythroid leukemia cell line (K562). Single (BC-E and BC-V) or polydonor (BC-V/T/E) $CD4^{IL-10}$ cells were co-cultured at a 1:1 ratio with ALL-CM or K562 cells. After 3 days the cells were harvested and surviving CD45low, CD3– target cells were counted and analyzed by FACS as described ((Locafaro et al. Mol Ther 2017, 25, 2254). The single donor and poly donor $CD4^{IL-10}$ cells also mediated strong direct cytotoxic effects on ALL-CM myeloid tumor cells, whereas they failed to kill the sensitive K562 cells, which lack Class I MHC expression required for their cytotoxic activity (FIG. 39). Single (BC-E and BC-V) or polydonor (BC-V/T/E) $CD4^{IL-10}$ cells had comparable cytotoxic activities against these two target cell lines (ALL-CM and K562).

Cytotoxic effects of single-donor (BC-E) and polydonor (BC-V/T/B) $CD4^{IL-10}$ cells were also tested in vivo, using a humanized xeno GvHD disease model—an NSG mouse intravenously injected with ALL-CM cells ($2.5\times10^6$). Their effect on GvHD induced by human PBMC from an allogeneic donor as well as their effect on the growth of acute myeloid leukemia in cell line ALL CM in a therapeutic setting were tested as illustrated in FIG. 36.

Eight to ten-week-old female NOD scid gamma, (NSG) mice were obtained from Charles-River Italia (Calco, Italy). The experimental protocol was approved by the internal committee for animal studies of the Ospedale San Raffaele (Institutional Animal Care and Use Committee (IACUC). At day 0, the mice received total body irradiation from a linear accelerator. ALL-CM cells ($2.5\times10^6$) were injected at day 0. On day 0, different groups of mice were injected with nothing, allogeneic PBMC ($2.5\times10^6$), single donor (BC-E, $2.5\times10^6$) or polydonor $CD4^{IL-10}$ cells pooled at 1:1:1 ratio from 3 different donors (BC-V/T/E, $2.5\times10^6$) in combination with allogeneic PBMC ($2.5\times10^6$) or polydonor $CD4^{IL-10}$ cells ($2.5\times10^6$) on day 3. All cells were administered i.v. in volumes of 250 μL of Iscove's modified Dulbecco's medium. Mice were monitored 3-4 times per week.

The NSG mice were divided into five cohorts of 5 mice and each group was treated on day 0 with (i) none as a control; (ii) allogeneic mononuclear cells (PBMC); (iii) allogeneic PBMC and polydonor $CD4^{IL-10}$ cells (BC-V/T/E); (iv) allogeneic PBMC and single-donor $CD4^{IL-10}$ cells (BC-E); or (v) polydonor (BC-V/T/E) $CD4^{IL-10}$ cells administered at day 3 Myeloid leukemia progression was measured as previously described ((Locafaro et al. Mol Ther 2017, 25, 2254).

Administration of ALL-CM cells to NSG mice resulted in a rapid expansion of these cells and all the mice died or had to be sacrificed on day 20. Injection of PBMC prevented leukemia progression as expected. Both single- and poly-donor $CD4^{IL-10}$ cells given in combination with allogeneic PBMC did not interfere with anti myeloid leukemia effects of the PBMC.

Injection of polydonor $CD4^{IL-10}$ (BC-V/T/E) cells 3 days after administration of the ALL-CM cells (when already massive expansion of these cells is ongoing) resulted in inhibition of tumor growth. These results indicate that polydonor $CD4^{IL-10}$ cells have direct therapeutic anti myeloid leukemia effects in vivo (FIG. 40).

However, despite their beneficial anti myeloid leukemia effects, the PBMC induced a very severe form of xeno-GvHD and all mice died by day 24 (FIG. 41). In the study, single-donor (BC-E) and polydonor (BC-V/T/E) $CD4^{IL-10}$ cells were tested on their capacity to inhibit xeno-GvHD induced by PBMC following administration in NSG mice. On day 0, the NSG mice were injected with ALL-CM cells ($2.5\times10^6$). The mice were divided into five groups and each group was treated with (i) none as a control; (ii) allogeneic mononuclear cells (PBMC); (iii) allogeneic PBMC and polydonor (BC-V/T/B) $CD4^{IL-10}$ cells (BC-E, BC-V, BC-T); (iv) allogeneic PBMC and single-donor $CD4^{IL-10}$ cells (BC-E) or polydonor (BC-V/T/E) $CD4^{IL-10}$ cells injected at day 3. In the animals, xeno-GvHD was measured by survival and weight loss. In addition, hunching, fur condition and skin integrity were monitored as described (Bondanza et al, Blood, 2006, 107, 1828). If weight loss reached more than 20%, the mice were sacrificed for ethical reasons. FIG. 41 shows % of NSG mice free of GvHD in each day following day 1 injection with ALL-CM cells ($2.5\times10^6$) and subsequent treatment with PBMC with or without single-donor or polydonor $CD4^{IL-10}$ cells.

The results show that polydonor $CD4^{IL-10}$ cells did not induce xeno-GvHD, and down regulated xeno-GvHD induced by allogeneic PBMC. Collectively these results indicate that polydonor $CD4^{IL-10}$ cells downregulate severe xeno-GvHD, have direct anti myeloid leukemia effects in a therapeutic setting and do not interfere with the protective anti myeloid leukemia effects of the PBMC.

6.9.15. Example 14: Adoptive Transfer of Polydonor $CD4^{IL-10}$ Cells Derived from Four Different Donors Adoptive transfer of polydonor $CD4^{IL-10}$ cells derived from four different donors was tested for the transfer's ability to inhibit PBMC-induced xeno-GvHD.

In these experiments, single-donor $CD4^{IL-10}$ cells (donor C; lot C) and polydonor $CD4^{IL-10}$ cells derived from 4 different donors (donors C, E, F, and H; lot CEFH) were tested in a humanized mouse model of GvHD induced by allogeneic PBMC. In this model, NSG mice were sub-lethally irradiated at day 0 and injected at day 3 (slow bolus i.v.) with (i) 2.5E+06 allogeneic PBMC, (ii) 2.5E+06 allogeneic PBMC in combination with 2.5E+06 single-donor $CD4^{IL-10}$ cells (lot C), (iii) 2.5E+06 allogeneic PBMC in combination with 2.5E+06 cells polydonor $CD4^{IL-10}$ cells (lot CEFH), or (iv) 2.5E+06 cells polydonor $CD4^{IL-10}$ cells (lot CEFH) alone. GvHD was determined using a composite score of weight loss, fur appearance, skin appearance, hunch, and activity (see Bondanza A, et al. Blood 2006; 107:1828-36]. As shown in FIG. 42, only mice administered with the polydonor $CD4^{IL-10}$ cells were 100% free of GvHD at the end of the study.

In summary, this data demonstrated that adoptive transfer of polydonor CD4$^{IL-10}$ cells derived from four different donors inhibits PBMC-induced xeno-GvHD and does not induce xeno GvHD.

6.9.16. Example 15: Generation of a Variant of IL-10

Variants of human IL-10 are generated by introducing amino acid modification(s) (e.g., substitution, insertion, deletion) in view of IL-10 sequences of other species. Modification sites are determined by sequence alignment as provided in FIG. 43A. Amino acid positions having different amino acids among species are identified from the alignment and modified by introducing substitution, insertion, or deletion of amino acids.

Two examples of the variant of human IL-10 are provided in FIG. 43B. Possible huIL-10 HYBRID #1 (SEQ ID NO: 21) is generated by substituting three amino acids (D, I and A) of human IL-10 with three different amino acids (B, A, and D) of viral IL-10 (EBVB9) at the corresponding positions. Possible huIL-10 HYBRID #2 (SEQ ID NO: 22) is generated by substituting one amino acid (1105) of human IL-10 with another amino acid (A105) of viral IL-10 (EBVB9) at the corresponding position. FIG. 43C shows alignment of human IL-10 (SEQ ID NO: 1) with IL10 EBVB9 (SEQ ID NO: 18) with "*" indicating the one or more amino acid positions that are substituted in IL-10 hybrid #1 and "#" indicating the preferred 1105 to A105 amino acid substitution for IL-10 hybrid #2.

The variants of human IL-10 are cloned into an expression vector as described in the above section and tested for the expression and function of the variant proteins. Selected variants of human IL-10 are used to generate CD4$^{IL-10}$ cells. Efficiency of CD4$^{IL-10}$ cells are tested as provided herein.

6.9.17. Additional Experimental Methods and Materials for Examples 1-11

Cell preparation and cell lines. Peripheral blood mononuclear cells (PBMC) were prepared by centrifugation over Ficoll-Hypaque gradients. CD4$^+$ T cells were purified with a CD4 T cell isolation kit (Miltenyi Biotec, Bergisch Gladbach, Germany) with a resulting purity of >95%. Mature dendritic cells (DC) were generated from peripheral blood CD14$^+$ monocytes positively selected using CD14$^+$ MicroBeads (Miltenyi Biotech, Germany) according to the manufacturer's instructions and cultured in RPMI 1640 (Lonza, Italy) supplemented with 10% fetal bovine serum (FBS; Lonza, Italy), 100 U/mL penicillin/streptomycin (Lonza, Italy), 2 mM L-glutamine (Lonza, Italy), at 37° C. in the presence of 10 ng/mL recombinant human (rh) IL-4 (R&D Systems, Minneapolis MN, USA) and 100 ng/mL rhGM-CSF (Genzyme, Seattle, WA, USA) for 5 days and matured with 1 mg/mL of lipopolysaccharide (LPS, Sigma, CA, USA) for an additional two days.

Plasmid construction. The coding sequence of human IL-10 was excised from pH15C (ATCC n° 68192), and the 549 bp fragment was cloned into the multiple cloning site of pBluKSM (Invitrogen) to obtain pBluKSM-hIL-10. A fragment of 555 bp was obtained by excision of hIL-10 from pBluKSM-hIL-10 and ligation to 1074.1071.hPGK.GFP.WPRE.mhCMV.dNGFR.SV40PA (here named LV-ΔNGFR), to obtain LV-IL-10/ΔNGFR. The presence of the bidirectional promoter (human PGK promoter plus minimal core element of the CMV promoter in opposite direction) allows co-expression of the two transgenes (Locafaro et al. Mol Ther. 2017; 25(10):2254-2269). The sequence of LV-IL-10/ΔNGFR was verified by pyrosequencing (Primm).

Vector production and titration. VSV-G-pseudotyped third generation bidirectional lentiviral vectors were produced by Ca$_3$PO$_4$ transient four-plasmid co-transfection into 293T cells and concentrated by ultracentrifugation as described (Locafaro et al. Mol Ther, 2017; 25(10):2254-2269). Titer was estimated by limiting dilution, vector particles were measured by HIV-1 Gag p24 antigen immune capture (NEN Life Science Products; Waltham, MA), and vector infectivity was calculated as the ratio between titer and particle. Titers ranged from 5×10$^8$ to 6×10$^9$ transducing units/mL, and infectivity from 5×10$^4$ to 10$^5$ transducing units/ng of p24.

Generation of CD4$^{IL-}$18 cell lines. Polyclonal CD4-transduced cells were obtained as previously described (Andolfi et al. Mol Ther. 2012; 20(9):1778-1790). Briefly, CD4 purified T cells were activated for 48 hours with soluble anti-CD3 monoclonal antibody (mAb, 30 ng/ml, OKT3, Janssen-Cilag, Raritan, NJ, USA), anti-CD28 mAb (1 pg/mL, BD) and rhIL-2 (50 U/mL, PROLEUKIN, Novartis, Italy). T cells were transduced with LV-IL-10/ΔNGFR (CD4$^{IL-10}$) with multiplicity of infection (MOI) of 20. At day 11, CD4$^+$ΔNGER$^+$ cells were beads-sorted using CD271$^+$ Microbeads (Miltenyi Biotec, Bergisch Gladbach, Germany) and expanded in X-VIVO15 medium with 5% human serum (BioWhittaker-Lonza, Washington), 100 U/mL penicillin-streptomycin (BioWhittaker), and 50 U/mL rhIL-2 (PROLEUKIN, Novartis, Italy). At day 7 and 10, medium was replaced by fresh medium supplemented with 50U/mL of rhIL-2. At day 14, cells were collected, washed, and restimulated with allogeneic feeder mixture as previously described (Andolfi et al. Mol Ther. 2012; 20(9):1778-1790). After 14 days, cells were collected and frozen. Thawed CD4$^{IL-10}$ cells were restimulated and after the 2$^{nd}$ and 314 re-stimulation and expansion were functionally characterized in vitro and used for in vivo experiments.

Vector Copy Number Analysis. Cells were cultured for at 11 days after transduction in order to get rid of non-integrated vector forms. Genomic DNA was isolated with QIAamp DNA Blood Mini Kit (QIAGEN, 51106), according to the manufacturer's instructions. Vector integrations were quantified by QX200 Droplet Digital PCR System (Bio-Rad), according to the manufacturer's instructions.

Cytokine determination. To measure cytokine production, after 2$^{nd}$ and 3$^{rd}$ re-stimulation single donor and polydonor CD4$^{IL-10}$ cells were left unstimulated or stimulated with immobilized anti-CD3 (10 μg/mL) and soluble anti-CD28 (1 μg/mL) mAbs in a final volume of 200 μL of medium (96 well round-bottom plates, 2×10$^5$/well). Supernatants were harvested after 48 hours of culture and levels of IL-10, IL-4, IL-5, IFN-γ, and IL-22 were determined by ELISA according to the manufacturer's instructions (BD Biosciences).

Flow cytometry analysis. For the expression of Granzyme B (clone MHGB04, Invitrogen, USA) after surface staining with CD4, CD4$^{IL-10}$ cells were fixed, permeabilized, and stained using the BD Cytofix/Cytoperm™ Kit according to the manufacturer's instructions (Cat. No. 554714, Biolegend, USA). Stained cells were washed two times with PBS supplemented with 1% FBS and analysed with a BD LSR-Fortessa analysed utilizing FlowJo 10 software.

Killing assays. After 2$^{nd}$ and 3$^{rd}$ re-stimulation, cytotoxicity of single-donor and polydonor CD4$^{IL-10}$ cells was analysed in co-culture experiments. Briefly, non-myeloid leukemia and a myeloid leukemia cell lines, K562 and ALL-CM respectively, were used as target cells and plated with CD4$^{IL-10}$ cells at 1:1 ratio (10$^5$ target cells and 10$^5$ CD4$^{IL-10}$ cells) for 3 days. At the end of co-culture, cells were harvested and K562 and ALL-CM cells were analysed and counted by FACS.

Suppression assays. To measure the suppressive capacity of single donor and polydonor CD4$^{IL-10}$ cells, allogeneic PBMC were labeled with Cell Proliferation Dye eFluor® 670 (Invitrogen, CA, USA), according to manufacturer's instructions prior to stimulation with allogeneic mature DC (5×10$^4$ cells/well) and soluble anti-CD3 (50 ng/ml) mAb. PBMC and suppressor cells were added at a 1:1 ratio (10$^5$ PBMC and 10$^5$ CD4$^{IL-10}$ cells). After 3 days of culture, proliferation of responder cells was determined by analyzing the eFluor670 dilution of CD4+ΔNGER or CD8 ΔNGFR T cells by FACS.

Graft-versus Host Disease models: In all experiments 6/8 week-old female NSG mice were used. On day 0 mice received total body irradiation with a single dose of 175-200 cGy from a linear accelerator according to the weight of the mice, and were intravenously with PBMC cells) (5×10$^6$), or CD4$^{IL-10}$ cells (single-donors or polydonor—pool of three donors—5×10$^6$ or 2.5×10$^6$), or with PBMC (5×10$^6$) in combination with CD4$^{IL-10}$ cells (5×10$^6$ or 2.5×10$^6$). Survival, weight loss, activity, fur, skin, and hunch were monitored at least 3 times per week as previously described (Bondanza et al. Blood. 2006; 107(5):1828-1836). Mice were euthanized for ethical reasons when their loss of bodyweight was 20%.

Alternatively, on day 0 mice received total body irradiation as above. On day 3 mice were injected with CD4$^+$ T cells (5×10$^6$ or 2.5×10$^6$), single and polydonor (pool of three donors) CD4$^{IL-10}$ cells (5×10$^6$ or 2.5×10$^6$), or CD4$^+$ T cells 5×10$^6$ or 2.5×10$^6$) in combination with single and polydonor (pool of three donors) CD4$^{IL-10}$ cells (5×10$^6$ or 2.5×10$^6$). GvHD induction was monitored as indicated above.

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

While various specific embodiments have been illustrated and described, the above specification is not restrictive. It will be appreciated that various changes can be made without departing from the spirit and scope of the invention (s). Many variations will become apparent to those skilled in the art upon review of this specification.

9. SEQUENCES
SEQ ID NO: 1 (Human IL-10 amino acid sequence--
Protein Sequence: Ref P22301)
MHSSALLCCLVLLTGVRASPGQGTQSENSCTHFPGNLPNMLRDLRDAFSRVKTFFQMKDQLDNL

LLKESLLEDFKGYLGCQALSEMIQFYLEEVMPQAENQDPDIKAHVNSLGENLKTLRLRLRRCHR

FLPCENKSKAVEQVKNAFNKLQEKGIYKAMSEFDIFINYIEAYMTMKIRN

SEQ ID NO: 2 (Human IL-10 exemplary polynucleotide sequence)
ATGCACAGCTCAGCACTGCTCTGTTGCCTGGTCCTCCTGACTGGGGTGAGGGCCAGCCCAGGCC

AGGGCACCCAGTCTGAGAACAGCTGCACCCACTTCCCAGGCAACCTGCCTAACATGCTTCGAGA

TCTCCGAGATGCCTTCAGCAGAGTGAAGACTTTCTTTCAAATGAAGGATCAGCTGGACAACTTG

TTGTTAAAGGAGTCCTTGCTGGAGGACTTTAAGGGTTACCTGGGTTGCCAAGCCTTGTCTGAGA

TGATCCAGTTTTACCTGGAGGAGGTGATGCCCCAAGCTGAGAACCAAGACCCAGACATCAAGGC

GCATGTGAACTCCCTGGGGGAGAACCTGAAGACCCTCAGGCTGAGGCTACGGCGCTGTCATCGA

TTTCTTCCCTGTGAAAACAAGAGCAAGGCCGTGGAGCAGGTGAAGAATGCCTTTAATAAGCTCC

AAGAGAAAGGCATCTACAAAGCCATGAGTGAGTTTGACATCTTCATCAACTACATAGAAGCCTA

CATGACAATGAAGATACGAAACTGA

SEQ ID NO: 3 (ΔNGFR amino acid sequence)
MGAGATGRAMDGPRLLLLLLLGVSLGGAKEACPTGLYTHSGECCKACNLGEGVAQPCGANQTVC

EPCLDSVTFSDVVSATEPCKPCTECVGLQSMSAPCVEADDAVCRCAYGYYQDETTGRCEACRVC

EAGSGLVFSCQDKQNTVCEECPDGTYSDEANHVDPCLPCTVCEDTERQLRECTRWADAECEEIP

GRWITRSTPPEGSDSTAPSTQEPEAPPEQDLIASTVAGVVTTVMGSSQPVVTRGTTDNLIPVYC

SILAAVVVGLVAYIAFKRWNRGIL

SEQ ID NO: 4 (ΔNGFR exemplary polynucleotide sequence)
ATGGGGGCAGGTGCCACCGGCCGCGCCATGGACGGGCCGCGCCTGCTGCTGTTGCTGCTTCTGG

GGGTGTCCCTTGGAGGTGCCAAGGAGGCATGCCCCACAGGCCTGTACACACACAGCGGTGAGTG

CTGCAAAGCCTGCAACCTGGGCGAGGGTGTGGCCCAGCCTTGTGGAGCCAACCAGACCGTGTGT

GAGCCCTGCCTGGACAGCGTGACGTTCTCCGACGTGGTGAGCGCGACCGAGCCGTGCAAGCCGT

-continued

GCACCGAGTGCGTGGGGCTCCAGAGCATGTCGGCGCCGTGCGTGGAGGCCGACGACGCCGTGTG

CCGCTGCGCCTACGGCTACTACCAGGATGAGACGACTGGGCGCTGCGAGGCGTGCCGCGTGTGC

GAGGCGGGCTCGGGCCTCGTGTTCTCCTGCCAGGACAAGCAGAACACCGTGTGCGAGGAGTGCC

CCGACGGCACGTATTCCGACGAGGCCAACCACGTGGACCCGTGCCTGCCCTGCACCGTGTGCGA

GGACACCGAGCGCCAGCTCCGCGAGTGCACACGCTGGGCCGACGCCGAGTGCGAGGAGATCCCT

GGCCGTTGGATTACACGGTCCACACCCCCAGAGGGCTCGGACAGCACAGCCCCCAGCACCCAGG

AGCCTGAGGCACCTCCAGAACAAGACCTCATAGCCAGCACGGTGGCAGGTGTGGTGACCACAGT

GATGGGCAGCTCCCAGCCCGTGGTGACCCGAGGCACCACCGACAACCTCATCCCTGTCTATTGC

TCCATCCTGGCTGCTGTGGTTGTGGGCCTTGTGGCCTACATAGCCTTCAAGAGGTGGAACAGGG

GGATCCTCTAG

SEQ ID NO: 5 (nucleotide sequence of pLV-IL10):
TGGCCATTGCATACGTTGTATCCATATCATAATATGTACATTTATATTGGCTCATGTCCAACAT

TACCGCCATGTTGACATTGATTATTGACTAGTTATTAATAGTAATCAATTACGGGGTCATTAGT

TCATAGCCCATATATGGAGTTCCGCGTTACATAACTTACGGTAAATGGCCCGCCTGGCTGACCG

CCCAACGACCCCCGCCCATTGACGTCAATAATGACGTATGTTCCCATAGTAACGCCAATAGGGA

CTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTAT

GCCCAGTACATGACCTTATGGGACTTTCCTACTTGGCAGTACATCTACGTATTAGTCATCGCTA

TTACCATGGTGATGCGGTTTTGGCAGTACATCAATGGGCGTGGATAGCGGTTTGACTCACGGGG

ATTTCCAAGTCTCCACCCCATTGACGTCAATGGGAGTTTGTTTTGGCACCAAAATCAACGGGAC

TTTCCAAAATGTCGTAACAACTCCGCCCCATTGACGCAAATGGGGGGTAGGCGTGTACGGTGGG

AGGTCTATATAAGCAGAGCTCGTTTAGTGAACCGGGGTCTCTCTGGTTAGACCAGATCTGAGCC

TGGGAGCTCTCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAGACCCTTTTA

GTCAGTGTGGAAAATCTCTAGCAGTGGCGCCCGAACAGGGACTTGAAAGCGAAAGGGAAACCAG

AGGAGCTCTCTCGACGCAGGACTCGGCTTGCTGAAGCGCGCACGGCAAGAGGCGAGGGGCGGCG

ACTGGTGAGTACGCCAAAAATTTTGACTAGCGGAGGCTAGAAGGAGAGAGATGGGTGCGAGAGC

GTCAGTATTAAGCGGGGGAGAATTAGATCGCGATGGGAAAAAATTCGGTTAAGGCCAGGGGGAA

AGAAAAAATATAAATTAAAACATATAGTATGGGCAAGCAGGGAGCTAGAACGATTCGCAGTTAA

TCCTGGCCTGTTAGAAACATCAGAAGGCTGTAGACAAATACTGGGACAGCTACAACCATCCCTT

CAGACAGGATCAGAAGAACTTAGATCATTATATAATACAGTAGCAACCCTCTATTGTGTGCATC

AAAGGATAGAGATAAAAGACACCAAGGAAGCTTTAGACAAGATAGAGGAAGAGCAAAACAAAAG

TAAGACCACCGCACAGCAAGCGGCCGCTGATCTTCAGACCTGGAGGAGGAGATATGAGGGACAA

TTGGAGAAGTGAATTATATAAATATAAAGTAGTAAAAATTGAACCATTAGGAGTAGCACCCACC

AAGGCAAAGAGAAGAGTGGTGCAGAGAGAAAAAAGAGCAGTGGGAATAGGAGCTTTGTTCCTTG

GGTTCTTGGGAGCAGCAGGAAGCACTATGGGCGCAGCGTCAATGACGCTGACGGTACAGGCCAG

ACAATTATTGTCTGGTATAGTGCAGCAGCAGAACAATTTGCTGAGGGCTATTGAGGCGCAACAG

CATCTGTTGCAACTCACAGTCTGGGGCATCAAGCAGCTCCAGGCAAGAATCCTGGCTGTGGAAA

GATACCTAAAGGATCAACAGCTCCTGGGGATTTGGGGTTGCTCTGGAAAACTCATTTGCACCAC

TGCTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGAAT

-continued

```
CGCAAAACCAGCAAGAAAAGAATGAACAAGAATTATTGGAATTAGATAAATGGGCAAGTTTGTG

GAATTGGTTTAACATAACAAATTGGCTGTGGTATATAAAATTATTCATAATGATAGTAGGAGGC

TTGGTAGGTTTAAGAATAGTTTTTGCTGTACTTTCTATAGTGAATAGAGTTAGGCAGGGATATT

CACCATTATCGTTTCAGACCCACCTCCCAACCCCGAGGGGACCCGACAGGCCCGAAGGAATAGA

AGAAGAAGGTGGAGAGAGAGACAGAGACAGATCCATTCGATTAGTGAACGGATCTCGACGGTAT

CGGTTAACTTTTAAAAGAAAAGGGGGGATTGGGGGGTACAGTGCAGGGGAAAGAATAGTAGACA

TAATAGCAACAGACATACAAACTAAAGAATTACAAAAACAAATTACAAAAATTCAAAATTTTAT

CGATCACGAGACTAGCCTCGAGAGATCTGATCATAATCAGCCATACCACATTTGTAGAGGTTTT

ACTTGCTTTAAAAAACCTCCCACACCTCCCCCTGAACCTGAAACATAAAATGAATGCAATTGTT

GTTGTTAACTTGTTTATTGCAGCTTATAATGGTTACAAATAAGGCAATAGCATCACAAATTTCA

CAAATAAGGCATTTTTTTCACTGCATTCTAGTTTTGGTTTGTCCAAACTCATCAATGTATCTTA

TCATGTCTGGATCTCAAATCCCTCGGAAGCTGCGCCTGTCTTAGGTTGGAGTGATACATTTTTA

TCACTTTTACCCGTCTTTGGATTAGGCAGTAGCTCTGACGGCCCTCCTGTCTTAGGTTAGTGAA

AAATGTCACTCTCTTACCCGTCATTGGCTGTCCAGCTTAGCTCGCAGGGGAGGTGGTCTGGATC

CACCATGTCTAGAGGATCCCCCTGTTCCACCTCTTGAAGGCTATGTAGGCCACAAGGCCCACAA

CCACAGCAGCCAGGATGGAGCAATAGACAGGGATGAGGTTGTCGGTGGTGCCTCGGGTCACCAC

GGGCTGGGAGCTGCCCATCACTGTGGTCACCACACCTGCCACCGTGCTGGCTATGAGGTCTTGT

TCTGGAGGTGCCTCAGGCTCCTGGGTGCTGGGGGCTGTGCTGTCCGAGCCCTCTGGGGGTGTGG

ACCGTGTAATCCAACGGCCAGGGATCTCCTCGCACTCGGCGTCGGCCCAGCGTGTGCACTCGCG

GAGCTGGCGCTCGGTGTCCTCGCACACGGTGCAGGGCAGGCACGGGTCCACGTGGTTGGCCTCG

TCGGAATACGTGCCGTCGGGGCACTCCTCGCACACGGTGTTCTGCTTGTCCTGGCAGGAGAACA

CGAGGCCCGAGCCCGCCTCGCACACGCGGCACGCCTCGCAGCGCCCAGTCGTCTCATCCTGGTA

GTAGCCGTAGGCGCAGCGGCACACGGCGTCGTCGGCCTCCACGCACGGCGCCGACATGCTCTGG

AGCCCCACGCACTCGGTGCACGGCTTGCACGGCTCGGTCGCGCTCACCACGTCGGAGAACGTCA

CGCTGTCCAGGCAGGGCTCACACACGGTCTGGTTGGCTCCACAAGGCTGGGCCACACCCTCGCC

CAGGTTGCAGGCTTTGCAGCACTCACCGCTGTGTGTGTACAGGCCTGTGGGGCATGCCTCCTTG

GCACCTCCAAGGGACACCCCCAGAAGCAGCAACAGCAGCAGGCGCGGCCCGTCCATGGCGCGGC

CGGTGGCACCTGCCCCCATCGCCCGCCTCCCGCGGCAGCGCTCGACTTCCAGCTCGGTCCGCTT

TGCGGACTGATGGGGCTGCGCTGCGCTGCGCTCCAGCGCCCCCCCTGCCCGCCGGAGCTGGCCG

CGGCCCGAATTCCTGCAGGAATTCGATGGAGGCTGGATCGGTCCCGGTGTCTTCTATGGAGGTC

AAAACAGCGTGGATGGCGTCTCCAGGCGATCTGACGGTTCACTAAACGAGCTCTGCTTATATAG

GCCTCCCACCGTACACGCCTACCCTCGAGAAGCTTGATATCGAATTCCCACGGGGTTGGGGTTG

CGCCTTTTCCAAGGCAGCCCTGGGTTTGCGCAGGGACGCGGCTGCTCTGGGCGTGGTTCCGGGA

AACGCAGCGGCGCCGACCCTGGGTCTCGCACATTCTTCACGTCCGTTCGCAGCGTCACCCGGAT

CTTCGCCGCTACCCTTGTGGGCCCCCCGGCGACGCTTCCTGCTCCGCCCCTAAGTCGGGAAGGT

TCCTTGCGGTTCGCGGCGTGCCGGACGTGACAAACGGAAGCCGCACGTCTCACTAGTACCCTCG

CAGACGGACAGCGCCAGGGAGCAATGGCAGCGCGCCGACCGCGATGGGCTGTGGCCAATAGCGG

CTGCTCAGCGGGGCGCGCCGAGAGCAGCGGCCGGGAAGGGGCGGTGCGGGAGGCGGGGTGTGGG

GCGGTAGTGTGGGCCCTGTTCCTGCCCGCGCGGTGTTCCGCATTCTGCAAGCCTCCGGAGCGCA

CGTCGGCAGTCGGCTCCCTCGTTGACCGAATCACCGACCTCTCTCCCCAGGGGGATCCCCGGTC
```

-continued

```
TGCAGGAATTCATGCACAGCTCAGCACTGCTCTGTTGCCTGGTCCTCCTGACTGGGGTGAGGGC

CAGCCCAGGCCAGGGCACCCAGTCTGAGAACAGCTGCACCCACTTCCCAGGCAACCTGCCTAAC

ATGCTTCGAGATCTCCGAGATGCCTTCAGCAGAGTGAAGACTTTCTTTCAAATGAAGGATCAGC

TGGACAACTTGTTGTTAAAGGAGTCCTTGCTGGAGGACTTTAAGGGTTACCTGGGTTGCCAAGC

CTTGTCTGAGATGATCCAGTTTTACCTGGAGGAGGTGATGCCCCAAGCTGAGAACCAAGACCCA

GACATCAAGGCGCATGTGAACTCCCTGGGGGAGAACCTGAAGACCCTCAGGCTGAGGCTACGGC

GCTGTCATCGATTTCTTCCCTGTGAAAACAAGAGCAAGGCCGTGGAGCAGGTGAAGAATGCCTT

TAATAAGCTCCAAGAGAAAGGCATCTACAAAGCCATGAGTGAGTTTGACATCTTCATCAACTAC

ATAGAAGCCTACATGACAATGAAGATACGAAACTGAGTCGAGAATCAACCTCTGGATTACAAAA

TTTGTGAAAGATTGACTGGTATTCTTAACTATGTTGCTCCTTTTACGCTATGTGGATACGCTGC

TTTAATGCCTTTGTATCATGCTATTGCTTCCCGTATGGCTTTCATTTTCTCCTCCTTGTATAAA

TCCTGGTTGCTGTCTCTTTATGAGGAGTTGTGGCCCGTTGTCAGGCAACGTGGCGTGGTGTGCA

CTGTGTTTGCTGACGCAACCCCCACTGGTTGGGGCATTGCCACCACCTGTCAGCTCCTTTCCGG

GACTTTCGCTTTCCCCCTCCCTATTGCCACGGCGGAACTCATCGCCGCCTGCCTTGCCCGCTGC

TGGACAGGGGCTCGGCTGTTGGGCACTGACAATTCCGTGGTGTTGTCGGGGAAATCATCGTCCT

TTCCTTGGCTGCTCGCCTGTGTTGCCACCTGGATTCTGCGCGGGACGTCCTTCTGCTACGTCCC

TTCGGCCCTCAATCCAGCGGACCTTCCTTCCCGCGGCCTGCTGCCGGCTCTGCGGCCTCTTCCG

CGTCTTCGCCTTCGCCCTCAGACGAGTCGGATCTCCCTTTGGGCCGCCTCCCCGCCTGGAATTC

GAGCTCGGTACCTTTAAGACCAATGACTTACAAGGCAGCTGTAGATCTTAGCCACTTTTTAAAA

GAAAAGGGGGGACTGGAAGGGCTAATTCACTCCCAACGAAGACAAGATCTGCTTTTTGCTTGTA

CTGGGTCTCTCTGGTTAGACCAGATCTGAGCCTGGGAGCTCTCTGGCTAACTAGGGAACCCACT

GCTTAAGCCTCAATAAAGCTTGCCTTGAGTGCTTCAAGTAGTGTGTGCCCGTCTGTTGTGTGAC

TCTGGTAACTAGAGATCCCTCAGACCCTTTTAGTCAGTGTGGAAAATCTCTAGCAGTAGTAGTT

CATGTCATCTTATTATTCAGTATTTATAACTTGCAAAGAAATGAATATCAGAGAGTGAGAGGAA

CTTGTTTATTGCAGCTTATAATGGTTACAAATAAAGCAATAGCATCACAAATTTCACAAATAAA

GCATTTTTTTCACTGCATTCTAGTTGTGGTTTGTCCAAACTCATCAATGTATCTTATCATGTCT

GGCTCTAGCTATCCCGCCCCTAACTCCGCCCATCCCGCCCCTAACTCCGCCCAGTTCCGCCCAT

TCTCCGCCCCATGGCTGACTAATTTTTTTTATTTATGCAGAGGCCGAGGCCGCCTCGGCCTCTG

AGCTATTCCAGAAGTAGTGAGGAGGCTTTTTTGGAGGCCTAGGCTTTTGCGTCGAGACGTACCC

AATTCGCCCTATAGTGAGTCGTATTACGCGCGCTCACTGGCCGTCGTTTTACAACGTCGTGACT

GGGAAAACCCTGGCGTTACCCAACTTAATCGCCTTGCAGCACATCCCCCTTTCGCCAGCTGGCG

TAATAGCGAAGAGGCCCGCACCGATCGCCCTTCCCAAGCGGCCGCACGCTCAGTGGAACGAAAA

CTCACGTTAAGGGATTTTGGTCATGAACAATAAAACTGTCTGCTTACATAAACAGTAATACAAG

GGGTGTTATGAGCCATATTCAACGGGAAACGTCTTGCTCTAGGCCGCGATTAAATTCCAACATG

GATGCTGATTTATATGGGTATAAATGGGCTCGCGATAATGTCGGGCAATCAGGTGCGACAATCT

ATCGATTGTATGGGAAGCCCGATGCGCCAGAGTTGTTTCTGAAACATGGCAAAGGTAGCGTTGC

CAATGATGTTACAGATGAGATGGTCAGACTAAACTGGCTGACGGAATTTATGCCTCTTCCGACC

ATCAAGCATTTTATCCGTACTCCTGATGATGCATGGTTACTCACCACTGCGATCCCCGGGAAAA

CAGCATTCCAGGTATTAGAAGAATATCCTGATTCAGGTGAAAACATTGTTGATGCGCTGGCAGT

GTTCCTGCGCCGGTTGCATTCGATTCCTGTTTGTAATTGTCCTTTTTAACAGCGATCGCGTATTT

CGTCTCGCTCAGGCGCAATCACGAATGAATAACGGTTTGGTTGATGCGAGTGATTTTGATGACG
```

-continued

AGCGTAATGGCTGGCCTGTTGAACAAGTCTGGAAAGAAATGCATAAACTTTTGCCATTCTCACC

GGATTCAGTCGTCACTCATGGTGATTTCTCACTTGATAACCTTATTTTTGACGAGGGGAAATTA

ATAGGTTGTATTGATGTTGGACGAGTCGGAATCGCAGACCGATACCAGGATCTTGCCATCCTAT

GGAACTGCCTCGGTGAGTTTTCTCCTTCATTACAGAAACGGCTTTTTCAAAAATATGGTATTGA

TAATCCTGATATGAATAAATTGCAGTTTCATTTGATGCTCGATGAGTTTTTCTAAGAATTAATT

CATGAGCGGATACATATTTGAATGTATTTAGAAAAATAAACAAATAGGGGTTCCGCGACTATGT

CTTTGATAATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCTTGCAAA

CAAAAAAACCACCGCTACCAGCGGTGGTTTGTTTGCCGGATCAAGAGCTACCAACTCTTTTTCC

GAAGGTAACTGGCTTCAGCAGAGCGCAGATACCAAATACTGTCCTTCTAGTGTAGCCGTAGTTA

GGCCACCACTTCAAGAACTCTGTAGCACCGCCTACATACCTCGCTCTGCTAATCCTGTTACCAG

TGGCTGCTGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGCGAACGACC

TACACCGAACTGAGATACCTACAGCGTGAGCTATGAGAAAGCGCCACGCTTCCCGAAGGGAGAA

AGGCGGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCGATTT

TTGTGATGCTCGTCAGGGGGGCGGAGCCTATGGAAAAACGCCAGCAACGCGGCCTTTTTACGGT

TCCTGGCCTTTTGCTGGCCTTATCCCCTGATTCTGTGGATAACCGTATTACCGCCTTTGAGTGA

GCTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGTATGCTTCCGGCTCGTATGTTGTGTGG

AATTGTGAGCGGATAACAATTTCACACAGGAAACAGCTATGACCATGATTACGCCAAGCCGAAT

TAACCCTCACTAAAGGGAACAGCTAGC

SEQ ID NO: 6 (Viral interleukin-10 homolog aka interleukin-10
BCRF1 aka IL10H_EBVB9) Protein Sequence: Ref: P03180
MERRLVVTLQCLVLLYLAPECGGTDQCDNFPQMLRDLRDAFSRVKTFFQTKDEVDNLLLKESLL

EDFKGYLGCQALSEMIQFYLEEVMPQAENQDPEAKDHVNSLGENLKTLRLRLRRCHRFLPCENK

SKAVEQIKNAFNKLQEKGIYKAMSEFDIFINYIEAYMTIKAR

SEQ ID NO: 7 (Viral interleukin-10 homolog cDNA sequence)
Nucleotide sequence (cDNA): Ref: NC_007605.1
5'_ATGGAGCGAAGGTTAGTGGTCACTCTGCAGTGCCTGGTGCTGCTTTACCTGGCACCTGAGT

GTGGAGGTACAGACCAATGTGACAATTTTCCCCAAATGTTGAGGGACCTAAGAGATGCCTTCAG

TCGTGTTAAAACCTTTTTCCAGACAAAGGACGAGGTAGATAACCTTTTGCTCAAGGAGTCTCTG

CTAGAGGACTTTAAGGGCTACCTTGGATGCCAGGCCCTGTCAGAAATGATCCAATTCTACCTGG

AGGAAGTCATGCCACAGGCTGAAAACCAGGACCCTGAAGCCAAGACCATGTCAATTCTTTGGG

TGAAAATCTAAAGACCCTACGGCTCCGCCTGCGCAGGTGCCACAGGTTCCTGCCGTGTGAGAAC

AAGAGTAAAGCTGTGGAACAGATAAAAAATGCCTTTAACAAGCTGCAGGAAAAAGGAATTTACA

AAGCCATGAGTGAATTTGACATTTTTATTAACTACATAGAAGCATACATGACAATTAAAGCCAG

GTGA_3'

SEQ ID NO: 9 (anti-CD19 CAR amino acid sequence)
MLLLVTSLLLCELPHPAFLLIPDIQMTQTTSSLSASLGDRVTISCRASQDISKYLNWYQQKPDG

TVKLLIYHTSRLHSGVPSRFSGSGSGTDYSLTISNLEQEDIATYFCQQGNTLPYTFGGGTKLEI

TGGGGSGGGGSGGGGSEVKLQESGPGLVAPSQSLSVTCTVSGVSLPDYGVSWIRQPPRKGLEWL

GVIWGSETTYYNSALKSRLTIIKDNSKSQVFLKMNSLQTDDTAIYYCAKHYYYGGSYAMDYWGQ

-continued

GTSVTVSSAAAPAPRPPTPAPTIASQPLSLRPEACRPAAGGAVHTRGLDFDTALAAVICSALAT

VLLALLILCVIYCKRQPRRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAEAY

SEIGMKGERRRGKGHDGLYQGLSTATKDTYDALHMQALPPR

SEQ ID NO: 10 (anti-CD19 CAR polynucleotide sequence)
ATGCTGCTGCTGGTCACCAGCCTGCTGCTGTGCGAGCTCCCTCACCCCGCCTTTCTGCTTATCC

CGGACATTCAGATGACACAGACCACCTCGAGCTTGTCCGCGTCGCTGGGCGATCGCGTGACCAT

CTCCTGCCGGGCCTCCCAAGACATTTCAAAGTATCTCAACTGGTACCAGCAGAAGCCGGACGGA

ACCGTGAAACTGCTGATCTACCATACCAGCCGCCTGCACTCCGGCGTGCCGTCCCGCTTCTCCG

GATCGGGTTCCGGAACTGACTACTCACTGACTATCTCCAACTTGGAACAAGAGGACATCGCCAC

TTACTTCTGTCAACAAGGAAATACCCTTCCCTACACCTTCGGGGGGGGTACCAAGCTGGAGATC

ACTGGGGGCGGAGGCTCCGGTGGAGGCGGATCCGGCGGTGGAGGGGAGCGAAGTCAAGCTGCAGG

AATCAGGACCAGGACTCGTGGCGCCATCCCAGTCCCTGTCGGTGACCTGTACTGTCTCCGGAGT

CAGCCTCCCCGATTACGGAGTGTCATGGATTAGGCAACCCCCAAGAAAAGGGCTGGAATGGCTC

GGAGTGATCTGGGGCTCCGAAACCACCTACTACAACTCGGCGCTGAAGTCCCGGCTGACCATCA

TCAAGGACAACTCCAAGAGCCAAGTGTTCTTGAAGATGAACAGCTTGCAGACCGACGATACCGC

AATCTACTACTGTGCCAAGCACTATTACTACGGGGGGGTCTTACGCCATGGACTACTGGGGACAG

GGCACCTCCGTGACTGTGTCGTCCGCGGCCGCGCCCGCCCCTCGGCCCCCGACTCCTGCCCCGA

CGATCGCTTCCCAACCTCTCTCGCTGCGCCCGGAAGCATGCCGGCCCGCCGCCGGTGGCGCTGT

CCACACTCGCGGACTGGACTTTGATACCGCACTGGCGGCCGTGATCTGTAGCGCCCTGGCCACC

GTGCTGCTGGCGCTGCTCATCCTTTGCGTGATCTACTGCAAGCGGCAGCCTAGGCGAAAGAAGC

TCCTCTACATTTTCAAGCAACCCTTCATGCGCCCCGTGCAAACCACCCAGGAGGAGGATGGATG

CTCATGCCGGTTCCCTGAGGAAGAAGAGGGCGGTTGCGAGCTCAGAGTGAAATTCAGCCGGTCG

GCTGACGCCCCGGCGTACCAGCAGGGCCAGAACCAGCTGTACAATGAGCTCAACCTGGGGCGCC

GCGAAGAGTACGACGTGCTGGACAAGAGGAGAGGCAGAGATCCGGAAATGGGCGGAAAGCCAAG

GCGGAAGAACCCGCAGGAAGGTCTTTACAACGAACTGCAGAAGGACAAGATGGCCGAGGCCTAC

TCCGAGATTGGGATGAAGGGAGAAAGACGGAGGGGAAAGGGACATGACGGACTTTACCAGGGCC

TGAGCACTGCCACGAAGGACACCTATGATGCCCTGCACATGCAGGCGCTGCCGCCTCGG

SEQ ID NO: 11 (anti-CD19 scFV amino acid sequence for FMC63)
MLLLVTSLLLCELPHPAFLLIPDIQMTQTTSSLSASLGDRVTISCRASQDISKYLNWYQQKPDG

TVKLLIYHTSRLHSGVPSRFSGSGSGTDYSLTISNLEQEDIATYFCQQGNTLPYTFGGGTKLEI

TGGGGSGGGGSGGGGSEVKLQESGPGLVAPSQSLSVTCTVSGVSLPDYGVSWIRQPPRKGLEWL

GVIWGSETTYYNSALKSRLTIIKDNSKSQVFLKMNSLQTDDTAIYYCAKHYYYGGSYAMDYWGQ

GTSVTVSS

SEQ ID NO: 12 (anti-CD19 scFV polynucleotide sequence)
ATGCTTCTCCTGGTCACCTCCCTGCTCCTCTGCGAACTGCCTCACCCTGCCTTCCTTCTGATTC

CTGACATTCAGATGACTCAGACCACCTCTTCCTTGTCCGCGTCACTGGGAGACAGAGTGACCAT

CTCGTGTCGCGCAAGCCAGGATATCTCCAAGTACCTGAACTGGTACCAACAGAAGCCCGACGGG

ACTGTGAAGCTGCTGATCTACCACACCTCACGCCTGCACAGCGGAGTGCCAAGCAGATTCTCCG

GCTCCGGCTCGGGAACCGATTACTCGCTTACCATTAGCAACCTCGAGCAGGAGGACATCGCTAC

CTACTTCTGCCAGCAAGGAAATACCCTGCCCTACACCTTCGGCGGAGGAACCAAATTGGAAATC

ACCGGCGGAGGAGGCTCCGGGGGAGGAGGTTCCGGGGGCGGGGGTTCCGAAGTGAAGCTCCAGG

-continued

AGTCCGGCCCCGGCCTGGTGGCGCCGTCGCAATCACTCTCTGTGACCTGTACCGTGTCGGGAGT

GTCCCTGCCTGATTACGGCGTGAGCTGGATTCGGCAGCCGCCGCGGAAGGGCCTGGAATGGCTG

GGTGTCATCTGGGGATCCGAGACTACCTACTACAACTCGGCCCTGAAGTCCCGCCTGACTATCA

TCAAAGACAACTCGAAGTCCCAGGTCTTTCTGAAGATGAACTCCCTGCAAACTGACGACACCGC

CATCTATTACTGTGCTAAGCACTACTACTACGGTGGAAGCTATGCTATGGACTACTGGGGGCAA

GGCACTTCGGTGACTGTGTCAAGCGCGGCCGCAACTACCACCCCTGCCCCTCGGCCGCCGACTC

CGGCCCCAACCATCGCAAGCCAACCCCTCTCCTTGCGCCCCGAAGCTTGCCGCCCGGCCGCGGG

TGGAGCCGTGCATACCCGGGGGCTGGACTTTGCCTGCGATATCTACATTTGGGCCCCGCTGGCC

GGCACTTGCGGCGTGCTCCTGCTGTCGCTGGTCATCACCCTTTACTGCAAGAGGGGCCGGAAGA

AGCTGCTTTACATCTTCAAGCAGCCGTTCATGCGGCCCGTGCAGACGACTCAGGAAGAGGACGG

ATGCTCGTGCAGATTCCCTGAGGAGGAAGAGGGGGGATGCGAACTGCGCGTCAAGTTCTCACGG

TCCGCCGACGCCCCCGCATATCAACAGGGCCAGAATCAGCTCTACAACGAGCTGAACCTGGGAA

GGAGAGAGGAGTACGACGTGCTGGACAAGCGACGCGGACGCGACCCGGAGATGGGGGGGAAACC

ACGGCGGAAAAACCCTCAGGAAGGACTGTACAACGAACTCCAGAAAGACAAGATGGCGGAAGCC

TACTCAGAAATCGGGATGAAGGGAGAGCGGAGGAGGGGAAAGGGTCACGACGGGCTGTACCAGG

GACTGAGCACCGCCACTAAGGATACCTACGATGCCTTGCATATGCAAGCACTCCCACCCCGG

SEQ ID NO: 13 (anti-CD19 scFV VH for FMC63)
MLLLVTSLLLCELPHPAFLLIPDIQMTQTTSSLSASLGDRVTISCRASQDISKYLNWYQQKPDG

TVKLLIYHTSRLHSGVPSRFSGSGSGTDYSLTISNLEQEDIATYFCQQGNTLPYTFGGGTKLEI

T

SEQ ID NO: 14 (anti-CD19 scFV VL for FMC63)
EVKLQESGPGLVAPSQSLSVTCTVSGVSLPDYGVSWIRQPPRKGLEWLGVIWGSETTYYNSALK

SRLTIIKDNSKSQVFLKMNSLQTDDTAIYYCAKHYYYGGSYAMDYWGQGTSVTVSS

SEQ ID NO: 16 (anti-CD20 CAR amino acid sequence)
MLLLVTSLLLCELPHPAFLLIPEVQLQQSGAELVKPGASVKMSCKASGYTFTSYNMHWVKQTPG

QGLEWIGAIYPGNGDTSYNQKFKGKATLTADKSSSTAYMQLSSLTSEDSADYYCARSNYYGSSY

WFFDVWGAGTTVTVSSGGGGSGGGGSGGGGSDIVLTQSPAILSASPGEKVTMTCRASSSVNYMD

WYQKKPGSSPKPWIYATSNLASGVPARFSGSGSGTSYSLTISRVEAEDAATYYCQQWSFNPPTF

GGGTKLEIKAAATTTPAPRPPTPAPTIASQPLSLRPEACRPAAGGAVHTRGLDFACDIYIWAPL

AGTCGVLLLSLVITLYCKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPR

SEQ ID NO: 17 (anti-CD20 CAR polynucleotide sequence)
ATGCTCCTTCTCGTGACCTCCCTGCTTCTCTGCGAACTGCCCCATCCTGCCTTCCTGCTGATTC

CCGAGGTGCAGTTGCAACAGTCAGGAGCTGAACTGGTCAAGCCAGGAGCCAGCGTGAAGATGAG

CTGCAAGGCCTCCGGTTACACCTTCACCTCCTACAACATGCACTGGGTGAAACAGACCCCGGGA

CAAGGGCTCGAATGGATTGGCGCCATCTACCCCGGGAATGGCGATACTTCGTACAACCAGAAGT

TCAAGGGAAAGGCCACCCTGACCGCCGACAAGAGCTCCTCCACCGCGTATATGCAGTTGAGCTC

CCTGACCTCCGAGGACTCCGCCGACTACTACTGCGCACGGTCCAACTACTATGGAAGCTCGTAC

TGGTTCTTCGATGTCTGGGGGGCCGGCACCACTGTGACCGTCAGCTCCGGGGGCGGAGGATCCG

GTGGAGGCGGAAGCGGGGGTGGAGGATCCGACATTGTGCTGACTCAGTCCCCGGCAATCCTGTC

GGCCTCACCGGGCGAAAAGGTCACGATGACTTGTAGAGCGTCGTCCAGCGTGAACTACATGGAT

-continued
TGGTACCAAAAGAAGCCTGGATCGTCACCCAAGCCTTGGATCTACGCTACATCTAACCTGGCCT

CCGGCGTGCCAGCGCGGTTCAGCGGGTCCGGCTCGGGCACCTCATACTCGCTGACCATCTCCCG

CGTGGAGGCTGAGGACGCCGCGACCTACTACTGCCAGCAGTGGTCCTTCAACCCGCCGACTTTT

GGAGGCGGTACTAAGCTGGAGATCAAAGCGGCCGCAACTACCACCCCTGCCCCTCGGCCGCCGA

CTCCGGCCCCAACCATCGCAAGCCAACCCCTCTCCTTGCGCCCCGAAGCTTGCCGCCCGGCCGC

GGGTGGAGCCGTGCATACCCGGGGGCTGGACTTTGCCTGCGATATCTACATTTGGGCCCCGCTG

GCCGGCACTTGCGGCGTGCTCCTGCTGTCGCTGGTCATCACCCTTTACTGCAAGAGGGGCCGGA

AGAAGCTGCTTTACATCTTCAAGCAGCCGTTCATGCGGCCCGTGCAGACGACTCAGGAAGAGGA

CGGATGCTCGTGCAGATTCCCTGAGGAGGAAGAGGGGGGATGCGAACTGCGCGTCAAGTTCTCA

CGGTCCGCCGACGCCCCCGCATATCAACAGGGCCAGAATCAGCTCTACAACGAGCTGAACCTGG

GAAGGAGAGAGGAGTACGACGTGCTGGACAAGCGACGCGGACGCGACCCGGAGATGGGGGGGAA

ACCACGGCGGAAAAACCCTCAGGAAGGACTGTACAACGAACTCCAGAAAGCAAGATGGCGGAA

GCCTACTCAGAAATCGGGATGAAGGGAGAGCGGAGGAGGGGAAAGGGTCACGACGGGCTGTACC

AGGGACTGAGCACCGCCACTAAGGATACCTACGATGCCTTGCATATGCAAGCACTCCCACCCCG

G

SEQ ID NO: 18 (anti-CD20 scFV amino acid sequence)
EVQLQQSGAELVKPGASVKMSCKASGYTFTSYNMEIWVKQTPGQGLEWIGAIYPGNGDTSYNQK

FKGKATLTADKSSSTAYMQLSSLTSEDSADYYCARSNYYGSSYWFFDVWGAGTTVTVSSGGGGS

GGGGSGGGGSDIVLTQSPAILSASPGEKVTMTCRASSSVNYMDWYQKKPGSSPKPWIYATSNLA

SGVPARFSGSGSGTSYSLTISRVEAEDAATYYCQQWSFNPPTFGGGTKLEIK

SEQ ID NO: 19 (anti-CD20 scFV polynucleotide sequence)
GAGGTGCAGTTGCAACAGTCAGGAGCTGAACTGGTCAAGCCAGGAGCCAGCGTGAAGATGAGCT

GCAAGGCCTCCGGTTACACCTTCACCTCCTACAACATGCACTGGGTGAAACAGACCCCGGGACA

AGGGCTCGAATGGATTGGCGCCATCTACCCCGGGAATGGCGATACTTCGTACAACCAGAAGTTC

AAGGGAAAGGCCACCCTGACCGCCGACAAGAGCTCCTCCACCGCGTATATGCAGTTGAGCTCCC

TGACCTCCGAGGACTCCGCCGACTACTACTGCGCACGGTCCAACTACTATGGAAGCTCGTACTG

GTTCTTCGATGTCTGGGGGGCCGGCACCACTGTGACCGTCAGCTCCGGGGGCGGAGGATCCGGT

GGAGGCGGAAGCGGGGGTGGAGGATCCGACATTGTGCTGACTCAGTCCCCGGCAATCCTGTCGG

CCTCACCGGGCGAAAAGGTCACGATGACTTGTAGAGCGTCGTCCAGCGTGAACTACATGGATTG

GTACCAAAAGAAGCCTGGATCGTCACCCAAGCCTTGGATCTACGCTACATCTAACCTGGCCTCC

GGCGTGCCAGCGCGGTTCAGCGGGTCCGGCTCGGGCACCTCATACTCGCTGACCATCTCCCGCG

TGGAGGCTGAGGACGCCGCGACCTACTACTGCCAGCAGTGGTCCTTCAACCCGCCGACTTTTGG

AGGCGGTACTAAGCTGGAGATCAAA

SEQ ID NO: 20 (anti-CD20 scFV VH)
EVQLQQSGAELVKPGASVKMSCKASGYTFTSYNMEIWVKQTPGQGLEWIGAIYPGNGDTSYNQK

FKGKATLTADKSSSTAYMQLSSLTSEDSADYYCARSNYYGSSYWFFDVWGAGTTVTVSS

SEQ ID NO: 21 (anti-CD20 scFV VL)
DIVLTQSPAILSASPGEKVTMTCRASSSVNYMDWYQKKPGSSPKPWIYATSNLASGVPARFSGS

GSGTSYSLTISRVEAEDAATYYCQQWSFNPPTFGGGTKLEIK

SEQ ID NO: 22 (anti-CD22 CAR amino acid sequence)
MLLLVTSLLLCELPHPAFLLIPQVQLQQSGPGLVKPSQTLSLTCAISGDSVSSNSAAWNWIRQS

PSRGLEWLGRTYYRSKWYNDYAVSVKSRITINPDTSKNQFSLQLNSVTPEDTAVYYCAREVTGD

LEDAFDIWGQGTMVTVSSGGGGSGGGGSGGGGSDIQMTQSPSSLSASVGDRVTITCRASQTIWS

-continued

YLNWYQQRPGKAPNLLIYAASSLQSGVPSRFSGRGSGTDFTLTISSLQAEDFATYYCQQSYSIP

QTFGQGTKLEIKAAATTTPAPRPPTPAPTIASQPLSLRPEACRPAAGGAVHTRGLDFACDIYIW

APLAGTCGVLLLSLVITLYCKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

SEQ ID NO: 23 (anti-CD22 CAR polynucleotide sequence)
ATGCTTCTTTTGGTGACTTCCCTTTTGCTGTGCGAGTTGCCACACCCCGCCTTCCTGCTTATTC

CCCAGGTACAGCTCCAGCAGAGTGGCCCAGGGCTCGTGAAGCCAAGCCAGACGCTGTCCCTGAC

TTGTGCAATTTCAGGGGATTCAGTTTCATCAAATAGCGCGGCGTGGAATTGGATTCGACAATCT

CCTTCCCGAGGGTTGGAATGGCTTGGACGAACATATTACAGATCCAAATGGTATAACGACTATG

CGGTATCAGTAAAGTCAAGAATAACCATTAACCCCGACACAAGCAAGAACCAATTCTCTTTGCA

GCTTAACTCTGTCACGCCAGAAGACACGGCAGTCTATTATTGCGCTCGCGAGGTAACGGGTGAC

CTGGAAGACGCTTTTGACATTTGGGGGCAGGGTACGATGGTGACAGTCAGTTCAGGGGGCGGTG

GGAGTGGGGGAGGGGGTAGCGGGGGGGGAGGGTCAGACATTCAGATGACCCAGTCCCCTTCATC

CTTGTCTGCCTCCGTCGGTGACAGGGTGACAATAACATGCAGAGCAAGCCAAACAATCTGGAGC

TATCTCAACTGGTACCAGCAGCGACCAGGAAAAGCGCCAAACCTGCTGATTTACGCTGCTTCCT

CCCTCCAATCAGGCGTGCCTAGTAGATTTAGCGGTAGGGGCTCCGGCACCGATTTTACGCTCAC

TATAAGCTCTCTTCAAGCAGAAGATTTTGCGACTTATTACTGCCAGCAGTCCTATAGTATACCT

CAGACTTTCGGACAGGGTACCAAGTTGGAGATTAAGGCGGCCGCAACTACCACCCCTGCCCCTC

GGCCGCCGACTCCGGCCCCAACCATCGCAAGCCAACCCCTCTCCTTGCGCCCCGAAGCTTGCCG

CCCGGCCGCGGGTGGAGCCGTGCATACCCGGGGGCTGGACTTTGCCTGCGATATCTACATTTGG

GCCCCGCTGGCCGGCACTTGCGGCGTGCTCCTGCTGTCGCTGGTCATCACCCTTTACTGCAAGA

GGGGCCGGAAGAAGCTGCTTTACATCTTCAAGCAGCCGTTCATGCGGCCCGTGCAGACGACTCA

GGAAGAGGACGGATGCTCGTGCAGATTCCCTGAGGAGGAAGAGGGGGGATGCGAACTGCGCGTC

AAGTTCTCACGGTCCGCCGACGCCCCCGCATATCAACAGGGCCAGAATCAGCTCTACAACGAGC

TGAACCTGGGAAGGAGAGAGGAGTACGACGTGCTGGACAAGCGACGCGGACGCGACCCGGAGAT

GGGGGGGAAACCACGGCGGAAAAACCCTCAGGAAGGACTGTACAACGAACTCCAGAAAGACAAG

ATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACT

CCCACCCCGG

SEQ ID NO: 24 (anti-CD22 scFV amino acid sequence)
QVQLQQSGPGLVKPSQTLSLTCAISGDSVSSNSAAWNWIRQSPSRGLEWLGRTYYRSKWYNDYA

VSVKSRITINPDTSKNQFSLQLNSVTPEDTAVYYCAREVTGDLEDAFDIWGQGTMVTVSSGGGG

SGGGGSGGGGSDIQMTQSPSSLSASVGDRVTITCRASQTIWSYLNWYQQRPGKAPNLLIYAASS

LQSGVPSRFSGRGSGTDFTLTISSLQAEDFATYYCQQSYSIPQTFGQGTKLEIKAAA

SEQ ID NO: 25 (anti-CD22 scFV polynucleotide sequence)
CAGGTACAGCTCCAGCAGAGTGGCCCAGGGCTCGTGAAGCCAAGCCAGACGCTGTCCCTGACTT

GTGCAATTTCAGGGGATTCAGTTTCATCAAATAGCGCGGCGTGGAATTGGATTCGACAATCTCC

TTCCCGAGGGTTGGAATGGCTTGGACGAACATATTACAGATCCAAATGGTATAACGACTATGCG

GTATCAGTAAAGTCAAGAATAACCATTAACCCCGACACAAGCAAGAACCAATTCTCTTTGCAGC

TTAACTCTGTCACGCCAGAAGACACGGCAGTCTATTATTGCGCTCGCGAGGTAACGGGTGACCT

GGAAGACGCTTTTGACATTTGGGGGCAGGGTACGATGGTGACAGTCAGTTCAGGGGGCGGTGGG

-continued

AGTGGGGGAGGGGGTAGCGGGGGGGGAGGGTCAGACATTCAGATGACCCAGTCCCCTTCATCCT

TGTCTGCCTCCGTCGGTGACAGGGTGACAATAACATGCAGAGCAAGCCAAACAATCTGGAGCTA

TCTCAACTGGTACCAGCAGCGACCAGGAAAAGCGCCAAACCTGCTGATTTACGCTGCTTCCTCC

CTCCAATCAGGCGTGCCTAGTAGATTTAGCGGTAGGGGCTCCGGCACCGATTTTACGCTCACTA

TAAGCTCTCTTCAAGCAGAAGATTTTGCGACTTATTACTGCCAGCAGTCCTATAGTATACCTCA

GACTTTCGGACAGGGTACCAAGTTGGAGATTAAGGCGGCCGCA

SEQ ID NO: 26 anti-CD22 scFV VH)
QVQLQQSGPGLVKPSQTLSLTCAISGDSVSSNSAAWNWIRQSPSRGLEWLGRTYYRSKWYNDYA

VSVKSRITINPDTSKNQFSLQLNSVTPEDTAVYYCAREVTGDLEDAFDIWGQGTMVTVSS

SEQ ID NO: 27 (anti-CD22 scFV VL)
DIQMTQSPSSLSASVGDRVTITCRASQTIWSYLNWYQQRPGKAPNLLIYAASSLQSGVPSRFSG

RGSGTDFTLTISSLQAEDFATYYCQQSYSIPQTFGQGTKLEIKAAA

SEQ ID NO: 28 (human CD8 hinge region)
AAATTTPAPRPPTPAPTIASQPLSLRPEACRPAAGGAVHTRGLDFACDIYIWAPLAGTCGVLLL

SLVITLYC

SEQ ID NO: 29 (TNFRSF 19 transmembrane domain)
DTALAAVICSALATVLLALLILCVIYCKRQ

SEQ ID NO: 30 (CD3zeta)
RVKFSRSADAPAYQQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

SEQ ID NO: 31 (4-1BB co-stimulatory domain)
KRGRKKLLYIFKQPFMRPVQTTQEEDGCSCRFPEEEEGGCEL SEQ ID NO: 32 (CD28 co-stimulatory domain)
RSKRSRLLHSDYMNMTPRRPGPTRKHYQPYAPPRDFAAYRS SEQ ID NO: 33 (2A sequence)
RAKRGSGATNFSLLKQAGDVEENPGPRAKR SEQ ID NO: 34 (anti-B7-H3 CAR amino acid sequence)
MLLLVTSLLLCELPHPAFLLIPQVQLQQSGAEVKKPGSSVKVSCKASGGTFSSYAISWVRQAPG

QGLEWMGGIIPILGIANYAQKFQGRVTITADESTSTAYMELSSLRSEDTAVYYCARGGAGGSGS

YYPLIWGQGTTVTVSSGGGGSGGGGSGGGGSEIVLTQSPATLSLSPGERATLSCGASQSVSSSY

LAWYQQKPGQAPRLLIYDASSRATGIPARFSGSGSGTDFTLTISSLEPEDFAVYYCQQRSSWPP

TWTFGQGTKLEIKRAAAIEVMYPPPYLDNEKSNGTIIHVKGKHLCPSPLFPGPSKPFWVLVVVG

GVLACYSLLVTVAFIIFWVRSKRSRLLHSDYMNMTPRRPGPTRKHYQPYAPPRDFAAYRSRVKF

SRSADAPAYQQGQNQLYNELNLGRREEYDVLDKRRGRDPEMGGKPRRKNPQEGLYNELQKDKMA

EAYSEIGMKGERRRGKGHDGLYQGLSTATKDTYDALHMQALPPR

SEQ ID NO: 35 (anti-B7-H3 CAR polynucleotide sequence)
ATGCTGCTGCTGGTGACCAGCCTGCTGCTGTGCGAACTGCCGCATCCGGCGTTTCTGCTGATTC

CGCAGGTGCAGCTGCAGCAGAGCGGCGCGGAAGTGAAAAAACCGGGCAGCAGCGTGAAAGTGAG

CTGCAAAGCGAGCGGCGGCACCTTTAGCAGCTATGCGATTAGCTGGGTGCGCCAGGCGCCGGGC

CAGGGCCTGGAATGGATGGGCGGCATTATTCCGATTCTGGGCATTGCGAACTATGCGCAGAAAT

TTCAGGGCCGCGTGACCATTACCGCGGATGAAAGCACCAGCACCGCGTATATGGAACTGAGCAG

CCTGCGCAGCGAAGATACCGCGGTGTATTATTGCGCGCGCGGCGGCGCGGGCGGCAGCGGCAGC

TATTATCCGCTGATTTGGGGCCAGGGCACCACCGTGACCGTGAGCAGCGGCGGCGGCGGCAGCG

GCGGCGGCGGCAGCGGCGGCGGCGGCAGCGAAATTGTGCTGACCCAGAGCCCGGCGACCCTGAG

CCTGAGCCCGGGCGAACGCGCGACCCTGAGCTGCGGCGCGAGCCAGAGCGTGAGCAGCAGCTAT

CTGGCGTGGTATCAGCAGAAACCGGGCCAGGCGCCGCGCCTGCTGATTTATGATGCGAGCAGCC

-continued

GCGCGACCGGCATTCCGGCGCGCTTTAGCGGCAGCGGCAGCGGCACCGATTTTACCCTGACCAT

TAGCAGCCTGGAACCGGAAGATTTTGCGGTGTATTATTGCCAGCAGCGCAGCAGCTGGCCGCCG

ACCTGGACCTTTGGCCAGGGCACCAAACTGGAAATTAAACGCGCGGCGGCGATTGAAGTGATGT

ATCCGCCGCCGTATCTGGATAACGAAAAAAGCAACGGCACCATTATTCATGTGAAAGGCAAACA

TCTGTGCCCGAGCCCGCTGTTTCCGGGCCCGAGCAAACCGTTTTGGGTGCTGGTGGTGGTGGGC

GGCGTGCTGGCGTGCTATAGCCTGCTGGTGACCGTGGCGTTTATTATTTTTTGGGTGCGCAGCA

AACGCAGCCGCCTGCTGCATAGCGATTATATGAACATGACCCCGCGCCGCCCGGGCCCGACCCG

CAAACATTATCAGCCGTATGCGCCGCCGCGCGATTTTGCGGCGTATCGCAGCCGCGTGAAATTT

AGCCGCAGCGCGGATGCGCCGGCGTATCAGCAGGGCCAGAACCAGCTGTATAACGAACTGAACC

TGGGCCGCCGCGAAGAATATGATGTGCTGGATAAACGCCGCGGCCGCGATCCGGAAATGGGCGG

CAAACCGCGCCGCAAAAACCCGCAGGAAGGCCTGTATAACGAACTGCAGAAAGATAAAATGGCG

GAAGCGTATAGCGAAATTGGCATGAAAGGCGAACGCCGCCGCGGCAAAGGCCATGATGGCCTGT

ATCAGGGCCTGAGCACCGCGACCAAAGATACCTATGATGCGCTGCATATGCAGGCGCTGCCGCC

GCGC

SEQ ID NO: 36 (anti-B7-H3 scFV amino acid sequence)
QVQLQQSGAEVKKPGSSVKVSCKASGGTFSSYAISWVRQAPGQGLEWMGGIIPILGIANYAQKF

QGRVTITADESTSTAYMELSSLRSEDTAVYYCARGGAGGSGSYYPLIWGQGTTVTVSSGGGGSG

GGGSGGGGSEIVLTQSPATLSLSPGERATLSCGASQSVSSSYLAWYQQKPGQAPRLLIYDASSR

ATGIPARFSGSGSGTDFTLTISSLEPEDFAVYYCQQRSSWPPTWTFGQGTKLEIKRAAA

SEQ ID NO: 37 (anti-B7-H3 scFV polynucleotide sequence)
CAGGTGCAGCTGCAGCAGAGCGGCGCGGAAGTGAAAAAACCGGGCAGCAGCGTGAAAGTGAGCT

GCAAAGCGAGCGGCGGCACCTTTAGCAGCTATGCGATTAGCTGGGTGCGCCAGGCGCCGGGCCA

GGGCCTGGAATGGATGGGCGGCATTATTCCGATTCTGGGCATTGCGAACTATGCGCAGAAATTT

CAGGGCCGCGTGACCATTACCGCGGATGAAAGCACCAGCACCGCGTATATGGAACTGAGCAGCC

TGCGCAGCGAAGATACCGCGGTGTATTATTGCGCGCGCGGCGGCGCGGGCGGCAGCGGCAGCTA

TTATCCGCTGATTTGGGGCCAGGGCACCACCGTGACCGTGAGCAGCGGCGGCGGCGGCAGCGGC

GGCGGCGGCAGCGGCGGCGGCGGCAGCGAAATTGTGCTGACCCAGAGCCCGGCGACCCTGAGCC

TGAGCCCGGGCGAACGCGCGACCCTGAGCTGCGGCGCGAGCCAGAGCGTGAGCAGCAGCTATCT

GGCGTGGTATCAGCAGAAACCGGGCCAGGCGCCGCGCCTGCTGATTTATGATGCGAGCAGCCGC

GCGACCGGCATTCCGGCGCGCTTTAGCGGCAGCGGCAGCGGCACCGATTTTACCCTGACCATTA

GCAGCCTGGAACCGGAAGATTTTGCGGTGTATTATTGCCAGCAGCGCAGCAGCTGGCCGCCGAC

CTGGACCTTTGGCCAGGGCACCAAACTGGAAATTAAACGCGCGGCGGCG

SEQ ID NO: 38 (anti-B7-H3 scFV VH)
QVQLQQSGAEVKKPGSSVKVSCKASGGTFSSYAISWVRQAPGQGLEWMGGIIPILGIANYAQKF

QGRVTITADESTSTAYMELSSLRSEDTAVYYCARGGAGGSGSYYPLIWGQGTTVTVSS

SEQ ID NO: 39 (anti-B7-H3 scFV VL)
EIVLTQSPATLSLSPGERATLSCGASQSVSSSYLAWYQQKPGQAPRLLIYDASSRATGIPARFS

GSGSGTDFTLTISSLEPEDFAVYYCQQRSSWPPTWTFGQGTKLEIKRAAA

SEQ ID NO: 40 (CD8α transmembrane region)
IYIWAPLAGTCGVLLLSLVITLYC

SEQ ID NO: 41 (anti-BCMA CAR amino acid sequence)
MALPVTALLLPLALLLHAARPDIVLTQSPPSLAMSLGKRATISCRASESVTILGSHLIYWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFRHYSMNWVKQAPG

KGLKWMGRINTESGVPIYADDFKGRFAFSVETSASTAYLVINNLKDEDTASYFCSNDYLYSLDF

WGQGTALTVSSFVPVFLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTPRRPGPTRKHYQPYAPPR

DFAAYRSRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

SEQ ID NO: 42 (anti-BCMA CAR amino acid sequence)
MALPVTALLLPLALLLHAARPDIVLTQSPPSLAMSLGKRATISCRASESVTILGSHLIHWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTDYSINWVKRAPG

KGLKWMGWINTETREPAYAYDFRGRFAFSLETSASTAYLQINNLKYEDTATYFCALDYSYAMDY

WGQGTSVTVSSFVPVFLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTPRRPGPTRKHYQPYAPPR

DFAAYRSRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

SEQ ID NO: 43 (anti-BCMA CAR amino acid sequence)
MALPVTALLLPLALLLHAARPDIVLTQSPPSLAMSLGKRATISCRASESVTILGSHLIYWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTHYSMNWVKQAPG

KGLKWMGRINTETGEPLYADDFKGRFAFSLETSASTAYLVINNLKNEDTATFFCSNDYLYSCDY

WGQGTTLTVSSFVPVFLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTPRRPGPTRKHYQPYAPPR

DFAAYRSRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

SEQ ID NO: 44 (anti-BCMA CAR amino acid sequence)
MLLLVTSLLLCELPHPAFLLIPDIVLTQSPPSLAMSLGKRATISCRASESVTILGSHLIHWYQQ

KPGQPPTLLIQLASNVQTGVPARFSGSGSRTDFTLTIDPVEEDDVAVYYCLQSRTIPRTFGGGT

KLEIKGSTSGSGKPGSGEGSTKGQIQLVQSGPELKKPGETVKISCKASGYTFTDYSINWVKRAP

GKGLKWMGWINTETREPAYAYDFRGRFAFSLETSASTAYLQINNLKYEDTATYFCALDYSYAMD

YWGQGTSVTVSSAAAFVPVFLPAKPTTTPAPRPPTPAPTIASQPLSLRPEACRPAAGGAVHTRG

LDFACDIYIWAPLAGTCGVLLLSLVITLYCNHRNRSKRSRLLHSDYMNMTPRRPGPTRKHYQPY

APPRDFAAYRSRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

SEQ ID NO: 45 (anti-BCMA CAR amino acid sequence)
MALPVTALLLPLALLLHAARPDIVLTQSPPSLAMSLGKRATISCRASESVTILGSHLIHWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTDYSINWVKRAPG

KGLKWMGWINTETREPAYAYDERGRFAFSLETSASTAYLQINNLKYEDTATYFCALDYSYAMDY

WGQGTSVTVSSAAAFVPVFLPAKPTTTPAPRPPTPAPTIASQPLSLRPEACRPAAGGAVHTRGL

DFACDIYIWAPLAGTCGVLLLSLVITLYCNHRNRSKRSRLLHSDYMNMTPRRPGPTRKHYQPYA

PPRDFAAYRSRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

-continued

SEQ ID NO: 46 (anti-BCMA CAR amino acid sequence)
MALPVTALLLPLALLLHAARPDIVLTQSPPSLAMSLGKRATISCRASESVTILGSHLIHWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTDYSINWVKRAPG

KGLKWMGWINTETREPAYAYDERGRFAFSLETSASTAYLQINNLKYEDTATYFCALDYSYAMDY

WGQGTSVTVSSAAAFVPVFLPAKPTTTPAPRPPTPAPTIASQPLSLRPEACRPAAGGAVHTRGL

DFACDIYIWAPLAGTCGVLLLSLVITLYCNHRNRFSVVKRGRKKLLYIFKQPFMRPVQTTQEED

GCSCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALPPR

SEQ ID NO: 47 (anti-BCMA CAR amino acid sequence)
MALPVTALLLPLALLLHAARPDIVLTQSPPSLAMSLGKRATISCRASESVTILGSHLIHWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTDYSINWVKRAPG

KGLKWMGWINTETREPAYAYDFRGRFAFSLETSASTAYLQINNLKYEDTATYFCALDYSYAMDY

WGQGTSVTVSSAAAFVPVFLPAKPTTTPAPRPPTPAPTIASQPLSLRPEACRPAAGGAVHTRGL

DFACDIYIWAPLAGTCGVLLLSLVITLYCNHRNRRDQRLPPDAHKPPGGGSFRTPIQEEQADAH

STLAKIRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

SEQ ID NO: 48 (anti-BCMA CAR amino acid sequence)
MALPVTALLLPLALLLHAARPDIVLTQSPPSLAMSLGKRATISCRASESVTILGSHLIHWYQQK

PGQPPTLLIQLASNVQTGVPARFSGSGSRTDFTLTIDPVEEDDVAVYYCLQSRTIPRTFGGGTK

LEIKGSTSGSGKPGSGEGSTKGQIQLVQSGPELKKPGETVKISCKASGYTFTDYSINWVKRAPG

KGLKWMGWINTETREPAYAYDFRGRFAFSLETSASTAYLQINNLKYEDTATYFCALDYSYAMDY

WGQGTSVTVSSAAAFVPVFLPAKPTTTPAPRPPTPAPTIASQPLSLRPEACRPAAGGAVHTRGL

DFACDIYIWAPLAGTCGVLLLSLVITLYCNHRNRFSVVKRGRKKLLYIFKQPFMRPVQTTQEED

GCSCRFPEEEEGGCELRRDQRLPPDAHKPPGGGSFRTPIQEEQADAHSTLAKIRVKFSRSADAP

AYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

SEQ ID NO: 49 (anti-BCMA CAR amino acid sequence)
DIVLTQSPPSLAMSLGKRATISCRASESVTILGSHLIHWYQQKPGQPPTLLIQLASNVQTGVPA

RFSGSGSRTDFTLTIDPVEEDDVAVYYCLQSRTIPRTFGGGTKLEIKGSTSGSGKPGSGEGSTK

GQIQLVQSGPELKKPGETVKISCKASGYTFTDYSINWVKRAPGKGLKWMGWINTETREPAYAYD

FRGRFAFSLETSASTAYLQINNLKYEDTATYFCALDYSYAMDYWGQGTSVTVSSAAATTTPAPR

PPTPAPTIASQPLSLRPEACRPAAGGAVHTRGLDFACDIYIWAPLAGTCGVLLLSLVITLYCKR

GRKKLLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRGKGHDG

LYQGLSTATKDTYDALHMQALPPR

SEQ ID NO: 50 (anti-BCMA Heavy Chain amino acid sequence)
QLQLQESGPGLVKPSETLSLTCTVSGGSISSGSYFWGWIRQPPGKGLEWIGSIYYSGITYYNPS

LKSRVTISVDTSKNQFSLKLSSVTAADTAVYYCARHDGAVAGLFDYWGQGTLVTVSSASTKGPS

VFPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEAAGGPSVFLFPPKPKDTLMISR

TPEVTCVVVDVSQEDPEVQFNWYVDGVEVHNAKTKPREEQFNSTYRVVSVLIVLHQDWLNGKEY

-continued
KCKVSNKGLPSSIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHNHYTQKSLSLSLGK

SEQ ID NO: 51 (anti-BCMA Light Chain amino acid sequence)
SYVLTQPPSVSVAPGQTARITCGGNNIGSKSVHWYQQPPGQAPVVVVYDDSDRPSGIPERFSGS

NSGNTATLTISRVEAGDEAVYYCQVWDSSSDHVVFGGGTKLTVLGQPKAAPSVTLFPPSSEELQ

ANKATLVCLISDFYPGAVTVAWKGDSSPVKAGVETTTPSKQSNNKYAASSYLSLTPEQWKSHRS

YSCQVTHEGSTVEKTVAPTECS

SEQ ID NO: 52 (anti-BCMA CAR Heavy Chain amino acid sequence)
QVQLVQSGAEVKKPGSSVKVSCKASGGTFSNYWMHWVRQAPGQGLEWMGATYRGHSDTYYNQKF

KGRVTITADKSTSTAYMELSSLRSEDTAVYYCARGAIYDGYDVLDNWGQGTLVTVSSASTKGPS

VFPLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSLS

PGK

SEQ ID NO: 53 (anti-BCMA Light Chain amino acid sequence)
DIQMTQSPSSLSASVGDRVTITCSASQDISNYLNWYQQKPGKAPKLLIYYTSNLHSGVPSRFSG

SGSGTDFTLTISSLQPEDFATYYCQQYRKLPWTFGQGTKLEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

SEQ ID NO: 54 (anti-BCMA CAR amino acid sequence)
MALPVTALLLPLALLLHAARPQVKLEESGGGLVQAGRSLRLSCAASEHTFSSHVMGWFRQAPGK

ERESVAVIGWRDISTSYADSVKGRFTISRDNAKKTLYLQMNSLKPEDTAVYYCAARRIDAADFD

SWGQGTQVTVSSGGGGSEVQLVESGGGLVQAGGSLRLSCAASGRTFTMGWFRQAPGKEREFVAA

ISLSPTLAYYAESVKGRFTISRDNAKNTVVLQMNSLKPEDTALYYCAADRKSVMSIRPDYWGQG

TQVTVSSTSTTTPAPRPPTPAPTIASQPLSLRPEACRPAAGGAVHTRGLDFACDIYIWAPLAGT

CGVLLLSLVITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID NO: 55 (nucleic acid sequence comprising anti-BCMA CAR
coding sequence)
TGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGC

CTGGGAGCTCTCTGGCTAACTAGGGAACCCACTGCTTAAGCCTCAATAAAGCTTGCCTTGAGTG

CTTCAAGTAGTGTGTGCCCGTCTGTTGTGTGACTCTGGTAACTAGAGATCCCTCAGACCCTTTT

AGTCAGTGTGGAAAATCTCTAGCAGTGGCGCCCGAACAGGGACTTGAAAGCGAAAGGGAAACCA

GAGGAGCTCTCTCGACGCAGGACTCGGCTTGCTGAAGCGCGCACGGCAAGAGGCGAGGGGCGGC

GACTGGTGAGTACGCCAAAAATTTTGACTAGCGGAGGCTAGAAGGAGAGAGATGGGTGCGAGAG

CGTCAGTATTAAGCGGGGGAGAATTAGATCGCGATGGGAAAAAATTCGGTTAAGGCCAGGGGGA

AAGAAAAAATATAAATTAAAACATATAGTATGGGCAAGCAGGGAGCTAGAACGATTCGCAGTTA

ATCCTGGCCTGTTAGAAACATCAGAAGGCTGTAGACAAATACTGGGACAGCTACAACCATCCCT

-continued

```
TCAGACAGGATCAGAAGAACTTAGATCATTATATAATACAGTAGCAACCCTCTATTGTGTGCAT

CAAAGGATAGAGATAAAAGACACCAAGGAAGCTTTAGACAAGATAGAGGAAGAGCAAAACAAAA

GTAAGACCACCGCACAGCAAGCGGCCGGCCGCTGATCTTCAGACCTGGAGGAGGAGATATGAGG

GACAATTGGAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGGAGCTTTGTT

CCTTGGGTTCTTGGGAGCAGCAGGAAGCACTATGGGCGCAGCGTCAATGACGCTGACGGTACAG

GCCAGACAATTATTGTCTGGTATAGTGCAGCAGCAGAACAATTTGCTGAGGGCTATTGAGGCGC

AACAGCATCTGTTGCAACTCACAGTCTGGGGCATCAAGCAGCTCCAGGCAAGAATCCTGGCTGT

GGAAAGATACCTAAAGGATCAACAGCTCCTGGGGATTTGGGGTTGCTCTGGAAAACTCATTTGC

ACCACTGCTGTGCCTTGGAATGCTAGTTGGAGTAATAAATCTCTGGAACAGATTTGGAATCACA

CGACCTGGATGGAGTGGGACAGAGAAATTAACAATTACACAAGCTTAATACACTCCTTAATTGA

AGAATCGCAAAACCAGCAAGAAAAGAATGAACAAGAATTATTGGAATTAGATAAATGGGCAAGT

TTGTGGAATTGGTTTAACATAACAAATTGGCTGTGGTATATAAAATTATTCATAATGATAGTAG

GAGGCTTGGTAGGTTTAAGAATAGTTTTTGCTGTACTTTCTATAGTGAATAGAGTTAGGCAGGG

ATATTCACCATTATCGTTTCAGACCCACCTCCCAACCCCGAGGGGACCCGACAGGCCCGAAGGA

ATAGAAGAAGAAGGTGGAGAGAGAGACAGAGACAGATCCATTCGATTAGTGAACGGATCTCGAC

GGTATCGCCTTTAAAAGAAAAGGGGGGATTGGGGGGTACAGTGCAGGGGAAAGAATAGTAGACA

TAATAGCAACAGACATACAAACTAAAGAATTACAAAAACAAATTACAAAAATTCAAAATTTTCG

GGTTTATTACAGGGACAGCAGAGATCCAGTTTATCGATGAGTAATTCATACAAAAGGACTCGCC

CCTGCCTTGGGGAATCCCAGGGACCGTCGTTAAACTCCCACTAACGTAGAACCCAGAGATCGCT

GCGTTCCCGCCCCCTCACCCGCCCGCTCTCGTCATCACTGAGGTGGAGAAGAGCATGCGTGAGG

CTCCGGTGCCCGTCAGTGGGCAGAGCGCACATCGCCCACAGTCCCCGAGAAGTTGGGGGGAGGG

GTCGGCAATTGAACCGGTGCCTAGAGAAGGTGGCGCGGGGTAAACTGGGAAAGTGATGTCGTGT

ACTGGCTCCGCCTTTTTCCCGAGGGTGGGGGAGAACCGTATATAAGTGCAGTAGTCGCCGTGAA

CGTTCTTTTTCGCAACGGGTTTGCCGCCAGAACACAGGTAAGTGCCGTGTGTGGTTCCCGCGGG

CCTGGCCTCTTTACGGGTTATGGCCCTTGCGTGCCTTGAATTACTTCCACGCCCCTGGCTGCAG

TACGTGATTCTTGATCCCGAGCTTCGGGTTGGAAGTGGGTGGGAGAGTTCGAGGCCTTGCGCTT

AAGGAGCCCCTTCGCCTCGTGCTTGAGTTGAGGCCTGGCTTGGGCGCTGGGGCCGCCGCGTGCG

AATCTGGTGGCACCTTCGCGCCTGTCTCGCTGCTTTCGATAAGTCTCTAGCCATTTAAAATTTT

TGATGACCTGCTGCGACGCTTTTTTTCTGGCAAGATAGTCTTGTAAATGCGGGCCAAGATCTGC

ACACTGGTATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTCAAGCTGGC

CGGCCTGCTCTGGTGCCTGGCCTCGCGCCGCCGTGTATCGCCCCGCCCTGGGCGGCAAGGCTGG

CCCGGTCGGCACCAGTTGCGTGAGCGGAAAGATGGCCGCTTCCCGGCCCTGCTGCAGGGAGCTC

AAAATGGAGGACGCGGCGCTCGGGAGAGCGGGCGGGTGAGTCACCCACACAAAGGAAAAGGGCC

TTTCCGTCCTCAGCCGTCGCTTCATGTGACTCCACGGAGTACCGGGCGCCGTCCAGGCACCTCG

ATTAGTTCTCGAGCTTTTGGAGTACGTCGTCTTTAGGTTGGGGGGAGGGGTTTTATGCGATGGA

GTTTCCCCACACTGAGTGGGTGGAGACTGAAGTTAGGCCAGCTTGGCACTTGATGTAATTCTCC

TTGGAATTTGCCCTTTTTGAGTTTGGATCTTGGTTCATTCTCAAGCCTCAGACAGTGGTTCAAA

GTTTTTTTTCTTCCATTTCAGGTGTCGTGAGGATCGCTAGCGCTACCGGACTCAGATCTCGAGCT
```

-continued

CAAGCTTCGAATTCGCCGCCACCATGGCTCTGCCCGTCACCGCTCTGCTGCTGCCTCTGGCTCT

GCTGCTGCACGCTGCTCGCCCTCAGGTCAAACTGGAAGAATCTGGCGGAGGCCTGGTGCAGGCA

GGACGGAGCCTGCGCCTGAGCTGCGCAGCATCCGAGCACACCTTCAGCTCCCACGTGATGGGCT

GGTTTCGGCAGGCCCCAGGCAAGGAGAGAGAGAGCGTGGCCGTGATCGGCTGGAGGGACATCTC

CACATCTTACGCCGATTCCGTGAAGGGCCGGTTCACCATCAGCCGGGACAACGCCAAGAAGACA

CTGTATCTGCAGATGAACAGCCTGAAGCCCGAGGACACCGCCGTGTACTATTGCGCAGCAAGGA

GAATCGACGCAGCAGACTTTGATTCCTGGGGCCAGGGCACCCAGGTGACAGTGTCTAGCGGAGG

AGGAGGATCTGAGGTGCAGCTGGTGGAGAGCGGAGGCGGCCTGGTGCAGGCCGGAGGCTCTCTG

AGGCTGAGCTGTGCAGCATCCGGAAGAACCTTCACAATGGGCTGGTTTAGGCAGGCACCAGGAA

AGGAGAGGGAGTTCGTGGCAGCAATCAGCCTGTCCCCTACCCTGGCCTACTATGCCGAGAGCGT

GAAGGGCAGGTTTACCATCTCCCGCGATAACGCCAAGAATACAGTGGTGCTGCAGATGAACTCC

CTGAAACCTGAGGACACAGCCCTGTACTATTGTGCCGCCGATCGGAAGAGCGTGATGAGCATTA

GACCAGACTATTGGGGGCAGGGAACACAGGTGACCGTGAGCAGCACTAGTACCACGACGCCAGC

GCCGCGACCACCAACACCGGCGCCCACCATCGCGTCGCAGCCCCTGTCCCTGCGCCCAGAGGCG

TGCCGGCCAGCGGCGGGGGGCGCAGTGCACACGAGGGGGGCTGGACTTCGCCTGTGATATCTACA

TCTGGGCGCCCTTGGCCGGGACTTGTGGGGTCCTTCTCCTGTCACTGGTTATCACCCTTTACTG

CAAACGGGGCAGAAAGAAACTCCTGTATATATTCAAACAACCATTTATGAGACCAGTACAAACT

ACTCAAGAGGAAGATGGCTGTAGCTGCCGATTTCCAGAAGAAGAAGAAGGAGGATGTGAACTGA

GAGTGAAGTTCAGCAGGAGCGCAGACGCCCCCGCGTACCAGCAGGGCCAGAACCAGCTCTATAA

CGAGCTCAATCTAGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATGAACTGCAGAAAG

ATAAGATGGCGGAGGCCTACAGTGAGATTGGGATGAAAGGCGAGCGCCGGAGGGGCAAGGGGCA

CGATGGCCTTTACCAGGGTCTCAGTACAGCCACCAAGGACACCTACGACGCCCTTCACATGCAG

GCCCTGCCCCCTCGCTAATCTAGATCCGCGTCTGGAACAATCAACCTCTGGATTACAAAATTTG

TGAAAGATTGACTGGTATTCTTAACTATGTTGCTCCTTTTACGCTATGTGGATACGCTGCTTTA

ATGCCTTTGTATCATGCTATTGCTTCCCGTATGGCTTTCATTTTCTCCTCCTTGTATAAATCCT

GGTTGCTGTCTCTTTATGAGGAGTTGTGGCCCGTTGTCAGGCAACGTGGCGTGGTGTGCACTGT

GTTTGCTGACGCAACCCCCACTGGTTGGGGCATTGCCACCACCTGTCAGCTCCTTTCCGGGACT

TTCGCTTTCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAGCTGACGTCCTTTCC

ATGGCTGCTCGCCTGTGTTGCCACCTGGATTCTGCGCGGGACGTCCTTCTGCTACGTCCCTTCG

GCCCTCAATCCAGCGGACCTTCCTTCCCGCGGCCTGCTGCCGGCTCTGCGGCCTCTTCCGCGTC

TTCGCCTTCGCCCTCAGACGAGTCGGATCTCCCTTTGGGCCGCCTCCCCGCCTGGAATTAATTC

TGCAGTCGAGACCTAGAAAAACATGGAGCAATCACAAGTAGCAATACAGCAGCTACCAATGCTG

ATTGTGCCTGGCTAGAAGCACAAGAGGAGGAGGAGGTGGGTTTTCCAGTCACACCTCAGGTACC

TTTAAGACCAATGACTTACAAGGCAGCTGTAGATCTTAGCCACTTTTTAAAAGAAAAGAGGGGA

CTGGAAGGGCTAATTATCTGAGCCTGGGAGCTCTCTCTGCTTTTTGCTTGTACTGGGTCTCTCT

GGTTAGACCAGCACTCCCAACGAAGACAAGATGGCTAACTAGGGAACCCACTGCTTAAGCCTCA

ATAAAGCTTGCCTTGAGTGCTTCAAGTAGTGTGTGCCCGTCTGTTGTGTGACTCTGGTAACTAG

AGATCCCTCAGACCCTTTTAGTCAGTGTGGAAAATCTCTAGCAGT

SEQ ID NO: 56 (exemplary human IL-10 variant substitutions based
on viral IL-10)
MHSSALLCCLVLLTGVRASPGQGTQSENSCTHFPGNLPNMLRDLRDAFSRVKTFFQTKDEVDNL

LLKESLLEDFKGYLGCQALSEMIQFYLEEVMPQAENQDPEAKDHVNSLGENLKTLRLRLRRCHR

FLPCENKSKAVEQIKNAFNKLQEKGIYKAMSEFDIFINYIEAYMTMKIRN

SEQ ID NO: 57 (exemplary human IL-10 variant with amino acid
substitutions based on viral IL-10)
MHSSALLCCLVLLTGVRASPGQGTQSENSCTHFPGNLPNMLRDLRDAFSRVKTFFQMKDQLDNL

LLKESLLEDFKGYLGCQALSEMIQFYLEEVMPQAENQDPDAKAHVNSLGENLKTLRLRLRRCHR

FLPCENKSKAVEQVKNAFNKLQEKGIYKAMSEFDIFINYIEAYMIMKIRN

SEQ ID NO: 58 (*Mus musculus*; "MOUSE")
MPGSALLCCLLLLTGMRISRGQYSREDNNCTHFPVGQSHMLLELRTAFSQVKTFFQTKDQLDNI

LLTDSLMQDFKGYLGCQALSEMIQFYLVEVMPQAEKHGPEIKEHLNSLGEKLKTLRMRLRRCHR

FLPCENKSKAVEQVKSDFNKLQDQGVYKAMNEFDIFINCIEAYMMIKMKS

SEQ ID NO: 59 (*Rattus norvegicus*; "RAT")
MPGSALLCCLLLLAGVKTSKGHSIRGDNNCTHFPVSQTHMLRELRAAFSQVKTFFQKKDQLDNI

LLTDSLLQDFKGYLGCQALSEMIKFYLVEVMPQAENHGPEIKEHLNSLGEKLKTLWIQLRRCHR

FLPCENKSKAVEQVKNDFNKLQDKGVYKAMNEFDIFINCIEAYVTLKMKN

SEQ ID NO: 60 (*Macaca mulatta*; "MACMU")
MHSSALLCCLVLLTGVRASPGQGTQSENSCTRFPGNLPHMLRDLRDAFSRVKTFFQMKDQLDNI

LLKESLLEDFKGYLGCQALSEMIQFYLEEVMPQAENHDPDIKEHVNSLGENLKTLRLRLRRCHR

FLPCENKSKAVEQVKNAFSKLQEKGVYKAMSEFDIFINYIEAYMTMKIQN

SEQ ID NO: 61 (*Gorilla gorilla*; "GORILLA")
MHSSALLCCLVLLTGVRASPGHGTQSENSCTHFPGNLPNMLRDLRDAFSRVKTFFQMKDQLDNL

LLKESLLEDFKGYLGCQALSEMIQFYLEEVMPQAENQDPDIKAHVNSLGENLKTLRLRLRRCHR

FLPCENKSKAVEQVKNAFNKLQEKGVYKAMSEFDIFINYIEAYMTMKIRN

SEQ ID NO: 62 (*Macaca fascicularis*; "CYNO")
MHSSALLCCLVLLTGVRASPGQGTQSENSCTRFPGNLPHMLRDLRDAFSRVKTFFQMKDQLDNI

LLKESLLEDFKGYLGCQALSEMIQFYLEEVMPQAENHDPDIKEHVNSLGENLKTLRLRLRRCHR

FLPCENKSKAVEQVKNAFSKLQEKGVYKAMSEFDIFINYIEAYMTMKIQN

SEQ ID NO: 63 (*Papio Anubis*; "OLIVE BABOON")
MHSSALLCCLVVLTGVRASPGQGTQSENSCTRFPGNLPHMLRDLRDAFSRVKTFFQMKDQLDNI

LLKESLLEDFKGYLGCQALSEMIQFYLEEVMPQAENHDPDIKEHVNSLGENLKTLRLRLRRCHR

FLPCENKSKAVEQVKNAFSKLQEKGVYKAMSEFDIFINYIEAYMTMKIQN

SEQ ID NO: 64 (*Pan paniscus*; "BONOBO")
MHSSALLCCLVLLTGVRASPGQGTQSENSCTHFPGNLPNMLRDLRDAFSRVKTFFQMKDQLDNL

LLKESLLEDFKGYLGCQALSEMIQFYLEEVMPQAENQDPDIKVHVNSLGENLKTLRLRLRRCHR

FLPCENKSKAVEQVKNAFNKLQEKGIYKAMSEFDIFINYIEAYMTMKIRN

SEQ ID NO: 65 (*Pan troglodytes*; "CHIMP")
MHSSALLCCLVLLTGVRASPGQGTQSENSCTHFPGNLPNMLRDLRDAFSRVKTFFQMKDQLDNL

LLKESLLEDFKGYLGCQALXEMIQFYLEEVMPQAENQDPDIKVHVNSLGENLKTLRLRLRRCHR

FLPCENKSKAVEQVKNAFNKLQEKGIVKAMSEFDIFINYIEAYMTMKIRN

SEQ ID NO: 66 (EBVB9)
MERRLVVTLQCLVLLYLAPECGGTDQCDNFPQMLRDLRDAFSRVKTFFQTKDEVDNLLLKESLL

EDFKGYLGCQALSEMIQFYLEEVMPQAENQDPEAKDHVNSLGENLKTLRLRLRRCHRFLPCENK

SKAVEQIKNAFNKLQEKGIYKAMSEFDIFINYIEAYMTIKAR

-continued

SEQ ID NO: 67 huIL-10 HYBRID#1
MHSSALLCCLVLLTGRASPGQGTQSENSCTHFPGNIPNMLRDIRDAFSRVKTEFQTKDEVDNLL

LKESLLEDEKGYLGCQALSEMIQFYLEEVMPQAENQDPEAKDHVNSLGENLKTLRLRIRRCHRF

LPCENKSKAVEQIKNAFNKLQEKGIYKAMSEFDIFINYIEAYMTMKIRN

SEQ ID NO: 68 huIL-10 HYBRID#2
MHSSALLCCLVLLTGRASPGQGTQSENSCTHFPGNIPNMLRDIRDAFSRVKTEFQMKDQLDNLL

LKESLLEDEKGYLGCQALSEMIQFYLEEVMPQAENQDPDAKAHVNSLGENLKTLRLRIRRCHRF

LPCENKSKAVEQVKNAFNKLQEKGIYKAMSEFDIFINYIEAYMTMKIRN

---

What is claimed is:

1. A population of genetically modified CD4$^+$ cells (CD4$^{IL\text{-}10/CAR}$ cells), wherein the CD4IL-10/CAR cells in the population comprise:

(a) a first exogenous polynucleotide segment encoding a chimeric antigen receptor (CAR), wherein the CAR comprises an antigen-binding domain targeting an autoantigen or antigen associated with an inflammatory or autoimmune disease; and (b) a second exogenous polynucleotide segment encoding interleukin-10 (IL-10), wherein the CD4$^{IL\text{-}10/CAR}$ cells express the CAR and secrete IL-10, and wherein the population of CD4$^{IL\text{-}10/CAR}$ cells reduce hyperactivity of NLRP3 inflammasome or inhibit the production of a pro-inflammatory cytokine when administered in a therapeutically sufficient amount to a patient who has an inflammatory or autoimmune disease.

2. The CD4$^{IL-10/CAR}$ cell population of claim 1, wherein the pro-inflammatory cytokine is IL-1β or IL-18.

3. The CD4$^{IL-10/CAR}$ cell population of claim 1, wherein the CAR-targeted autoantigen or antigen associated with an inflammatory or autoimmune disease is CD19.

4. The CD4$^{IL-10/CAR}$ cell population of claim 1, wherein the CD4$^{IL-10/CAR}$ cells are cytotoxic to cells expressing the CAR-targeted autoantigen or antigen.

5. The CD4$^{IL-10/CAR}$ cell population of claim 3, wherein the CD4$^{IL-10/CAR}$ cells are cytotoxic to cells expressing CD19.

\* \* \* \* \*